(12) United States Patent
Hasvold et al.

(10) Patent No.: US 10,633,379 B2
(45) Date of Patent: Apr. 28, 2020

(54) BROMODOMAIN INHIBITORS

(71) Applicant: AbbVie Inc., North Chicago, IL (US)

(72) Inventors: Lisa A. Hasvold, Grayslake, IL (US); Dachun Liu, Vernon Hills, IL (US); Keith F. McDaniel, Wauconda, IL (US); John Pratt, Kenosha, WI (US); George Sheppard, Wilmette, IL (US); Le Wang, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 16/093,483

(22) PCT Filed: Apr. 14, 2017

(86) PCT No.: PCT/CN2017/080511
§ 371 (c)(1),
(2) Date: Oct. 12, 2018

(87) PCT Pub. No.: WO2017/177955
PCT Pub. Date: Oct. 19, 2017

(65) Prior Publication Data
US 2019/0345153 A1 Nov. 14, 2019

(30) Foreign Application Priority Data

Apr. 15, 2016 (WO) ............... PCT/CN2016/079362

(51) Int. Cl.
*C07D 471/04* (2006.01)
(52) U.S. Cl.
CPC ................. *C07D 471/04* (2013.01)
(58) Field of Classification Search
CPC .................................................. C07D 471/04
USPC ....................................................... 514/300
See application file for complete search history.

(56) References Cited

U.S. PATENT DOCUMENTS

| | | | |
|---|---|---|---|
| 4,004,012 A | 1/1977 | Lesher et al. | |
| 4,072,746 A | 2/1978 | Lesher et al. | |
| 4,093,812 A | 6/1978 | Rainer | |
| 4,107,315 A | 8/1978 | Lesher et al. | |
| 4,137,233 A | 1/1979 | Lesher et al. | |
| 4,199,586 A | 4/1980 | Lesher et al. | |
| 4,225,715 A | 9/1980 | Lesher et al. | |
| 4,289,774 A | 9/1981 | Schacht et al. | |
| 4,298,609 A | 11/1981 | Lesher et al. | |
| 4,304,776 A | 12/1981 | Lesher et al. | |
| 4,305,943 A | 12/1981 | Lesher et al. | |
| 4,337,253 A | 6/1982 | Lesher et al. | |
| 4,338,446 A | 7/1982 | Lesher et al. | |
| 4,346,221 A | 8/1982 | Lesher et al. | |
| 4,353,905 A | 10/1982 | Sircar et al. | |
| 4,397,854 A | 8/1983 | Sircar | |
| 4,404,203 A | 9/1983 | Sircar | |
| 4,465,686 A | 8/1984 | Lesher et al. | |
| 4,486,431 A | 12/1984 | Lesher et al. | |
| 4,515,797 A | 5/1985 | Lesher et al. | |
| 4,559,352 A | 12/1985 | Lesher et al. | |
| 4,599,423 A | 7/1986 | Lesher et al. | |
| 4,643,998 A | 2/1987 | Hilboll et al. | |
| 4,666,902 A | 5/1987 | Zoller et al. | |
| 4,667,033 A | 5/1987 | Hilboll et al. | |
| 4,678,786 A | 7/1987 | Roe et al. | |
| 4,734,415 A | 3/1988 | Sircar et al. | |
| 4,816,454 A | 3/1989 | Zoller et al. | |
| 4,820,819 A | 4/1989 | Roe et al. | |

(Continued)

FOREIGN PATENT DOCUMENTS

| | | |
|---|---|---|
| AU | 2014249025 A1 | 9/2015 |
| CN | 104136435 A | 11/2014 |

(Continued)

OTHER PUBLICATIONS

Banerjee C., et al., "BET Bromodomain Inhibition as a Novel Strategy for Reactivation of HIV-1," Journal of Leukocyte Biology, 2012, vol. 92 (6), pp. 1147-1154.

Berge S.M., et al., "Pharmaceutical Salts," Journal of Pharmaceutical Sciences, 1977, vol. 66 (1), pp. 1-19.

Best O.G., et al., "The Novel Hsp-90 Inhibitor SNX7081 is Significantly More Potent than 17-AAG Against Primary CLL Cells and a Range of Haematological Cell Lines, Irrespective of Lesions in the TP53 Pathway," British Journal of Haematalogy, 2010, vol. 151 (2), pp. 185-188.

Bhattacharya, S., et al., "Bromodomain Inhibitors: What Does the Future Hold?," Clinical Advances in Hematology & Oncology : H&O, Jul. 2018, vol. 16 (7), pp. 504-515.

(Continued)

*Primary Examiner* — Nizal S Chandrakumar
(74) *Attorney, Agent, or Firm* — Michael S. Montgomery

(57) ABSTRACT

The present invention provides for compounds of formula (I)

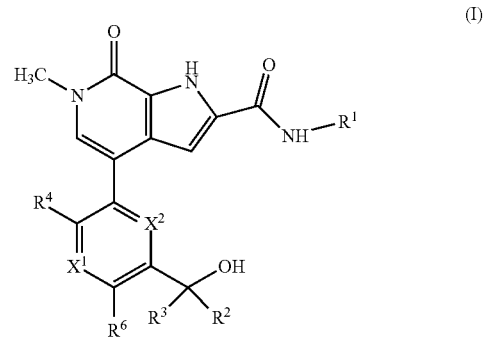

wherein $R^1$, $R^2$, $R^3$, $R^4$, $R^6$, $X^1$, and $X^2$ have any of the values defined in the specification, and pharmaceutically acceptable salts thereof, that are useful as agents in the treatment of diseases and conditions, including inflammatory diseases, cancer, and AIDS. Also provided are pharmaceutical compositions comprising compounds of formula (I).

2 Claims, No Drawings

(56) References Cited

U.S. PATENT DOCUMENTS

| | | |
|---|---|---|
| 4,863,745 A | 9/1989 | Zibell |
| 4,919,941 A | 4/1990 | Zibell |
| 5,112,625 A | 5/1992 | Zibell et al. |
| 5,192,563 A | 3/1993 | Patel et al. |
| 5,217,735 A | 6/1993 | Zibell |
| 5,221,543 A | 6/1993 | Zibell et al. |
| 5,385,925 A | 1/1995 | Narr et al. |
| 5,401,738 A | 3/1995 | Mederski et al. |
| 5,418,233 A | 5/1995 | Linz et al. |
| 5,455,348 A | 10/1995 | Austel et al. |
| 5,466,697 A | 11/1995 | Wilhelm et al. |
| 5,552,409 A | 9/1996 | Michelotti et al. |
| 5,563,268 A | 10/1996 | Linz et al. |
| 5,587,393 A | 12/1996 | Narr et al. |
| 5,631,254 A | 5/1997 | Michelotti et al. |
| 5,635,494 A | 6/1997 | Ross et al. |
| 5,668,279 A | 9/1997 | Chakravarty et al. |
| 5,684,029 A | 11/1997 | Narr et al. |
| 5,698,554 A | 12/1997 | Ishida et al. |
| 5,716,954 A | 2/1998 | Wilhelm et al. |
| 5,726,162 A | 3/1998 | Michelotti et al. |
| 5,726,176 A | 3/1998 | Michelotti et al. |
| 5,728,694 A | 3/1998 | Michelotti et al. |
| 5,728,698 A | 3/1998 | Michelotti et al. |
| 5,728,715 A | 3/1998 | Michelotti et al. |
| 5,741,793 A | 4/1998 | Young et al. |
| 5,753,642 A | 5/1998 | Michelotti et al. |
| 5,763,440 A | 6/1998 | Ross et al. |
| 5,808,065 A | 9/1998 | Ishida et al. |
| 5,814,651 A | 9/1998 | Duplantier et al. |
| 5,855,654 A | 1/1999 | Willingham et al. |
| 5,935,961 A | 8/1999 | Ross et al. |
| 5,958,925 A | 9/1999 | Ross et al. |
| 6,143,751 A | 11/2000 | Cheshire et al. |
| 6,245,804 B1 | 6/2001 | Lehmann et al. |
| 6,271,380 B1 | 8/2001 | Gilligan et al. |
| 6,307,047 B1 | 10/2001 | Black et al. |
| 6,344,454 B1 | 2/2002 | Lehmann et al. |
| 6,348,468 B1 | 2/2002 | Ohkuchi et al. |
| 6,403,586 B1 | 6/2002 | Ohkuchi et al. |
| 6,420,367 B1 | 7/2002 | Ueda et al. |
| 6,518,271 B1 | 2/2003 | Gilligan et al. |
| 6,548,534 B2 | 4/2003 | Lehmann et al. |
| 7,001,895 B2 | 2/2006 | Black et al. |
| 7,115,591 B2 | 10/2006 | Black et al. |
| 7,132,424 B2 | 11/2006 | Picard |
| 7,226,920 B2 | 6/2007 | Arnost et al. |
| 7,273,877 B2 | 9/2007 | Black et al. |
| 7,435,735 B2 | 10/2008 | Wai et al. |
| 7,459,453 B2 | 12/2008 | Dal et al. |
| 7,595,316 B2 | 9/2009 | Ohtake et al. |
| 7,598,245 B2 | 10/2009 | Arnost et al. |
| 7,838,523 B2 | 11/2010 | Blomgren et al. |
| 7,884,108 B2 | 2/2011 | Blomgren et al. |
| 7,915,267 B2 | 3/2011 | Nara et al. |
| 7,943,618 B2 | 5/2011 | Dewdney et al. |
| 7,994,325 B2 | 8/2011 | Paone et al. |
| 8,263,612 B2 | 9/2012 | Bondy et al. |
| 8,980,879 B2 | 3/2015 | Liu et al. |
| 9,050,346 B2 | 6/2015 | Hasvold et al. |
| 9,296,741 B2 * | 3/2016 | Wang ............... A61K 31/5377 |
| 9,321,764 B2 | 4/2016 | Wang et al. |
| 9,321,765 B2 | 4/2016 | Gong |
| 9,399,640 B2 | 7/2016 | Yue et al. |
| 9,428,514 B2 | 8/2016 | Bogdan et al. |
| 9,493,411 B2 | 11/2016 | Hasvold et al. |
| 9,776,990 B2 | 10/2017 | Pratt et al. |
| 9,918,990 B2 | 3/2018 | Yue et al. |
| 9,957,263 B2 | 5/2018 | Dai et al. |
| 9,994,581 B2 | 6/2018 | Wang et al. |
| 10,035,800 B2 | 7/2018 | Fidanze et al. |
| 10,085,985 B2 | 10/2018 | Bogdan et al. |
| 10,131,657 B2 | 11/2018 | Dai et al. |
| 2002/0013318 A1 | 1/2002 | Black et al. |
| 2002/0016365 A1 | 2/2002 | Lehmann et al. |
| 2002/0028938 A1 | 3/2002 | Black et al. |
| 2002/0099055 A1 | 7/2002 | Bantick et al. |
| 2002/0123496 A1 | 9/2002 | Ohkuchi et al. |
| 2003/0114448 A1 | 6/2003 | Zhang et al. |
| 2003/0203902 A1 | 10/2003 | Lehmann et al. |
| 2003/0225276 A1 | 12/2003 | Black et al. |
| 2004/0043979 A1 | 3/2004 | Picard |
| 2004/0063673 A1 | 4/2004 | Johnson |
| 2004/0147516 A1 | 7/2004 | Ohkuchi et al. |
| 2004/0158064 A1 | 8/2004 | Black et al. |
| 2005/0026964 A1 | 2/2005 | Black et al. |
| 2005/0065155 A1 | 3/2005 | Ohkuchi et al. |
| 2005/0222034 A1 | 10/2005 | Hsu et al. |
| 2005/0261268 A1 | 11/2005 | Arnost et al. |
| 2005/0267113 A1 | 12/2005 | Ohkuchi et al. |
| 2006/0002379 A1 | 1/2006 | Koyama |
| 2006/0160804 A1 | 7/2006 | Ohkuchi et al. |
| 2006/0178375 A1 | 8/2006 | Ohtake et al. |
| 2006/0276496 A1 | 12/2006 | Goldberg et al. |
| 2007/0049595 A1 | 3/2007 | Ohkuchi et al. |
| 2007/0093496 A1 | 4/2007 | Wai et al. |
| 2007/0142414 A1 | 6/2007 | Vanotti et al. |
| 2007/0208025 A1 | 9/2007 | Ohkuchi et al. |
| 2008/0027041 A1 | 1/2008 | Hudkins et al. |
| 2008/0090827 A1 | 4/2008 | Taylor et al. |
| 2008/0096901 A1 | 4/2008 | Arnost et al. |
| 2008/0119457 A1 | 5/2008 | Huang et al. |
| 2008/0119474 A1 | 5/2008 | Ohkuchi et al. |
| 2008/0153834 A1 | 6/2008 | Blomgren et al. |
| 2008/0207678 A1 | 8/2008 | Bondy et al. |
| 2008/0261972 A1 | 10/2008 | Paone et al. |
| 2008/0269235 A1 | 10/2008 | Dal et al. |
| 2008/0269287 A1 | 10/2008 | Ohtake et al. |
| 2008/0312307 A1 | 12/2008 | Adams et al. |
| 2009/0042888 A1 | 2/2009 | Black et al. |
| 2009/0069332 A1 | 3/2009 | Ohkuchi et al. |
| 2009/0082330 A1 | 3/2009 | Blomgren et al. |
| 2009/0105209 A1 | 4/2009 | Dewdney et al. |
| 2009/0111824 A1 | 4/2009 | Bratt et al. |
| 2009/0137603 A1 | 5/2009 | Nara et al. |
| 2009/0163545 A1 | 6/2009 | Goldfarb |
| 2009/0181983 A1 | 7/2009 | Corte |
| 2009/0270399 A1 | 10/2009 | Ohkuchi et al. |
| 2010/0137320 A1 | 6/2010 | Huang et al. |
| 2010/0190773 A1 | 7/2010 | Abeywardane et al. |
| 2010/0210637 A1 | 8/2010 | Ohtake et al. |
| 2010/0256363 A1 | 10/2010 | Xu |
| 2010/0273779 A1 | 10/2010 | Bacon et al. |
| 2010/0280007 A1 | 11/2010 | Bacon et al. |
| 2010/0286127 A1 | 11/2010 | Miyoshi et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0059944 A1 | 3/2011 | Blomgren et al. |
| 2011/0098269 A1 | 4/2011 | Becknell et al. |
| 2011/0124635 A1 | 5/2011 | Claremon et al. |
| 2011/0224198 A1 | 9/2011 | Kuduk et al. |
| 2011/0263532 A1 | 10/2011 | Keller et al. |
| 2013/0045229 A1 | 2/2013 | Iadonato et al. |
| 2013/0188311 A1 | 7/2013 | Martens et al. |
| 2013/0281450 A1 | 10/2013 | Pratt et al. |
| 2013/0331382 A1 | 12/2013 | Hubbard et al. |
| 2014/0094456 A1 | 4/2014 | Buckman et al. |
| 2014/0107110 A1 | 4/2014 | Buckman et al. |
| 2014/0162971 A1 | 6/2014 | Wang et al. |
| 2014/0256705 A1 | 9/2014 | Hasvold et al. |
| 2014/0275026 A1 | 9/2014 | Wang et al. |
| 2014/0275079 A1 | 9/2014 | Hasvold et al. |
| 2015/0111890 A1 | 4/2015 | Hasvold et al. |
| 2015/0148342 A1 | 5/2015 | Yue et al. |
| 2015/0150884 A1 | 6/2015 | Liu et al. |
| 2016/0143916 A1 | 5/2016 | Wang et al. |
| 2016/0237084 A1 | 8/2016 | Wang et al. |
| 2016/0237085 A1 | 8/2016 | Gong |
| 2017/0066765 A1 | 3/2017 | Gong |
| 2018/0296566 A1 | 10/2018 | Wang et al. |

(56) References Cited

U.S. PATENT DOCUMENTS

| | | |
|---|---|---|
| 2018/0298003 A1 | 10/2018 | Fidanze et al. |
| 2019/0008866 A1 | 1/2019 | Bogdan et al. |
| 2019/0084981 A1 | 3/2019 | Dai et al. |

FOREIGN PATENT DOCUMENTS

| | | |
|---|---|---|
| CN | 108690020 A | 10/2018 |
| DE | 10010423 A1 | 9/2001 |
| EP | 0010156 A1 | 4/1980 |
| EP | 0316279 A2 | 5/1989 |
| EP | 0612321 A1 | 8/1994 |
| EP | 0634404 A1 | 1/1995 |
| EP | 0634413 A1 | 1/1995 |
| EP | 0652218 A1 | 5/1995 |
| EP | 0711759 A1 | 5/1996 |
| EP | 0760208 A2 | 3/1997 |
| EP | 0856255 A2 | 8/1998 |
| EP | 0934933 A1 | 8/1999 |
| EP | 0984961 A1 | 3/2000 |
| EP | 0989131 A1 | 3/2000 |
| EP | 1887008 A1 | 2/2008 |
| EP | 2239264 A1 | 10/2010 |
| FR | 2478640 A1 | 9/1981 |
| JP | H08337583 A | 12/1996 |
| JP | 2003313169 A | 11/2003 |
| JP | 2008156311 A | 7/2008 |
| JP | 2017159837 A | 9/2017 |
| WO | WO-9112251 A1 | 8/1991 |
| WO | WO-9206087 A1 | 4/1992 |
| WO | WO-9701551 A1 | 1/1997 |
| WO | WO-0138377 A1 | 5/2001 |
| WO | WO-0172812 A1 | 10/2001 |
| WO | WO-0201935 A1 | 1/2002 |
| WO | WO-02096873 A1 | 12/2002 |
| WO | WO-2006032470 A1 | 3/2006 |
| WO | WO-2006038734 A1 | 4/2006 |
| WO | WO-2006112331 A1 | 10/2006 |
| WO | WO-2006129623 A1 | 12/2006 |
| WO | WO-2007008144 A1 | 1/2007 |
| WO | WO-2007008145 A1 | 1/2007 |
| WO | WO-2007068728 A2 | 6/2007 |
| WO | WO-2008064018 A1 | 5/2008 |
| WO | WO-2008148034 A1 | 12/2008 |
| WO | WO-2009084693 A1 | 7/2009 |
| WO | WO-2009134387 A1 | 11/2009 |
| WO | WO-2010019210 A2 | 2/2010 |
| WO | WO-2010069504 A1 | 6/2010 |
| WO | WO-2011054553 A1 | 5/2011 |
| WO | WO-2011054843 A1 | 5/2011 |
| WO | WO-2011054844 A1 | 5/2011 |
| WO | WO-2011054845 A1 | 5/2011 |
| WO | WO-2011054846 A1 | 5/2011 |
| WO | WO-2011054848 A1 | 5/2011 |
| WO | WO-2011054851 A1 | 5/2011 |
| WO | WO-2011060067 A2 | 5/2011 |
| WO | WO-2011133722 A2 | 10/2011 |
| WO | WO-2011143669 A2 | 11/2011 |
| WO | WO-2011161031 A1 | 12/2011 |
| WO | WO-2012075456 A1 | 6/2012 |
| WO | WO-2013086357 A2 | 6/2013 |
| WO | WO-2013097052 A1 | 7/2013 |
| WO | WO-2013097601 A1 | 7/2013 |
| WO | WO-2013155695 A1 | 10/2013 |
| WO | WO-2013158952 A1 | 10/2013 |
| WO | WO-2013188311 A1 | 12/2013 |
| WO | WO-2014125408 A2 | 8/2014 |
| WO | WO-2014139324 A1 | 9/2014 |
| WO | WO-2014164771 A1 | 10/2014 |
| WO | WO-2014164780 A1 | 10/2014 |
| WO | WO-2014165127 A1 | 10/2014 |
| WO | WO-2014165143 A1 | 10/2014 |
| WO | WO-2014206150 A1 | 12/2014 |
| WO | WO-2014206345 A1 | 12/2014 |
| WO | WO-2014210425 A1 | 12/2014 |
| WO | WO-2015081189 A1 | 6/2015 |
| WO | WO-2015081203 A1 | 6/2015 |
| WO | WO-2015081246 A1 | 6/2015 |
| WO | WO-2015081280 A1 | 6/2015 |
| WO | WO-2015085925 A1 | 6/2015 |
| WO | WO-2015089075 A1 | 6/2015 |
| WO | WO-2015164480 A1 | 10/2015 |
| WO | WO-2016077380 A1 | 5/2016 |
| WO | WO-2016183114 A1 | 11/2016 |
| WO | WO-2016183115 A1 | 11/2016 |
| WO | WO-2017178416 A1 | 10/2017 |
| WO | WO-2017178582 A1 | 10/2017 |
| WO | WO-2017181117 A1 | 10/2017 |
| WO | WO-2017181177 A1 | 10/2017 |
| WO | WO-2017214565 A1 | 12/2017 |
| WO | WO-2017216772 A2 | 12/2017 |
| WO | WO-2017223268 A1 | 12/2017 |
| WO | WO-2018068282 A1 | 4/2018 |
| WO | WO-2018068283 A1 | 4/2018 |
| WO | WO-2018095933 A1 | 5/2018 |
| WO | WO-2018130174 A1 | 7/2018 |
| WO | WO-2018188047 A1 | 10/2018 |
| WO | WO-2018223909 A1 | 12/2018 |

OTHER PUBLICATIONS

Braun, T and Gardin, C "Investigational Bet Bromodomain Protein Inhibitors in Early Stage Clinical Trials for Acute Myelogenous Leukemia (Aml)," Expert Opinion on Investigational Drugs, Jul. 2017, vol. 26 (7), pp. 803-811.

Bui M.H. et al., "Preclinical characterization or BET Family Bromodomain Inhibitor ABBV-075 Suggests Combination Therapeutic Strategies," Cancer Research, 2017, vol. 77 (11), pp. 2976-2989.

Chandarlapaty S., et al., "SNX2112, A Synthetic Heat Shock Protein 90 Inhibitor, has Potent Antitumor Activity against HER Kinase-Dependent Cancers," Clinical Cancer Research, 2008, vol. 14 (1), pp. 240-248.

Chung C.W., et al., "Discovery and Characterization of Small Molecule Inhibitors of the BET Family Bromodomains," Journal of Medicinal Chemistry, 2011, vol. 54 (11), pp. 3827-3838.

Chung C.W., "Small Molecule Bromodomain Inhibitors: Extending the Druggable Genome," Progress in Medicinal Chemistry, 2012, vol. 51, pp. 1-55.

Dal Piaz V., et al., "Synthesis and Evaluation of Noval Pyrrolo[2,3-d] and Thieno [2,3-d] Pyridazinones as in Vitro Antiproliferative Agents," Acta Chimica Slovenica, 2009, vol. 56 (3), pp. 571-579.

Dawson M.A., et al., "Inhibition of BET Recruitment to Chromatin as an Effective Treatment for MLL-fusion Leukaemia," Nature, 2011, vol. 478 (7370), pp. 529-533.

Delmore J.E., et al., "BET Bromodomain Inhibition as a Therapeutic Strategy to Target c-Myc," Cell, 2011, vol. 146 (6), pp. 904-917.

Denis G.V., "Bromodomain Coactivators in Cancer, Obesity, type 2 Diabetes, and Inflammation," Discovery Medicine, 2010, vol. 10 (55), pp. 489-499.

Doroshow D.B. et al., "BET inhibitors: a novel epigenetic approach.," Annals of Oncology, 2017, vol. 28 (8), pp. 1776-1787.

Faivre et al., "Abstract 4960: First-in-Class, Highly BDII-Selective BET Family Inhibitor ABBV-744 Displays Potent Anti-Tumor Activity in Androgen Receptor Positive Prostate Cancer Models and an Improved Tolerability Profile," Cancer Research, Proceedings: AACR Annual Meeting 2018, Apr. 14-18, 2018, vol. 78 (13), 2 pages.

Ferri et al., "Bromodomains: Structure, Function and Pharmacology of Inhibition," Biochemical Pharmacology, Apr. 2016, vol. 106, pp. 18 pages.

Filippakopoulos P., et al., "Selective Inhibition of BET Bromodomains," Nature, 2010, vol. 468 (7327), pp. 1067-1073.

Fong et al., "BET Inhibitor Resistance Emerges From Leukaemia Stem Cells," Nature, Sep. 24, 2015, vol. 525, pp. 538-542.

French C.A. et al., "Small-Molecule Targeting of BET Proteins in Cancer," Advance Cancer Research, 2016, vol. 131, pp. 21-58.

Fu et al., "Inhibition of BET Bromodomains as a Therapeutic Strategy for Cancer Drug Discovery," Oncotarget, 2015, vol. 6(8), pp. 5501-5516.

(56) References Cited

OTHER PUBLICATIONS

Furniss B.S., et al., Vogel's Textbook of Practical Organic Chemistry, 5th Edition, Longman Scientific & Technical, 1989, Essex CM20 2JE, England, Table of Contents.
Greene T.W., et al., Protective Groups in Organic Synthesis, 3rd Edition, John Wiley and Sons, Inc., 1999, Preface, Table of Contents, Abbreviations.
Hewings D.S., et al., "Progress in the Development and Application of Small Molecule Inhibitors of Bromodomain-acetyl-lysine Interactions," Journal of Medicinal Chemistry, 2012, vol. 55 (22), pp. 9393-9413.
Ikeura Y., et al., "Potent NK1 Receptor Antagonists: Synthesis and Antagonistic Activity of Various Heterocycles with an N-[3,5-bis(trifluoromethyl)benzyl]-N-methylcarbamoyl Substituent," Chemical and Pharmaceutical Bulletin, 1997, vol. 45 (10), pp. 1642-1652.
International Search Report and Written Opinion for Application No. PCT/CN2017/080511, dated Sep. 29, 2017, 16 pages.
IUPAC 1974 Recommendations for Section E, Fundamental Stereochemistry, Pure and Applied Chemistry, 1976, vol. 45, pp. 13-30.
Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.
Jimenez I et al., "Bromodomain and Extraterminal Protein Inhibitors in Pediatrics: a Review of the Literature," Pediatric Blood & Cancer, 2017, vol. 64, pp. 01-11.
Jung et al., "Affinity Map of Bromodomain Protein 4 (BRD4) Interactions With the Histone H4 Tail and the Small Molecule Inhibitor JQ1," The Journal of Biological Chemistry, 2014, vol. 289(13), pp. 9304-9319.
Jung et al., "Targeting BET Bromodomains for Cancer Treatment," Epigenomics, 2015, vol. 7(3), pp. 487-501.
Kati W., "Abstract DDT01-05: ABBV-744: a First-in-Class Highly BDII-Selective BET Bromodomain Inhibitor," Cancer Research, Proceedings: AACR Annual Meeting 2018, Apr. 14-18, 2018, vol. 78 (13), 2 pages . . . .
Lee, W., et al., Structure Based Design: Identification of the Clinical Candidate Abbv-744, a First-in-class Highly BDII-selective BET Bromodomain Inhibitor, 256th American Chemical Society National Meeting, 2018.
Leroy G., et al., "The Double Bromodomain Proteins Brd2 and Brd3 Couple Histone Acetylation to Transcription," Molecular Cell, 2008, vol. 30 (1), pp. 51-60.
Lim J., et al., "New Strategies in Sarcoma: Linking Genomic and Immunotherapy Approaches to Molecular Subtype," Clinical Cancer Research, 2015, vol. 21(21), pp. 4753-4759.
Lin X. et al., "Abstract 800, ABBV-744, a first-in-class and highly selective inhibitor of the second bromodomain of BET family proteins displays robust activities in preclinical model of acute myelogenous leukemia," Cancer Research, Proceedings: AACR Annual Meeting 2018, vol. 78 (13), 2 pages . . . .
Liu Z. et al., "Drug Discovery Targeting Bromodomain-Containing Protein 4.," Journal of Medical Chemistry, 2017, vol. 60 (11), pp. 4533-4558.
Matzuk M.M., et al., "Small-molecule Inhibition of BRDT for Male Contraception," Cell, 2012, vol. 150 (4), pp. 673-684.
McDaniel K.F. et al., "Discovery of N-(2,4-Difluorophenoxy)-3-(6-methyl-7-oxo-6,7-dihydro-1H-pyrrolo[2,3-c]pyridin-4-yl)phenyl)ethanesulfonamide(ABBV-075/Mivebresib), a potent and Orally Available Bromodomain and Extraterminal Domain (BET) Family Bromodomain Inhibitor," Journal of Medical Chemistry, 2017, vol. 60, pp. 8369-8384.
Mertz J.A., et al., "Targeting MYC Dependence in Cancer by Inhibiting BET Bromodomains," Proceedings of the National Academy of Sciences, 2011, vol. 108 (40), pp. 16669-16674.
Miyaura N., et al., "Palladium-Catalyzed Cross-Coupling Reactions of Organoboron Compounds," Chemical Reviews, 1995, vol. 95 (7), pp. 2457-2483.

Nicodeme E., et al., "Suppression of Inflammation by a Synthetic Histone Mimic," Nature, 2010, vol. 468 (7327), pp. 1119-1123.
Noguchi-Yachide T., "BET Bromodomain as a Target of Epigenetic Therapy," Chemical & Pharmaceutical Bulletin, 2016, vol. 64(6), pp. 540-547.
Paulson C.N. et al., "Design, Synthesis, and Characterization of Fluorescence Polarization Pan-BET Bromodomain Probe," ACS Medical Chemistry Letters , 2018, vol. 9 (12), pp. 1223-1229.
Perez-Salvia, M and Esteller, M "Bromodomain Inhibitors and Cancer Therapy: From Structures to Applications," Epigenetics, May 2017, vol. 12 (5), pp. 323-339.
Piha-Paul S.A. et al., "Results of the first-in-human study of ABBV-075 (mivebresib), a pan-inhibitor of bromodomain (BD) and extra terminal (BET) proteins, in patients (pts) with relapsed/refractory (R/R) solid tumors.," Journal of Clinical Oncology, 2018, vol. 36 (15), pp. 2510-2510.
Prescott, Ed., Methods in Cell Biology, vol. XIV, Academic Press, New York, 1976, pp. 33.
Prinjha R.K., et al., "Place your BETs: the Therapeutic Potential of Bromodomains," Trends in Pharmacological Sciences, 2012, vol. 33 (3), pp. 146-153.
Huang B., et al., "Brd4 Coactivates Transcriptional Activation of NF-κB via Specific Binding to Acetylated RelA," Molecular and Cellular Biology, 2009, vol. 29 (5), pp. 1375-1387.
Zhang G., et al., "Down-regulation of NF-κB Transcriptional Activity in HIV-associated Kidney Disease by BRD4 Inhibition," Journal of Biological Chemistry, 2012, vol. 287 (34), pp. 28840-28851.
Ramadoss M. et al., "Targeting the cancer epigenome: synergistic therapy with bromodomain inhibitors," Drug Discovery Today, 2018, vol. 23 (1), pp. 76-89.
Sahai V. et al., "Targeting BET bromodomain proteins in solid tumors," Oncotarget, 2016, vol. 7 (33), pp. 53997-54009.
Sheppard G.S. et al., "Abstract 931: Discovery of ABBV-744, a first-in-class highly BDII-selective BET bromodomain inhibitor," Cancer Research, 2018, vol. 78 (13), pp. 931-931.
Shi, J and Vakoc, C.R "The Mechanisms Behind the Therapeutic Activity of Bet Bromodomain Inhibition," Molecular Cell, Jun. 2014, vol. 54 (5), pp. 728-736.
Shi J., et al., "Disrupting the Interaction of BRD4 with Diacetylated Twist Suppresses Tumorigenesis in Basal-like Breast Cancer," Cancer Cell, Feb. 2014, vol. 25(2), pp. 210-225.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Suzuki A., et al., "Recent advances in the cross-coupling reactions of organoboron derivatives with organic electrophiles, 1995-1998," Journal of Organometallic Chemistry, 1999, 576 (1-2), 147-168.
Taniguchi, Y. "The Bromodomain and Extra-terminal Domain (Bet) Family: Functional Anatomy of Bet Paralogous Proteins," International Journal of Molecular Sciences, Nov. 2016, vol. 17 (11), pp. 1-24.
Wang F., et al., "Brd2 Disruption in Mice Causes Severe Obesity without Type 2 Diabetes," Biochemical Journal, 2010, vol. 425, pp. 71-83.
Wyce, A., et al., "Bet Inhibition Silences Expression of MYCN and BCL2 and Induces Cytotoxicity in Neuroblastoma Tumor Models," PLoS One, Aug. 2013, vol. 8 (8), pp. 1-16.
Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.
Zuber J., et al., "RNAi Screen Identifies Brd4 as a Therapeutic Target in Acute Myeloid Leukaemia," Nature, 2011, vol. 478 (7370), pp. 524-528.
Picaud, S., et al., "RVX-208, an Inhibitor of BET Transcriptional Regulators with Selectivity for the Second Bromodomain," Proceedings of the National Academy of Sciences of the United States of America, Dec. 3, 2013, vol. 110 (49), pp. 19754-19759.
European Search Report for Application No. 17781931.5, dated Aug. 6, 2019, 5 pages.
Baud, et al. "New Synthetic Routes to Triazolo-benzodiazepine Analogues: Expanding the Scope of the Bump-and-Hole Approach

(56) References Cited

OTHER PUBLICATIONS for Selective Bromo and Extra-Terminal (BET) Bromodomain Inhibition", Journal of Medicinal Chemistry (2016), 59, pp. 1492-1500.

Chen, et al. "Discovery, structural insight, and bioactivities of BY27 as a selective inhibitor of the second bromodomains of BET proteins," European Journal of Medicinal Chemistry, 182 (2019) pp. 111633.

Kharenko, et al., "RVX-297—a novel BD2 selective inhibitor of BET bromodomains," Biochemical and Biophysical Research Communications, 477 (2016) pp. 62-67.

Law, et al., "Discovery of Tetrahydroquinoxalines as Bromodomain and Extra-Terminal Domain (BET) Inhibitors with Selectivity for the Second Bromodomain," J. Med. Chem. (2018), 61, pp. 4317-4334.

Shadrick, et al., "Exploiting a water network to achieve enthalpy-driven, bromodomain-selective BET inhibitors," Bioorganic & Medicinal Chemistry, (2018), 26, pp. 25-36.

Sharp, et al., "Design, Synthesis, and Biological Activity of 1,2,3-Triazolobenzodiazepine BET Bromodomain Inhibitors," ACS Medicinal Chemistry Letters (2017) 8, pp. 1298-1303.

\* cited by examiner

BROMODOMAIN INHIBITORS

BACKGROUND

Bromodomains refer to conserved protein structural folds which bind to N-acetylated lysine residues that are found in some proteins. The BET family of bromodomain containing proteins comprises four members (BRD2, BRD3, BRD4 and BRDt). Each member of the BET family employs two bromodomains to recognize N-acetylated lysine residues typically, but not exclusively those found on transcription factors (Shi, J., et al. Cancer Cell 25(2): 210-225 (2014)) or on the amino-terminal tails of histone proteins. Numbering from the N-terminal end of each BET protein the tandem bromodomains are typically labelled Binding Domain I (BDI) and Binding Domain II (BDII). These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to pre-disposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect the present invention provides for compounds of formula (I) or a pharmaceutically acceptable salt thereof,

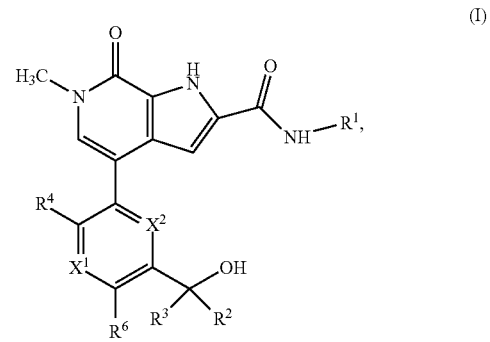

wherein
$R^1$ is hydrogen, $CD_2CD_3$, $C_1$-$C_6$ alkyl, $C_1$-$C_6$ haloalkyl, a $C_3$-$C_6$ cycloalkyl, a phenyl, or a 5-6 membered monocyclic heteroaryl; wherein the $C_3$-$C_6$ cycloalkyl, the phenyl, and the 5-6 membered monocyclic heteroaryl are each optionally substituted with 1, 2, 3, or 4 independently selected $R^x$ groups;
$R^2$ is $G^{2a}$, $C_1$-$C_6$ haloalkyl, or $C_1$-$C_6$ alkyl wherein the $C_1$-$C_6$ alkyl is optionally substituted with one substituent selected from the group consisting of $G^{2b}$ and —OH;
  $G^{2a}$ is a phenyl or a $C_3$-$C_6$ monocyclic cycloalkyl; wherein each $G^{2a}$ is optionally substituted with 1, 2, 3, or 4 independently selected $R^x$ groups;
  $G^{2b}$ is phenyl optionally substituted with 1, 2, 3, or 4 independently selected $R^x$ groups;
$R^3$ is $C_1$-$C_6$ haloalkyl, $C_1$-$C_6$ alkyl, or a $C_3$-$C_6$ monocyclic cycloalkyl wherein the $C_3$-$C_6$ monocyclic cycloalkyl is optionally substituted with 1, 2, 3, or 4 independently selected $R^x$ groups; or
$R^2$ and $R^3$, together with the carbon atom to which they are attached, form a $C_3$-$C_6$ monocyclic cycloalkyl, a $C_4$-$C_6$ monocyclic cycloalkenyl, or a 4-6 membered monocyclic heterocycle; wherein the $C_3$-$C_6$ monocyclic cycloalkyl, the $C_4$-$C_6$ monocyclic cycloalkenyl, and the 4-6 membered monocyclic heterocycle are each optionally substituted with 1, 2, 3, or 4 independently selected $R^x$ groups;
$R^4$ is phenyl, pyridinyl, a $C_3$-$C_6$ monocyclic cycloalkyl, or a $C_4$-$C_6$ monocyclic cycloalkenyl; wherein each $R^4$ is optionally substituted with 1, 2, 3, or 4 independently selected $R^y$ groups; or
$R^4$ is formula (a)

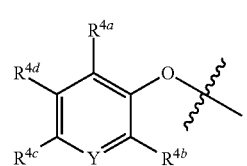

$R^{4a}$ and $R^{4b}$ are each independently halogen, $C_1$-$C_6$ alkyl, or $C_1$-$C_6$ haloalkyl;
$R^{4c}$ and $R^{4d}$ are each independently hydrogen, halogen, —CN, $C_1$-$C_6$ alkyl, $C_1$-$C_6$ haloalkyl, —S($C_1$-$C_6$ alkyl), —S(O)$_2$($C_1$-$C_6$ alkyl), or —($C_1$-$C_6$ alkylenyl)-OH;
Y is C($R^{4e}$) or N; wherein $R^{4e}$ is hydrogen, halogen, —CN, $C_1$-$C_6$ alkyl, or $C_1$-$C_6$ haloalkyl;

$R^x$, at each occurrence, is independently halogen, $C_1$-$C_6$ alkyl, or $C_1$-$C_6$ haloalkyl;

$R^y$, at each occurrence, is independently halogen, $C_1$-$C_6$ alkyl, $C_1$-$C_6$ haloalkyl, —O($C_1$-$C_6$ alkyl), —O($C_1$-$C_6$ haloalkyl), or —($C_1$-$C_6$ alkylenyl)-OH;

$X^1$ and $X^2$ are C($R^5$); or one of $X^1$ and $X^2$ is N and the other is C($R^5$);

$R^5$, at each occurrence, is independently hydrogen or halogen; and $R^6$ is hydrogen, halogen, —CN, $C_1$-$C_6$ haloalkyl, or $C_1$-$C_6$ alkyl.

In another aspect, the present invention provides for methods for treating or preventing disorders that are ameliorated by inhibition of BET. Such methods comprise of administering to the subject a therapeutically effective amount of a compound of formula (I), alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, and Wilms' tumor. In certain embodiments, the methods further comprise administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to methods of treating a disease or condition in a subject comprising administering a therapeutically effective amount of a compound of formula (I), or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I), or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease, and tubular interstitial nephritis. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I), or a pharmaceutically acceptable salt thereof, to a subject in need thereof, wherein said acute kidney injury or disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy, or diabetic neuropathy in a subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

In another aspect, the present invention relates to methods of preventing conception by inhibiting spermatogenesis in a subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with at least one additional therapeutic agent, in the manufacture of a medicament for treating or preventing conditions and disorders disclosed herein, with or without a pharmaceutically acceptable carrier.

Pharmaceutical compositions comprising a compound of formula (I), or a pharmaceutically acceptable salt, alone or in combination with at lease one additional therapeutic agent, are also provided.

DETAILED DESCRIPTION

Disclosed herein are compounds of formula (I)

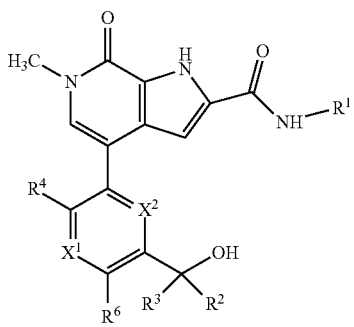

(I)

wherein $R^1$, $R^2$, $R^3$, $R^4$, $R^6$, $X^1$, and $X^2$ are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "alkyl" as used herein, means a saturated, straight or branched hydrocarbon chain radical. In some instances, the number of carbon atoms in an alkyl moiety is indicated by the prefix "$C_x$-$C_y$," wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl. The terms "alkyl," "$C_1$-$C_6$ alkyl," and "$C_1$-$C_3$ alkyl" used herein are unsubstituted, unless otherwise indicated.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms ($C_1$-$C_4$ alkylenyl) or of 1 to 3 carbon atoms ($C_1$-$C_3$ alkylenyl) or of 2 to 6 carbon atoms ($C_2$-$C_6$ alkylenyl). Examples of $C_1$-$C_6$ alkylenyl include, but are not limited to, —CH$_2$—, —CH$_2$CH$_2$—, —C((CH$_3$)$_2$)—CH$_2$CH$_2$CH$_2$—, —C((CH$_3$)$_2$)—CH$_2$CH$_2$, —CH$_2$CH$_2$CH$_2$CH$_2$—, and —CH$_2$CH(CH$_3$)CH$_2$—.

The term "$C_3$-$C_6$ cycloalkyl" as used herein, means a hydrocarbon ring radical containing 3-6 carbon atoms, zero heteroatom, and zero double bond. The $C_3$-$C_6$ cycloalkyl group may be a single-ring (monocyclic) or have two rings (bicyclic). $C_3$-$C_6$ monocyclic cycloalkyls means cyclopropyl, cyclobutyl, cyclopentyl, and cyclohexyl. The rings within the bicyclic cycloalkyl groups are in a bridged orientation. In a bridged cycloalkyl, the rings share at least two non-adjacent atoms. An example of a bridged $C_3$-$C_6$ cycloalkyl is bicyclo[1.1.1]pentanyl.

The term "$C_4$-$C_6$ monocyclic cycloalkenyl" as used herein, means a monocyclic hydrocarbon ring radical containing 4-6 carbon atoms, zero heteroatom, and one or two double bonds. Examples of $C_4$-$C_6$ monocyclic cycloalkenyl groups are cyclobutenyl, cyclopentenyl, cyclohexenyl, and cycloheptyl.

The term "halo" or "halogen" as used herein, means Cl, Br, I, and F.

The term "haloalkyl" as used herein, means an alkyl group, as defined herein, in which one, two, three, four, five, or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Examples of haloalkyl include, but are not limited to, chloromethyl, 2-fluoroethyl, 2,2-difluoroethyl, fluoromethyl, 1,1,1-trifluoro-2-methylpropan-2-yl, 2,2,2-trifluoroethyl, trifluoromethyl, difluoromethyl, pentafluoroethyl, 2-chloro-3-fluoropentyl, and 1,1,1-trifluoro-2-methylpropanyl.

The term "4-6 membered monocyclic heterocycle" is a four-, five- or six-membered hydrocarbon ring wherein at least one carbon atom is replaced by heteroatom independently selected from the group consisting of O, N, and S. A four-membered monocyclic heterocycle contains zero or one double bond, and one heteroatom selected from the group consisting of O, N, and S. Examples of four-membered monocyclic heterocycles include, but not limited to, azetidinyl and oxetanyl. A five-membered monocyclic heterocycle contains zero or one double bond and one, two, or three heteroatoms selected from the group consisting of O, N, and S. Examples of five-membered monocyclic heterocycles include those containing in the ring: 1 O; 1 S; 1 N; 2 N; 3 N; 1 S and 1 N; 1 S, and 2 N; 1 O and 1 N; or 1 O and 2 N. Non limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three heteroatoms selected from the group consisting of O, N, and S. Examples of six-membered monocyclic heterocycles include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of six-membered monocyclic heterocycles include tetrahydropyranyl, dihydropyranyl, dioxanyl, 1,4-dithianyl, hexahydropyrimidine, morpholinyl, piperazinyl, piperidinyl, tetrahydropyridinyl, tetrahydrothiopyranyl, thiomorpholinyl, thioxanyl, and trithianyl. The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl) and the nitrogen atoms may optionally be quarternized.

The term "5-6 membered monocyclic heteroaryl" is a five- or six-membered hydrocarbon ring wherein at least one carbon atom is replaced by heteroatom independently selected from the group consisting of O, N, and S. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Examples of 5-6 membered monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The nitrogen atom in the heteroaryl rings may optionally be oxidized and may optionally be quarternized.

The phenyl, the $C_3$-$C_6$ cycloalkyls, the $C_3$-$C_6$ monocyclic cycloalkyls, the $C_4$-$C_6$ cycloalkenyls, the 4-6 membered monocyclic heterocycles, and the 5-6 membered monocyclic heteroaryls, including the exemplary rings, are optionally substituted unless otherwise indicated; and are attached to the parent molecular moiety through any substitutable atom contained within the ring system.

The term "heteroatom" as used herein, means a nitrogen, oxygen, and sulfur.

The term "radiolabel" means a compound of the invention in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^3H$ (tritium), $^{14}C$, $^{11}C$, $^{15}O$, $^{18}F$, $^{35}S$, $^{123}I$, and $^{126}I$.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In one embodiment, the subject is a human. The terms "human," "patient," and "subject" are used interchangeably herein.

The term 'at least one additional therapeutic agent' means one to four therapeutic agents other than the compounds of the invention. In one embodiment it means one to three additional therapeutic agents. In further embodiments it means one or two additional therapeutic agents. In a yet further embodiment it means one additional therapeutic agent. In a yet further embodiment it means two additional therapeutic agents. In a yet further embodiment it means three additional therapeutic agents.

b. Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments, $R^1$ is hydrogen.

In certain embodiments, $R^1$ is $CD_2CD_3$, $C_1$-$C_6$ alkyl, $C_1$-$C_6$ haloalkyl, or a $C_3$-$C_6$ cycloalkyl; wherein the $C_3$-$C_6$ cycloalkyl is optionally substituted with 1, 2, 3, or 4 independently selected $R^x$ groups.

In certain embodiments, $R^1$ is $CD_2CD_3$, $C_1$-$C_6$ alkyl, $C_1$-$C_6$ haloalkyl, cyclopropyl, or bicyclo[1.1.1]pentanyl; wherein the cyclopropyl and the bicyclo[1.1.1]pentanyl are each optionally substituted with 1, 2, 3, or 4 independently selected $R^x$ groups.

In certain embodiments, $R^1$ is $CD_2CD_3$.

In certain embodiments, $R^1$ is $C_1$-$C_6$ alkyl or $C_1$-$C_6$ haloalkyl. In some such embodiments, $R^1$ is $CH_3$, $CH_2CH_3$, $C(CH_3)_3$, or $C(CH_3)_2CF_3$.

In certain embodiments, $R^1$ is $C_1$-$C_6$ alkyl. In some such embodiments, $R^1$ is $CH_3$, $CH_2CH_3$, or $C(CH_3)_3$. In some further embodiments, $R^1$ is $CH_3$ or $CH_2CH_3$. In some further embodiments, $R^1$ is $CH_3$. In some further embodiments, $R^1$ is $CH_2CH_3$.

In certain embodiments, $R^1$ is $C_1$-$C_6$ haloalkyl. In some such embodiments, $R^1$ is $C(CH_3)_2CF_3$.

In certain embodiments, $R^1$ is a $C_3$-$C_6$ cycloalkyl; wherein the $C_3$-$C_6$ cycloalkyl is optionally substituted with 1, 2, 3, or 4 independently selected $R^x$ groups. In some such embodiments, the $C_3$-$C_6$ cycloalkyl is cyclopropyl or bicyclo[1.1.1]pentanyl; wherein the cyclopropyl and the bicyclo[1.1.1]pentanyl are each optionally substituted with 1, 2, 3, or 4 independently selected $R^x$ groups. In some further embodiments, the $C_3$-$C_6$ cycloalkyl is cyclopropyl wherein the cyclopropyl is optionally substituted with 1, 2, 3, or 4 independently selected $R^x$ groups. In some further embodiments, the $C_3$-$C_6$ cycloalkyl is bicyclo[1.1.1]pentanyl wherein the bicyclo[1.1.1]pentanyl is optionally substituted with 1, 2, 3, or 4 independently selected $R^x$ groups.

In certain embodiments, $R^1$ is a phenyl or a 5-6 membered monocyclic heteroaryl; wherein the phenyl and the 5-6 membered monocyclic heteroaryl are each optionally substituted with 1, 2, 3, or 4 independently selected $R^x$ groups.

In certain embodiments, $R^2$ is phenyl, cyclopropyl, cyclopentyl, $C_1$-$C_6$ haloalkyl, or $C_1$-$C_6$ alkyl wherein the $C_1$-$C_6$ alkyl is optionally substituted with one substituent selected from the group consisting of $G^{2b}$ and —OH; and wherein the phenyl, the cyclopropyl, and the cyclopentyl are each optionally substituted with 1, 2, 3, or 4 independently selected $R^x$ groups.

In certain embodiments, $R^2$ is $G^{2a}$. In some such embodiments, $G^{2a}$ is phenyl, cyclopropyl, or cyclopentyl; wherein each $G^{2a}$ is optionally substituted with 1, 2, 3, or 4 independently selected $R^x$ groups. In some such embodiments, $G^{2a}$ is phenyl; wherein the phenyl is optionally substituted with 1, 2, 3, or 4 independently selected $R^x$ groups.

In certain embodiments, $R^2$ is $C_1$-$C_6$ haloalkyl or $C_1$-$C_6$ alkyl wherein the $C_1$-$C_6$ alkyl is optionally substituted with one substituent selected from the group consisting of $G^{2b}$ and —OH. In some such embodiments, $R^2$ is $C_1$-$C_6$ haloalkyl, $C_1$-$C_6$ alkyl, —$CH_2$— phenyl, —$CH_2CH_2$-phenyl, $CH_2OH$, or $CH_2CH_2OH$; wherein the phenyl moiety of —$CH_2$-phenyl and —$CH_2CH_2$-phenyl is optionally substituted with 1, 2, 3, or 4 independently selected $R^x$ groups.

In certain embodiments, $R^2$ is —$CH_2$-phenyl or —$CH_2CH_2$-phenyl; wherein the phenyl moiety of —$CH_2$-phenyl and —$CH_2CH_2$-phenyl is optionally substituted with 1, 2, 3, or 4 independently selected $R^x$ groups.

In certain embodiments, $R^2$ is $C_1$-$C_6$ haloalkyl or $C_1$-$C_6$ alkyl wherein the $C_1$-$C_6$ alkyl is optionally substituted with one —OH. In some such embodiments, $R^2$ is $CF_3$, $CH_2F$, $CH_3$, $CH_2CH_3$, $C(H)(CH_3)_2$, $C(CH_3)(H)CH_2CH_3$, $CH_2C(H)(CH_3)_2$, $CH_2OH$, or $CH_2CH_2OH$.

In certain embodiments, $R^2$ is $C_1$-$C_6$ haloalkyl. In some such embodiments, $R^2$ is $CF_3$ or $CH_2F$.

In certain embodiments, $R^2$ is $C_1$-$C_6$ alkyl wherein the $C_1$-$C_6$ alkyl is optionally substituted with one —OH. In some such embodiments, $R^2$ is $CH_3$, $CH_2CH_3$, $C(H)(CH_3)_2$, $C(CH_3)(H)CH_2CH_3$, $CH_2C(H)(CH_3)_2$, $CH_2OH$, or $CH_2CH_2OH$.

In certain embodiments, $R^2$ is $C_1$-$C_6$ alkyl. In some such embodiments, $R^2$ is $CH_3$, $CH_2CH_3$, $C(H)(CH_3)_2$, $C(CH_3)(H)CH_2CH_3$, or $CH_2C(H)(CH_3)_2$. In some such embodiments, $R^2$ is $CH_3$.

In certain embodiments, $R^2$ is $C_1$-$C_6$ alkyl which is substituted with one —OH. In some such embodiments, $R^2$ is $CH_2OH$ or $CH_2CH_2OH$.

In certain embodiments, $R^3$ is $C_1$-$C_6$ haloalkyl, $C_1$-$C_6$ alkyl, or a $C_3$-$C_6$ monocyclic cycloalkyl wherein the $C_3$-$C_6$ monocyclic cycloalkyl is optionally substituted with 1, 2, 3, or 4 independently selected $R^x$ groups.

In certain embodiments, $R^3$ is $C_1$-$C_6$ haloalkyl, $C_1$-$C_6$ alkyl, or a cyclopropyl wherein the cyclopropyl is optionally substituted with 1, 2, 3, or 4 independently selected $R^x$ groups.

In certain embodiments, $R^3$ is a $C_3$-$C_6$ monocyclic cycloalkyl wherein the $C_3$-$C_6$ monocyclic cycloalkyl is optionally substituted with 1, 2, 3, or 4 independently selected $R^x$ groups. In some such embodiments, $R^3$ is cyclopropyl wherein the cyclopropyl is optionally substituted with 1, 2, 3, or 4 independently selected $R^x$ groups.

In certain embodiments, $R^3$ is $C_1$-$C_6$ haloalkyl or $C_1$-$C_6$ alkyl. In some such embodiments, $R^3$ is $CF_3$, $CH_3$, or $CH_2CH_3$.

In certain embodiments, $R^3$ is $C_1$-$C_6$ haloalkyl. In some such embodiments, $R^3$ is $CF_3$.

In certain embodiments, $R^3$ is $C_1$-$C_6$ alkyl. In some such embodiments, $R^3$ is $CH_3$ or $CH_2CH_3$. In some such embodiments, $R^3$ is $CH_3$.

In certain embodiments, $R^2$ and $R^3$, together with the carbon atom to which they are attached, form a $C_3$-$C_6$ monocyclic cycloalkyl, a $C_4$-$C_6$ monocyclic cycloalkenyl, or a 4-6 membered monocyclic heterocycle; wherein the $C_3$-$C_6$ monocyclic cycloalkyl, the $C_4$-$C_6$ monocyclic cycloalkenyl, and the 4-6 membered monocyclic heterocycle are each optionally substituted with 1, 2, 3, or 4 independently selected $R^x$ groups.

In certain embodiments, $R^2$ and $R^3$, together with the carbon atom to which they are attached, is a cyclobutyl, a cyclopentyl, a cyclopentenyl, or an oxetanyl; wherein the cyclobutyl, the cyclopentyl, the cyclopentenyl, and the oxetanyl are each optionally substituted with 1, 2, 3, or 4 independently selected $R^x$ groups.

In certain embodiments, $R^4$ is phenyl, pyridinyl, $C_3$-$C_6$ monocyclic cycloalkyl, or $C_4$-$C_6$ monocyclic cycloalkenyl; wherein each $R^4$ is optionally substituted with 1, 2, 3, or 4 independently selected $R^y$ groups.

In certain embodiments, $R^4$ is phenyl, cyclopentenyl, or cyclohexenyl; wherein each $R^4$ is optionally substituted with 1, 2, 3, or 4 independently selected $R^y$ groups.

In certain embodiments, $R^4$ is formula (a)

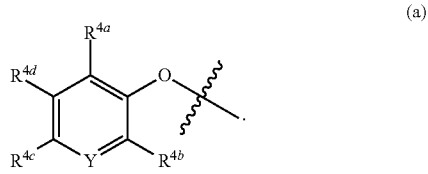

(a)

In certain embodiments, $R^{4a}$ is halogen, $C_1$-$C_6$ alkyl, or $C_1$-$C_6$ haloalkyl. In some such embodiments, $R^{4a}$ is F, Cl, $C_1$-$C_3$ alkyl, or $C_1$-$C_3$ haloalkyl. In some such embodiments, $R^{4a}$ is F, Cl, $CH_3$, $CF_3$, or $CHF_2$.

In certain embodiments, $R^{4a}$ is $C_1$-$C_3$ alkyl. In some such embodiments, $R^{4a}$ is $CH_3$.

In certain embodiments, $R^{4b}$ is halogen or $C_1$-$C_6$ alkyl. In some such embodiments, $R^{4b}$ is Cl or $C_1$-$C_3$ alkyl. In some such embodiments, $R^{4b}$ is Cl or $CH_3$.

In certain embodiments, $R^{4b}$ is $C_1$-$C_3$ alkyl. In some such embodiments, $R^{4b}$ is $CH_3$.

In certain embodiments, $R^{4c}$ is hydrogen, halogen, —CN, $C_1$-$C_6$ alkyl, $C_1$-$C_6$ haloalkyl, —S($C_1$-$C_6$ alkyl), —S(O)$_2$($C_1$-$C_6$ alkyl), or —($C_1$-$C_6$ alkylenyl)-OH.

In certain embodiments, $R^{4c}$ is hydrogen, halogen, —CN, —S($C_1$-$C_6$ alkyl), —S(O)$_2$($C_1$-$C_6$ alkyl), or ($C_1$-$C_6$ alkylenyl)-OH.

In certain embodiments, $R^{4c}$ is hydrogen, F, Cl, Br, —CN, —SCH$_3$, —S(O)$_2$CH$_3$, or —C(CH$_3$)$_2$—OH.

In certain embodiments, $R^{4c}$ is hydrogen or halogen. In some such embodiments, the halogen is F, Cl, or Br. In some such embodiments, the halogen is F.

In certain embodiments, $R^{4c}$ is halogen. In some such embodiments, the halogen is F, Cl, or Br. In some such embodiments, the halogen is F.

In certain embodiments, $R^{4c}$ is F.

In certain embodiments, $R^{4d}$ is hydrogen or halogen. In some such embodiments, the halogen is F or Cl.

In certain embodiments, $R^{4d}$ is hydrogen.

In certain embodiments, Y is C($R^{4e}$) or N; wherein $R^{4e}$ is hydrogen.

In certain embodiments, Y is N.

In certain embodiments, Y is C($R^{4e}$). In some such embodiments, $R^{4e}$ is hydrogen or halogen. In some such embodiments, $R^{4e}$ is hydrogen.

In certain embodiments, $R^6$ is hydrogen or halogen. In some such embodiments, the halogen is F.

In certain embodiments, $R^6$ is hydrogen.

In certain embodiments, $R^6$ is halogen. In some such embodiments, the halogen is F.

Various embodiments of substituents $R^1$, $R^2$, $R^3$, $R^4$, $R^{4a}$, $R^{4b}$, $R^{4c}$, $R^{4d}$, $R^{4e}$, $R^5$, $R^6$, $X^1$, $X^2$, and Y have been discussed above. These substituents embodiments can be combined to form various embodiments of compounds of formula (I). All embodiments of compounds of formula (I), formed by combining the substituent embodiments discussed above are within the scope of Applicant's invention, and some illustrative embodiments of the compounds of formula (I) are provided below.

In one embodiment, the invention is directed to compounds of formula (I), wherein
$R^2$ is phenyl, cyclopropyl, cyclopentyl, $C_1$-$C_6$ haloalkyl, or $C_1$-$C_6$ alkyl wherein the $C_1$-$C_6$ alkyl is optionally substituted with one substituent selected from the group consisting of $G^{2b}$ and —OH; and wherein the phenyl, the cyclopropyl, and the cyclopentyl are each optionally substituted with 1, 2, 3, or 4 independently selected $R^x$ groups; and
$R^3$ is $C_1$-$C_6$ haloalkyl, $C_1$-$C_6$ alkyl, or a cyclopropyl wherein the cyclopropyl is optionally substituted with 1, 2, 3, or 4 independently selected $R^x$ groups.

In one embodiment, the invention is directed to compounds of formula (I), wherein
$R^2$ is $C_1$-$C_6$ haloalkyl or $C_1$-$C_6$ alkyl wherein the $C_1$-$C_6$ alkyl is optionally substituted with one —OH; and
$R^3$ is $C_1$-$C_6$ haloalkyl or $C_1$-$C_6$ alkyl.

In one embodiment, the invention is directed to compounds of formula (I), wherein
$R^2$ is $C_1$-$C_6$ alkyl wherein the $C_1$-$C_6$ alkyl is optionally substituted with one —OH; and
$R^3$ is $C_1$-$C_6$ alkyl.

In one embodiment, the invention is directed to compounds of formula (I), wherein
$R^2$ is $C_1$-$C_6$ alkyl; and $R^3$ is $C_1$-$C_6$ alkyl. In some such embodiment, $R^2$ is $CH_3$; and $R^3$ is $CH_3$.

In one embodiment, the invention is directed to compounds of formula (I), wherein
$R^4$ is formula (a); wherein
$R^{4a}$ is halogen, $C_1$-$C_6$ alkyl, or $C_1$-$C_6$ haloalkyl;
$R^{4b}$ is halogen or $C_1$-$C_6$ alkyl;
$R^{4d}$ is hydrogen or halogen; and
Y is C($R^{4e}$) or N; wherein $R^{4e}$ is hydrogen.

In one embodiment, the invention is directed to compounds of formula (I), wherein
$R^4$ is formula (a); wherein
$R^{4a}$ is halogen, $C_1$-$C_6$ alkyl, or $C_1$-$C_6$ haloalkyl;
$R^{4b}$ is halogen or $C_1$-$C_6$ alkyl;
$R^{4c}$ is hydrogen or halogen;
$R^{4d}$ is hydrogen or halogen; and
Y is C($R^{4e}$) or N; wherein $R^{4e}$ is hydrogen.
In some such embodiments, $R^{4c}$ is hydrogen or F. In some such embodiments, $R^{4c}$ is F. In some such embodiments, $R^{4c}$ is hydrogen.

In one embodiment, the invention is directed to compounds of formula (I), wherein
$R^4$ is formula (a); wherein
$R^{4a}$ is $C_1$-$C_3$ alkyl;
$R^{4b}$ is $C_1$-$C_3$ alkyl;
$R^{4c}$ is hydrogen or halogen;
$R^{4d}$ is hydrogen; and
Y is C($R^{4e}$) wherein $R^{4e}$ is hydrogen.
In some such embodiments, $R^{4c}$ is hydrogen or F. In some such embodiments, $R^{4c}$ is F. In some such embodiments, $R^{4c}$ is hydrogen.

In one embodiment, the invention is directed to compounds of formula (I), wherein $X^1$ is N or C($R^5$); $X^2$ is C($R^5$); and $R^5$ is hydrogen.

In one embodiment, the invention is directed to compounds of formula (I), wherein $X^1$ and $X^2$ are C($R^5$); and $R^5$ is hydrogen.

In one embodiment, the invention is directed to compounds of formula (I), wherein $X^1$ is N; $X^2$ is C($R^5$); and $R^5$ is hydrogen.

In one embodiment, the invention is directed to compounds of formula (I), wherein $X^1$ is $C(R^5)$; $X^2$ is N; and $R^5$ is hydrogen.

In one embodiment, the invention is directed to compounds of formula (I), wherein
  $X^1$ is N or $C(R^5)$;
  $X^2$ is $C(R^5)$;
  $R^5$ is hydrogen; and
  $R^2$ and $R^3$, together with the carbon atom to which they are attached, form a $C_3$-$C_6$ monocyclic cycloalkyl, a $C_4$-$C_6$ monocyclic cycloalkenyl, or a 4-6 membered monocyclic heterocycle; wherein the $C_3$-$C_6$ monocyclic cycloalkyl, the $C_4$-$C_6$ monocyclic cycloalkenyl, and the 4-6 membered monocyclic heterocycle are each optionally substituted with 1, 2, 3, or 4 independently selected $R^x$ groups.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
  $X^1$ is N or $C(R^5)$;
  $X^2$ is $C(R^5)$;
  $R^5$ is hydrogen;
  $R^2$ and $R^3$, together with the carbon atom to which they are attached, form a $C_3$-$C_6$ monocyclic cycloalkyl, a $C_4$-$C_6$ monocyclic cycloalkenyl, or a 4-6 membered monocyclic heterocycle; wherein the $C_3$-$C_6$ monocyclic cycloalkyl, the $C_4$-$C_6$ monocyclic cycloalkenyl, and the 4-6 membered monocyclic heterocycle are each optionally substituted with 1, 2, 3, or 4 independently selected $R^x$ groups;
  $R^4$ is formula (a); wherein
    $R^{4a}$ is halogen, $C_1$-$C_6$ alkyl, or $C_1$-$C_6$ haloalkyl;
    $R^{4b}$ is halogen or $C_1$-$C_6$ alkyl;
    $R^{4d}$ is hydrogen or halogen; and
    Y is $C(R^{4e})$ or N; wherein $R^{4e}$ is hydrogen; and
  $R^6$ is hydrogen or halogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
  $X^1$ is N or $C(R^5)$;
  $X^2$ is $C(R^5)$;
  $R^5$ is hydrogen;
  $R^1$ is $C_1$-$C_6$ alkyl, or $R^1$ is $C_3$-$C_6$ cycloalkyl optionally substituted with 1, 2, 3, or 4 independently selected $R^x$ groups;
  $R^2$ and $R^3$, together with the carbon atom to which they are attached, form a $C_3$-$C_6$ monocyclic cycloalkyl, a $C_4$-$C_6$ monocyclic cycloalkenyl, or a 4-6 membered monocyclic heterocycle; wherein the $C_3$-$C_6$ monocyclic cycloalkyl, the $C_4$-$C_6$ monocyclic cycloalkenyl, and the 4-6 membered monocyclic heterocycle are each optionally substituted with 1, 2, 3, or 4 independently selected $R^x$ groups;
  $R^4$ is formula (a); wherein
    $R^{4a}$ is $C_1$-$C_3$ alkyl;
    $R^{4b}$ is $C_1$-$C_3$ alkyl;
    $R^{4c}$ is hydrogen or halogen;
    $R^{4d}$ is hydrogen; and
    Y is $C(R^{4e})$; wherein $R^{4e}$ is hydrogen; and
  $R^6$ is hydrogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In some such embodiments, $R^1$ is $C_1$-$C_6$ alkyl.

In some such embodiments, $R^1$ is optionally substituted cyclopropyl.

In one embodiment, the invention is directed to compounds of formula (I), wherein
  $X^1$ is N or $C(R^5)$;
  $X^2$ is $C(R^5)$;
  $R^5$ is hydrogen;
  $R^2$ is phenyl, cyclopropyl, cyclopentyl, $C_1$-$C_6$ haloalkyl, or $C_1$-$C_6$ alkyl wherein the $C_1$-$C_6$ alkyl is optionally substituted with one substituent selected from the group consisting of $G^{2b}$ and —OH; and wherein the phenyl, the cyclopropyl, and the cyclopentyl are each optionally substituted with 1, 2, 3, or 4 independently selected $R^x$ groups; and
  $R^3$ is $C_1$-$C_6$ haloalkyl, $C_1$-$C_6$ alkyl, or a cyclopropyl wherein the cyclopropyl is optionally substituted with 1, 2, 3, or 4 independently selected $R^x$ groups.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
  $X^1$ is N or $C(R^5)$;
  $X^2$ is $C(R^5)$;
  $R^5$ is hydrogen;
  $R^2$ is phenyl, cyclopropyl, cyclopentyl, $C_1$-$C_6$ haloalkyl, or $C_1$-$C_6$ alkyl wherein the $C_1$-$C_6$ alkyl is optionally substituted with one substituent selected from the group consisting of $G^{2b}$ and —OH; and wherein the phenyl, the cyclopropyl, and the cyclopentyl are each optionally substituted with 1, 2, 3, or 4 independently selected $R^x$ groups;
  $R^3$ is $C_1$-$C_6$ haloalkyl, $C_1$-$C_6$ alkyl, or a cyclopropyl wherein the cyclopropyl is optionally substituted with 1, 2, 3, or 4 independently selected $R^x$ groups;
  $R^4$ is phenyl, pyridinyl, a $C_3$-$C_6$ monocyclic cycloalkyl, or a $C_4$-$C_6$ monocyclic cycloalkenyl; wherein each $R^4$ is optionally substituted with 1, 2, 3, or 4 independently selected $R^y$ groups; and
  $R^6$ is hydrogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
  $X^1$ is N or $C(R^5)$;
  $X^2$ is $C(R^5)$;
  $R^5$ is hydrogen;
  $R^2$ is $C_1$-$C_6$ alkyl wherein the $C_1$-$C_6$ alkyl is optionally substituted with one —OH;
  $R^3$ is $C_1$-$C_6$ alkyl;
  $R^4$ is phenyl, pyridinyl, a $C_3$-$C_6$ monocyclic cycloalkyl, or a $C_4$-$C_6$ monocyclic cycloalkenyl; wherein each $R^4$ is optionally substituted with 1, 2, 3, or 4 independently selected $R^y$ groups; and
  $R^6$ is hydrogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
$X^1$ is $C(R^5)$;
$X^2$ is $C(R^5)$;
$R^5$ is hydrogen;
$R^1$, $R^2$, and $R^3$ are $C_1$-$C_6$ alkyl;
$R^4$ is phenyl, pyridinyl, a $C_3$-$C_6$ monocyclic cycloalkyl, or a $C_4$-$C_6$ monocyclic cycloalkenyl; wherein each $R^4$ is optionally substituted with 1, 2, 3, or 4 independently selected $R^y$ groups; and
$R^6$ is hydrogen.

In one embodiment, the invention is directed to compounds of formula (I), wherein
$X^1$ is N or $C(R^5)$;
$X^2$ is $C(R^5)$;
$R^5$ is hydrogen;
$R^2$ is phenyl, cyclopropyl, cyclopentyl, $C_1$-$C_6$ haloalkyl, or $C_1$-$C_6$ alkyl wherein the $C_1$-$C_6$ alkyl is optionally substituted with one substituent selected from the group consisting of $G^{2b}$ and —OH; and wherein the phenyl, the cyclopropyl, and the cyclopentyl are each optionally substituted with 1, 2, 3, or 4 independently selected $R^x$ groups;
$R^3$ is $C_1$-$C_6$ haloalkyl, $C_1$-$C_6$ alkyl, or a cyclopropyl wherein the cyclopropyl is optionally substituted with 1, 2, 3, or 4 independently selected $R^x$ groups;
$R^4$ is formula (a); and
$R^6$ is hydrogen or halogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
$X^1$ is N or $C(R^5)$;
$X^2$ is $C(R^5)$;
$R^5$ is hydrogen;
$R^2$ is phenyl, cyclopropyl, cyclopentyl, $C_1$-$C_6$ haloalkyl, or $C_1$-$C_6$ alkyl wherein the $C_1$-$C_6$ alkyl is optionally substituted with one substituent selected from the group consisting of $G^{2b}$ and —OH; and wherein the phenyl, the cyclopropyl, and the cyclopentyl are each optionally substituted with 1, 2, 3, or 4 independently selected $R^x$ groups;
$R^3$ is $C_1$-$C_6$ haloalkyl, $C_1$-$C_6$ alkyl, or a cyclopropyl wherein the cyclopropyl is optionally substituted with 1, 2, 3, or 4 independently selected $R^x$ groups;
$R^4$ is formula (a); wherein
$R^{4a}$ is halogen, $C_1$-$C_6$ alkyl, or $C_1$-$C_6$ haloalkyl;
$R^{4b}$ is halogen or $C_1$-$C_6$ alkyl;
$R^{4d}$ is hydrogen or halogen; and
Y is $C(R^{4e})$ or N; wherein $R^{4e}$ is hydrogen; and
$R^6$ is hydrogen or halogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
$X^1$ is N or $C(R^5)$;
$X^2$ is $C(R^5)$;
$R^5$ is hydrogen;
$R^2$ is phenyl, cyclopropyl, cyclopentyl, $C_1$-$C_6$ haloalkyl, or $C_1$-$C_6$ alkyl wherein the $C_1$-$C_6$ alkyl is optionally substituted with one substituent selected from the group consisting of $G^{2b}$ and —OH; and wherein the phenyl, the cyclopropyl, and the cyclopentyl are each optionally substituted with 1, 2, 3, or 4 independently selected $R^x$ groups;
$R^3$ is $C_1$-$C_6$ haloalkyl, $C_1$-$C_6$ alkyl, or a cyclopropyl wherein the cyclopropyl is optionally substituted with 1, 2, 3, or 4 independently selected $R^x$ groups;
$R^4$ is formula (a); wherein
$R^{4a}$ is $C_1$-$C_3$ alkyl;
$R^{4b}$ is $C_1$-$C_3$ alkyl;
$R^{4c}$ is hydrogen or halogen;
$R^{4d}$ is hydrogen; and
Y is $C(R^{4e})$ or N; wherein $R^{4e}$ is hydrogen; and
$R^6$ is hydrogen or halogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
$X^1$ is N or $C(R^5)$;
$X^2$ is $C(R^5)$;
$R^5$ is hydrogen;
$R^2$ is $C_1$-$C_6$ haloalkyl or $C_1$-$C_6$ alkyl wherein the $C_1$-$C_6$ alkyl is optionally substituted with one —OH;
$R^3$ is $C_1$-$C_6$ haloalkyl or $C_1$-$C_6$ alkyl;
$R^4$ is formula (a); wherein
$R^{4a}$ is $C_1$-$C_3$ alkyl;
$R^{4b}$ is $C_1$-$C_3$ alkyl;
$R^{4c}$ is hydrogen or halogen;
$R^{4d}$ is hydrogen; and
Y is $C(R^{4e})$ or N; wherein $R^{4e}$ is hydrogen; and
$R^6$ is hydrogen or halogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
$X^1$ is N or $C(R^5)$;
$X^2$ is $C(R^5)$;
$R^5$ is hydrogen;
$R^1$ is $C_1$-$C_6$ alkyl or cyclopropyl which is optionally substituted with 1, 2, 3, or 4 independently selected $R^x$ groups;
$R^2$ and $R^3$ are $C_1$-$C_6$ alkyl;
$R^4$ is formula (a); wherein
$R^{4a}$ is $C_1$-$C_3$ alkyl;
$R^{4b}$ is $C_1$-$C_3$ alkyl;
$R^{4c}$ is hydrogen or halogen;
$R^{4d}$ is hydrogen; and
Y is $C(R^{4e})$ wherein $R^{4e}$ is hydrogen; and
$R^6$ is hydrogen or halogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
$X^1$ is $C(R^5)$;
$X^2$ is $C(R^5)$;
$R^5$ is hydrogen;
$R^1$ is cyclopropyl which is optionally substituted with 1, 2, 3, or 4 independently selected $R^x$ groups;
$R^2$ and $R^3$ are $C_1$-$C_6$ alkyl;
$R^4$ is formula (a); wherein
$R^{4a}$ is $C_1$-$C_3$ alkyl;
$R^{4b}$ is $C_1$-$C_3$ alkyl;

$R^{4c}$ is hydrogen or halogen;
$R^{4d}$ is hydrogen; and
Y is $C(R^{4e})$ wherein $R^{4e}$ is hydrogen; and
$R^6$ is hydrogen.

In some such embodiments, $R^{4c}$ is halogen. In some such embodiments, $R^{4c}$ is F.

In one embodiment, the invention is directed to compounds of formula (I), wherein
$X^1$ is N or $C(R^5)$;
$X^2$ is $C(R^5)$;
$R^5$ is hydrogen;
$R^1$, $R^2$ and $R^3$ are $C_1$-$C_6$ alkyl;
$R^4$ is formula (a); wherein
$R^{4a}$ is $C_1$-$C_3$ alkyl;
$R^{4b}$ is $C_1$-$C_3$ alkyl;
$R^{4c}$ is hydrogen or halogen;
$R^{4d}$ is hydrogen; and
Y is $C(R^{4e})$ wherein $R^{4e}$ is hydrogen; and
$R^6$ is hydrogen or halogen.

In some such embodiments, $X^1$ and $X^2$ are $C(R^5)$; and $R^5$ is hydrogen.

In some such embodiments, $X^1$ is N; $X^2$ is $C(R^5)$; and $R^5$ is hydrogen.

In one embodiment, the invention is directed to compounds of formula (I), wherein
$X^1$ is $C(R^5)$;
$X^2$ is $C(R^5)$;
$R^5$ is hydrogen;
$R^1$, $R^2$ and $R^3$ are $C_1$-$C_6$ alkyl;
$R^4$ is formula (a); wherein
$R^{4a}$ is $C_1$-$C_3$ alkyl;
$R^{4b}$ is $C_1$-$C_3$ alkyl;
$R^{4c}$ is halogen;
$R^{4d}$ is hydrogen; and
Y is $C(R^{4e})$ wherein $R^{4e}$ is hydrogen; and
$R^6$ is hydrogen.

In some such embodiments, $R^{4c}$ is F.

In one embodiment, the invention is directed to a process for preparing compound of formula (A) wherein the process comprises bromination of compound of formula (B)

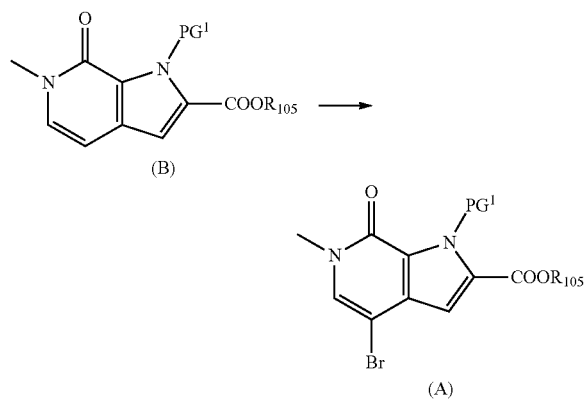

wherein $PG^1$ is a nitrogen protecting group; and $R_{105}$ is $C_1$-$C_6$ alkyl.

In certain embodiments, $PG^1$ is selected from the group consisting of p-toluenesulfonyl, benzyl, and 2-(trimethylsilyl)ethoxymethyl. In certain embodiments, $PG^1$ is p-toluenesulfonyl.

In certain embodiments, $R_{105}$ is ethyl.

Compound (B) may be brominated using a brominating agent and in the presence of an acid. In certain embodiments, the brominating agent may include, for example, bromine or N-bromosuccinimide. In certain embodiments, the brominating agent is N-bromosuccinimide. Examples of the acid may include acetic acid and p-toluenesulfonic acid. In certain embodiments, the acid is p-toluenesulfonic acid. In certain embodiments, compound (B) is brominated using N-bromosuccinimide and p-toluenesulfonic acid.

In certain embodiments, compound (B) may be brominated with or without the presence of a solvent. In certain embodiments, the bromination is conducted in the presence of a solvent. Solvents may include, for example, tetrahydrofuran, N,N-dimethylformamide, N,N-dimethylacetamide, N-methyl-pyrrolidone, dimethyl sulfoxide, 1,2-dimethoxyethane, 1,4-dioxane, acetonitrile, cyclopentyl methyl ether, toluene, benzene, tert-amyl alcohol, tert-butyl alcohol, 2-methyltetrahydrofuran, ethyl acetate, isopropyl acetate, anisole, trifluorotoluene, and any other suitable solvent and combinations thereof. In certain embodiments, the solvent is tetrahydrofuran. In certain embodiments, the solvent is acetonitrile.

In certain embodiments, compound (B) may be brominated without the presence of a solvent, for example, compound (B) may be reacted with bromine in neat acetic acid to provide compound (A).

In certain embodiments, compound (B) may be brominated at a temperature from about 20° C. to about 50° C. In certain embodiments, compound (B) is brominated at a temperature of about 20° C. to about 25° C. In certain embodiments, compound (B) is brominated at a temperature of about 25° C.

In an embodiment, compound (B) is reacted with N-bromosuccinimide in the presence of p-toluenesulfonic acid to give compound (A).

In an embodiment, compound (B) is reacted with N-bromosuccinimide in the presence of p-toluenesulfonic acid and tetrahydrofuran to give compound (A).

In an embodiment, compound (B) is reacted with N-bromosuccinimide in the presence of p-toluenesulfonic acid and acetonitrile to give compound (A).

In an embodiment, compound (B) is reacted with N-bromosuccinimide in the presence of acetic acid to give compound (A).

In an embodiment, compound (B) is reacted with N-bromosuccinimide in the presence of p-toluenesulfonic acid and tetrahydrofuran at about 25° C. to give compound (A).

In an embodiment, compound (B) is reacted with N-bromosuccinimide in the presence of p-toluenesulfonic acid and acetonitrile at about 25° C. to give compound (A).

Compound of the invention are named by using Name 2015 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) may generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Exemplary compounds of formula (I) include, but are not limited to:
4-[2-(2,6-dimethylphenoxy)-5-(2-hydroxypropan-2-yl)pyridin-3-yl]-N-ethyl-6-methyl-7-oxo-6,7-dihydro-1H-pyrrolo[2,3-I]pyridine-2-carboxamide;
4-[2-(2,6-dimethylphenoxy)-5-(3-hydroxypentan-3-yl)pyridin-3-yl]-N-ethyl-6-methyl-7-oxo-6,7-dihydro-1H-pyrrolo[2,3-c]pyridine-2-carboxamide;
4-[2-(2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide;
4-[2-(2,6-dimethylphenoxy)-5-(1-hydroxycyclopent-3-en-1-yl)pyridin-3-yl]-N-ethyl-6-methyl-7-oxo-6,7-dihydro-1H-pyrrolo[2,3-c]pyridine-2-carboxamide;
4-[2-(2,6-dimethylphenoxy)-5-(1-hydroxycyclopent-3-en-1-yl)phenyl]-N-ethyl-6-methyl-7-oxo-6,7-dihydro-1H-pyrrolo[2,3-c]pyridine-2-carboxamide;
4-[2-(2,6-dimethylphenoxy)-5-(1-hydroxycyclopentyl)pyridin-3-yl]-N-ethyl-6-methyl-7-oxo-6,7-dihydro-1H-pyrrolo[2,3-c]pyridine-2-carboxamide;
4-[2-(2,6-dimethylphenoxy)-5-(1-hydroxy-1-phenylpropyl)pyridin-3-yl]-N-ethyl-6-methyl-7-oxo-6,7-dihydro-1H-pyrrolo[2,3-c]pyridine-2-carboxamide;
4-[2-(2,6-dimethylphenoxy)-5-(2-hydroxybutan-2-yl)pyridin-3-yl]-N-ethyl-6-methyl-7-oxo-6,7-dihydro-1H-pyrrolo[2,3-c]pyridine-2-carboxamide;
4-{2-(2,6-dimethylphenoxy)-5-[1-(4-fluorophenyl)-1-hydroxypropyl]pyridin-3-yl}-N-ethyl-6-methyl-7-oxo-6,7-dihydro-1H-pyrrolo[2,3-c]pyridine-2-carboxamide;
4-[2-(2,6-dimethylphenoxy)-5-(3-hydroxy-5-methyl hexan-3-yl)pyridin-3-yl]-N-ethyl-6-methyl-7-oxo-6,7-dihydro-1H-pyrrolo[2,3-c]pyridine-2-carboxamide;
4-[5-(1-cyclopentyl-1-hydroxypropyl)-2-(2,6-dimethylphenoxy)pyridin-3-yl]-N-ethyl-6-methyl-7-oxo-6,7-dihydro-1H-pyrrolo[2,3-c]pyridine-2-carboxamide;
4-[5-(1-cyclopropyl-1-hydroxypropyl)-2-(2,6-dimethylphenoxy)pyridin-3-yl]-N-ethyl-6-methyl-7-oxo-6,7-dihydro-1H-pyrrolo[2,3-c]pyridine-2-carboxamide;
4-[2-(2,6-dimethylphenoxy)-5-(3-hydroxy-4-methyl hexan-3-yl)pyridin-3-yl]-N-ethyl-6-methyl-7-oxo-6,7-dihydro-1H-pyrrolo[2,3-c]pyridine-2-carboxamide;
4-[2-(2,6-dimethylphenoxy)-5-(3-hydroxy-1-phenylpentan-3-yl)pyridin-3-yl]-N-ethyl-6-methyl-7-oxo-6,7-dihydro-1H-pyrrolo[2,3-c]pyridine-2-carboxamide;
4-{2-(2,6-dimethylphenoxy)-5-[1-(4-fluorophenyl)-2-hydroxybutan-2-yl]pyridin-3-yl}-N-ethyl-6-methyl-7-oxo-6,7-dihydro-1H-pyrrolo[2,3-c]pyridine-2-carboxamide;
4-[2-(2,6-dimethylphenoxy)-5-(1-hydroxy-1-phenyl ethyl)pyridin-3-yl]-N-ethyl-6-methyl-7-oxo-6,7-dihydro-1H-pyrrolo[2,3-c]pyridine-2-carboxamide;
4-{2-(2,6-dimethylphenoxy)-5-[1-(4-fluorophenyl)-1-hydroxyethyl]pyridin-3-yl}-N-ethyl-6-methyl-7-oxo-6,7-dihydro-1H-pyrrolo[2,3-c]pyridine-2-carboxamide;
4-[2-(2,6-dimethylphenoxy)-5-(2-hydroxy-4-methyl pentan-2-yl)pyridin-3-yl]-N-ethyl-6-methyl-7-oxo-6,7-dihydro-1H-pyrrolo[2,3-c]pyridine-2-carboxamide;
4-[2-(2,6-dimethylphenoxy)-5-(2-hydroxy-3-methylbutan-2-yl)pyridin-3-yl]-N-ethyl-6-methyl-7-oxo-6,7-dihydro-1H-pyrrolo[2,3-c]pyridine-2-carboxamide;
4-[2-(2,6-dimethylphenoxy)-5-(2-hydroxy-3-methyl pentan-2-yl)pyridin-3-yl]-N-ethyl-6-methyl-7-oxo-6,7-dihydro-1H-pyrrolo[2,3-c]pyridine-2-carboxamide;

4-[2-(2,6-dimethylphenoxy)-5-(2-hydroxy-4-phenylbutan-2-yl)pyridin-3-yl]-N-ethyl-6-methyl-7-oxo-6,7-dihydro-1H-pyrrolo[2,3-c]pyridine-2-carboxamide;

4-{2-(2,6-dimethylphenoxy)-5-[1-(4-fluorophenyl)-2-hydroxypropan-2-yl]pyridin-3-yl}-N-ethyl-6-methyl-7-oxo-6,7-dihydro-1H-pyrrolo[2,3-c]pyridine-2-carboxamide;

4-{5-[cyclopropyl(4-fluorophenyl)hydroxymethyl]-2-(2,6-dimethylphenoxy)pyridin-3-yl}-N-ethyl-6-methyl-7-oxo-6,7-dihydro-1H-pyrrolo[2,3-c]pyridine-2-carboxamide;

4-{5-[cyclopentyl(cyclopropyl)hydroxymethyl]-2-(2,6-dimethylphenoxy)pyridin-3-yl}-N-ethyl-6-methyl-7-oxo-6,7-dihydro-1H-pyrrolo[2,3-c]pyridine-2-carboxamide;

4-{5-[di cyclopropyl(hydroxy)methyl]-2-(2,6-dimethylphenoxy)pyridin-3-yl}-N-ethyl-6-methyl-7-oxo-6,7-dihydro-1H-pyrrolo[2,3-c]pyridine-2-carboxamide;

4-[5-(1-cyclopropyl-1-hydroxy-2-methylpropyl)-2-(2,6-dimethylphenoxy)pyridin-3-yl]-N-ethyl-6-methyl-7-oxo-6,7-dihydro-1H-pyrrolo[2,3-c]pyridine-2-carboxamide;

4-[5-(1-cyclopropyl-1-hydroxy-2-methylbutyl)-2-(2,6-dimethylphenoxy)pyridin-3-yl]-N-ethyl-6-methyl-7-oxo-6,7-dihydro-1H-pyrrolo[2,3-c]pyridine-2-carboxamide;

N-ethyl-4-{5-(2-hydroxypropan-2-yl)-2-[2-methyl-6-(trifluoromethyl)phenoxy]phenyl}-6-methyl-7-oxo-6,7-dihydro-1H-pyrrolo[2,3-c]pyridine-2-carboxamide;

4-[2-(2-chloro-6-methylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide;

4-[2-(2-chloro-6-methylphenoxy)-5-(2-hydroxypropan-2-yl)phenyl]-N-ethyl-6-methyl-7-oxo-6,7-dihydro-1H-pyrrolo[2,3-c]pyridine-2-carboxamide;

N-tert-butyl-4-[2-(2-chloro-6-methylphenoxy)-5-(2-hydroxypropan-2-yl)phenyl]-6-methyl-7-oxo-6,7-dihydro-1H-pyrrolo[2,3-c]pyridine-2-carboxamide;

N-tert-butyl-4-[2-(2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

N-tert-butyl-4-[2',4'-difluoro-4-(2-hydroxypropan-2-yl)[1,1'-biphenyl]-2-yl]-6-methyl-7-oxo-6,7-dihydro-1H-pyrrolo[2,3-c]pyridine-2-carboxamide;

N-(2,2-difluoro-1-methyl cyclopropyl)-4-[2-(2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide;

N-ethyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

N-tert-butyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

N-tert-butyl-4-[2-(2-chloro-6-methylphenoxy)-5-(2-hydroxypropan-2-yl)pyridin-3-yl]-6-methyl-7-oxo-6,7-dihydro-1H-pyrrolo[2,3-c]pyridine-2-carboxamide;

4-[2-(2-chloro-6-methylphenoxy)-5-(2-hydroxypropan-2-yl)pyridin-3-yl]-6-methyl-7-oxo-N-(1,1,1-trifluoro-2-methylpropan-2-yl)-6,7-dihydro-1H-pyrrolo[2,3-c]pyridine-2-carboxamide;

4-[2-(2-chloro-6-methylphenoxy)-5-(2-hydroxypropan-2-yl)pyridin-3-yl]-N-(2,2-difluoro-1-methyl cyclopropyl)-6-methyl-7-oxo-6,7-dihydro-1H-pyrrolo[2,3-c]pyridine-2-carboxamide;

4-{2-[2,6-dimethyl-4-(methyl sulfanyl)phenoxy]-5-(2-hydroxypropan-2-yl)phenyl}-N-ethyl-6-methyl-7-oxo-6,7-dihydro-1H-pyrrolo[2,3-c]pyridine-2-carboxamide;

4-[2-(2-chloro-6-methylphenoxy)-5-(2-hydroxypropan-2-yl)phenyl]-6-methyl-7-oxo-N-(1,1,1-trifluoro-2-methylpropan-2-yl)-6,7-dihydro-1H-pyrrolo[2,3-c]pyridine-2-carboxamide;

4-[2-(2-chloro-6-methylphenoxy)-5-(2-hydroxypropan-2-yl)phenyl]-N-(2,2-difluoro-1-methylcyclopropyl)-6-methyl-7-oxo-6,7-dihydro-1H-pyrrolo[2,3-c]pyridine-2-carboxamide;

N-ethyl-4-[2-(4-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide;

N-tert-butyl-4-[2-(4-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide;

N-tert-butyl-4-{5-(2-hydroxypropan-2-yl)-2-[2-methyl-6-(trifluoromethyl)phenoxy]pyridin-3-yl}-6-methyl-7-oxo-6,7-dihydro-1H-pyrrolo[2,3-c]pyridine-2-carboxamide;

4-{5-(2-hydroxypropan-2-yl)-2-[2-methyl-6-(trifluoromethyl)phenoxy]pyridin-3-yl}-6-methyl-7-oxo-N-(1,1,1-trifluoro-2-methylpropan-2-yl)-6,7-dihydro-1H-pyrrolo[2,3-c]pyridine-2-carboxamide;

N-(2,2-difluoro-1-methyl cyclopropyl)-4-{5-(2-hydroxypropan-2-yl)-2-[2-methyl-6-(trifluoromethyl)phenoxy]pyridin-3-yl}-6-methyl-7-oxo-6,7-dihydro-1H-pyrrolo[2,3-c]pyridine-2-carboxamide;

N-ethyl-4-{5-(2-hydroxypropan-2-yl)-2-[2-methyl-6-(trifluoromethyl)phenoxy]pyridin-3-yl}-6-methyl-7-oxo-6,7-dihydro-1H-pyrrolo[2,3-c]pyridine-2-carboxamide;

4-[2-(2-chloro-4-fluoro-6-methylphenoxy)-5-(2-hydroxypropan-2-yl)phenyl]-N-ethyl-6-methyl-7-oxo-6,7-dihydro-1H-pyrrolo[2,3-c]pyridine-2-carboxamide;

N-tert-butyl-4-[2-(2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide;

N-tert-butyl-4-[2-(2-chloro-4-fluoro-6-methylphenoxy)-5-(2-hydroxypropan-2-yl)pyridin-3-yl]-6-methyl-7-oxo-6,7-dihydro-1H-pyrrolo[2,3-c]pyridine-2-carboxamide;

4-[2-(2-chloro-4-fluoro-6-methylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide;

N-tert-butyl-4-[2-(2-chloro-4-fluoro-6-methylphenoxy)-5-(2-hydroxypropan-2-yl)phenyl]-6-methyl-7-oxo-6,7-dihydro-1H-pyrrolo[2,3-c]pyridine-2-carboxamide;

N-tert-butyl-4-{5-(2-hydroxypropan-2-yl)-2-[2-methyl-6-(trifluoromethyl)phenoxy]phenyl}-6-methyl-7-oxo-6,7-dihydro-1H-pyrrolo[2,3-c]pyridine-2-carboxamide;

4-[2-(4-fluoro-2,6-dimethylphenoxy)-5-(2-hydroxypropan-2-yl)phenyl]-6-methyl-7-oxo-N-(1,1,1-trifluoro-2-methylpropan-2-yl)-6,7-dihydro-1H-pyrrolo[2,3-c]pyridine-2-carboxamide;

4-[2-(4-fluoro-2,6-dimethylphenoxy)-5-(2-hydroxypropan-2-yl)pyridin-3-yl]-6-methyl-7-oxo-N-(1,1,1-trifluoro-2-methylpropan-2-yl)-6,7-dihydro-1H-pyrrolo[2,3-c]pyridine-2-carboxamide;

4-[2-(2-chloro-4-fluoro-6-methylphenoxy)-5-(2-hydroxypropan-2-yl)phenyl]-6-methyl-7-oxo-N-(1,1,1-trifluoro-2-methylpropan-2-yl)-6,7-dihydro-1H-pyrrolo[2,3-c]pyridine-2-carboxamide;

4-[2-(2-chloro-4-fluoro-6-methylphenoxy)-5-(2-hydroxypropan-2-yl)pyridin-3-yl]-6-methyl-7-oxo-N-(1,1,1-trifluoro-2-methylpropan-2-yl)-6,7-dihydro-1H-pyrrolo[2,3-c]pyridine-2-carboxamide;

4-[2-(2-chloro-4-fluoro-6-methylphenoxy)-5-(2-hydroxypropan-2-yl)phenyl]-N-(2,2-difluoro-1-methyl cyclopropyl)-6-methyl-7-oxo-6,7-dihydro-1H-pyrrolo[2,3-c]pyridine-2-carboxamide;

N-(2,2-difluoro-1-methyl cyclopropyl)-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

N-(2,2-difluoro-1-methyl cyclopropyl)-4-[2-(4-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide;

4-[2-(2-chloro-4-fluoro-6-methylphenoxy)-5-(2-hydroxypropan-2-yl)pyridin-3-yl]-N-(2,2-difluoro-1-methyl cyclopropyl)-6-methyl-7-oxo-6,7-dihydro-1H-pyrrolo[2,3-c]pyridine-2-carboxamide;

N-(bicyclo[1.1.1]pentan-1-yl)-4-[2-(2-chloro-6-methylphenoxy)-5-(2-hydroxypropan-2-yl)pyridin-3-yl]-6-methyl-7-oxo-6,7-dihydro-1H-pyrrolo[2,3-c]pyridine-2-carboxamide;

4-[2-(2,6-dimethylphenoxy)-4-fluoro-5-(2-hydroxypropan-2-yl)phenyl]-N-ethyl-6-methyl-7-oxo-6,7-dihydro-1H-pyrrolo[2,3-c]pyridine-2-carboxamide;

N-ethyl-4-[4-fluoro-2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

4-[5-(1,2-dihydroxypropan-2-yl)-2-(2,6-dimethyl phenoxy)phenyl]-N-ethyl-6-methyl-7-oxo-6,7-dihydro-1H-pyrrolo[2,3-c]pyridine-2-carboxamide;

4-[5-(2,4-dihydroxybutan-2-yl)-2-(2,6-dimethylphenoxy)phenyl]-N-ethyl-6-methyl-7-oxo-6,7-dihydro-1H-pyrrolo[2,3-c]pyridine-2-carboxamide;

4-{5-[(2R)-1,2-dihydroxypropan-2-yl]-2-(2,6-dimethylphenoxy)phenyl}-N-ethyl-6-methyl-7-oxo-6,7-dihydro-1H-pyrrolo[2,3-c]pyridine-2-carboxamide;

4-{5-[(2)-1,2-dihydroxypropan-2-yl]-2-(2,6-dimethylphenoxy)phenyl}-N-ethyl-6-methyl-7-oxo-6,7-dihydro-1H-pyrrolo[2,3-c]pyridine-2-carboxamide;

4-{2-[2-(difluoromethyl)-6-methylphenoxy]-5-(2-hydroxypropan-2-yl)phenyl}-N-ethyl-6-methyl-7-oxo-6,7-dihydro-1H-pyrrolo[2,3-c]pyridine-2-carboxamide;

N-tert-butyl-4-{2-[2-(difluoromethyl)-6-methylphenoxy]-5-(2-hydroxypropan-2-yl)phenyl}-6-methyl-7-oxo-6,7-dihydro-1H-pyrrolo[2,3-c]pyridine-2-carboxamide;

4-[2-(4-bromo-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide;

4-[2-(4-cyano-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide;

4-{2-[(2,4-dimethylpyridin-3-yl)oxy]-5-(2-hydroxypropan-2-yl)phenyl}-N-ethyl-6-methyl-7-oxo-6,7-dihydro-1H-pyrrolo[2,3-c]pyridine-2-carboxamide;

N-(bicyclo[1.1.1]pentan-1-yl)-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

N-tert-butyl-4-[3-(2,6-dimethylphenoxy)-6-(2-hydroxypropan-2-yl)pyridin-2-yl]-6-methyl-7-oxo-6,7-dihydro-1H-pyrrolo[2,3-c]pyridine-2-carboxamide;

4-[3-(2,6-dimethylphenoxy)-6-(2-hydroxypropan-2-yl)pyridin-2-yl]-N-ethyl-6-methyl-7-oxo-6,7-dihydro-1H-pyrrolo[2,3-c]pyridine-2-carboxamide;

N-ethyl-4-[2-(4-fluoro-2,6-dimethylphenoxy)-5-(1-fluoro-2-hydroxypropan-2-yl)pyridin-3-yl]-6-methyl-7-oxo-6,7-dihydro-1H-pyrrolo[2,3-c]pyridine-2-carboxamide;

N-ethyl-4-[2-(4-fluoro-2,6-dimethylphenoxy)-5-(1,1,1-trifluoro-2-hydroxypropan-2-yl)pyridin-3-yl]-6-methyl-7-oxo-6,7-dihydro-1H-pyrrolo[2,3-c]pyridine-2-carboxamide;

N-ethyl-4-[2-(4-fluoro-2,6-dimethylphenoxy)-5-(1,1,1,3,3,3-hexafluoro-2-hydroxypropan-2-yl)pyridin-3-yl]-6-methyl-7-oxo-6,7-dihydro-1H-pyrrolo[2,3-c]pyridine-2-carboxamide;

N-ethyl-4-[2-(2-fluoro-6-methylphenoxy)-5-(2-hydroxypropan-2-yl)phenyl]-6-methyl-7-oxo-6,7-dihydro-1H-pyrrolo[2,3-c]pyridine-2-carboxamide;

N-($d_5$)ethyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

N-ethyl-4-[2-(4-fluoro-2,6-dimethylphenoxy)-5-(1-fluoro-2-hydroxypropan-2-yl)phenyl]-6-methyl-7-oxo-6,7-dihydro-1H-pyrrolo[2,3-c]pyridine-2-carboxamide;

4-[2-(4-chloro-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide;

N-ethyl-4-{5-(2-hydroxypropan-2-yl)-2-[4-(methanesulfonyl)-2,6-dimethylphenoxy]phenyl}-6-methyl-7-oxo-6,7-dihydro-1H-pyrrolo[2,3-c]pyridine-2-carboxamide;

N-ethyl-4-[2-(4-fluoro-2,6-dimethylphenoxy)-5-(1,1,1-trifluoro-2-hydroxypropan-2-yl)phenyl]-6-methyl-7-oxo-6,7-dihydro-1H-pyrrolo[2,3-c]pyridine-2-carboxamide;

N-tert-butyl-4-[2-(4-fluoro-2,6-dimethylphenoxy)-5-(1-fluoro-2-hydroxypropan-2-yl)phenyl]-6-methyl-7-oxo-6,7-dihydro-1H-pyrrolo[2,3-c]pyridine-2-carboxamide;

4-[2-(4-chloro-2,6-dimethylphenoxy)-5-(1-fluoro-2-hydroxypropan-2-yl)phenyl]-N-ethyl-6-methyl-7-oxo-6,7-dihydro-1H-pyrrolo[2,3-c]pyridine-2-carboxamide;

4-[2-(2,4-difluorophenyl)-5-(2-hydroxypropan-2-yl)pyridin-3-yl]-N-ethyl-6-methyl-7-oxo-6,7-dihydro-1H-pyrrolo[2,3-c]pyridine-2-carboxamide;

N-tert-butyl-4-{5-(2-hydroxypropan-2-yl)-2-[4-(methanesulfonyl)-2,6-dimethylphenoxy]phenyl}-6-methyl-7-oxo-6,7-dihydro-1H-pyrrolo[2,3-c]pyridine-2-carboxamide;

N-ethyl-4-[2-(3-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide;

N-tert-butyl-4-{5-(2-hydroxypropan-2-yl)-2-[4-(methanesulfonyl)-2,6-dimethylphenoxy]pyridin-3-yl}-6-methyl-7-oxo-6,7-dihydro-1H-pyrrolo[2,3-c]pyridine-2-carboxamide;

N-ethyl-4-{5-(2-hydroxypropan-2-yl)-2-[4-(methanesulfonyl)-2,6-dimethylphenoxy]pyridin-3-yl}-6-methyl-7-oxo-6,7-dihydro-1H-pyrrolo[2,3-c]pyridine-2-carboxamide;

4-[2-(4-chloro-2,6-dimethylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide;

N-tert-butyl-4-[2-(4-chloro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide;

N-ethyl-4-[3-(4-fluoro-2,6-dimethylphenoxy)-6-(2-hydroxypropan-2-yl)pyridin-2-yl]-6-methyl-7-oxo-6,7-dihydro-1H-pyrrolo[2,3-c]pyridine-2-carboxamide;

N-tert-butyl-4-[3-(4-fluoro-2,6-dimethylphenoxy)-6-(2-hydroxypropan-2-yl)pyridin-2-yl]-6-methyl-7-oxo-6,7-dihydro-1H-pyrrolo[2,3-c]pyridine-2-carboxamide;

4-{2-[2-(difluoromethyl)-4-fluoro-6-methylphenoxy]-5-(2-hydroxypropan-2-yl)phenyl}-N-ethyl-6-methyl-7-oxo-6,7-dihydro-1H-pyrrolo[2,3-c]pyridine-2-carboxamide;

4-[2-(3-chloro-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide;

N-tert-butyl-4-[2-(2,6-di chloro-4-fluorophenoxy)-5-(2-hydroxypropan-2-yl)pyridin-3-yl]-6-methyl-7-oxo-6,7-dihydro-1H-pyrrolo[2,3-c]pyridine-2-carboxamide;

4-[2-(2,6-di chloro-4-fluorophenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide;

4-[2-(4-chloro-2,6-dimethylphenoxy)-5-(1-fluoro-2-hydroxypropan-2-yl)pyridin-3-yl]-N-ethyl-6-methyl-7-oxo-6,7-dihydro-1H-pyrrolo[2,3-c]pyridine-2-carboxamide;

N-tert-butyl-4-[2-(4-chloro-2,6-dimethylphenoxy)-5-(1-fluoro-2-hydroxypropan-2-yl)pyridin-3-yl]-6-methyl-7-oxo-6,7-dihydro-1H-pyrrolo[2,3-c]pyridine-2-carboxamide;

N-ethyl-4-[2-(3-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

4-[2-(2,6-dimethylphenoxy)-5-(2-hydroxy-4-methyl pentan-2-yl)phenyl]-N-ethyl-6-methyl-7-oxo-6,7-dihydro-1H-pyrrolo[2,3-c]pyridine-2-carboxamide;

N-tert-butyl-4-[2-(2,6-dimethylphenoxy)-5-(2-hydroxy-4-methylpentan-2-yl)phenyl]-6-methyl-7-oxo-6,7-dihydro-1H-pyrrolo[2,3-c]pyridine-2-carboxamide;

N-ethyl-4-{5-(2-hydroxypropan-2-yl)-2-[4-(2-hydroxypropan-2-yl)-2,6-dimethylphenoxy]phenyl}-6-methyl-7-oxo-6,7-dihydro-1H-pyrrolo[2,3-c]pyridine-2-carboxamide;

N-tert-butyl-4-{5-(2-hydroxypropan-2-yl)-2-[4-(2-hydroxypropan-2-yl)-2,6-dimethylphenoxy]phenyl}-6-methyl-7-oxo-6,7-dihydro-1H-pyrrolo[2,3-c]pyridine-2-carboxamide;

4-[2-(3-chloro-2,6-dimethylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide;

N-ethyl-4-[4-(2-hydroxypropan-2-yl)-4'-(trifluoromethoxy)[1,1'-biphenyl]-2-yl]-6-methyl-7-oxo-6,7-dihydro-1H-pyrrolo[2,3-c]pyridine-2-carboxamide;

4-[4',4'-difluoro-4-(2-hydroxypropan-2-yl)[2',3',4',5'-tetrahydro[1,1'-biphenyl]]-2-yl]-N-ethyl-6-methyl-7-oxo-6,7-dihydro-1H-pyrrolo[2,3-c]pyridine-2-carboxamide;

4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

N-ethyl-4-[4-(2-hydroxypropan-2-yl)-4'-methyl[2',3',4',5'-tetrahydro[1,1'-biphenyl]]-2-yl]-6-methyl-7-oxo-6,7-dihydro-1H-pyrrolo[2,3-c]pyridine-2-carboxamide;

4-[2-(cyclopent-1-en-1-yl)-5-(2-hydroxypropan-2-yl)phenyl]-N-ethyl-6-methyl-7-oxo-6,7-dihydro-1H-pyrrolo[2,3-c]pyridine-2-carboxamide;

4-[2-(2-chloro-6-methylphenoxy)-5-(1,2-dihydroxypropan-2-yl)phenyl]-N-ethyl-6-methyl-7-oxo-6,7-dihydro-1H-pyrrolo[2,3-c]pyridine-2-carboxamide;

N-tert-butyl-4-[2-(2-chloro-6-methylphenoxy)-5-(1,2-dihydroxypropan-2-yl)phenyl]-6-methyl-7-oxo-6,7-dihydro-1H-pyrrolo[2,3-c]pyridine-2-carboxamide;

4-[2-(2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

N-tert-butyl-4-[2-(2-chloro-4-fluoro-6-methylphenoxy)-5-(1,2-dihydroxypropan-2-yl)phenyl]-6-methyl-7-oxo-6,7-dihydro-1H-pyrrolo[2,3-c]pyridine-2-carboxamide;

4-[2-(2-chloro-4-fluoro-6-methylphenoxy)-5-(1,2-dihydroxypropan-2-yl)phenyl]-N-ethyl-6-methyl-7-oxo-6,7-dihydro-1H-pyrrolo[2,3-c]pyridine-2-carboxamide;

4-[2-(4-fluoro-2,6-dimethylphenoxy)-5-(2-hydroxypropan-2-yl)phenyl]-N,6-dimethyl-7-oxo-6,7-dihydro-1H-pyrrolo[2,3-c]pyridine-2-carboxamide;

N-cyclopropyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide;

N-ethyl-4-[2-(4-fluoro-2,6-dimethylphenoxy)-5-(1-hydroxycyclobutyl)phenyl]-6-methyl-7-oxo-6,7-dihydro-1H-pyrrolo[2,3-c]pyridine-2-carboxamide; and N-ethyl-4-[2-(4-fluoro-2,6-dimethylphenoxy)-5-(3-hydroxyoxetan-3-yl)phenyl]-6-methyl-7-oxo-6,7-dihydro-1H-pyrrolo[2,3-c]pyridine-2-carboxamide.

Examples of formula (I) also include:

N-ethyl-4-{5-(2-hydroxypropan-2-yl)-2-[4-(2-hydroxypropan-2-yl)-2,6-dimethylphenoxy]pyridin-3-yl}-6-methyl-7-oxo-6,7-dihydro-1H-pyrrolo[2,3-c]pyridine-2-carboxamide;

N-tert-butyl-4-{5-(2-hydroxypropan-2-yl)-2-[4-(2-hydroxypropan-2-yl)-2,6-dimethylphenoxy]pyridin-3-yl}-6-methyl-7-oxo-6,7-dihydro-1H-pyrrolo[2,3-c]pyridine-2-carboxamide;

4-{5-(1,2-dihydroxypropan-2-yl)-2-[2-methyl-6-(trifluoromethyl)phenoxy]phenyl}-N-ethyl-6-methyl-7-oxo-6,7-dihydro-1H-pyrrolo[2,3-c]pyridine-2-carboxamide;

N-tert-butyl-4-{5-(1,2-dihydroxypropan-2-yl)-2-[2-methyl-6-(trifluoromethyl)phenoxy]phenyl}-6-methyl-7-oxo-6,7-dihydro-1H-pyrrolo[2,3-c]pyridine-2-carboxamide;

4-[5-(2,5-dihydroxypentan-2-yl)-2-(4-fluoro-2,6-dimethylphenoxy)phenyl]-N-ethyl-6-methyl-7-oxo-6,7-dihydro-1H-pyrrolo[2,3-c]pyridine-2-carboxamide; and N-ethyl-4-[2-(4-fluoro-2,6-dimethylphenoxy)-5-(4-hydroxyoxan-4-yl)phenyl]-6-methyl-7-oxo-6,7-dihydro-1H-pyrrolo[2,3-c]pyridine-2-carboxamide.

Compounds of formula (I) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and may be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethyl amine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

c. General Synthesis

The compounds described herein, including compounds of general formula (I) and specific examples, may be prepared, for example, through the reaction routes depicted in schemes 1-9. The variables $X^1$, $X^2$, $R^1$, $R^2$, $R^3$, $R^4$, $R^5$, $R^6$, $R^{4a}$, $R^{4b}$, $R^{4c}$, $R^{4d}$, and Y used in the following schemes have the meanings as set forth in the summary and detailed description sections unless otherwise noted.

Abbreviations used in the descriptions of the schemes and the specific examples have the following meanings: DMF for N,N-dimethylformamide, DMSO for dimethyl sulfoxide, psi for pounds per square inch, HPLC for high performance liquid chromatography, and SFC for Supercritical Fluid Chromatography.

Scheme 1

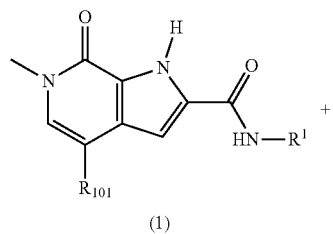

(1)

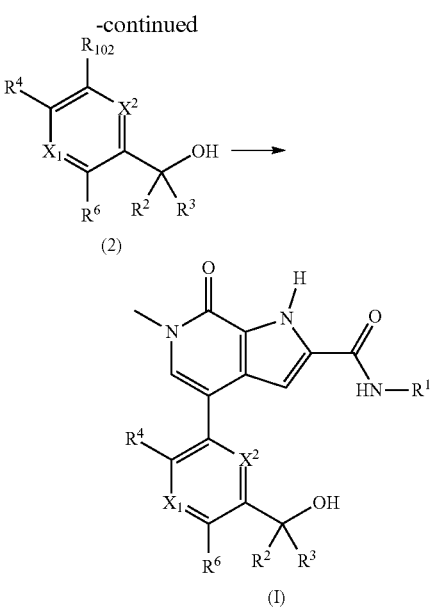

Compounds of general formula (I) may be prepared by reaction of boronic acids or a derivative thereof (e.g., a pinacol ester) of formula (1) wherein $R_{101}$ is boronic acid or a derivative thereof (e.g., a pinacol ester) with compounds of formula (2), wherein $R_{102}$ is halo (Cl, Br, or I) or triflate, under Suzuki coupling conditions (N. Miyama and A. Suzuki, Chem. Rev. 1995, 95:2457-2483, J. Organomet. Chem. 1999, 576:147-148). For example, the coupling reaction may be conducted in the presence of a palladium catalyst and a base, and optionally in the presence of a ligand, and in a suitable solvent at elevated temperature (about 60° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamante, 2-dicyclohexylphosphino-2',4',6'-triisopropylbiphenyl (X-phos), and 1,1'-bis(diphenylphosphanyl) ferrocene. Non-limiting examples of suitable solvent include methanol, ethanol, dimethoxyethane, N,N-dimethylformamide, dimethylsulfoxide, dioxane, tetrahydrofuran, toluene, and water, or a mixture thereof.

Similar transformation may be conducted for compounds of formula (1) wherein $R_{101}$ is halo (Cl, Br, or I) or triflate and compounds of formula (2) wherein $R_{102}$ is boronic acid or a derivative thereof (e.g., a pinacol ester).

Scheme 2

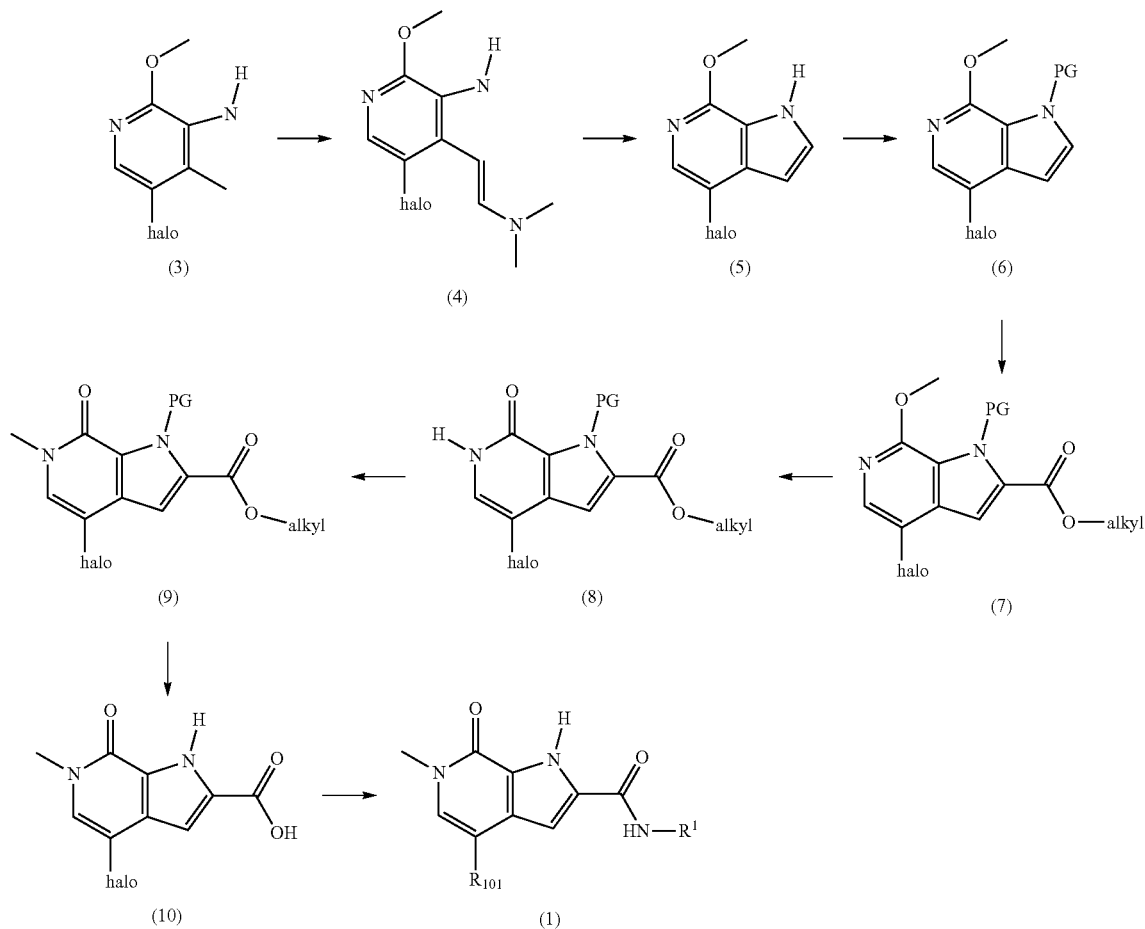

Compounds of formula (1) may be prepared using general synthetic route as shown in Scheme 2. Treatment of compounds of formula (3) wherein halo is Br, Cl, or I, with 1,1-dimethoxy-N,N-dimethylmethanamine at elevated temperature (for example, at about 60° C. to about 100° C.), in the absence or presence of a base, and in a solvent such as, but not limited to, N,N-dimethylformamide, provide compounds of formula (4). Examples of bases that may be employed include, but not limited to, lithium or sodium methanolate. Catalytic hydrogenation of (4) in the presence of a catalyst such as, but not limited to, Raney-Nickel and under hydrogen atmosphere (about 30 psi) and in a solvent such as, but not limited to, ethyl acetate, at about room temperature generally affords compounds of formula (5). Protection of the nitrogen atom with protecting group (PG) such as, but not limited to, benzyl, p-tolunesulfonyl, and (trimethylsilyl)ethoxy)methyl group may be derived from reaction with an appropriate halide, in the presence of a strong base such as, but not limited to, sodium hydride, to provide compounds of formula (6). Conversion of (6) to (7) may be achieved by reaction with alkyl carbonochloridate in the presence of a base such as, but not limited to, lithium diisopropylamide. Treatment of (7) with an acid such as, but not limited to, hydrochloric acid or hydrobromic acid and in a solvent such as, but not limited to, dioxane or water, at about 40° C. to about 100° C., provides compounds of formula (8).

Alkylation of (8) with methyl iodide, in the presence of a base such as, but not limited to, sodium hydride, cesium carbonate, or potassium carbonate, and in a solvent such as, but not limited to, N,N-dimethylformamide or dimethylsulfoxide at a temperature of about 0° C. to about 50° C. provides compounds of formula (9). Hydrolysis of esters (9) provides acids of formula (1).

Acids of formula (10) may be transformed to the appropriate acid chloride by treatment with oxalyl chloride in the presence of catalytic amount of N,N-dimethylformamide at about room temperature, and in a suitable solvent such as, but not limited to, tetrahydrofuran or dichloromethane. The resulting acid chloride may be converted to amides of formula (1) wherein $R_{101}$ is halo by treatment with an amine of formula $R^1NH_2$ in a solvent such as, but not limited to, tetrahydrofuran, N,N-dimethylformamide, or dichloromethane at a temperature from about room temperature to about 50° C., optionally in the presence of a base such as, but not limited to, triethylamine, N,N-diisopropylethylamine, or potassium carbonate, and optionally in the presence of a catalyst such as 4-dimethylaminopyridine.

Alternatively, acids of formula (10) may be reacted with the amine of formula $R^1NH_2$ in a solvent such as, but not limited to, tetrahydrofuran or N,N-dimethylformamide in the presence of a coupling reagent such as 1,1'-carbonyldiimidazole (CDI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU), in the presence or absence of a coupling auxiliary such as, but not limited to, 1-hydroxy-7-azabenzotriazole (HOAT) or 1-hydroxybenzotriazole hydrate (HOBT). The reaction may be generally conducted in the presence or absence of a base such as, but not limited to, N-methyl morpholine, triethylamine, or N,N-diisopropylethylamine.

Treatment of the compounds of formula (1) wherein $R_{101}$ is halo with 4,4,4',4',5,5,5',5'-octamethyl-2,2'-bi(1,3,2-dioxaborolane) generally affords compounds of formula (1) wherein $R_{101}$ is 4,4,5,5-tetramethyl-1,3,2-dioxaborolan-2-yl. In general, the conversion may be facilitated by a palladium catalyst such as, but not limited to, tetrakis(triphenylphosphine)palladium(0), tris(dibenzylideneacetone)dipalladium(0), or palladium(II)acetate, an optional ligand such as, but not limited to, 2-dicyclohexylphosphino-2',4',6'-triisopropylbiphenyl, 2-dicyclohexylphosphino-2',4',6'-triisopropylbiphenyl (X-phos), or 1,1'-bis(diphenylphosphanyl) ferrocene, and a base such as, but not limited to, carbonates, acetates, or phosphates of sodium, potassium, and cesium; and cesium fluoride. Non-limiting examples of suitable solvents include methanol, dimethoxyethane, N,N-dimethylformamide, dimethylsulfoxide, dioxane, tetrahydrofuran, and water, or a mixture thereof.

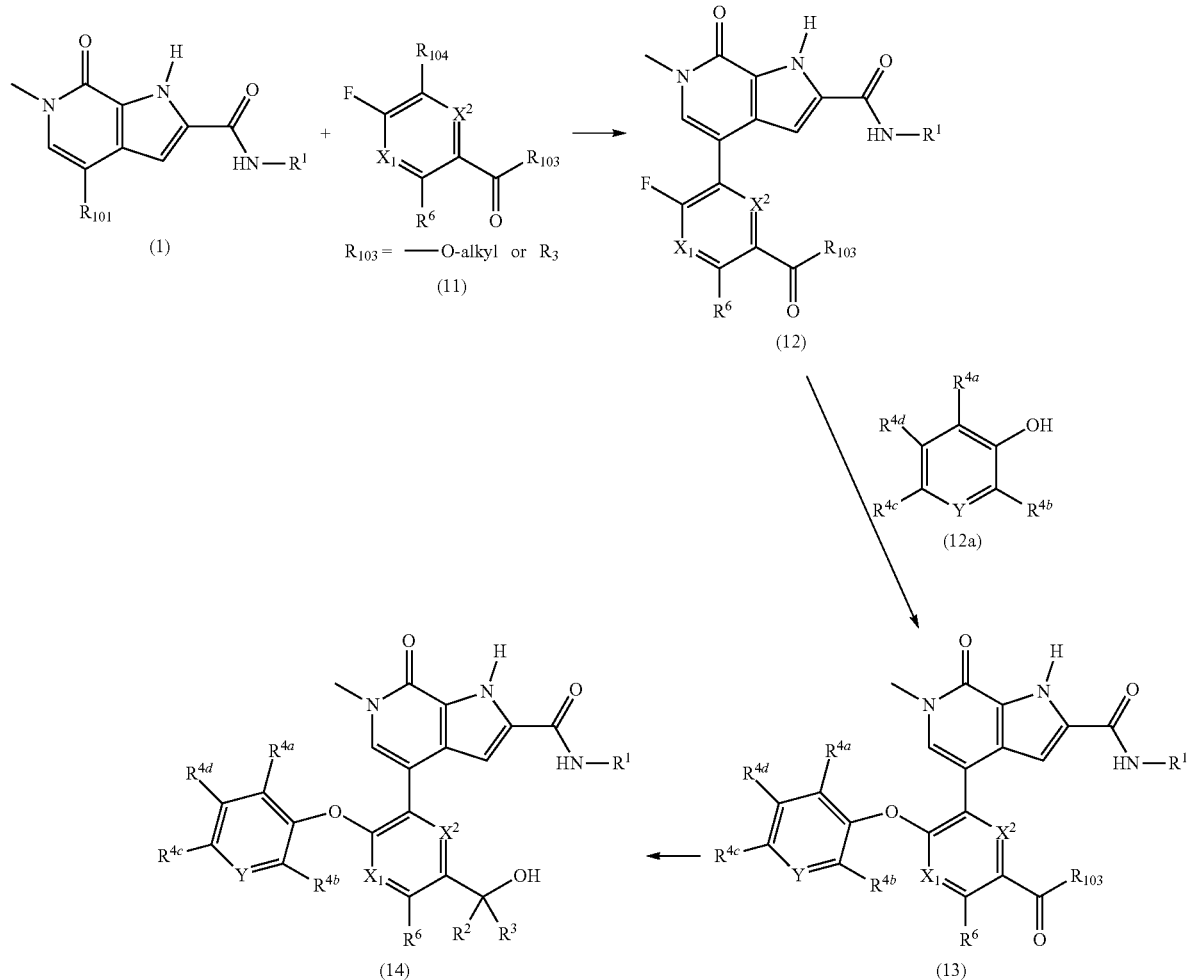

Scheme 3

Compounds of general formula (I) wherein $R^4$ is formula (a) may also be prepared by the route shown in Scheme 3. Reaction of formula (1) wherein $R_{101}$ is boronic acid or a derivative thereof (e.g., a pinacol ester) with compounds of formula (11), wherein $R_{104}$ is halo (Cl, Br, or I) or triflate, under Suzuki coupling conditions (N. Miyama and A. Suzuki, Chem. Rev. 1995, 95:2457-2483, J. Organomet. Chem. 1999, 576:147-148), as described above, to provide compounds of formula (12). Compounds of formula (13) may be prepared by displacement of the fluorine atom of the intermediates (12) with an appropriate alcohol (12a). Displacement of the fluorine atom may be accomplished in a solvent such as, but not limited to, dimethylsulfoxide, dimethylformamide, dioxane, or tetrahydrofuran and in the presence of a base such as, but not limited to, carbonate of cesium, potassium, or sodium, or sodium hydride, and at a temperature from about 40° C. to about 120° C. Compounds of formula (14) wherein $R^2$ and $R^3$ are different may be prepared by reaction of compounds of formula (13) wherein $R_{103}$=$R^3$ with a Grignard reagent of formula $R^2MgX$ in a solvent such as tetrahydrofuran, diether ether, or dioxane at about ambient temperatures. Compounds of formula (14) wherein $R^2$ and $R^3$ are the same may be prepared by reaction of compounds of formula (13) wherein $R_{103}$=Oalkyl with greater than two equivalents of a Grignard reagent of formula $R^2MgX$ in a solvent such as tetrahydrofuran, diether ether, or dioxane at about ambient temperatures.

Compounds of general formula (I) wherein $R^4$ is optionally substituted phenyl, optionally substituted pyridinyl, or optionally substituted $C_3$-$C_6$ monocyclic cycloalkyl, may be prepared according to Scheme 4. Using reaction conditions outlined in Scheme 3, the alcohols (16) may be prepared from compounds of formula (15). Reaction of compounds of formula (16) with compounds of formula (1a) under Suzuki coupling conditions (N. Miyama and A. Suzuki, Chem. Rev. 1995, 95:2457-2483, J. Organomet. Chem. 1999, 576:147-148), as described in Scheme 1, provides compounds of formula (17). Compounds of formula (19) may then be Scheme 4

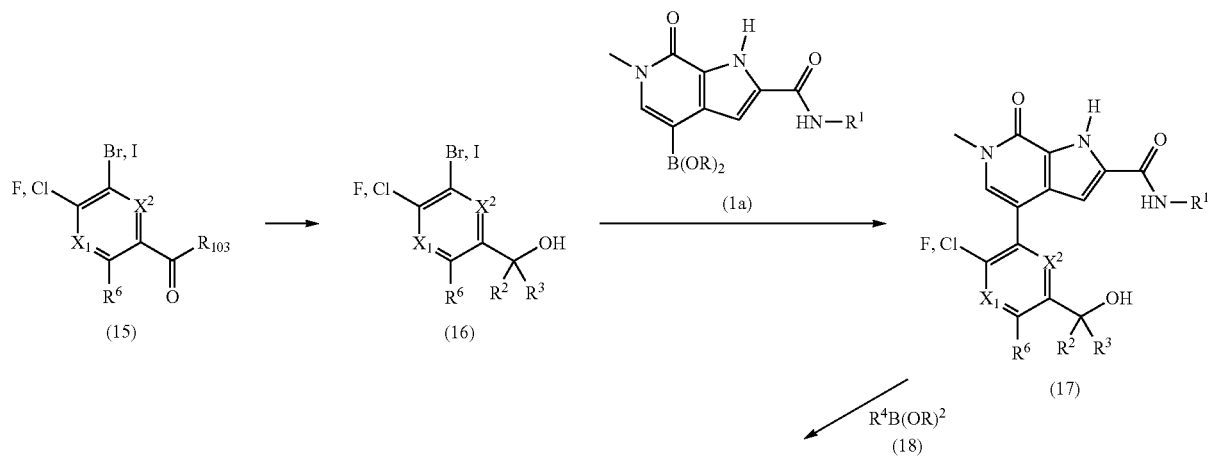

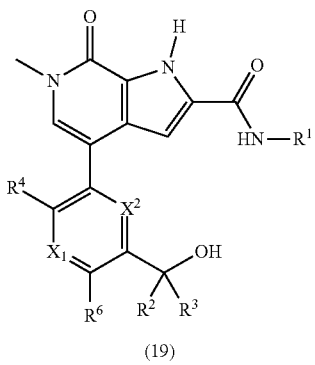

(19)

prepared from compounds of formula (17) by a subsequent Suzuki coupling reaction with compounds of formula (18).

Scheme 5

(7)

(20)

(2a)

(21)

Compounds of general formula (I) may also be prepared according to Scheme 5. Treatment of the compounds of formula (7) with 4,4,4',4',5,5,5',5'-octamethyl-2,2'-bi(1,3,2-dioxaborolane) under cross-coupling conditions as described in Scheme 2 generally affords compounds of formula (20). Reaction of compounds of formula (20) with compounds of formula (2a) under Suzuki coupling conditions (N. Miyama and A. Suzuki, Chem. Rev. 1995, 95:2457-2483, J. Organomet. Chem. 1999, 576:147-148), as described in Scheme 1, provides compounds of formula (21). Hydrolysis of the ester of compounds of formula (21), along with concomitant removal of the protecting group (PG) provides compounds of formula (22). Conversion of the acids (22) to the corresponding amides of formula (I) may be achieved with reaction conditions as outlined in Scheme 2.

(I)

(22)

Scheme 6

(23)

(15a)

(24)

(2a)

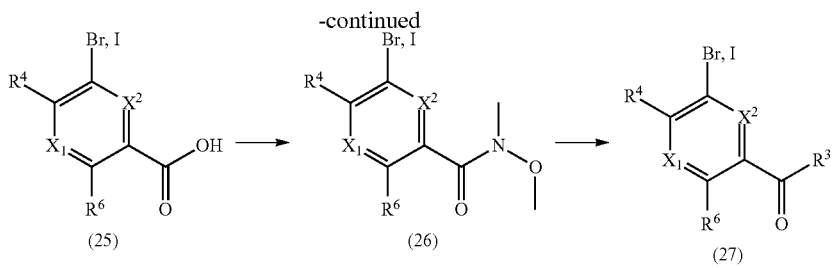

Compounds of general formula (2a) may be prepared as described in Scheme 7. Compounds of formula (23) may be esterified under general conditions known to one skilled in the art to provide compounds of formula (15a). Compounds of formula (24) wherein $R^4$ is formula (a) may be prepared by displacement of the Cl or F atom of the intermediates (15a) with an alcohol as described in Scheme 3. Suzuki coupling of (15a) with an appropriate boronic acid or esters (or derivatives thereof) as described in Scheme 1. Reaction of (24) with about two equivalents of Grignard reagent of formula $R^3MgX$ provides compounds of formula (2a) wherein $R^2$ and $R^3$ are the same.

Hydrolysis of esters (24) provides acids of formula (25), which may be treated with N,O-dimethylhydroxylamine in a solvent such as, but not limited to, tetrahydrofuran or N,N-dimethylformamide in the presence of a coupling reagent such as 1,1'-carbonyldiimidazole (CDI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU), in the presence or absence of a coupling auxiliary such as, but not limited to, 1-hydroxy-7-azabenzotriazole (HOAT) or 1-hydroxybenzotriazole hydrate (HOBT), to provide compounds of formula (26). Reaction of compounds of formula (26) with a Grignard reagent of formula $R^3MgX$ in a solvent such as tetrahydrofuran, diether ether, or dioxane at about ambient temperatures provides compounds of formula (27). Reaction of compounds of formula (27) with a Grignard reagent of formula $R^2MgX$ in a solvent such as tetrahydrofuran, diether ether, or dioxane at about ambient temperatures provides compounds of general formula (2a).

Alternatively, compounds of general formula (2a) may be prepared as described in Scheme 7. Conversion of (27) to compounds (28) may be achieved using reaction conditions as described in Scheme 4. Reduction of the nitro group of compounds of formula (28) provides amines of formula (29). Compounds of general formula (2a) may be prepared from compounds (29) under Sandmeyer conditions.

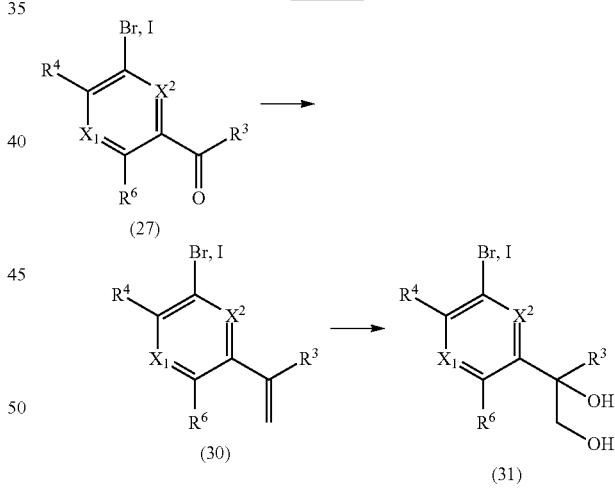

Alternatively, compounds of general formula (2a) wherein $R^2$ is —$CH_2OH$ may be prepared as described in Scheme 8. Reaction of compounds of formula (27) with a Wittig reagent such as methyltriphenylphosphonium bromide in a solvent such as but not limited to tetrahydrofuran or dioxane in the presence of a base, such as but not limited to n-butyllithium or sodium hydride at temperatures ranging from about −20° C. to ambient temperature, provides compounds of formula (30). Oxidation of compounds of formula (30) with reagents such as but not limited to potassium hexacyanoferrate (III) and potassium osmate hydrate in a solvent combination such as but not limited to water and tert-butanol in the presence of a base such as but not limited to potassium carbonate or sodium carbonate, provides compounds of formula (31).

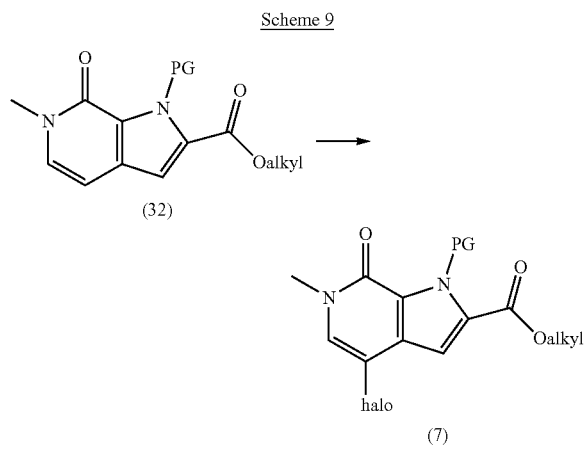

Scheme 9

Intermediates (7) may also be prepared as described in Scheme 9 by halogenation of compounds (32). The reaction may be conducted in the presence of a halogenating agent such as, but not limited to, N-bromosuccinimide, N-iodosuccinimide, or N-chlorosuccinimide, an acid such as, but not limited to, p-toluenesulofonic acid, and a solvent such as, but not limited to, tetrahydrofuran and acetonitrile.

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

d. Pharmaceutical Compositions

When employed as a pharmaceutical, a compound of the invention is typically administered in the form of a pharmaceutical composition. Such composition may be prepared in a manner well known in the pharmaceutical art and comprise a therapeutically effective amount of a compound of formula (I), or a pharmaceutically acceptable salt thereof, alone or or in combination with at least one additional therapeutic agent, together with a pharmaceutically acceptable carrier. The phrase "pharmaceutical composition" refers to a composition suitable for administration in medical or veterinary use.

The pharmaceutical compositions that comprise a compound of formula (I), alone or or in combination with at least one additional therapeutic agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous, and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it may be desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms may be made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula (I) may be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules may be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula (I) may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

e. Methods of Use

The compounds of formula (I), or pharmaceutically acceptable salts thereof, and pharmaceutical compositions comprising a compound of formula (I), or a pharmaceutically acceptable salt thereof, may be administered to a subject suffering from a bromodomain-mediated disorder or condition. The term "administering" refers to the method of contacting a compound with a subject. Thus, the compounds of formula (I) may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds of formula (I) may be administered transdermally, topically, via implantation, and transdermaly. In certain embodiments, the compounds of the formula (I) may be delivered orally. The compounds may also be delivered rectally, bucally, intravaginally, ocularly, andially, or by insufflation. Bromodomain-mediated disorders and conditions may be treated prophylactically, acutely, and chronically using compounds of formula (I), depending on the nature of the disorder or condition. Typically, the host or subject in each of these methods is human, although other mammals may also benefit from the administration of a compound of formula (I).

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, the invention provides a method for treating cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor. The method comprises the step of administering to a subject in need thereof a therapeutically effective amount of a compound of formula (I) or a preferred embodiment thereof, with or without a pharmaceutically acceptable carrier.

The invention further provides a method for treating inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. The method comprises the step of administering to a subject in need thereof a therapeutically effective amount of a compound of formula (I) or a preferred embodiment thereof, with or without a pharmaceutically acceptable carrier.

The invention further provides a method for treating diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease, or tubular interstitial nephritis. The method comprises the step of administering to a subject in need thereof a therapeutically effective amount of a compound of formula (I) or a preferred embodiment thereof, with or without a pharmaceutically acceptable carrier.

The invention further provides a method for treating acute kidney injury or disease or condition, wherein said acute kidney injury or disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease. The method comprises the step of administering to a subject in need thereof a therapeutically effective amount of a compound of formula (I) or a preferred embodiment thereof, with or without a pharmaceutically acceptable carrier.

The invention further provides a method for treating chronic kidney disease or condition, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease, and tubular interstitial nephritis. The method comprises the step of administering to a subject in need thereof a therapeutically effective amount of a compound of formula (I), or a preferred embodiment thereof, with or without a pharmaceutically acceptable carrier.

The invention further provides a method for treating AIDS. The method comprises the step of administering to a subject in need thereof a therapeutically effective amount of a compound of formula (I), or a preferred embodiment thereof, with or without a pharmaceutically acceptable carrier.

In another embodiment, the present invention provides compounds of the invention, or pharmaceutical compositions comprising a compound of the invention, for use in medicine. In a particular embodiment, the present invention provides compounds of the invention, or pharmaceutical compositions comprising a compound of the invention, for use in the treatment of diseases or disorders as described herein above.

One embodiment is directed to the use of a compound according to formula (I), or a pharmaceutically acceptable salt thereof in the preparation of a medicament. The medicament optionally can comprise at least one additional therapeutic agent. In some embodiments the medicament is for use in the treatment of diseases and disorders as described herein above.

This invention is also directed to the use of a compound according to formula (I), or a pharmaceutically acceptable salt thereof in the manufacture of a medicament for the treatment of the diseases and disorders as described herein above. The medicament optionally can comprise at least one additional therapeutic agent.

The compounds of formula (I) may be administered as the sole active agent or it may be co-administered with other therapeutic agents, including other compounds that demonstrate the same or a similar therapeutic activity and that are determined to be safe and efficacious for such combined administration. The term "co-administered" means the administration of two or more different therapeutic agents or treatments (e.g., radiation treatment) that are administered to a subject in a single pharmaceutical composition or in separate pharmaceutical compositions. Thus co-administration involves administration at the same time of a single pharmaceutical composition comprising two or more different therapeutic agents or administration of two or more different compositions to the same subject at the same or different times.

The compounds of the invention may be co-administered with a therapeutically effective amount of at least one additional therapeutic agent to treat cancer, where examples of the therapeutic agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/ deltoids plant alkaloids, small inhibitory ribonucleic acids (siRNAs), topoisomerase inhibitors, ubiquitin ligase inhibitors, and the like, and in combination with at least one of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-(3-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (*Bacillus* Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention may also be used as radio-sensitizers that enhance the efficacy of radiotherapy. Examples of radiotherapy include external beam radiotherapy, teletherapy, brachytherapy and sealed, unsealed source radiotherapy and the like.

Additionally, compounds of formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MIEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine) (ONCOVIN®; P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICIINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide, lonafarnib, 5,10-methyl enetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from *ginseng* comprising 20(S)protopanaxadiol (aPPD) and 20(S)protopanaxatriol (aPPT)), panitumumab, PANVAC®—VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention may also be co-administered with a therapeutically effective amount of at least one additional therapeutic agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-10 converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of formula (I) may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-10 monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; anti-thrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of formula (I) may be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of formula (I) may be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon (β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, anti-thrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of formula (I) may be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCUpseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Examples of therapeutic agents for SLE (Lupus) with which a compound of formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of formula (I) may also be used with LW 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of at least one additional therapeutic agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, lamivudine, nevirapine, stavudine zalcitabine, and zidovudine. Examples of protease inhibitors include, but are not limited to, amprenavir, indinavir, lopinavir, nelfinavir, ritonavir, and saquinavir.

The following Examples may be used for illustrative purposes and should not be deemed to narrow the scope of the invention.

f. Examples

All reagents were of commercial grade and were used as received without further purification, unless otherwise stated. Commercially available anhydrous solvents were used for reactions conducted under inert atmosphere. Reagent grade solvents were used in all other cases, unless otherwise specified. Chemical shifts (δ) for $^1$HNMR spectra were reported in parts per million (ppm) relative to tetramethylsilane (δ 0.00) or the appropriate residual solvent peak, i.e. CHCl$_3$ (δ 7.27), as internal reference. Multiplicities were given as singlet (s), doublet (d), triplet (t), quartet (q), quintuplet (quin), multiplet (m) and broad (br).

Example 1

4-[2-(2,6-dimethylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide Method A for the Preparation of ethyl 4-bromo-6-methyl-7-oxo-1-tosyl-6,7-dihydro-1H-pyrrolo[2,3-c]pyridine-2-carboxylate

Example 1a (E)-2-(5-bromo-2-methoxy-3-nitropyridin-4-yl)-N,N-dimethylethenamine 5-Bromo-2-methoxy-4-methyl-3-nitropyridine (15.0 g, 60.7 mmol) was dissolved in dimethylformamide (300 mL), and lithium methanolate (6.07 mL, 6.07 mmol, 1 M) was added. The reaction mixture was heated at 100° C. To this mixture was added 1,1-dimethoxy-N,N-dimethylmethanamine (64.5 mL, 486 mmol) over 10 minutes. The reaction mixture was stirred at 95° C. for 16 hours. The reaction mixture was cooled to ambient temperature and water was added carefully (300 mL, exothermic). The resulting precipitate was collected by vacuum filtration, washed with water, and dried to provide the title compound (13.9 g, 45.9 mmol, 76% yield).

Example 1b 4-bromo-7-methoxy-1H-pyrrolo[2,3-c]pyridine

Example 1a (13.9 g, 45.8 mmol) and ethyl acetate (150 mL) were added to Ra—Ni 2800 (pre-washed with ethanol) water slurry (6.9 g, 118 mmol) in a stainless steel pressure bottle and stirred for 30 minutes at 30 psi of $H_2$ and ambient temperature. The reaction mixture was filtered, and concentrated. The residue was triturated with dichloromethane, and the solid filtered to provide the title compound (5.82 g). The mother liquor was concentrated and the residue triturated again with dichloromethane and filtered to provide an additional 1.63 g of the title compound. Total yield=7.45 g, 72% yield.

Example 1c 4-bromo-7-methoxy-1-tosyl-1H-pyrrolo[2,3-c]pyridine

A solution of Example 1b (7.42 g, 32.7 mmol) in dimethylformamide (235 mL) was stirred at ambient temperature. To this solution was added sodium hydride (1.18 g, 1.96 g of 60% dispersion in oil, 49.0 mmol), and the reaction mixture was stirred for 10 minutes. P-toluenesulfonyl chloride (9.35 g, 49.0 mmol) was then added portion-wise, and the mixture was stirred at ambient temperature under nitrogen for 16 hours. The reaction mixture was quenched with water. The resulting beige solid was collected by vacuum filtration on a Buchner funnel, and washed with water. The solid was collected and dried in a vacuum oven at 50° C. to provide 12.4 g (100%) of the title compound.

Example 1d ethyl 4-bromo-7-methoxy-1-tosyl-1H-pyrrolo[2,3-c]pyridine-2-carboxylate To a solution of Example 1c (12 g, 31.5 mmol) in tetrahydrofuran (150 mL) was added lithium diisopropylamide (24.3 mL, 47.2 mmol) drop wise at −70° C. The mixture was stirred at −70° C. to −50° C. for 45 minutes, followed by drop wise addition of ethyl carbonochloridate (5.12 g, 47.2 mmol). After 1.5 hours, the reaction mixture was quenched with saturated aqueous ammonium chloride solution, the organic layer was separated, and the aqueous phase was extracted with ethyl acetate (3×300 mL). The combined organic layers was dried over anhydrous sodium sulfate, filtered, and concentrated under reduced pressure. The crude product was triturated with dichloromethane and methanol (1:10) to provide the title compound (13 g, 91% yield).

Example $R^1$ ethyl 4-bromo-7-oxo-1-tosyl-6,7-dihydro-1H-pyrrolo[2,3-c]pyridine-2-carboxylate To a mixture of Example 1d (29 g, 64.0 mmol) and sodium iodide (14.38 g, 96 mmol) in acetonitrile (400 mL), chlorotrimethylsilane (10.43 g, 96 mmol) was added dropwise at ambient temperature. The resulting mixture was stirred at ambient temperature for 1 hour. Water (0.576 g, 32.0 mmol) was added dropwise to the reaction mixture and the mixture was stirred at 65° C. for 3 hours. The reaction mixture was cooled to ambient temperature and filtered. The precipitate was dissolved in dichloromethane, filtered, and concentrated to provide a solid which was triturated with petroleum ether and dichloromethane to provide the title compound (32 g, 97%).

Example 1f ethyl 4-bromo-6-methyl-7-oxo-1-tosyl-6,7-dihydro-1H-pyrrolo[2,3-c]pyridine-2-carboxylate To a solution of Example $R^1$ (18.72 g, 42.6 mmol) in anhydrous dimethylformamide (200 mL) was added cesium carbonate (16.66 g, 51.1 mmol), followed by the dropwise addition of iodomethane (3.20 mL, 51.1 mmol). The reaction mixture was stirred for 72 hours at ambient temperature. Water was added to the reaction mixture (500 mL) and the precipitate was filtered off, washed with water, and dried overnight in a vacuum oven at 55° C. to provide 17.9 g (93%) of the title compound.

Method B for the Preparation of ethyl 4-bromo-6-methyl-7-oxo-1-tosyl-6,7-dihydro-1H-pyrrolo[2,3-c]pyridine-2-carboxylate

Example 1f-i

N-(2,2-dimethoxyethyl)-N-methyl-1H-pyrrole-2-carboxamide

A solution of 1H-pyrrole-2-carboxylic acid (50.0 g, 450 mmol) in 500 mL of tetrahydrofuran was cooled to −5 to −8° C., followed by the addition of 2,2-dimethoxy-N-methylethanamine (64.4 g, 540 mmol) and diisopropylethylamine (171 mL, 128 mmol). The reaction mixture was stirred at this temperature, while propylphosphonic anhydride (315 g, 495 mmol) was added dropwise over 20 minutes. After the addition, the reaction mixture was warmed to 23° C. over 15 minutes. The reaction mixture was stirred for 1 hour at ambient temperature, and then heated to 40° C. After 18 hours at 40° C., the reaction mixture was cooled in an ice bath and diluted with 1000 mL of water and 500 mL of ethyl acetate. The organic layer was separated. The aqueous layer was back extracted three times with 250 mL of ethyl acetate. The combined ethyl acetate layers were washed with 250 mL of water and 250 mL of brine. The resulting organic layer was reduced under house high vacuum with a jacket temperature of 30-40° C. After the volume was reduced by 50% to 850 mL, an additional 850 mL of heptane was added and the distillation continued under house high vacuum with a jacket temperature of 30-40° C. Heptane (550 mL) was distilled off and the reaction mixture was cooled to 15° C. The product began to precipitate and then 500 mL of heptane was added to generate a slurry, which was heated to 30-40° C. to remove all the solids that adhered to the vessel wall. The slurry was cooled to 25° C. An additional 500 mL of heptane was added to thin out the slurry. The slurry was cooled in an ice bath and filtered at 0° C. The solid was quickly washed with heptane, and then dried in the vacuum oven at 40° C. overnight to give the title compound (63.6 g, 70.1% yield) as a fluffy, white solid.

Example 1f-ii 6-methyl-1H-pyrrolo[2,3-c]pyridin-7(6H)-one

To Example 1f-i (50 g, 236 mmol) in 500 mL of tetrahydrofuran, was added p-toluenesulfonic acid monohydrate (8.96 g, 47.1 mmol) and the reaction mixture was stirred at 60° C. for 5 hours. After this time, the reaction mixture was stirred for 12 hours, and allowed to cool to 23° C. During this time, the product began to precipitate from the reaction mixture. A solution of sodium bicarbonate (0.2 N, 500 mL) was added, and the reaction mixture was extracted with 250 mL of ethyl acetate. The organic layer was separated, and the aqueous layer was back-extracted three times with 188 mL of ethyl acetate. The combined organic layers were washed with brine (188 mL). The resulting organic layer was dried with anhydrous magnesium sulfate, filtered through a 0.45 micron filter, and the organic layer was reduced to 850 mL under vacuum with a jacket temperature of 40° C. After this time, 500 mL of heptane was added slowly over 10 minutes at 25° C. A slurry formed, which was cooled to 10° C. and stirred at this temperature for 14 hours. The resulting solid was filtered, washed with heptane, and dried in the vacuum oven at 50° C. to yield the title compound (27.9 g, 80% yield) as a tan solid.

Example 1f-iii 6-methyl-1-tosyl-1H-pyrrolo[2,3-c]pyridin-7(6H)-one

A jacketed 3000 mL round bottom flask was flushed with nitrogen and charged with Example 1f-ii (121 g, 817 mmol). Tetrahydrofuran (1200 mL) was added and the reaction mixture was cooled to −8° C. A tetrahydrofuran solution of lithium bis(trimethylsilyl)amide (1M, 1022 mL, 1022 mmol) was added to the resulting suspension at a rate that maintained an internal reaction temperature below 10° C. The solution was cooled to −8° C. and stirred for 1 hour. After this time, p-toluenesulfonyl chloride (238 g, 1225 mmol) was added in several portions. Once the internal temperature of the reaction mixture was stabilized, the contents of the flask were allowed to warm to 20° C., at which point the product began to precipitate. The reaction mixture was stirred for 2 hours, and held for an additional 14 hour. After this time, heptane (600 mL) was added and the reaction mixture was distilled to a total volume of approximately 1200 mL. The solution was cooled to 0° C., and the precipitated solid was filtered in a 2 L filter funnel with a medium-pore frit. The collected solid was then slurried in 1200 mL of water and re-filtered. Additional slurry was generated using the solid and 1200 mL of methanol. After stirring the slurry for 15 minutes the solid was filtered and dried at 35° C. to give the title compound (215 g, 86% yield) as an off-white solid.

Example 1f-iv ethyl 6-methyl-7-oxo-1-tosyl-6,7-dihydro-1H-pyrrolo[2,3-c]pyridine-2-carboxylate To a 500 mL three-neck round bottom flask was added Example 1f-iii (10.0 g, 33.1 mmol). The flask was fit with a thermocouple and purged with nitrogen. After 30 minutes the flask was sealed with septa, and a nitrogen inlet. The solid was then suspended in 70 mL of tetrahydrofuran. The off-white suspension was stirred and cooled to −15° C. After holding at this temperature for 2 minutes, n-butyllithium in hexanes (2.5 M, 13.0 ml, 32.5 mmol) was added at a rate to maintain the temperature at +/−5° C., which gave a light brown suspension. After addition, the reaction mixture was stirred for 5 minutes, and then cooled to −55° C. After holding at this temperature for 1 minute, ethyl carbonochloridate (4.6 ml, 50.7 mmol) was added at a rate to maintain the temperature +/−10° C. After complete addition, the reaction mixture was stirred for 5 minutes and then the cold bath was removed. The reaction mixture was stirred for an additional 180 minutes or until the reaction mixture warmed to 20° C. After this time, the reaction mixture was quenched with 50 mL of water and added to a separatory funnel with about 100 mL of additional water. Ethyl acetate was then added (200 mL) and the layers were separated. The aqueous layer was then extracted 2×100 mL with ethyl acetate. After removal of the ethyl acetate, the crude dark brown solid was slurried in 100 mL of acetonitrile, which produced a tan precipitate. The solid was collected, washed with 20 mL of acetonitrile, and dried. The acetonitrile filtrate was distilled until precipitation began once again. The tan solid was collected by filtration, washed with acetonitrile (1×20 mL), and dried. The collected solids were combined to give the title compound (6.94 g, 57% yield) as a tan solid.

Example 1f ethyl 4-bromo-6-methyl-7-oxo-1-tosyl-6,7-dihydro-1H-pyrrolo[2,3-c]pyridine-2-carboxylate A 250 mL round-bottom flask was charged with a stir bar and Example 1f-iv (3.00 g, 8.02 mmol). To the flask was added 100 mL of tetrahydrofuran, and the reaction mixture was stirred until complete dissolution (about 1 minute). To the stirring reaction mixture was added p-toluenesulfonic acid hydrate (0.763 g, 4.01 mmol), followed by N-bromosuccinimide (1.455 g, 8.17 mmol). The reaction mixture was stirred at 23° C. for 12.5 hours. After this time, the tetrahydrofuran was removed on a rotary evaporator, leaving a yellow residue. The residue was suspended in 200 proof ethanol (75 mL), and stirred as a slurry for 80 minutes. The slurry was filtered and washed with ethanol (200 proof, 1×50 mL), to provide the title compound (3.06 g, 84% yield) as an off-white solid.

Example 1g 4-bromo-N-ethyl-6-methyl-7-oxo-6,7-dihydro-1H-pyrrolo[2,3-c]pyridine-2-carboxamide To a solution of Example 1f (10 g, 22.06 mmol) and 2 M ethanamine in tetrahydrofuran (90 mL, 180 mmol) at 20° C.

was added 8% wt % magnesium methanolate (88 mL, 66.7 mmol) in methanol. The reaction mixture was heated at 55° C. for 15 hours with the system sealed. Then the mixture was cooled to ambient temperature and diluted with 0.5 N HCl (800 mL), stirred for 5 minutes, and filtered. The solid was washed with ice water and dried to provide 6.8 g (98%) of the title compound.

Example 1h

N-ethyl-6-methyl-7-oxo-4-(4,4,5,5-tetramethyl-1,3,2-dioxaborolan-2-yl)-6,7-dihydro-1H-pyrrolo[2,3-c]pyridine-2-carboxamide A 1 L three-necked round bottom flask was charged with dried potassium acetate (17.18 g, 175 mmol), Example 1g (17.4 g, 58.4 mmol), 4,4,4',4',5,5,5',5'-octamethyl-2,2'-bi(1,3,2-dioxaborolane) (29.6 g, 117 mmol), chloro(2-dicyclohexylphosphino-2',4',6'-triisopropyl-1,1'-biphenyl)[2-(2'-amino-1,1'-biphenyl)]palladium(II) (1.837 g, 2.335 mmol), and 2-dicyclohexylphosphino-2',4',6'-triisopropylbiphenyl (1.113 g, 2.335 mmol), and placed under nitrogen. Degassed anhydrous 2-methyl tetrahydrofuran (500 mL) was added and the mixture was heated at 75° C. overnight. The mixture was cooled to ambient temperature, diluted with water and ethyl acetate and the biphasic mixture was stirred for about one hour with 1.2 g. (3.0 equiv. based on moles of palladium) of ammonium pyrrolidine dithiocarbamate. The mixture was filtered through a plug of Diatomaceous earth with ethyl acetate and 10% methanol/ethyl acetate washes. The filtrate was diluted further with ethyl acetate and brine, the layers separated, and the organic layer washed with water and brine, dried with anhydrous sodium sulfate, filtered, and concentrated. The crude product was triturated with 300 mL of 20% ethyl acetate/heptane. The dried solids provided 17.4 g (86%) of the title compound.

Example 1i 5-bromo-6-(2,6-dimethylphenoxy)nicotinic acid

A solution of 5-bromo-6-chloronicotinic acid (12 g, 50.8 mmol), 2,6-dimethylphenol (7.44 g, 60.9 mmol) and cesium carbonate (49.6 g, 152 mmol) in dimethyl sulfoxide (100 mL) was heated at 100° C. for 40 hours, cooled to ambient temperature, and poured into 500 mL of ice water. The pH was adjusted to a constant pH of 2 by careful addition of 12 M HCl. The aqueous mixture was extracted with ethyl acetate (3×200 mL). The combined organics were washed twice with saturated aqueous sodium chloride, dried over anhydrous magnesium sulfate, treated with decolorizing charcoal, filtered, and concentrated. The crude material was adsorbed on silica gel and chromatographed on a 330 g silica cartridge, eluting with 10-70% 3:1 ethyl acetate/ethanol: heptanes to provide 10.74 g (66%) of the title compound.

Example 1j 5-bromo-6-(2,6-dimethylphenoxy)-N-methoxy-N-methylnicotinamide

A solution of Example 1i (8.5 g, 26.4 mmol), $N^1$-((ethylimino)methylene)-$N^3$,$N^3$-dimethylpropane-1,3-diamine hydrochloride (6.05 g, 31.6 mmol), 1H-benzo[d][1,2,3]triazol-1-ol hydrate (5.12 g, 33.4 mmol), N,O-dimethylhydroxylamine hydrochloride (5.21 g, 53.4 mmol) and 4-methylmorpholine (10 mL, 91 mmol) in dichloromethane (130 mL) was stirred at 25° C. for 3 hours. The mixture was washed into a separatory funnel with 50 mL of dichloromethane, extracted with water, washed with aqueous sodium bicarbonate, and dried over anhydrous sodium sulfate, filtered, and concentrated. The residue was purified by chromatography (silica gel, 0-50% ethyl acetate in heptane) to provide the title compound (8.56 g, 89%).

Example 1k 1-(5-bromo-6-(2,6-dimethylphenoxy)pyridin-3-yl)ethanone

A solution of Example 1j (1.51 g, 4.13 mmol) in tetrahydrofuran (30 mL) was treated with a solution of methylmagnesium chloride (3.0 M solution in tetrahydrofuran, 1.8 mL, 5.40 mmol) and stirred at 25° C. for 90 minutes. The solution was poured into aqueous ammonium chloride and extracted into ethyl acetate (100 mL), dried over anhydrous sodium sulfate, filtered, and concentrated. The residue was purified by chromatography (silica gel, 0-100% ethyl acetate in heptane) to provide 0.875 g (66%) of the title compound.

Example 1l 2-(5-bromo-6-(2,6-dimethylphenoxy)pyridin-3-yl)propan-2-ol

A solution of Example 1k (0.239 g, 0.746 mmol) in tetrahydrofuran (5 mL) was treated with a solution of methylmagnesium chloride (3.0 M solution in tetrahydrofuran, 0.4 mL, 1.2 mmol) and stirred at 25° C. for 3.5 hours. The solution was poured into aqueous ammonium chloride and extracted into ethyl acetate (60 mL), dried over anhydrous sodium sulfate, filtered, and concentrated. The residue was purified by chromatography (silica gel, 0-100% ethyl acetate in heptane) to provide 0.195 g (78%) of the title compound.

Example 1m 4-(2-(2,6-dimethylphenoxy)-5-(2-hydroxypropan-2-yl)pyridin-3-yl)-N-ethyl-6-methyl-7-oxo-6,7-dihydro-1H-pyrrolo[2,3-c]pyridine-2-carboxamide Example 1h (222 mg, 0.643 mmol), Example 1l (195 mg, 0.580 mmol), potassium phosphate (363 mg, 1.710 mmol), tris(dibenzylideneacetone)dipalladium(0) (16.7 mg, 0.018 mmol) and 1,3,5,7-tetramethyl-6-phenyl-2,4,8-trioxa-6-phosphaadamantane (18.3 mg, 0.063 mmol) were combined and sparged with nitrogen for 15 minutes, followed by addition of a degassed mixture of tetrahydrofuran (4.80 mL)/water (1.20 mL). The mixture was heated at 60° C. for 3 hours. The mixture was diluted with 20 mL of ethyl acetate, washed with saturated aqueous sodium chloride, dried with anhydrous sodium sulfate, filtered and evaporated. The residues were purified by reverse phase HPLC (C18, $CH_3CN$/water (0.1% trifluoroacetic acid), 0-100% gradient) to provide the title compound as a trifluoroacetic acid salt. $^1$H NMR (400 MHz, DMSO-$d_6$) δ 12.31 (bs, 1H), 8.35 (t, J=5.3 Hz, 1H), 8.10 (d, J=2.4 Hz, 1H), 7.95 (d, J=2.4 Hz, 1H), 7.45 (s, 1H), 7.06 (m, 1H), 7.01 (m, 1H), 6.88 (d, J=2.1 Hz, 1H), 3.61 (s, 3H), 3.28 (m, 2H), 1.99 (s, 6H), 1.48 (s, 6H), 1.12 (t, J=7.2 Hz, 3H). MS (ESI+) m/z 475.2 $(M+H)^+$.

Example 2

4-[2-(2,6-dimethylphenoxy)-5-(3-hydroxypentan-3-yl)pyridin-3-yl]-N-ethyl-6-methyl-7-oxo-6,7-dihydro-1H-pyrrolo[2,3-c]pyridine-2-carboxamide The trifluoroacetic acid salt of Example 2 was prepared according to the procedure used for the preparation of Example 7, substituting ethyl magnesium bromide for phenyl magnesium bromide. $^1$H NMR (400 MHz, DMSO-d$_6$) δ 7.97 (d, J=2.4 Hz, 1H), 7.83 (d, J=2.4 Hz, 1H), 7.42 (s, 1H), 7.07 (d, J=1.9 Hz, 1H), 7.03-6.99 (m, 1H), 6.91 (s, 1H), 3.61 (s, 3H), 3.28 (t, J=7.2 Hz, 2H), 1.96 (s, 6H), 1.76 (dh, J=13.8, 7.1 Hz, 4H), 1.12 (t, J=7.2 Hz, 3H), 0.71 (t, J=7.3 Hz, 6H). MS (ESI+) m/z 503 (M+H)$^+$.

Example 3

4-[2-(2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide

Example 3a

3-bromo-4-(2,6-dimethylphenoxy)benzoic acid

A mixture of methyl 3-bromo-4-fluorobenzoate (10.80 g, 46.3 mmol), 2,6-dimethylphenol (6.24 g, 51.1 mmol) and cesium carbonate (16.6 g, 50.9 mmol) in dimethyl sulfoxide (95 mL) was heated at 190° C. for 20 hours. The mixture was allowed to cool, then poured into 400 mL of brine, acidified with HCl and extracted with 500 mL of ethyl acetate. The organic extracts were washed with brine and dried over anhydrous magnesium sulfate. After filtration the crude material was adsorbed on silica gel and chromatographed on a 220 g silica cartridge eluting with 10-70% 3:1 ethyl acetate/ethanol:heptanes to provide 13.54 g (91%) of the title compound.

Example 3b

3-bromo-4-(2,6-dimethylphenoxy)-N-methoxy-N-methylbenzamide

Example 3b was prepared according to the procedure used for the preparation of Example 1j, substituting Example 3a for Example 1i.

Example 3c

1-(3-bromo-4-(2,6-dimethylphenoxy)phenyl)ethanone

Method A
To a mixture of Example 3b (1.19 g, 3.27 mmol) in tetrahydrofuran (24 mL) was added by syringe methylmagnesium chloride (3.0 M solution in tetrahydrofuran, 1.4 mL, 4.20 mmol) and the mixture was stirred at ambient temperature. After 90 minutes, the solution was poured into saturated aqueous ammonium chloride and extracted into ethyl acetate (100 mL). The organics were dried over anhydrous sodium sulfate, filtered, and concentrated under reduced pressure. The residue was purified by flash chromatography (silica gel, 0-100% ethyl acetate/heptane) to provide the title compound (0.631 g, 61% yield).
Method B:
A mixture of potassium carbonate (4.78 g, 34.6 mmol) 2,6-dimethylphenol (2.96 g, 24.19 mmol) 1-(3-bromo-4-fluorophenyl)ethanone (5 g, 23.04 mmol) in dimethylacetamide (50 mL) was stirred at 80° C. for 1.5 hours. After cooling to ambient temperature, water (40 mL) was added. The mixture was extracted with ethyl acetate, and the combined organic phase was washed with water, brine, and concentrated to provide the title compound (7.1 g, 22.24 mmol, 97% yield).

Example 3d

2-(3-bromo-4-(2,6-dimethylphenoxy)phenyl)propan-2-ol

Method A:
To a solution of Example 3c (0.365 g, 1.144 mmol) in tetrahydrofuran (10.00 mL) was added by syringe methylmagnesium chloride (3.0 M solution in tetrahydrofuran, 1 mL, 3.00 mmol), and the mixture was stirred at ambient temperature. After 3.5 hours, the solution was partitioned between saturated aqueous ammonium chloride (50 mL) and ethyl acetate (75 mL). The organics were dried over anhydrous sodium sulfate, filtered, and concentrated under reduced pressure. The residue was purified by flash chromatography (silica gel, 0-100% ethyl acetate/heptane) to provide the title compound (0.247 g, 64% yield).
Method B:
To a solution of 2,6-dimethylphenol (11.53 g, 94 mmol) and methyl 3-bromo-4-fluorobenzoate (20 g, 86 mmol) in dimethyl sulfoxide (80 mL) was added cesium carbonate (41.9 g, 129 mmol). The mixture was stirred at 80° C. under nitrogen for 2 hours, cooled, diluted with 200 mL of water, and stirred for 10 minutes. The mixture was transferred to a separatory funnel and extracted 4×200 mL with methyl tert-butyl ether. The organic extracts were combined, dried over anhydrous sodium sulfate, filtered and concentrated. Purification by chromatography (silica, 0-10% ethyl acetate in heptanes) provided methyl 3-bromo-4-(2,6-dimethylphenoxy)benzoate as an oil that solidified upon standing (25.7 g, 82%). To a solution of this material (11.08 g, 33.1 mmol) in tetrahydrofuran (165 mL) under nitrogen at 23° C. was added methylmagnesium bromide (33.1 mL, 99 mmol, 3.0 M in diethyl ether) in a drop wise manner. The reaction was exothermic. The reaction mixture was stirred for 1 hour allowing the internal temperature to cool to about ambient temperature. The mixture was poured into cold 5% aqueous ammonium chloride and partitioned with 400 mL diethyl ether. The organic layer was washed with saturated aqueous sodium chloride, dried over anhydrous sodium sulfate, filtered, and concentrated. Purification by chromatography (silica, 0-25% ethyl acetate in heptanes) afforded the title compound (9.0 g, 81%).

Example 3e

4-(2-(2,6-dimethylphenoxy)-5-(2-hydroxypropan-2-yl)phenyl)-N-ethyl-6-methyl-7-oxo-6,7-dihydro-1H-pyrrolo[2,3-c]pyridine-2-carboxamide Example 3e was prepared according to the procedure used for the preparation of Example 1m, substituting Example 3d for Example 1l. $^1$H NMR (400 MHz, DMSO-d$_6$) δ 12.21 (bds, 1H), 8.34 (t, J=5.4 Hz, 1H), 7.52 (d, J=2.4 Hz, 1H), 7.34 (s, 1H), 7.31 (dd, J=8.6, 2.4 Hz, 1H), 7.12 (d, J=7.2 Hz, 1H), 7.04 (m, 1H), 6.86 (d, J=2.1 Hz, 1H), 6.28 (d, J=8.6 Hz, 1H), 3.60 (s, 3H), 3.28 (m 2H), 2.02 (s, 6H), 1.44 (s, 6H), 1.12 (t, J=7.2 Hz, 3H). MS (ESI+) m/z 474.2 (M+H)$^+$.

Example 4

4-[2-(2,6-dimethylphenoxy)-5-(1-hydroxycyclopent-3-en-1-yl)pyridin-3-yl]-N-ethyl-6-methyl-7-oxo-6,7-dihydro-1H-pyrrolo[2,3-c]pyridine-2-carboxamide

Example 4a 1-(5-bromo-6-(2,6-dimethylphenoxy)pyridin-3-yl)but-3-en-1-one

Example 4a was prepared according to the procedure used for the preparation of Example 1k, substituting allylmagnesium chloride for methylmagnesium chloride.

Example 4b 4-(5-bromo-6-(2,6-dimethylphenoxy)pyridin-3-yl)hepta-1,6-dien-4-ol Example 4b was prepared according to the procedure used for the preparation of Example 1l, substituting Example 4a for Example 1k, and substituting allylmagnesium chloride for methylmagnesium chloride.

Example 4c 1-(5-bromo-6-(2,6-dimethylphenoxy)pyridin-3-yl)cyclopent-3-enol

A flask with stir bar was charged with (1,3-bis(2,4,6-trimethylphenyl)-2-imidazolidinylidene)dichloro(phenylmethylene)(tricyclohexylphosphine)-ruthenium (21.5 mg, 0.025 mmol), sealed with a septum and swept with nitrogen. A solution of Example 4b (176 mg, 0.453 mmol) in degassed 1,2-dichloroethane (4.5 mL) was added to the reaction vessel. The solution was stirred at ambient temperature for 3 hours, concentrated, and the residue was taken up in 4 mL dichloromethane, filtered through a syringe filter, and chromatographed (silica gel, 0-100% ethyl acetate/heptanes) to provide 0.138 g (85%) of the title compound.

Example 4d 4-(2-(2,6-dimethylphenoxy)-5-(1-hydroxycyclopent-3-en-1-yl)pyridin-3-yl)-N-ethyl-6-methyl-7-oxo-6,7-dihydro-1H-pyrrolo[2,3-c]pyridine-2-carboxamide The trifluoroacetic acid salt of Example 4d was prepared according to the procedure used for the preparation of Example 1m, substituting Example 4c for Example 1l. $^1$H NMR (400 MHz, DMSO-$d_6$) δ 12.31 (d, J=2.4 Hz, 1H), 8.34 (t, J=5.3 Hz, 1H), 8.09 (d, J=2.5 Hz, 1H), 7.89 (d, J=2.3 Hz, 1H), 7.46 (s, 1H), 7.06 (m, 2H), 7.00 (dd, J=8.6, 6.0 Hz, 1H), 6.89 (d, J=2.2 Hz, 1H), 5.75 (s, 1H), 3.61 (s, 3H), 3.27 (m, 2H), 2.86-2.61 (m, 4H), 1.99 (s, 6H), 1.12 (t, J=7.2 Hz, 3H). MS (ESI+) m/z 499.2 (M+H)$^+$.

Example 5

4-[2-(2,6-dimethylphenoxy)-5-(1-hydroxycyclopent-3-en-1-yl)phenyl]-N-ethyl-6-methyl-7-oxo-6,7-dihydro-1H-pyrrolo[2,3-c]pyridine-2-carboxamide

Example 5a 1-(5-bromo-6-(2,6-dimethylphenoxy)pyridin-3-yl)but-3-en-1-one

Example 5a was prepared according to Method A of Example 3c, substituting allylmagnesium chloride for methylmagnesium chloride.

Example 5b 4-(3-bromo-4-(2,6-dimethylphenoxy)phenyl)hepta-1,6-dien-4-ol

Example 5b was prepared according to Method A of Example 3d, substituting Example 5a for Example 3c, and substituting allylmagnesium chloride for methylmagnesium chloride.

Example 5c 1-(5-bromo-6-(2,6-dimethylphenoxy)pyridin-3-yl)cyclopent-3-enol

Example 5c was prepared according to the procedure used for the preparation of Example 4c, substituting Example 5b for Example 4b.

Example 5d 4-(2-(2,6-dimethylphenoxy)-5-(1-hydroxycyclopent-3-en-1-yl)phenyl)-N-ethyl-6-methyl-7-oxo-6,7-dihydro-1H-pyrrolo[2,3-c]pyridine-2-carboxamide Example 5d was prepared according to the procedure used for the preparation of Example 1m, substituting Example 5c for Example 1l. $^1$H NMR (400 MHz, DMSO-$d_6$) δ 12.22 (bs, 1H), 8.34 (m, 1H), 7.48 (m, 1H), 7.35 (s, 1H), 7.28 (dd, J=8.5, 2.3 Hz, 1H), 7.18-6.97 (m, 2H), 6.88 (m, 1H), 6.31 (d, J=8.6 Hz, 1H), 5.73 (s, 2H), 3.60 (s, 3H), 3.26 (m, 2H), 2.75 (d, J=16.2 Hz, 2H), 2.56 (d, J=16.2 Hz, 2H), 2.03 (s, 6H), 1.12 (td, J=7.3, 1.9 Hz, 3H). MS (ESI+) m/z 498.1 (M+H)$^+$.

Example 6

4-[2-(2,6-dimethylphenoxy)-5-(1-hydroxycyclopentyl)pyridin-3-yl]-N-ethyl-6-methyl-7-oxo-6,7-dihydro-1H-pyrrolo[2,3-c]pyridine-2-carboxamide Example 4d (48 mg, 0.096 mmol) and tetrahydrofuran (10 mL) were added to 5% Pd/C (wet JM#9) (9 mg, 0.038 mmol) in a 50 mL pressure bottle and shaken for 30 minutes at 30 psi of hydrogen, and at ambient temperature. The mixture was filtered, and concentrated. The residues were purified by reverse phase HPLC (C18, CH$_3$CN/water (0.1% trifluoroacetic acid), 0-100% gradient) to provide the title compound as a trifluoroacetic acid salt. $^1$H NMR (400 MHz, DMSO-$d_6$) δ 12.31 (d, J=2.4 Hz, 1H), 8.34 (t, J=5.4 Hz, 1H), 8.11 (d, J=2.4 Hz, 1H), 7.92 (d, J=2.4 Hz, 1H), 7.45 (s, 1H), 7.11-6.93 (m, 2H), 6.88 (d, J=2.1 Hz, 1H), 3.61 (s, 3H), 3.27

(m, 2H), 1.99 (s, 6H), 1.97-1.68 (m, 8H), 1.12 (t, J=7.2 Hz, 3H). MS (ESI) m/z 501.2 (M+H)+.

Example 7

4-[2-(2,6-dimethylphenoxy)-5-(1-hydroxy-1-phenyl-propyl)pyridin-3-yl]-N-ethyl-6-methyl-7-oxo-6,7-dihydro-1H-pyrrolo[2,3-c]pyridine-2-carboxamide A 4 mL vial was charged with Example 1j (75 mg, 0.20 mmol) in tetrahydrofuran (1.5 mL) and treated with phenyl magnesium bromide, 1.0 M solution in tetrahydrofuran (0.3 mL, 0.3 mmol) and the mixture stirred at ambient temperature for 3 hours. After 3 hours, aqueous ammonium chloride was added and the intermediate ketone was extracted with dichloromethane using a phase separator. The organic layer was concentrated. The resulting residue was dissolved in tetrahydrofuran (1.5 mL) and treated with ethyl magnesium bromide (3.0 M solution in tetrahydrofuran, 0.1 mL, 0.32 mmol) and allowed to stir at ambient temperature for 3 hours. After 3 hours, aqueous ammonium chloride was added to the reaction mixture and the intermediate tertiary alcohol was extracted with dichloromethane using a phase separator. After filtration and solvent removal, the crude material was combined with Example 1h (9 mg, 0.027 mmol), potassium phosphate (20 mg, 0.027 mmol), tris(dibenzylideneacetone)dipalladium(0) (0.75 mg, 0.82 µmol) and 1,3,5,7-tetramethyl-6-phenyl-2,4,8-trioxa-6-phosphoadamantane (0.70 mg, 0.0025 mmol). The mixture was purged with nitrogen for 15 minutes and dissolved in a degassed mixture of 0.5 mL tetrahydrofuran and 0.1 mL of water. This mixture was heated at 60° C. for 3 hours, filtered through diatomaceous earth, and concentrated under reduced pressure. The residue was dissolved in 1:1 dimethyl sulfoxide/methanol and purified by reverse phase HPLC HPLC on a Phenomenex Luna C8(2) 5 µm 100 Å AXIA column (30 mm×150 mm) with a gradient of acetonitrile (A) and 0.1% trifluoroacetic acid in water (B), at a flow rate of 50 mL/min (0-0.5 min 5% A, 0.5-8.5 min linear gradient 5-100% A, 8.7-10.7 min 100% A, 10.7-11.0 min linear gradient 100-5% A) to provide the title compound as a trifluoroacetic acid salt (3.8 mg, 21% yield). $^1$H NMR (400 MHz, DMSO-d$_6$) δ 8.06 (d, J=2.5 Hz, 1H), 7.85 (d, J=2.4 Hz, 1H), 7.50-7.43 (m, 2H), 7.39 (s, 1H), 7.31 (dd, J=8.4, 7.1 Hz, 2H), 7.22-7.17 (m, 1H), 7.06 (s, 1H), 7.04-6.99 (m, 2H), 6.81 (s, 1H), 3.59 (s, 3H), 3.28 (t, J=7.2 Hz, 2H), 2.28 (q, J=7.3 Hz, 2H), 1.94 (s, 6H), 1.12 (t, J=7.2 Hz, 3H), 0.78 (t, J=7.2 Hz, 3H). MS (ESI+) m/z 551 (M+H)+.

Example 8

4-[2-(2,6-dimethylphenoxy)-5-(2-hydroxybutan-2-yl)pyridin-3-yl]-N-ethyl-6-methyl-7-oxo-6,7-dihydro-1H-pyrrolo[2,3-c]pyridine-2-carboxamide The trifluoroacetic acid salt of Example 8 was prepared according to the procedure used for the preparation of Example 7, substituting methyl magnesium bromide for phenyl magnesium bromide. $^1$H NMR (500 MHz, DMSO-d$_6$) δ 8.05 (d, J=2.4 Hz, 1H), 7.91 (s, 1H), 7.08 (d, J=7.4 Hz, 2H), 7.03 (dd, J=8.4, 6.3 Hz, 1H), 3.64 (s, 3H), 3.30 (q, J=7.2 Hz, 2H), 2.00 (s, 6H), 1.75 (dt, J=8.9, 6.7 Hz, 2H), 1.48 (s, 3H), 1.13 (d, J=7.2 Hz, 3H), 0.76 (t, J=7.3 Hz, 3H). MS (ESI) m/z 489 (M+H)+.

Example 9

4-{2-(2,6-dimethylphenoxy)-5-[1-(4-fluorophenyl)-1-hydroxypropyl]pyridin-3-yl}-N-ethyl-6-methyl-7-oxo-6,7-dihydro-1H-pyrrolo[2,3-c]pyridine-2-carboxamide The trifluoroacetic acid salt of Example 9 was prepared according to the procedure used for the preparation of Example 7, substituting 4-fluorophenyl magnesium bromide for phenyl magnesium bromide. $^1$H NMR (400 MHz, DMSO-d$_6$) δ 8.07 (d, J=2.5 Hz, 1H), 7.85 (d, J=2.4 Hz, 1H), 7.51 (dd, J=8.9, 5.5 Hz, 2H), 7.41 (s, 1H), 7.13 (t, J=8.9 Hz, 2H), 7.05 (s, 1H), 7.03 (s, 1H), 6.81 (s, 1H), 3.60 (s, 3H), 3.28 (q, J=7.2 Hz, 2H), 2.28 (d, J=7.4 Hz, 2H), 1.96 (s, 6H), 1.13 (t, J=7.2 Hz, 3H), 0.78 (t, J=7.1 Hz, 3H). MS (ESI+) m/z 569 (M+H)+.

Example 10

4-[2-(2,6-dimethylphenoxy)-5-(3-hydroxy-5-methyl-hexan-3-yl)pyridin-3-yl]-N-ethyl-6-methyl-7-oxo-6,7-dihydro-1H-pyrrolo[2,3-c]pyridine-2-carboxamide The trifluoroacetic acid salt of Example 10 was prepared according to the procedure used for the preparation of Example 7, substituting 2-methyl-1-propyl magnesium bromide for phenyl magnesium bromide. $^1$H NMR (400 MHz, DMSO-d$_6$) δ 7.98 (d, J=2.4 Hz, 1H), 7.84 (d, J=2.4 Hz, 1H), 7.39 (s, 1H), 7.10-6.98 (m, 3H), 6.86 (s, 1H), 3.61 (s, 3H), 3.27 (q, J=7.3 Hz, 2H), 1.96 (s, 6H), 1.75 (ddd, J=25.4, 14.0, 6.6 Hz, 3H), 1.68-1.50 (m, 2H), 1.12 (t, J=7.2 Hz, 3H), 0.85 (d, J=6.5 Hz, 3H), 0.68 (t, J=7.3 Hz, 3H), 0.62 (d, J=6.5 Hz, 3H). MS (ESI+) m/z 531 (M+H)+.

Example 11

4-[5-(1-cyclopentyl-1-hydroxypropyl)-2-(2,6-dimethylphenoxy)pyridin-3-yl]-N-ethyl-6-methyl-7-oxo-6,7-dihydro-1H-pyrrolo[2,3-c]pyridine-2-carboxamide The trifluoroacetic acid salt of Example 11 was prepared according to the procedure used for the preparation of Example 7, substituting cyclopentyl magnesium bromide for phenyl magnesium bromide. $^1$H NMR (400 MHz, DMSO-d$_6$) δ 8.00 (d, J=2.3 Hz, 1H), 7.86 (d, J=2.4 Hz, 1H), 7.42 (s, 1H), 7.07 (d, J=7.2 Hz, 2H), 7.04-6.97 (m, 1H), 6.88 (s, 1H), 3.62 (s, 3H), 3.28 (q, J=7.2 Hz, 2H), 2.40-2.27 (m, 1H), 1.97 (s, 6H), 1.80 (dd, J=11.5, 7.1 Hz, 1H), 1.65 (m, 1H), 1.47 (d, J=33.2 Hz, 3H), 1.27-1.20 (m, 1H), 1.13 (t, J=7.2 Hz, 3H), 0.66 (t, J=7.3 Hz, 3H). MS (ESI+) m/z 543 (M+H)+.

Example 12

4-[5-(1-cyclopropyl-1-hydroxypropyl)-2-(2,6-dimethylphenoxy)pyridin-3-yl]-N-ethyl-6-methyl-7-oxo-6,7-dihydro-1H-pyrrolo[2,3-c]pyridine-2-carboxamide The trifluoroacetic acid salt of Example 12 was prepared according to the procedure used for the preparation of Example 7, substituting cyclopropyl magnesium bromide for phenyl magnesium bromide. $^1$H NMR (400 MHz, DMSO-d$_6$) δ 8.07 (d, J=2.4 Hz, 1H), 7.91 (d, J=2.4 Hz, 1H), 7.43 (s, 1H), 7.11-6.98 (m, 3H), 6.90 (s, 1H), 3.61 (s, 3H), 3.27 (q, J=7.2 Hz, 2H), 1.97 (s, 6H), 1.83 (dh, J=21.1, 7.3

Hz, 2H), 1.33-1.25 (m, 1H), 1.12 (t, J=7.2 Hz, 3H), 0.76 (q, J=7.4, 6.9 Hz, 3H), 0.43 (ddt, J=43.3, 9.1, 4.9 Hz, 2H), 0.31-0.21 (m, 2H). MS (ESI+) m/z 515 (M+H)$^+$.

Example 13

4-[2-(2,6-dimethylphenoxy)-5-(3-hydroxy-4-methyl hexan-3-yl)pyridin-3-yl]-N-ethyl-6-methyl-7-oxo-6, 7-dihydro-1H-pyrrolo[2,3-c]pyridine-2-carboxamide The trifluoroacetic acid salt of Example 13 was prepared according to the procedure used for the preparation of Example 7, substituting 2-butyl magnesium bromide for phenyl magnesium bromide. $^1$H NMR (400 MHz, DMSO-d$_6$) δ 7.96 (d, J=2.3 Hz, 1H), 7.85-7.81 (m, 1H), 7.42 (d, J=1.9 Hz, 1H), 7.07 (d, J=7.1 Hz, 2H), 7.04-6.98 (m, 1H), 6.88 (d, J=1.4 Hz, 1H), 3.62 (s, 3H), 3.28 (q, J=7.2 Hz, 2H), 1.97 (s, 6H), 1.88-1.74 (m, 1H), 1.65 (d, J=8.2 Hz, 1H), 1.35 (s, 1H), 1.13 (t, J=7.2 Hz, 3H), 0.90-0.82 (m, 3H), 0.79 (t, J=7.1 Hz, 2H), 0.68 (dd, J=14.7, 7.4 Hz, 3H). MS (ESI+) m/z 531 (M+H)$^+$.

Example 14

4-[2-(2,6-dimethylphenoxy)-5-(3-hydroxy-1-phenyl-pentan-3-yl)pyridin-3-yl]-N-ethyl-6-methyl-7-oxo-6, 7-dihydro-1H-pyrrolo[2,3-c]pyridine-2-carboxamide The trifluoroacetic acid salt of Example 14 was prepared according to the procedure used for the preparation of Example 7, substituting 2-phenylethyl magnesium bromide for phenyl magnesium bromide. $^1$H NMR (400 MHz, DMSO-d$_6$) δ 8.06 (s, 1H), 7.89 (s, 1H), 7.40 (s, 1H), 7.26-7.18 (m, 2H), 7.15-7.10 (m, 3H), 7.07 (d, J=1.8 Hz, 2H), 7.03-6.98 (m, 1H), 6.89 (s, 1H), 3.63 (s, 3H), 3.28 (q, J=7.3 Hz, 2H), 2.65 (dq, J=12.4, 7.6, 6.5 Hz, 1H), 2.36-2.25 (m, 1H), 2.11-2.02 (m, 1H), 1.97 (s, 6H), 1.81 (dt, J=13.6, 6.8 Hz, 2H), 1.11 (t, J=7.2 Hz, 3H), 0.73 (t, J=7.3 Hz, 3H). MS (ESI+) m/z 579 (M+H)$^+$.

Example 15

4-{2-(2,6-dimethylphenoxy)-5-[1-(4-fluorophenyl)-2-hydroxybutan-2-yl]pyridin-3-yl}-N-ethyl-6-methyl-7-oxo-6,7-dihydro-1H-pyrrolo[2,3-c]pyridine-2-carboxamide The trifluoroacetic acid salt of Example 15 was prepared according to the procedure used for the preparation of Example 7, substituting 4-fluorobenzyl magnesium bromide for phenyl magnesium bromide. $^1$H NMR (400 MHz, DMSO-d$_6$) δ 7.80 (d, J=2.4 Hz, 1H), 7.67 (d, J=2.4 Hz, 1H), 7.24 (s, 1H), 7.09-6.93 (m, 7H), 6.81 (s, 1H), 3.60 (s, 3H), 3.29 (t, J=7.2 Hz, 2H), 2.99 (q, J=13.5 Hz, 2H), 1.94 (s, 7H), 1.78 (dt, J=14.2, 7.2 Hz, 1H), 1.12 (t, J=7.2 Hz, 3H), 0.76 (t, J=7.3 Hz, 3H). MS (ESI+) m/z 514 (M+H)$^+$. MS (ESI+) 583 m/z (M+H)$^+$.

Example 16

4-[2-(2,6-dimethylphenoxy)-5-(1-hydroxy-1-phenyl-ethyl)pyridin-3-yl]-N-ethyl-6-methyl-7-oxo-6,7-dihydro-1H-pyrrolo[2,3-c]pyridine-2-carboxamide The trifluoroacetic acid salt of Example 16 was prepared according to the procedure used for the preparation of Example 7, substituting methyl magnesium bromide for ethyl magnesium bromide. $^1$H NMR (500 MHz, DMSO-d$_6$) δ 8.08 (s, 1H), 7.88 (d, J=2.4 Hz, 1H), 7.50 (d, J=7.5 Hz, 2H), 7.43 (s, 1H), 7.34 (t, J=7.6 Hz, 2H), 7.22 (t, J=7.3 Hz, 1H), 7.07 (d, J=7.3 Hz, 2H), 7.02 (dd, J=8.5, 6.1 Hz, 1H), 6.86 (s, 1H), 3.62 (s, 3H), 3.30 (q, J=7.3 Hz, 2H), 2.04 (s, 1H), 1.98 (s, 5H), 1.91 (s, 3H), 1.14 (t, J=7.2 Hz, 3H). MS (ESI+) m/z 536.9 (M+H)$^+$.

Example 17

4-{2-(2,6-dimethylphenoxy)-5-[1-(4-fluorophenyl)-1-hydroxyethyl]pyridin-3-yl}-N-ethyl-6-methyl-7-oxo-6,7-dihydro-1H-pyrrolo[2,3-c]pyridine-2-carboxamide The trifluoroacetic acid salt of Example 17 was prepared according to the procedure used for the preparation of Example 7, substituting 4-fluorophenyl magnesium bromide for phenyl magnesium bromide, and substituting methyl magnesium bromide for ethyl magnesium bromide. $^1$H NMR (500 MHz, DMSO-d$_6$) δ 8.07 (d, J=2.5 Hz, 1H), 7.87 (d, J=2.4 Hz, 1H), 7.55-7.50 (m, 2H), 7.44 (s, 1H), 7.14 (t, J=8.9 Hz, 2H), 7.07 (d, J=6.7 Hz, 2H), 7.02 (dd, J=8.5, 6.1 Hz, 1H), 6.85 (s, 1H), 3.62 (s, 3H), 3.30 (q, J=7.3 Hz, 2H), 2.04 (s, 1H), 1.98 (s, 5H), 1.90 (s, 3H), 1.14 (t, J=7.2 Hz, 3H). MS (ESI+) m/z 555.7 (M+H)$^+$.

Example 18

4-[2-(2,6-dimethylphenoxy)-5-(2-hydroxy-4-methyl-pentan-2-yl)pyridin-3-yl]-N-ethyl-6-methyl-7-oxo-6, 7-dihydro-1H-pyrrolo[2,3-c]pyridine-2-carboxamide The trifluoroacetic acid salt of Example 18 was prepared according to the procedure used for the preparation of Example 7, substituting 2-methyl1-propyl magnesium bromide for phenyl magnesium bromide, and substituting methyl magnesium bromide for ethyl magnesium bromide. $^1$H NMR (500 MHz, DMSO-d$_6$) δ 8.07 (d, J=2.4 Hz, 1H), 7.92 (d, J=2.5 Hz, 1H), 7.44 (s, 1H), 7.08 (d, J=7.4 Hz, 2H), 7.04-7.00 (m, 1H), 6.91 (s, 1H), 3.64 (s, 3H), 3.30 (q, J=7.2 Hz, 2H), 1.99 (s, 6H), 1.71-1.57 (m, 3H), 1.50 (s, 3H), 1.14 (t, J=7.2 Hz, 3H), 0.85 (d, J=6.4 Hz, 3H), 0.70 (d, J=6.6 Hz, 3H). MS (ESI+) m/z 517 (M+H)$^+$.

Example 19

4-[2-(2,6-dimethylphenoxy)-5-(2-hydroxy-3-methylbutan-2-yl)pyridin-3-yl]-N-ethyl-6-methyl-7-oxo-6,7-dihydro-1H-pyrrolo[2,3-c]pyridine-2-carboxamide The trifluoroacetic acid salt of Example 19 was prepared according to the procedure used for the preparation of Example 7, substituting isopropyl magnesium bromide for phenyl magnesium bromide, and substituting methyl magnesium bromide for ethyl magnesium bromide. $^1$H NMR (500 MHz, DMSO-d$_6$) δ 8.07 (d, J=2.5 Hz, 1H), 7.87 (d, J=2.4 Hz, 1H), 7.55-7.50 (m, 2H), δ 7.09 (d, J=7.4 Hz, 2H), 7.04-6.99 (m, 1H), 3.64 (s, 3H),), 6.9 (s, 1H) 3.30 (q, J=7.2 Hz, 2H), 1.99 (s, 6H), 1.91 (hept, J=6.8 Hz, 1H), 1.47 (s, 3H), 1.18-1.09 (m, 3H), 0.84 (d, J=6.8 Hz, 3H), 0.77 (d, J=6.8 Hz, 3H). MS (ESI+) m/z 503 (M+H)$^+$.

Example 20

4-[2-(2,6-dimethylphenoxy)-5-(2-hydroxy-3-methyl-pentan-2-yl)pyridin-3-yl]-N-ethyl-6-methyl-7-oxo-6,7-dihydro-1H-pyrrolo[2,3-c]pyridine-2-carboxamide The trifluoroacetic acid salt of Example 20 was prepared according to the procedure used for the preparation of Example 7, substituting 2-butyl magnesium bromide for phenyl magnesium bromide, and substituting methyl magnesium bromide for ethyl magnesium bromide. $^1$H NMR (500 MHz, DMSO-$d_6$) δ 8.02 (s, 1H), 7.89 (s, 1H), 7.45 (s, 1H), 7.08 (d, 2H), 7.04-7.00 (m, 1H), 6.9 (s, 1H), 3.64 (s, 3H), 3.29 (t, J=7.3 Hz, 2H), 1.99 (s, 6H), 1.59-1.53 (m, 1H), 1.47 (d, J=11.7 Hz, 3H), 1.14 (d, J=7.2 Hz, 2H), 0.83-0.75 (m, 5H). MS (ESI+) m/z 517 (M+H)$^+$.

Example 21

4-[2-(2,6-dimethylphenoxy)-5-(2-hydroxy-4-phenylbutan-2-yl)pyridin-3-yl]-N-ethyl-6-methyl-7-oxo-6,7-dihydro-1H-pyrrolo[2,3-c]pyridine-2-carboxamide The trifluoroacetic acid salt of Example 21 was prepared according to the procedure used for the preparation of Example 7, substituting 2-phenylethyl magnesium bromide for phenyl magnesium bromide, and substituting methyl magnesium bromide for ethyl magnesium bromide. $^1$H NMR (500 MHz, DMSO-$d_6$) δ 8.13 (d, J=2.4 Hz, 1H), 7.96 (d, J=2.4 Hz, 1H), 7.44 (s, 1H), 7.26-7.21 (m, 2H), 7.17-7.12 (m, 3H), 7.08 (d, J=7.9 Hz, 2H), 7.03 (dd, J=8.4, 6.3 Hz, 1H), 6.94 (s, 1H), 3.64 (s, 3H), 3.29 (q, J=7.3 Hz, 2H), 2.65 (ddd, J=13.6, 11.0, 6.0 Hz, 1H), 2.41 (ddd, J=13.4, 11.0, 5.6 Hz, 1H), 2.07-2.03 (m, 1H), 2.00 (s, 6H), 1.56 (s, 3H), 1.14 (t, J=7.2 Hz, 3H). MS (ESI+) m/z 565 (M+H)$^+$.

Example 22

4-{2-(2,6-dimethylphenoxy)-5-[1-(4-fluorophenyl)-2-hydroxypropan-2-yl]pyridin-3-yl}-N-ethyl-6-methyl-7-oxo-6,7-dihydro-1H-pyrrolo[2,3-c]pyridine-2-carboxamide The trifluoroacetic acid salt of Example 22 was prepared according to the procedure used for the preparation of Example 7, substituting 4-fluorobenzyl magnesium bromide for phenyl magnesium bromide, and substituting methyl magnesium bromide for ethyl magnesium bromide. $^1$H NMR (500 MHz, DMSO-$d_6$) δ 7.88 (s, 1H), 7.77 (d, J=2.4 Hz, 1H), 7.31 (s, 1H), 7.08 (d, J=7.4 Hz, 2H), 7.04-6.96 (m, 5H), 6.88 (s, 1H), 3.63 (s, 3H), 3.30 (q, J=7.3 Hz, 2H), 3.03-2.93 (m, 2H), 1.98 (s, 6H), 1.53 (s, 3H), 1.15 (t, J=7.2 Hz, 3H). MS (ESI+) m/z 568.9 (M+H)$^+$.

Example 23

4-{5-[cyclopropyl (4-fluorophenyl)hydroxymethyl]-2-(2,6-dimethylphenoxy)pyridin-3-yl}-N-ethyl-6-methyl-7-oxo-6,7-dihydro-1H-pyrrolo[2,3-c]pyridine-2-carboxamide The trifluoroacetic acid salt of Example 23 was prepared according to the procedure used for the preparation of Example 7, substituting 4-fluorophenyl magnesium bromide for phenyl magnesium bromide, and substituting cyclopropyl magnesium bromide for ethyl magnesium bromide. $^1$H NMR (400 MHz, Pyridine-$d_5$) δ 8.46 (s, 1H), 8.31 (d, J=2.4 Hz, 1H), 7.88 (s, 1H), 7.77-7.70 (m, 2H), 7.11-6.98 (m, 6H), 3.59 (s, 3H), 3.58-3.51 (m, 2H), 2.15 (s, 7H), 1.81 (tt, J=8.2, 5.4 Hz, 1H), 1.20 (t, J=7.2 Hz, 3H), 0.90-0.75 (m, 2H), 0.62 (dtdd, J=26.5, 9.1, 5.3, 3.7 Hz, 2H). MS (ESI+) m/z 581 (M+H)$^+$.

Example 24

4-{5-[cyclopentyl(cyclopropyl)hydroxymethyl]-2-(2,6-dimethylphenoxy)pyridin-3-yl}-N-ethyl-6-methyl-7-oxo-6,7-dihydro-1H-pyrrolo[2,3-c]pyridine-2-carboxamide The trifluoroacetic acid salt of Example 24 was prepared according to the procedure used for the preparation of Example 7, substituting cyclopentyl magnesium bromide for phenyl magnesium bromide, and substituting cyclopropyl magnesium bromide for ethyl magnesium bromide. $^1$H NMR (400 MHz, Pyridine-$d_5$) δ 8.47 (d, J=2.5 Hz, 1H), 8.36 (d, J=2.4 Hz, 1H), 7.43 (s, 1H), 7.25 (d, J=1.1 Hz, 1H), 7.08-7.03 (m, 2H), 7.03-6.96 (m, 1H), 3.65 (s, 3H), 3.55 (td, J=7.2, 5.6 Hz, 2H), 2.64 (h, J=9.0, 8.6 Hz, 1H), 2.17 (s, 6H), 1.85 (dt, J=9.6, 6.6 Hz, 2H), 1.75-1.40 (m, 7H), 1.18 (t, J=7.2 Hz, 3H), 0.88 (ddd, J=9.1, 5.4, 3.7 Hz, 1H), 0.57-0.31 (m, 3H). MS (ESI+) m/z 555 (M+H)$^+$.

Example 25

4-{5-[di cyclopropyl(hydroxy)methyl]-2-(2,6-dimethylphenoxy)pyridin-3-yl}-N-ethyl-6-methyl-7-oxo-6,7-dihydro-1H-pyrrolo[2,3-c]pyridine-2-carboxamide The trifluoroacetic acid salt of Example 25 was prepared according to the procedure used for the preparation of Example 7, substituting cyclopropyl magnesium bromide for phenyl magnesium bromide, and substituting cyclopropyl magnesium bromide for ethyl magnesium bromide $^1$H NMR (400 MHz, Pyridine-$d_5$) δ 8.58 (s, 1H), 8.48 (d, J=0.7 Hz, 1H), 7.42 (s, 2H), 7.23 (d, J=2.6 Hz, 1H), 7.06 (d, J=10.3 Hz, 2H), 7.03-6.98 (m, 1H), 3.65 (d, J=10.0 Hz, 3H), 3.59-3.51 (m, 2H), 2.16 (d, J=3.2 Hz, 6H), 1.43-1.29 (m, 1H), 1.19 (t, J=7.2 Hz, 3H), 0.88-0.78 (m, 2H), 0.72 (dtd, J=9.5, 5.5, 3.9 Hz, 2H), 0.54 (ddd, J=9.4, 7.4, 4.6 Hz, 2H), 0.42 (tdd, J=9.1, 5.6, 3.9 Hz, 2H). MS (ESI+) m/z 527 (M+H)$^+$.

Example 26

4-[5-(1-cyclopropyl-1-hydroxy-2-methylpropyl)-2-(2,6-dimethylphenoxy)pyridin-3-yl]-N-ethyl-6-methyl-7-oxo-6,7-dihydro-1H-pyrrolo[2,3-c]pyridine-2-carboxamide The trifluoroacetic acid salt of Example 26 was prepared according to the procedure used for the preparation of Example 7, substituting isopropyl magnesium bromide for phenyl magnesium bromide, and substituting cyclopropyl magnesium bromide for ethyl magnesium bromide. $^1$H NMR (400 MHz, Pyridine-$d_5$) δ 8.45 (d, J=2.5 Hz, 1H), 8.33 (d, J=2.4 Hz, 1H), 7.41 (s, 1H), 7.24 (d, J=1.2 Hz, 1H), 7.06 (s, 1H), 7.01 (d, J=5.9 Hz, 1H), 3.64 (s, 3H), 3.59-3.50 (m, 2H), 2.17 (s, 6H), 1.50-1.40 (m, 1H), 1.20-1.13 (t, 3H), 1.12 (d, 3H), 1.06 (d, J=6.8 Hz, 3H), 0.98-0.90 (m, 1H), 0.58-0.50 (m, 1H), 0.50-0.43 (m, 1H), 0.4-0.38 (m, 1H). MS (ESI+) m/z 529 (M+H)$^+$.

Example 27

4-[5-(1-cyclopropyl-1-hydroxy-2-methylbutyl)-2-(2, 6-dimethylphenoxy)pyridin-3-yl]-N-ethyl-6-methyl-7-oxo-6,7-dihydro-1H-pyrrolo[2,3-c]pyridine-2-carboxamide The trifluoroacetic acid salt of Example 27 was prepared according to the procedure used for the preparation of Example 7, substituting 2-butyl magnesium bromide for phenyl magnesium bromide, and substituting cyclopropyl magnesium bromide for ethyl magnesium bromide. $^1$H NMR (400 MHz, Pyridine-$d_5$) δ 8.47 (d, J=2.4 Hz, 1H), 8.35 (d, J=2.5 Hz, 1H), 7.42 (s, 1H), 7.23 (s, 1H), 7.07 (d, J=7.0 Hz, 2H), 7.05-6.95 (m, 1H), 3.64 (s, 2H), 3.57-3.50 (m, 2H), 2.17 (s, 7H), 2.06 (td, J=6.9, 3.6 Hz, 2H), 1.58-1.39 (m, 1H), 1.32-1.19 (m, 2H), 1.17 (d, J=7.2 Hz, 3H), 1.10 (dd, J=12.8, 6.9 Hz, 3H), 0.98-0.87 (m, 4H), 0.61-0.43 (m, 2H), 0.43-0.34 (m, 1H). MS (ESI+) m/z 543 (M+H)$^+$.

Example 28

N-ethyl-4-{5-(2-hydroxypropan-2-yl)-2-[2-methyl-6-(trifluoromethyl)phenoxy]phenyl}-6-methyl-7-oxo-6,7-dihydro-1H-pyrrolo[2,3-c]pyridine-2-carboxamide

Example 28a 2-(benzyloxy)-1-methyl-3-(trifluoromethyl)benzene

Phenylmethanol (3.24 g, 30.0 mmol) in 1-methylpyrrolidin-2-one (25 mL) was treated with 60% sodium hydride in oil (2.40 g, 60.0 mmol). The reaction mixture was stirred at ambient temperature for 10 minutes. To this solution was added 2-fluoro-1-methyl-3-(trifluoromethyl)benzene (1.781 g, 10 mmol). The reaction mixture was stirred at 100° C. for 4 hours. After cooling, the reaction mixture was partitioned between water and ethyl acetate. The aqueous layer was extracted with additional ethyl acetate three times. The combined organic layers were washed with brine, separated, dried over anhydrous magnesium sulfate, filtered, and concentrated. The residue was purified by flash chromatography on silica eluting with 5% ethyl acetate in heptanes to provide the title compound (1.56 g, 5.86 mmol, 58.6% yield) as a colorless oil.

Example 28b 2-methyl-6-(trifluoromethyl)phenol

Example 28a (1.1 g, 4.13 mmol) and methanol (25 mL) were added to 20% Pd(OH)$_2$ on carbon (wet, 0.22 g, 0.16 mmol) in a 50 mL pressure bottle and stirred for 3 hours at 30 psi of hydrogen and at 50° C. After cooling, the solid was removed by filtration. The filtrate was concentrated under reduced pressure to provide the title compound (0.35 g, 1.987 mmol, 48%).

Example 28c methyl 3-bromo-4-(2-methyl-6-(trifluoromethyl) phenoxy)benzoate

A mixture of methyl 3-bromo-4-fluorobenzoate (0.280 g, 1.2 mmol), Example 28b (0.211 g, 1.200 mmol), and cesium carbonate (0.391 g, 1.200 mmol) in dimethyl sulfoxide (5 mL) was heated at 110° C. overnight. After cooling, the reaction mixture was partitioned between water and ethyl acetate. The aqueous layer was extracted with additional ethyl acetate three times. The combined organic layers were washed with brine, separated, dried over anhydrous magnesium sulfate, filtered, and concentrated. The residue was purified by flash chromatography on silica eluting with 20% ethyl acetate in heptanes to provide the title compound (0.08 g, 0.206 mmol, 17.1% yield).

Example 28d 2-(3-bromo-4-(2-methyl-6-(trifluoromethyl)phenoxy)phenyl)propan-2-ol Example 28c (0.08 g, 0.206 mmol) in tetrahydrofuran (5 mL) was treated with methylmagnesium chloride (0.685 mL, 2.056 mmol) at 0° C. The reaction mixture was stirred at ambient temperature overnight. The reaction mixture was quenched with saturated aqueous ammonium chloride, and partitioned between water and ethyl acetate. The aqueous layer was extracted with additional ethyl acetate three times. The combined organic layers were washed with brine, separated, dried over anhydrous magnesium sulfate, filtered, and concentrated. The residue was purified by flash chromatography (silica eluting, 20% ethyl acetate in heptanes) to provide the title compound (0.056 g, 0.144 mmol, 70.0% yield).

Example 28e

N-ethyl-4-{5-(2-hydroxypropan-2-yl)-2-[2-methyl-6-(trifluoromethyl)phenoxy]phenyl}-6-methyl-7-oxo-6,7-dihydro-1H-pyrrolo[2,3-c]pyridine-2-carboxamide A mixture of Example 1h (0.069 g, 0.2 mmol), Example 28d (0.078 g, 0.200 mmol), tetrakis(triphenylphosphine) palladium(0) (0.023 g, 0.020 mmol), and cesium fluoride (0.091 g, 0.600 mmol) in 1,2-dimethoxyethane (1 mL) and methanol (0.500 mL) was heated at 120° C. for 40 minutes in a microwave reactor. After cooling, the reaction mixture was partitioned between water and ethyl acetate. The aqueous layer was extracted with additional ethyl acetate three times. The combined organic layers were washed with brine, separated, dried over anhydrous magnesium sulfate, filtered, and concentrated. The residue was purified by flash chromatography (silica gel, 5% methanol in ethyl acetate) to provide the crude product, which was then purified by reverse phase Preparative HPLC (C18 column, CH$_3$CN/water (0.1% trifluoroacetic acid), 20-80% gradient) to provide the title compound (0.039 g, 0.074 mmol, 37.0% yield). $^1$H NMR (500 MHz, DMSO-$d_6$) δ 12.25 (d, J=2.4 Hz, 1H), 8.35 (t, J=5.3 Hz, 1H), 7.72-7.53 (m, 3H), 7.42-7.21 (m, 3H), 6.81 (d, J=2.2 Hz, 1H), 6.33 (d, J=8.7 Hz, 1H), 3.60 (s, 3H), 3.27 (qdd, J=7.2, 4.9, 2.4 Hz, 2H), 1.94 (s, 3H), 1.45 (s, 6H), 1.12 (t, J=7.2 Hz, 3H). MS (ESI+) m/z 528.1 (M+H)$^+$.

Example 29

4-[2-(2-chloro-6-methylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide

Example 29a methyl 5-bromo-6-(2-chloro-6-methylphenoxy)nicotinate

A mixture of 2-chloro-6-methylphenol (1.195 g, 8.38 mmol), methyl 5-bromo-6-chloronicotinate (2 g, 7.98 mmol), and cesium carbonate (2.60 g, 7.98 mmol) in anhydrous dimethyl sulfoxide (20 mL) was stirred at 80° C. for 1.5 hours. After cooling to ambient temperature, water (40 mL) was added to the mixture, and the precipitated product was collected by filtration and dried to provide the title compound (2.6 g, 7.29 mmol, 91% yield) as off-white solid.

Example 29b 2-(5-bromo-6-(2-chloro-6-methylphenoxy)pyridin-3-yl)propan-2-ol

To a solution of Example 29a (1 g, 2.80 mmol) in anhydrous tetrahydrofuran (10 mL) at 0° C. was added 1 M methylmagnesium bromide (14.02 mmol) in tetrahydrofuran dropwise, and the mixture was stirred at room temperature for 16 hours. The reaction mixture was quenched with saturated aqueous ammonium chloride (20 mL) carefully, and extracted with ethyl acetate (20 mL×3). The combined organic phase was washed with brine (20 mL), dried over anhydrous sodium sulfate, filtered, and concentrated to dryness to provide the title compound (1 g, 2.80 mmol, 100% yield).

Example 29c 4-(2-(2-chloro-6-methylphenoxy)-5-(2-hydroxypropan-2-yl)pyridin-3-yl)-N-ethyl-6-methyl-7-oxo-6,7-dihydro-1H-pyrrolo[2,3-c]pyridine-2-carboxamide Example 29c was prepared according to the procedure used for the preparation of Example 1m, substituting Example 29b for Example 1l. $^1$H NMR (400 MHz, DMSO-$d_6$) δ 12.30 (s, 1H), 8.36 (t, J=5.4 Hz, 1H), 8.11 (d, J=2.4 Hz, 1H), 7.99 (d, J=2.4 Hz, 1H), 7.49 (s, 1H), 7.35 (dd, J=7.9, 1.6 Hz, 1H), 7.31-7.21 (m, 1H), 7.16 (t, J=7.8 Hz, 1H), 6.96 (s, 1H), 5.23 (s, 1H), 3.61 (s, 3H), 3.28 (td, J=7.2, 5.3 Hz, 2H), 2.09 (s, 3H), 1.49 (s, 6H), 1.12 (t, J=7.2 Hz, 3H). MS (ESI+) m/z 495.2 (M+H)$^+$.

Example 30

4-[2-(2-chloro-6-methylphenoxy)-5-(2-hydroxypropan-2-yl)phenyl]-N-ethyl-6-methyl-7-oxo-6,7-dihydro-1H-pyrrolo[2,3-c]pyridine-2-carboxamide Example 30a methyl 3-bromo-4-(2-chloro-6-methylphenoxy)benzoate A mixture of cesium carbonate (839 mg, 2.57 mmol), 2-chloro-6-methylphenol (294 mg, 2.060 mmol), and methyl 3-bromo-4-fluorobenzoate (400 mg, 1.716 mmol) in dimethyl sulfoxide (5 mL) was stirred at 100° C. for 1 hour under nitrogen. After cooling to ambient temperature, water (50 mL) was added. The resulting mixture was extracted with ethyl acetate (50 mL) twice. The organic layers were combined and dried over anhydrous sodium sulfate. After filtration and solvent removal the crude material was purified by flash chromatographed (silica gel, 0-50% ethyl acetate/petroleum ether) to provide the title compound (400 mg, 65.5% yield).

Example 30b 2-(3-bromo-4-(2-chloro-6-methylphenoxy)phenyl)propan-2-ol

Example 30b was prepared according to the procedure used for the preparation of Example 29b, substituting Example 30a for Example 29a.

Example 30c

4-[2-(2-chloro-6-methylphenoxy)-5-(2-hydroxypropan-2-yl)phenyl]-N-ethyl-6-methyl-7-oxo-6,7-dihydro-1H-pyrrolo[2,3-c]pyridine-2-carboxamide Example 30c was prepared according to the procedure used for the preparation of Example 1m, substituting Example 30b for Example 1l. $^1$H NMR (300 MHz, DMSO-$d_6$) δ 12.23 (s, 1H), 8.34 (b s, 1H), 7.53 (d, J=2.4 Hz, 1H), 7.45-7.25 (m, 4H), 7.19 (t, J=7.8 Hz, 1H), 6.91 (s, 1H), 6.30 (d, J=8.6 Hz, 1H), 5.01 (s, 1H), 3.59 (s, 3H), 3.30-3.21 (m, 2H), 2.08 (s, 3H), 1.44 (s, 6H), 1.11 (t, J=7.2 Hz, 3H). MS (ESI+) m/z 494.2 (M+H)$^+$.

Example 31

N-tert-butyl-4-[2-(2-chloro-6-methylphenoxy)-5-(2-hydroxypropan-2-yl)phenyl]-6-methyl-7-oxo-6,7-dihydro-1H-pyrrolo[2,3-c]pyridine-2-carboxamide A mixture of Example 30b (95 mg, 0.268 mmol), sodium carbonate (85 mg, 0.804 mmol), tris(dibenzylideneacetone)dipalladium(0) (24.5 mg, 0.027 mmol), Example 32c (100 mg, 0.268 mmol), and 1,3,5,7-tetramethyl-6-phenyl-2,4,8-trioxa-6-phosphaadamantane (9.40 mg, 0.032 mmol) was dissolved in tetrahydrofuran (4 mL) and water (1 mL). The mixture was heated at 60° C. for 3 hours under nitrogen. The mixture was cooled to ambient temperature and filtered and the filtrate was extracted with ethyl acetate. The organic layer was separated and dried over anhydrous magnesium sulfate, filtered, and evaporated. The crude residue was dissolved in dimethyl sulfoxide and purified by preparative-HPLC (Column:Waters HSS C18, 2.1*50 mm, 1.8 μm; Mobile Phase A:water/10 mmol NH$_4$HCO$_3$, Mobile Phase B: acetonitrile; Flow rate: 25 mL/min; gradient:25% B to 50% B in 5 min, hold 0.5 min; 254 nm) to provide the title compound (18.9 mg, 0.036 mmol, 13.5% yield). $^1$H NMR (300 MHz, DMSO-$d_6$) δ 12.36 (s, 1H), 7.86 (s, 1H), 7.54 (d, J=2.3 Hz, 1H), 7.41 (d, J=7.0 Hz, 1H), 7.37 (s, 1H), 7.31 (m, 2H), 7.19 (t, J=7.8 Hz, 1H), 6.91 (d, J=2.1 Hz, 1H), 6.29 (d, J=8.6 Hz, 1H), 5.01 (s, 1H), 3.60 (s, 3H), 2.08 (s, 3H), 1.44 (s, 6H), 1.36 (s, 9H). MS (ESI+) m/z 522.2 (M+H)$^+$.

Example 32

N-tert-butyl-4-[2-(2,6-dimethylphenoxy)-5-(2-hydroxypropan-2-yl)phenyl]-6-methyl-7-oxo-6,7-dihydro-1H-pyrrolo[2,3-c]pyridine-2-carboxamide Example 32a 4-bromo-6-methyl-7-oxo-6,7-dihydro-1H-pyrrolo[2,3-c]pyridine-2-carboxylic acid A 500 mL round bottom flask was charged with Example 1f (7.9 g, 17.43 mmol) and dioxane (100 mL). To this solution was added 2M NaOH (34.9 mL, 69.7 mmol), and the reaction mixture was heated at 80° C. for 2 hours. After cooling, the reaction mixture was diluted with HCl (0.1 N) to pH 2.1N HCl was then added dropwise to lower the pH to about 1. The resulting mixture was stirred vigorously for about one hour. The mixture was filtered and the resulting solid was washed with water and dried to provide the title compound (4.44 g, 94% yield).

Example 32b 4-bromo-N-(tert-butyl)-6-methyl-7-oxo-6,7-dihydro-1H-pyrrolo[2,3-c]pyridine-2-carboxamide To a slurry of Example 32a (2.98 g, 11.0 mmol) in dichloromethane (30 mL) was added 4 drops of dimethylformamide followed by the addition of oxalyl chloride (1.93 mL, 22.0 mmol). The mixture was stirred at ambient temperature for 3 hours and concentrated. To the residue were added tetrahydrofuran (30 mL) and 2-methylpropan-2-amine (3.47 mL, 33.0 mmol) and the mixture stirred at ambient temperature for 1 hour. The mixture was partitioned with ethyl acetate and water. The organic layer was washed with saturated aqueous sodium chloride, dried with anhydrous sodium sulfate, filtered, and concentrated. The resulting residue was triturated with ethyl acetate/heptanes (1:1) to provide the title compound (3.35 g, 10.27 mmol, 93%).

Example 32c

N-(tert-butyl)-6-methyl-7-oxo-4-(4,4,5,5-tetramethyl-1,3,2-dioxaborolan-2-yl)-6,7-dihydro-1H-pyrrolo[2,3-c]pyridine-2-carboxamide A mixture of anhydrous potassium acetate (26.6 g, 271 mmol), Example 32b (29.5 g, 90 mmol), 4,4,4',4',5,5,5',5'-octamethyl-2,2'-bi(1,3,2-dioxaborolane) (45.9 g, 181 mmol), chloro(2-dicyclohexylphosphino-2',4',6'-triisopropyl-1,1'-biphenyl)[2-(2'-amino-1,1'-biphenyl)]palladium(II) (2.85 g, 3.62 mmol), and 2-dicyclohexylphosphino-2',4',6'-triisopropylbiphenyl (1.725 g, 3.62 mmol) was degassed under a stream of nitrogen. To this mixture was added degassed anhydrous 2-methyl tetrahydrofuran (1 L). The resulting yellow slurry was heated at 80° C. overnight. The reaction mixture was cooled to ambient temperature and then diluted with water (500 mL) and ethyl acetate (500 mL) and stirred for 90 minutes with 1.8 g. (3.0 equivalents based on moles of palladium) of ammonium pyrrolidine dithiocarbamate. The resulting mixture was filtered through diatomaceous earth and the diatomaceous earth pad was rinsed with ethyl acetate. The filtrate was washed with brine. The organic layer was mixed with about 20 g. SiliaMetS Thiol® (a thiol attached on silica via an alkyl chain, a palladium scavenger from Silicycle), and this mixture was stirred for about one hour. The mixture was dried over anhydrous sodium sulfate, filtered, and concentrated under reduced pressure. The residue was purified on a Grace Reveleris X2 MPLC using a Teledyne-Isco RediSep Rf Gold 750 g. silica gel column, eluting with 50% to 60% to 70% to 80% ethyl acetate/heptane to provide the title compound. This material was sonicated in 250 mL of 20% ethyl acetate/heptane. The solid was collected by filtration, washed with 20% ethyl acetate/heptane, and dried to provide the title compound (17.6 g, 52% yield).

Example 32d

N-tert-butyl-4-[2-(2,6-dimethylphenoxy)-5-(2-hydroxypropan-2-yl)phenyl]-6-methyl-7-oxo-6,7-dihydro-1H-pyrrolo[2,3-c]pyridine-2-carboxamide A stream of nitrogen gas was blown over a mixture of Example 32c (15.0 g, 40.2 mmol), Example 3d (16.2 g, 48.2 mmol), 1,3,5,7-tetramethyl-6-phenyl-2,4,8-trioxa-6-phosphaadamantane (1.175 g, 4.02 mmol), potassium phosphate (21.33 g, 100 mmol), and tris(dibenzylideneacetone)dipalladium (1.104 g, 1.206 mmol) for one hour. In the meantime, in a 1 L. flask were mixed anhydrous dioxane (300 mL) and water (75 mL). This solution was degassed for one hour by bubbling nitrogen through it. After one hour, the solvents were transferred via cannula into the mixture of degassed solids. As the solvents were added an exotherm was observed and the temperature rose from 20.5° C. to 32.0° C. When the reaction mixture was sufficiently mixed, it was heated at 80° C. for 2.5 hours. The reaction mixture was cooled to ambient temperature and diluted with ethyl acetate and water. The mixture was stirred for one hour with about 600 mg. (3.0 equivalents. based on moles of palladium) of ammonium pyrrolidine dithiocarbamate. The resulting mixture was filtered through diatomaceous earth. The diatomaceous earth pad was washed with ethyl acetate. The resulting filtrate was poured into a separatory funnel and the mixture diluted further with ethyl acetate and brine. The organic layer was washed with water (2×) and brine. The organic layer was dried with anhydrous sodium sulfate, filtered, and concentrated under reduced pressure. The residue was purified on a Grace Reveleris X2 MPLC using a Teledyne Isco RediSep Rf Gold 330 g. silica gel column eluting with 70% to 80% to 90% ethyl acetate/heptanes to 100% ethyl acetate. The resulting pure material was dissolved with heating in ethanol, concentrated under reduced pressure, and dried to produce the title compound (18.0 g, 89% yield). $^1$H NMR (501 MHz, DMSO-$d_6$) δ 12.34 (s, 1H), 7.85 (s, 1H), 7.52 (d, J=2.3 Hz, 1H), 7.33 (s, 1H), 7.28 (dd, J=8.6, 2.4 Hz, 1H), 7.10 (d, J=7.8 Hz, 2H), 7.03 (dd, J=8.3, 6.6 Hz, 1H), 6.85 (s, 1H), 6.26 (d, J=8.6 Hz, 1H), 4.97 (s, 1H), 3.59 (s, 3H), 2.00 (s, 6H), 1.42 (s, 6H), 1.35 (s, 9H). MS (ESI+) m/z 502.1 (M+H)$^+$.

Example 33

N-tert-butyl-4-[2',4'-difluoro-4-(2-hydroxypropan-2-yl)[1,1'-biphenyl]-2-yl]-6-methyl-7-oxo-6,7-dihydro-1H-pyrrolo[2,3-c]pyridine-2-carboxamide Example 33a methyl 2',4'-difluoro-2-nitro-[1,1'-biphenyl]-4-carboxylate A mixture of methyl 4-bromo-3-nitrobenzoate (750 mg, 2.88 mmol), (2,4-difluorophenyl)boronic acid (683 mg, 4.33 mmol), tetrakis(triphenylphosphine)palladium(0) (333 mg, 0.288 mmol), and sodium carbonate (611 mg, 5.77 mmol) were combined in dioxane (15 mL) and water (4 mL), sparged with nitrogen gas for 10 minutes, and heated at 90° C. under nitrogen for 2 hours. The mixture was cooled to ambient temperature and partitioned between ethyl acetate and water. The organic layer was washed with saturated aqueous sodium chloride, dried over anhydrous sodium sulfate, treated with diatomaceous earth, filtered, and concentrated. The residue was purified by chromatography (silica gel, 0-100% ethyl acetate in petroleum ether) to provide the title compound (510 mg, 1.739 mmol, 60.3% yield).

Example 33b methyl 2-amino-2',4'-difluoro-[1,1'-biphenyl]-4-carboxylate

Example 33a (450 mg, 1.535 mmol), zinc (1003 mg, 15.35 mmol) and ammonia hydrochloride (821 mg, 15.35 mmol) were combined in tetrahydrofuran (4 mL), methanol (1 mL) and water (1 mL) with vigorous stirring at 26° C. for 3 hours. The mixture was filtered through a plug of diatomaceous earth to remove solids. The plug was rinsed repeatedly with methanol and tetrahydrofuran. The filtrate was concentrated and the residue partitioned between ethyl acetate and water. The ethyl acetate layer was washed with brine, dried (anhydrous sodium sulfate), filtered, and concentrated to provide the title compound (380 mg, 1.444 mmol, 94% yield).

Example 33c methyl 2',4'-difluoro-2-iodo-[1,1'-biphenyl]-4-carboxylate

A solution of Example 33b (200 mg, 0.760 mmol) in 1,4-dioxane (10 mL) at 0° C. was treated with concentrated HCl (27.7 mg, 0.760 mmol) and stirred for 15 minutes and then treated with a solution of sodium nitrite (62.9 mg, 0.912 mmol) in water (2 mL). The mixture was stirred for 1 hour at 0° C., treated with a solution of potassium iodide (252 mg, 1.52 mmol) in water (2 mL) and stirred for 1 hour at ambient temperature. The reaction mixture was partitioned between ethyl acetate and water. The organic layer was washed with saturated sodium thiosulfate, water, and brine, dried (anhydrous magnesium sulfate), filtered, and concentrated. The residue was purified by chromatography on silica gel (hexane) to provide the title compound (300 mg, 0.642 mmol, 84% yield).

Example 33d 2-(2',4'-difluoro-2-iodo-[1,1'-biphenyl]-4-yl)propan-2-ol

A mixture of Example 33c (100 mg, 0.267 mmol) in tetrahydrofuran (10 mL) was stirred at −10° C. To this solution was slowly added methylmagnesium bromide (0.356 mL, 1.069 mmol). The reaction mixture was stirred at 25° C. overnight. The mixture was diluted with ethyl ether, washed with 20 mL water (twice), and brine. The organic layer was dried over anhydrous sodium sulfate, filtered, and concentrated under reduced pressure. The residue was purified by silica gel chromatography (petroleum ether/ethyl acetate=33/1) to provide the title compound (50 mg, 0.134 mmol, 50.0% yield).

Example 33e

N-tert-butyl-4-[2',4'-difluoro-4-(2-hydroxypropan-2-yl)[1,1'-biphenyl]-2-yl]-6-methyl-7-oxo-6,7-dihydro-1H-pyrrolo[2,3-c]pyridine-2-carboxamide Example 33e was prepared according to the procedure used for the preparation of Example 32d, substituting Example 33d for Example 3d. $^1$H NMR (400 MHz, Methanol-$d_4$) δ 7.67 (d, J=2.0 Hz, 1H), 7.62 (dd, J=8.0, 2.1 Hz, 1H), 7.41 (d, J=8.1 Hz, 1H), 7.30-7.21 (m, 1H), 6.86 (s, 1H), 6.86-6.77 (m, 2H), 6.69 (s, 1H), 3.53 (s, 3H), 1.63 (s, 6H), 1.45 (s, 9H). MS (ESI+) m/z 494.2 (M+H)$^+$.

Example 34

N-(2,2-difluoro-1-methylcyclopropyl)-4-[2-(2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide

Example 34a 4-bromo-6-methyl-7-oxo-6,7-dihydro-1H-pyrrolo[2,3-c]pyridine-2-carbonyl chloride Example 32a (1.0 g, 3.69 mmol) in dichloromethane (18.45 mL) under nitrogen was treated with N,N-dimethylformamide (0.057 mL, 0.738 mmol) followed by dropwise addition of oxalyl dichloride (0.969 mL, 11.07 mmol). The reaction mixture was stirred under nitrogen at ambient temperature for 3 hours and concentrated. The residue was azeotroped three more times with 1:1 dichloromethane/toluene to provide the title compound (1.06 g, 99%) that was used without purification.

Example 34b 4-bromo-N-(2,2-difluoro-1-methylcyclopropyl)-6-methyl-7-oxo-6,7-dihydro-1H-pyrrolo[2,3-c]pyridine-2-carboxamide A mixture of Example 34a (1.06 g, 3.69 mmol) and 2,2-difluoro-1-methylcyclopropanamine hydrochloride (0.636 g, 4.43 mmol) in tetrahydrofuran (24.59 mL) under nitrogen was treated dropwise with N-ethyl-N-isopropylpropan-2-amine (6.44 mL, 36.9 mmol). The reaction mixture was stirred under nitrogen at ambient temperature for 18 hours. The mixture was partitioned between ethyl acetate and water. The organic layer was washed with saturated aqueous sodium chloride, dried over anhydrous sodium sulfate, filtered, and concentrated. Purification by trituration (2:1 dichloromethane/heptanes) provided the title compound (0.688 g, 52%).

Example 34c

N-(2,2-difluoro-1-methylcyclopropyl)-6-methyl-7-oxo-4-(4,4,5,5-tetramethyl-1,3,2-dioxaborolan-2-yl)-6,7-dihydro-1H-pyrrolo[2,3-c]pyridine-2-carboxamide Dicyclohexyl(2',4',6'-triisopropyl-[1,1'-biphenyl]-2-yl)phosphine (0.109 g, 0.229 mmol), potassium acetate (0.750 g, 7.64 mmol), tris(dibenzylideneacetone)dipalladium(0) (0.052 g, 0.057 mmol), Example 34b (0.688 g, 1.910 mmol) and 4,4,4',4',5,5,5',5'-octamethyl-2,2'-bi(1,3,2-dioxaborolane) (1.455 g, 5.73 mmol) were combined in dioxane (9.55 mL) and sparged with argon for 15 minutes. The mixture was then heated under nitrogen for 18 hours at 80° C., cooled, and partitioned between ethyl acetate and water. The organic layer was washed with saturated aqueous sodium chloride, dried (anhydrous sodium sulfate), treated with 3-mercaptopropyl functionalized silica gel, filtered, and concentrated. Purification by chromatography (silica gel, 20-100% ethyl acetate in heptanes) provided the crude desired product. Trituration in a minimal volume of 9:1 heptanes/diethyl ether provided the title compound (0.362 g, 46%).

Example 34d

N-(2,2-difluoro-1-methylcyclopropyl)-4-[2-(2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide Example 34c (0.06 g, 0.147 mmol), Example 11 (0.059 g, 0.177 mmol), tris(dibenzylideneacetone)dipalladium(0) (4.05 mg, 4.42 µmol), 1,3,5,7-tetramethyl-6-phenyl-2,4,8-trioxa-6-phosphaadamantane (4.31 mg, 0.015 mmol) and sodium carbonate (0.062 g, 0.589 mmol) were combined and sparged with argon for 15 minutes. Meanwhile a solution of 4:1 tetrahydrofuran/water (1.0 mL) was sparged with nitrogen for 15 minutes and transferred by syringe into the reaction vessel under argon. The mixture was stirred for 3 hours under argon at 60° C., cooled, and partitioned between ethyl acetate and water. The organic layer was washed with saturated aqueous sodium chloride, dried over anhydrous sodium sulfate, treated with 3-mercaptopropyl functionalized silica gel, filtered and concentrated. Purification by reverse phase HPLC (C18, CH$_3$CN/water (0.1% trifluoroacetic acid), 0-100%) provided the title compound (0.066 g, 83%). $^1$H NMR (400 MHz, DMSO-d$_6$) δ 12.38 (d, J=2.1 Hz, 1H), 8.77 (d, J=2.4 Hz, 1H), 8.08 (d, J=2.4 Hz, 1H), 7.92 (d, J=2.4 Hz, 1H), 7.43 (s, 1H), 7.07-6.89 (m, 4H), 3.59 (s, 3H), 1.96 (s, 6H), 1.72-1.54 (m, 2H), 1.46 (s, 6H), 1.43 (d, J=2.5 Hz, 3H). MS (ESI+) m/z 537 [M+H]$^+$.

Example 35

N-ethyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide

Example 35a 4-fluoro-2,6-dimethylphenol

A solution of 2-bromo-5-fluoro-1,3-dimethylbenzene (25 g, 123 mmol) in tetrahydrofuran (300 mL) was cooled to −78° C. and n-butyllithium (59.1 mL, 148 mmol) was added dropwise at a rate to keep the internal temperature at or below −75° C. The mixture was stirred for 2 hours and then trimethylborate (16.51 mL, 148 mmol) was added and the mixture stirred for 3 hours at −78° C., then warmed to ambient temperature. After 4 hours, the mixture was cooled to −10° C. and a precooled solution of NaOH (7.39 g, 185 mmol) and 30% hydrogen peroxide (201 mL, 1970 mmol) was added. Once the addition was complete the mixture was allowed to warm to ambient temperature overnight. The pH of the mixture was adjusted to pH 1 with 2M HCl. 400 mL of ethyl ether and 200 mL of water were added and the layers were separated. The aqueous layer was extracted with 3×200 mL of ether, and the combined organic layers were washed with saturated NaHCO$_3$ and saturated NaS$_2$O$_3$, then stirred with a saturated aqueous NaS$_2$O$_5$ solution (200 mL) for 15 minutes. The organic phase was dried with anhydrous magnesium sulfate, filtered, and concentrated. The residues were taken up in 1/1 diethyl ether/pentane and flushed through a silica plug. Concentration of the filtrate provided 11.47 g (67%) of the title compound.

Example 35b methyl 3-bromo-4-(4-fluoro-2,6-dimethylphenoxy)benzoate

To a solution of Example 35a (1.86 g, 13.27 mmol) and methyl 3-bromo-4-fluorobenzoate (2.099 mL, 14.20 mmol) in dimethyl sulfoxide (14 mL) was added cesium carbonate (6.49 g, 19.91 mmol). The mixture was heated at 80° C. for 2 hours, cooled, and diluted with water (100 mL), then extracted with methyl tert-butyl ether (200 mL). The aqueous phase was extracted with additional portions (2×100 mL) of methyl tert-butyl ether. The combined organics were dried over anhydrous sodium sulfate, filtered, and concentrated. The crude material was purified by chromatography (silica gel, eluting with 0-25% ethyl acetate/heptanes) to provide 4.56 g (97%) of the title compound.

Example 35c 2-(3-bromo-4-(4-fluoro-2,6-dimethylphenoxy)phenyl)propan-2-ol

A flask containing a solution of Example 35b (2.49 g, 7.05 mmol) in tetrahydrofuran (28.0 mL) was placed in a water bath, and then treated with 3 M methylmagnesium bromide in tetrahydrofuran (7.0 mL, 21.00 mmol). After 30 minutes, the mixture was quenched by addition of 100 mL of aqueous ammonium chloride and partitioned with 100 mL of diethyl ether. The organics were washed with water and dried over anhydrous sodium sulfate. After filtration and solvent removal, the crude material was chromatographed (silica cartridge, 0-100% ethyl acetate/heptanes) to provide 2.056 g (83%) of the title compound.

Example 35d

N-ethyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide Method A:

A mixture of Example 35c, Example 1h (0.280 g, 0.810 mmol), 1,3,5,7-tetramethyl-6-phenyl-2,4,8-trioxa-6-phosphaadamantane (0.021 g, 0.073 mmol), tris(dibenzylideneacetone)dipalladium(0) (4) (0.017 g, 0.019 mmol), and potassium phosphate (0.331 g, 1.557 mmol) in dioxane (4 mL) and water (1 mL) was degassed and back-filled with nitrogen six times. The reaction mixture was heated at 60° C. for 12 hours. The reaction mixture was partitioned between water and ethyl acetate. The aqueous layer was extracted with additional ethyl acetate (3×20 mL). The combined organic layers were washed with brine, dried over anhydrous magnesium sulfate, filtered, and concentrated. The residue was purified by flash column chromatography on silica gel eluting with 5% methanol in ethyl acetate. The crude product was further purified by reverse phase Preparative HPLC (C18, CH$_3$CN/water (0.1% trifluoroacetic acid), 20-80% gradient). The desired fractions were combined and freeze-dried to provide the title compound (0.14 g, 0.285 mmol, 45.7% yield). $^1$H NMR (400 MHz, DMSO-d$_6$) δ 12.20 (s, 1H), 8.32 (t, J=5.3 Hz, 1H), 7.50 (d, J=2.5 Hz, 1H), 7.46-7.21 (m, 2H), 6.96 (d, J=8.9 Hz, 2H), 6.83 (d, J=2.3 Hz, 1H), 6.29 (d, J=8.6 Hz, 1H), 3.58 (s, 3H), 3.24 (dt, J=12.6, 6.2 Hz, 2H), 2.00 (s, 6H), 1.42 (s, 6H), 1.10 (t, J=7.2 Hz, 2H). MS (ESI+) m/z 492.2 (M+H)$^+$.

Method B:

Step 1: Preparation of ethyl 4-(2-(4-fluoro-2,6-dimethylphenoxy)-5-(2-hydroxypropan-2-yl)phenyl)-6-methyl-7-oxo-1-tosyl-6,7-dihydro-1H-pyrrolo[2,3-c]pyridine-2-carboxylate A three-neck flask was charged with a stir bar, and fit with a thermocouple and reflux condenser. To the flask was added bis(pinacolato)diboron (27.0 g, 106 mmol), tris(dibenzylideneacetone)dipalladium(0) (605 mg, 0.661 mmol), 1,3,5,7-tetramethyl-6-phenyl-2,4,8-trioxa-6-phosphaadamantane (465 mg, 1.591 mmol), Example 1f prepared from Method B (38.832 g, 86 mmol), and potassium acetate (17.67 g, 180 mmol). The flask containing the solids was purged with nitrogen for 30 minutes and a separate flask containing 350 mL of tetrahydrofuran was sparged for 30 minutes. After this time, the three-neck flask was stoppered and 350 mL of the sparged tetrahydrofuran was transferred to the solids using a cannula. The reaction mixture was then stirred and heated to 60° C. until the reaction was judged complete by HPLC (22 hours). After this time, the reaction mixture was filtered through a pad of diatomaceous earth, and collected in a round-bottom flask. The diatomaceous earth pad was washed with tetrahydrofuran (1×50 mL) and added to the reaction. The reaction mixture was then sparged with nitrogen for 30 minutes. In a separate flask, tribasic potassium phosphate (52.0 g, 548 mmol) was dissolved in water (50 mL) and the solution was sparged with nitrogen for 30 minutes. After this time, the flask containing the reaction mixture was open (under high flow of nitrogen) and Example 35c (28.8 g, 82 mmol) was added as a solid. Immediately following the addition, the phosphate and water solution was added via cannula. The reaction mixture was then heated at 60° C. for 2 hours or until complete consumption of Example 35C was observed. The volatile components were then removed on a rotary evaporator. To the remaining mixture was added 300 mL of ethyl acetate to completely dissolve the crude residue. The aqueous and organic layer was separated, and the aqueous layer was extracted with ethyl acetate (2×250 mL). The organic layers were combined and washed with 5% cysteine/8% sodium bicarbonate (2×100 mL). The organic and aqueous layers were separated and the organic component was removed on a rotary evaporator leaving a yellow/light brown solid. The solid was dissolved in methyl tert-butyl ether (450 mL) to give a yellow solution and 900 mL of heptane was added to promote precipitation. The off-white solid was filtered and washed quickly with 200 mL of heptane. The filtrate was concentrated until precipitation began again. The solid was again filtered and washed. A final amount of solvent was removed from the second filtrate, and a precipitate began to form. Cooling the filtrate, followed by filtration and washing of the solid with heptane, gave a third and final batch of the title compound (41.69 g, 75%).

Step 2: Preparation of 4-(2-(4-fluoro-2,6-dimethylphenoxy)-5-(2-hydroxypropan-2-yl)phenyl)-6-methyl-7-oxo-6,7-dihydro-1H-pyrrolo[2,3-c]pyridine-2-carboxylic acid A 24 mL dram vial was charged with a stir bar and ethyl 4-(2-(4-fluoro-2,6-dimethylphenoxy)-5-(2-hydroxypropan-2-yl)phenyl)-6-methyl-7-oxo-1-tosyl-6,7-dihydro-1H-pyrrolo[2,3-c]pyridine-2-carboxylate (140 mg, 0.216 mmol). The solid was dissolved in 3 mL of tetrahydrofuran and aqueous potassium hydroxide (4.45 M, 0.60 mL, 2.67 mmol) was added. The mixture was stirred at 60° C. for 22 hours. To the vial was added 10 mL of ethyl acetate. The reaction mixture was transferred to a separatory funnel and shaken. The organic and aqueous layers were separated. The aqueous layer was extracted with additional ethyl acetate (2×10 mL). The aqueous layer was then adjusted to pH=3 using 1 M HCl, and extracted with ethyl acetate (3×10 mL). The ethyl acetate fractions collected after pH adjustment were combined and distilled from the reaction using a rotary evaporator to provide the title compound (80 mg, 80% yield).

Step 3: Preparation of N-ethyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide A 50 mL round-bottom flask was charged with a stir bar and 4-(2-(4-fluoro-2,6-dimethylphenoxy)-5-(2-hydroxypropan-2-yl)phenyl)-6-methyl-7-oxo-6,7-dihydro-1H-pyrrolo[2,3-c]pyridine-2-carboxylic acid (80 mg, 0.388 mmol). The flask was flushed with nitrogen, and 3.8 mL of anhydrous N,N-dimethylformamide was added. The light yellow solution was stirred as HATU (1-[bis(dimethylamino)methylene]-1H-1,2,3-triazolo[4,5-b]pyridinium 3-oxid hexafluorophosphate, 166 mg, 0.437 mmol) was added in one portion as a solid. The bright yellow reaction mixture was stirred for 10 minutes. After this time, ethanamine (0.40 ml, 0.800 mmol) was added and the reaction mixture was stirred an additional 20 minutes before diisopropylethylamine (0.20 ml, 1.145 mmol) was added. After 12 hours, 20 mL of water was added to the reaction mixture causing precipitation of the product as a white solid. The solid was washed quickly with additional water (2×10 mL) and dried to provide the title compound (70 mg, 83% yield).

Example 36

N-tert-butyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide Example 36 was prepared according to the procedure used for the preparation of Example 32d, substituting Example 35c for Example 3d. $^1$H NMR (400 MHz, DMSO-$d_6$) δ 12.35 (d, J=2.3 Hz, 1H), 7.86 (s, 1H), 7.53 (d, J=2.4 Hz, 1H), 7.41-7.25 (m, 2H), 6.99 (d, J=9.0 Hz, 2H), 6.84 (d, J=2.3 Hz, 1H), 6.31 (d, J=8.6 Hz, 1H), 3.61 (s, 3H), 2.02 (s, 6H), 1.44 (s, 6H), 1.37 (s, 9H). MS (ESI+) m/z 520.1 (M+H)$^+$.

Example 37

N-tert-butyl-4-[2-(2-chloro-6-methylphenoxy)-5-(2-hydroxypropan-2-yl)pyridin-3-yl]-6-methyl-7-oxo-6,7-dihydro-1H-pyrrolo[2,3-c]pyridine-2-carboxamide Example 32c (45 mg, 0.12 mmol), Example 29b (47 mg, 0.13 mmol), sodium carbonate (46 mg, 0.42 mmol), tris(dibenzylideneacetone)dipalladium(0) (3.3 mg, 3.6 μmol) and 1,3,5,7-tetramethyl-6-phenyl-2,4,8-trioxa-6-phosphaadamantane (3.2 mg, 11 μmol) were combined in a microwave tube and purged with nitrogen for 15 minutes. The mixture of tetrahydrofuran (2 mL) and water (0.5 mL) was purged with nitrogen for 15 minutes and transferred to the microwave tube. The reaction mixture was heated at 60° C. for 3 hours, cooled and partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20-40% 3:1 ethyl acetate/ethanol in heptanes) to provide the title compound (56 mg, 89%). $^1$H NMR (500 MHz, DMSO-$d_6$) δ 12.41 (s, 1H), 8.08 (d, J=2.4 Hz, 1H), 7.97 (d, J=2.4 Hz, 1H), 7.84 (s, 1H), 7.46 (s, 1H), 7.35-7.31 (m, 1H), 7.25-7.22 (m, 1H), 7.13 (t, J=7.8

Hz, 1H), 6.94 (d, J=2.1 Hz, 1H), 5.19 (s, 1H), 3.59 (s, 3H), 2.07 (s, 3H), 1.46 (s, 6H), 1.35 (s, 9H). MS (ESI+) m/z 523 (M+H)⁺.

Example 38

4-[2-(2-chloro-6-methylphenoxy)-5-(2-hydroxypropan-2-yl)pyridin-3-yl]-6-methyl-7-oxo-N-(1,1,1-trifluoro-2-methylpropan-2-yl)-6,7-dihydro-1H-pyrrolo[2,3-c]pyridine-2-carboxamide

Example 38a 4-bromo-6-methyl-7-oxo-N-(1,1,1-trifluoro-2-methylpropan-2-yl)-6,7-dihydro-1H-pyrrolo[2,3-c]pyridine-2-carboxamide Example 38a (1.04 g, 74%) was prepared according to the procedure used for the preparation of Example 34b, substituting 1,1,1-trifluoro-2-methylpropan-2-amine for 2,2-difluoro-1-methylcyclopropanamine hydrochloride.

Example 38b 6-methyl-7-oxo-4-(4,4,5,5-tetramethyl-1,3,2-dioxaborolan-2-yl)-N-(1,1,1-trifluoro-2-methylpropan-2-yl)-6,7-dihydro-1H-pyrrolo[2,3-c]pyridine-2-carboxamide Example 38b (0.404 g, 60%) was prepared according to the procedure used for the preparation of Example 34c, substituting Example 38a for Example 34b.

Example 38c

4-[2-(2-chloro-6-methylphenoxy)-5-(2-hydroxypropan-2-yl)pyridin-3-yl]-6-methyl-7-oxo-N-(1,1,1-trifluoro-2-methylpropan-2-yl)-6,7-dihydro-1H-pyrrolo[2,3-c]pyridine-2-carboxamide Example 38c (48 mg, 83%) was prepared according to the procedure used for the preparation of Example 37, substituting Example 38b for Example 32c. ¹H NMR (400 MHz, DMSO-d₆) δ 12.54 (s, 1H), 8.11-8.06 (m, 2H), 7.97 (d, J=2.3 Hz, 1H), 7.47 (s, 1H), 7.33 (d, J=7.9 Hz, 1H), 7.23 (d, J=7.2 Hz, 1H), 7.13 (t, J=7.8 Hz, 1H), 7.05 (s, 1H), 5.19 (s, 1H), 3.60 (s, 3H), 2.07 (s, 3H), 1.59 (s, 6H), 1.46 (s, 6H). MS (ESI+) m/z 577 (M+H)⁺.

Example 39

4-[2-(2-chloro-6-methylphenoxy)-5-(2-hydroxypropan-2-yl)pyridin-3-yl]-N-(2,2-difluoro-1-methylcyclopropyl)-6-methyl-7-oxo-6,7-dihydro-1H-pyrrolo[2,3-c]pyridine-2-carboxamide Example 39 (48 mg, 86%) was prepared according to the procedure used for the preparation of Example 37, substituting Example 34c for Example 32c. ¹H NMR (500 MHz, DMSO-d₆) δ 12.39 (s, 1H), 8.76 (s, 1H), 8.09 (d, J=2.4 Hz, 1H), 7.95 (d, J=2.4 Hz, 1H), 7.45 (s, 1H), 7.35-7.29 (m, 1H), 7.25-7.21 (m, 1H), 7.13 (t, J=7.8 Hz, 1H), 6.98 (d, J=1.7 Hz, 1H), 5.19 (s, 1H), 3.59 (s, 3H), 2.06 (s, 3H), 1.71-1.55 (m, 2H), 1.46 (s, 6H), 1.43 (s, 3H). MS (ESI+) m/z 557 (M+H)⁺.

Example 40

4-{2-[2,6-dimethyl-4-(methyl sulfanyl)phenoxy]-5-(2-hydroxypropan-2-yl)phenyl}-N-ethyl-6-methyl-7-oxo-6,7-dihydro-1H-pyrrolo[2,3-c]pyridine-2-carboxamide Example 40 was isolated as a byproduct from the preparation of Example 35. ¹H NMR (400 MHz, DMSO-d₆) δ 12.21 (d, J=2.2 Hz, 1H), 8.33 (t, J=5.4 Hz, 1H), 7.51 (d, J=2.4 Hz, 1H), 7.32 (d, J=8.9 Hz, 2H), 7.02 (s, 2H), 6.84 (d, J=2.2 Hz, 1H), 6.31 (d, J=8.7 Hz, 1H), 3.60 (s, 3H), 3.26 (qd, J=7.2, 5.2 Hz, 2H), 2.45 (s, 3H), 1.99 (s, 6H), 1.44 (s, 6H), 1.12 (t, J=7.2 Hz, 3H). MS (ESI+) m/z 520.1 (M+H)⁺.

Example 41

4-[2-(2-chloro-6-methylphenoxy)-5-(2-hydroxypropan-2-yl)phenyl]-6-methyl-7-oxo-N-(1,1,1-trifluoro-2-methylpropan-2-yl)-6,7-dihydro-1H-pyrrolo[2,3-c]pyridine-2-carboxamide Example 41 (44 mg, 76%) was prepared according to the procedure used for the preparation of Example 37, substituting Example 38b for Example 32c, and substituting Example 30b for Example 29b. ¹H NMR (400 MHz, DMSO-d₆) δ 12.45 (s, 1H), 8.07 (s, 1H), 7.53 (d, J=1.7 Hz, 1H), 7.43-7.35 (m, 2H), 7.34-7.25 (m, 2H), 7.17 (t, J=7.8 Hz, 1H), 7.02 (s, 1H), 6.28 (d, J=8.6 Hz, 1H), 4.98 (s, 1H), 3.59 (s, 3H), 2.07 (s, 3H), 1.59 (s, 6H), 1.42 (s, 6H). MS (ESI+) m/z 576 (M+H)⁺.

Example 42

4-[2-(2-chloro-6-methylphenoxy)-5-(2-hydroxypropan-2-yl)phenyl]-N-(2,2-difluoro-1-methylcyclopropyl)-6-methyl-7-oxo-6,7-dihydro-1H-pyrrolo[2,3-c]pyridine-2-carboxamide Example 42 (45 mg, 81%) was prepared according to the procedure used for the preparation of Example 34d, substituting Example 30b for Example 11. ¹H NMR (400 MHz, DMSO-d₆) δ 12.29 (s, 1H), 8.75 (s, 1H), 7.52 (d, J=2.3 Hz, 1H), 7.39 (dd, J=7.9, 1.0 Hz, 1H), 7.35 (s, 1H), 7.31 (dd, J=8.6, 2.4 Hz, 1H), 7.28 (d, J=6.9 Hz, 1H), 7.17 (t, J=7.8 Hz, 1H), 6.95 (d, J=1.7 Hz, 1H), 6.29 (d, J=8.6 Hz, 1H), 4.98 (s, 1H), 3.58 (s, 3H), 2.06 (s, 3H), 1.71-1.52 (m, 2H), 1.43 (s, 9H). MS (ESI+) m/z 556 (M+H)⁺.

Example 43

N-ethyl-4-[2-(4-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide

Example 43a methyl 5-bromo-6-(4-fluoro-2,6-dimethylphenoxy)nicotinate

Example 43a was prepared according to the procedure used for the preparation of Example 28c, substituting Example 35a for Example 28b, and substituting methyl 5-bromo-6-chloronicotinate for methyl 3-bromo-4-fluorobenzoate respectively.

Example 43b 2-(5-bromo-6-(4-fluoro-2,6-dimethylphenoxy)pyridin-3-yl)propan-2-ol

Example 43b was prepared according to the procedure used for the preparation of Example 28d, substituting Example 43a for Example 28c.

Example 43c

N-ethyl-4-[2-(4-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide Example 43c was prepared according to the procedure used for the preparation of Example 1m, substituting Example 43b for Example 1l. $^1$H NMR (400 MHz, DMSO-$d_6$) δ 12.31 (d, J=2.2 Hz, 1H), 8.34 (t, J=5.4 Hz, 1H), 8.11 (d, J=2.4 Hz, 1H), 7.95 (d, J=2.5 Hz, 1H), 7.44 (s, 1H), 6.92 (d, J=9.2 Hz, 2H), 6.86 (d, J=2.2 Hz, 1H), 3.61 (s, 3H), 3.27 (qd, J=7.3, 5.2 Hz, 2H), 1.99 (s, 6H), 1.48 (s, 6H), 1.12 (t, J=7.2 Hz, 3H). MS (ESI+) m/z 493.2 (M+H)$^+$.

Example 44

N-tert-butyl-4-[2-(4-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide Example 44 was prepared according to the procedure used for the preparation of Example 1m, substituting Example 43b for Example 1l, and substituting Example 32c for Example 1h, respectively. $^1$H NMR (400 MHz, DMSO-$d_6$) δ 12.43 (d, J=2.4 Hz, 1H), 8.10 (d, J=2.4 Hz, 1H), 7.96 (d, J=2.4 Hz, 1H), 7.87 (s, 1H), 7.44 (s, 1H), 6.98-6.82 (m, 3H), 3.61 (s, 3H), 1.99 (s, 6H), 1.48 (s, 6H), 1.37 (s, 9H). MS (ESI+) m/z 521.2 (M+H)$^+$.

Example 45

N-tert-butyl-4-{5-(2-hydroxypropan-2-yl)-2-[2-methyl-6-(trifluoromethyl)phenoxy]pyridin-3-yl}-6-methyl-7-oxo-6,7-dihydro-1H-pyrrolo[2,3-c]pyridine-2-carboxamide Example 45a 2-(benzyloxy)-1-methyl-3-(trifluoromethyl)benzene A 3-neck, oven-dried and nitrogen-flushed 250 mL round-bottom flask was charged with 60% sodium hydride (8.98 g, 225 mmol). The flask was equipped with a reflux condenser and a temperature probe and the system was degassed with nitrogen for 30 minutes. 1-methylpyrrolidin-2-one (150 mL) was added, and the suspension was cooled in an ice-water bath (to internal temp=4° C.). Benzyl alcohol (17.4 mL, 168 mmol) was added dropwise over about 5 minutes. The reaction mixture was warmed to ambient temperature for about 30 minutes. A solution of 2-fluoro-1-methyl-3-(trifluoromethyl)benzene (20.0 g, 112 mmol) in toluene (30 mL) was added. The reaction mixture was stirred at ambient temperature for about 5 minutes, then heated at 60° C. for 16 hours, cooled in an ice bath, carefully quenched with isopropyl alcohol (25 mL), diluted with water, and extracted with ethyl acetate four times. The combined organic layers were dried with anhydrous sodium sulfate, filtered, and evaporated. The residue was purified by flash chromatography (silica gel, 0-5% ethyl acetate in heptanes) to provide the title compound (27.6 g, 92%).

Example 45b 2-methyl-6-(trifluoromethyl)phenol

To a solution of Example 45a (35.3 g, 133 mmol) in methanol (200 mL) in a 500 mL stainless steel pressure bottle was added Pd(OH)$_2$/C (wet, 20%, 6.60 g, 10.2% wt, 4.79 mmol). The reaction mixture was shaken at 50° C. for 3 hours under 30 psi of hydrogen, filtered, and concentrated to provide the title compound (22.9 g, 98%).

Example 45c methyl 5-bromo-6-(2-methyl-6-(trifluoromethyl)phenoxy)nicotinate

Methyl 5-bromo-6-chloronicotinate (9.90 g, 39.5 mmol), Example 45b (8.70 g, 49.4 mmol) and cesium carbonate (25.8 g, 79.0 mmol) were combined in dimethyl sulfoxide (100 mL). The reaction mixture was heated at 100° C. for 2 hours, cooled, diluted with water, and extracted with ethyl acetate three times. The combined organic layers were washed with saturated aqueous sodium chloride, dried with anhydrous sodium sulfate, filtered, and concentrated. The residue was purified by flash chromatography (silica gel, 0-10% ethyl acetate in heptane) to provide the title compound (11.9 g, 77%).

Example 45d 2-(5-bromo-6-(2-methyl-6-(trifluoromethyl)phenoxy)pyridin-3-yl)propan-2-ol To a solution of Example 45c (11.9 g, 30.6 mmol) in tetrahydrofuran (300 mL) was added 3M methylmagnesium chloride in tetrahydrofuran (30.6 mL, 92.0 mmol) dropwise over 20 minutes at −74° C. The reaction mixture was stirred in the cold bath which was thawed overnight, cooled in an ice-water bath, quenched by the careful addition of water, diluted with water and extracted with ethyl acetate three times. The combined organic layers were dried with anhydrous sodium sulfate, filtered, and concentrated. The residue was purified by flash chromatography (silica gel, 0-25% ethyl acetate in heptane) to provide the title compound (6.1 g, 51%).

Example 45e

N-tert-butyl-4-{5-(2-hydroxypropan-2-yl)-2-[2-methyl-6-(trifluoromethyl)phenoxy]pyridin-3-yl}-6-methyl-7-oxo-6,7-dihydro-1H-pyrrolo[2,3-c]pyridine-2-carboxamide Example 45e was prepared according to the procedure used for the preparation of Example 37, substituting Example 45d for Example 29b. Purification by flash chromatography (silica gel, 2-4% methanol in dichloromethane) provided the title compound (57 mg, 85%). $^1$H NMR (400

MHz, DMSO-d$_6$) δ 12.44 (s, 1H), 8.07 (d, J=2.4 Hz, 1H), 7.98 (d, J=2.4 Hz, 1H), 7.84 (s, 1H), 7.55 (dd, J=7.7, 3.0 Hz, 2H), 7.38 (s, 1H), 7.31 (t, J=7.7 Hz, 1H), 6.79 (d, J=1.7 Hz, 1H), 5.19 (s, 1H), 3.56 (s, 3H), 1.97 (s, 3H), 1.44 (s, 6H), 1.34 (s, 9H). MS (ESI+) m/z 557 (M+H)$^+$.

Example 46

4-{5-(2-hydroxypropan-2-yl)-2-[2-methyl-6-(trifluoromethyl)phenoxy]pyridin-3-yl}-6-methyl-7-oxo-N-(1,1,1-trifluoro-2-methylpropan-2-yl)-6,7-dihydro-1H-pyrrolo[2,3-c]pyridine-2-carboxamide Example 46 was prepared according to the procedure used for the preparation of Example 37, substituting Example 38b for Example 32c, and substituting Example 45d for Example 29b. Purification by flash chromatography (silica gel, 2-4% methanol in dichloromethane) provided the title compound (61 mg, 83%). $^1$H NMR (400 MHz, DMSO-d$_6$) δ 12.56 (s, 1H), 8.09-8.06 (m, 2H), 7.98 (d, J=2.4 Hz, 1H), 7.55 (dd, J=7.7, 3.2 Hz, 2H), 7.39 (s, 1H), 7.30 (t, J=7.7 Hz, 1H), 6.89 (d, J=1.7 Hz, 1H), 5.18 (s, 1H), 3.56 (s, 3H), 1.97 (s, 3H), 1.58 (s, 6H), 1.44 (s, 6H). MS (ESI+) m/z 611 (M+H)$^+$.

Example 47

N-(2,2-difluoro-1-methyl cyclopropyl)-4-{5-(2-hydroxypropan-2-yl)-2-[2-methyl-6-(trifluoromethyl)phenoxy]pyridin-3-yl}-6-methyl-7-oxo-6,7-dihydro-1H-pyrrolo[2,3-c]pyridine-2-carboxamide Example 47 was prepared according to the procedure used for the preparation of Example 37, substituting Example 34c for Example 32c and substituting Example 45d for Example 29b. Purification by flash chromatography (silica gel, 2-4% methanol in dichloromethane) provided the title compound (53 mg, 75%). $^1$H NMR (400 MHz, DMSO-d$_6$) δ 12.39 (s, 1H), 8.76 (s, 1H), 8.08 (d, J=2.4 Hz, 1H), 7.97 (d, J=2.4 Hz, 1H), 7.55 (dd, J=7.7, 3.1 Hz, 2H), 7.37 (s, 1H), 7.30 (t, J=7.7 Hz, 1H), 6.85 (s, 1H), 5.18 (s, 1H), 3.55 (s, 3H), 1.97 (d, J=3.9 Hz, 3H), 1.70-1.53 (m, 2H), 1.45 (s, 6H), 1.42 (s, 3H). MS (ESI+) m/z 591 (M+H)$^+$.

Example 48

N-ethyl-4-{5-(2-hydroxypropan-2-yl)-2-[2-methyl-6-(trifluoromethyl)phenoxy]pyridin-3-yl}-6-methyl-7-oxo-6,7-dihydro-1H-pyrrolo[2,3-c]pyridine-2-carboxamide Example 48 was prepared according to the procedure used for the preparation of Example 1m, substituting Example 45d for Example 11. $^1$H NMR (400 MHz, Methanol-d$_4$) δ 8.12 (s, 2H), 7.54 (dd, J=16.8, 7.7 Hz, 2H), 7.48 (s, 1H), 7.31 (t, J=7.7 Hz, 1H), 6.97 (s, 1H), 3.70 (s, 3H), 3.41 (q, J=7.3 Hz, 2H), 2.02 (s, 3H), 1.60 (s, 6H), 1.23 (t, J=7.2 Hz, 3H). MS (ESI+) m/z 529.2 (M+H)$^+$.

Example 49

4-[2-(2-chloro-4-fluoro-6-methylphenoxy)-5-(2-hydroxypropan-2-yl)phenyl]-N-ethyl-6-methyl-7-oxo-6,7-dihydro-1H-pyrrolo[2,3-c]pyridine-2-carboxamide

Example 49a methyl 3-bromo-4-(2-chloro-4-fluoro-6-methylphenoxy)benzoate

Example 49a was prepared according to the procedure used for the preparation of Example 35b, substituting 2-chloro-4-fluoro-6-methylphenol for Example 35a.

Example 49b 2-(3-bromo-4-(2-chloro-4-fluoro-6-methylphenoxy)phenyl)propan-2-ol Example 49b was prepared according to the procedure used for the preparation of Example 35c, substituting Example 49a for Example 35b.

Example 49c

4-[2-(2-chloro-4-fluoro-6-methylphenoxy)-5-(2-hydroxypropan-2-yl)phenyl]-N-ethyl-6-methyl-7-oxo-6,7-dihydro-1H-pyrrolo[2,3-c]pyridine-2-carboxamide Example 49c was prepared according to the procedure used for the preparation of Example 1m, substituting Example 49b for Example 11. $^1$H NMR (400 MHz, Methanol-d$_4$) δ 7.55 (d, J=2.4 Hz, 1H), 7.31 (s, 1H), 7.26 (dd, J=8.7, 2.4 Hz, 1H), 7.08 (dd, J=8.1, 3.1 Hz, 1H), 6.94 (dd, J=8.9, 3.0 Hz, 1H), 6.91 (s, 1H), 6.33 (d, J=8.6 Hz, 1H), 3.62 (s, 3H), 3.31 (q, J=7.2 Hz, 2H), 2.01 (s, 3H), 1.47 (s, 6H), 1.12 (t, J=7.2 Hz, 3H). MS (ESI+) m/z 512.2 (M+H)$^+$.

Example 50

N-tert-butyl-4-[2-(2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide The trifluoroacetic acid salt of Example 50 was prepared according to the procedure used for the preparation of Example 1m, substituting Example 32c for Example 1h. $^1$H NMR (400 MHz, DMSO-d$_6$) δ 12.44 (s, 1H), 8.07 (d, J=2.3 Hz, 1H), 7.94 (d, J=2.4 Hz, 1H), 7.87 (s, 1H), 7.44 (s, 1H), 7.05 (d, J=7.1 Hz, 2H), 7.02-6.96 (m, 1H), 6.87 (d, J=2.0 Hz, 1H), 3.60 (s, 3H), 1.98 (s, 6H), 1.46 (s, 6H), 1.35 (s, 9H). MS (ESI+) m/z 512.2 (M+H)$^+$.

Example 51

N-tert-butyl-4-[2-(2-chloro-4-fluoro-6-methylphenoxy)-5-(2-hydroxypropan-2-yl)pyridin-3-yl]-6-methyl-7-oxo-6,7-dihydro-1H-pyrrolo[2,3-c]pyridine-2-carboxamide

Example 51a methyl 5-bromo-6-(2-chloro-4-fluoro-6-methylphenoxy)nicotinate

Example 51a was prepared according to the procedure used for the preparation of Example 35b, substituting methyl 5-bromo-6-chloronicotinate for methyl 3-bromo-4-fluorobenzoate, and substituting 2-chloro-4-fluoro-6-methylphenol for Example 35a.

Example 51b 2-(5-bromo-6-(2-chloro-4-fluoro-6-methylphenoxy)pyridin-3-yl)propan-2-ol Example 51b was prepared according to the procedure used for the preparation of Example 35c, substituting Example 51a for Example 35b.

Example 51c

N-tert-butyl-4-[2-(2-chloro-4-fluoro-6-methylphenoxy)-5-(2-hydroxypropan-2-yl)pyridin-3-yl]-6-methyl-7-oxo-6,7-dihydro-1H-pyrrolo[2,3-c]pyridine-2-carboxamide Example 51c was prepared according to the procedure used for the preparation of Example 37, substituting Example 51b for Example 29b. $^1$H NMR (400 MHz, Methanol-d$_4$) δ 8.03 (d, J=2.3 Hz, 1H), 7.97 (d, J=2.4 Hz, 1H), 7.38 (s, 1H), 7.04 (dd, J=8.2, 3.0 Hz, 1H), 6.96 (s, 1H), 6.91 (dd, J=8.9, 3.0 Hz, 1H), 3.62 (s, 3H), 2.02 (s, 3H), 1.50 (s, 6H), 1.36 (s, 9H). MS (ESI+) m/z 541.2 (M+H)$^+$.

Example 52

4-[2-(2-chloro-4-fluoro-6-methylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide The trifluoroacetic acid salt of Example 52 was prepared according to the procedure used for the preparation of Example 1m, substituting Example 51b for Example 1l. $^1$H NMR (400 MHz, DMSO-d$_6$) δ 12.30 (s, 1H), 8.32 (t, J=5.4 Hz, 1H), 8.10 (d, J=2.3 Hz, 1H), 7.97 (d, J=2.4 Hz, 1H), 7.45 (s, 1H), 7.33 (dd, J=8.3, 3.0 Hz, 1H), 7.17 (dd, J=9.3, 3.0 Hz, 1H), 6.91 (d, J=2.1 Hz, 1H), 3.59 (s, 3H), 3.25 (td, J=7.3, 5.4 Hz, 2H), 2.07 (s, 3H), 1.47 (s, 6H), 1.10 (t, J=7.2 Hz, 3H). MS (ESI+) m/z 513.2 (M+H)$^+$.

Example 53

N-tert-butyl-4-[2-(2-chloro-4-fluoro-6-methylphenoxy)-5-(2-hydroxypropan-2-yl)phenyl]-6-methyl-7-oxo-6,7-dihydro-1H-pyrrolo[2,3-c]pyridine-2-carboxamide Example 53 was prepared according to the procedure used for the preparation of Example 37, substituting Example 49b for Example 29b. $^1$H NMR (400 MHz, Methanol-d$_4$) δ 7.63 (d, J=2.4 Hz, 1H), 7.41-7.32 (m, 2H), 7.17 (dd, J=8.1, 3.0 Hz, 1H), 7.06-6.99 (m, 2H), 6.41 (d, J=8.6 Hz, 1H), 3.71 (s, 3H), 2.09 (s, 3H), 1.56 (s, 6H), 1.44 (s, 9H). MS (ESI+) m/z 540.2 (M+H)$^+$.

Example 54

N-tert-butyl-4-{5-(2-hydroxypropan-2-yl)-2-[2-methyl-6-(trifluoromethyl)phenoxy]phenyl}-6-methyl-7-oxo-6,7-dihydro-1H-pyrrolo[2,3-c]pyridine-2-carboxamide Example 54 was prepared according to the procedure used for the preparation of Example 37, substituting Example 28d for Example 29b. $^1$H NMR (400 MHz, DMSO-d$_6$) δ 12.37 (s, 1H), 7.84 (s, 1H), 7.64-7.58 (m, 2H), 7.56 (d, J=2.4 Hz, 1H), 7.36 (t, J=7.7 Hz, 1H), 7.31 (dd, J=8.6, 2.4 Hz, 1H), 7.28 (s, 1H), 6.78 (d, J=1.7 Hz, 1H), 6.31 (d, J=8.6 Hz, 1H), 5.01 (s, 1H), 3.57 (s, 3H), 1.92 (s, 3H), 1.43 (s, 6H), 1.36 (s, 9H). MS (ESI+) m/z 556.4 (M+H)$^+$.

Example 55

4-[2-(4-fluoro-2,6-dimethylphenoxy)-5-(2-hydroxypropan-2-yl)phenyl]-6-methyl-7-oxo-N-(1,1,1-trifluoro-2-methylpropan-2-yl)-6,7-dihydro-1H-pyrrolo[2,3-c]pyridine-2-carboxamide Example 55 was prepared according to the procedure used for the preparation of Example 35d, substituting Example 38b for Example 1h. $^1$H NMR (400 MHz, Methanol-d$_4$) δ 7.61 (d, J=2.4 Hz, 1H), 7.45-7.25 (m, 2H), 7.06 (s, 1H), 6.83 (d, J=8.9 Hz, 2H), 6.39 (d, J=8.6 Hz, 1H), 3.72 (s, 3H), 2.05 (s, 6H), 1.67 (s, 6H), 1.55 (s, 6H). MS (ESI+) m/z 574.2 (M+H)$^+$.

Example 56

4-[2-(4-fluoro-2,6-dimethylphenoxy)-5-(2-hydroxypropan-2-yl)pyridin-3-yl]-6-methyl-7-oxo-N-(1,1,1-trifluoro-2-methylpropan-2-yl)-6,7-dihydro-1H-pyrrolo[2,3-c]pyridine-2-carboxamide A mixture of Example 43b (80 mg, 0.226 mmol), Example 38b (106 mg, 0.248 mmol), tris(dibenzylideneacetone)dipalladium(0) (7.65 mg, 8.36 μmol), potassium phosphate tribasic (144 mg, 0.678 mmol) and 1,3,5,7-tetramethyl-6-phenyl-2,4,8-trioxa-6-phosphaadamantane (8.85 mg, 0.030 mmol) in tetrahydrofuran (2.5 mL) and water (0.6 mL) was heated in a microwave reactor at 70° C. for 2 hours under nitrogen. The reaction mixture was cooled, partitioned between ethyl acetate and water, and the aqueous phase was extracted twice with ethyl acetate. The combined organics were washed with water and brine, dried over anhydrous sodium sulfate and concentrated to provide the crude. The crude product was purified by preparative HPLC (Column: Waters HSS C18, 2.1*50 mm, 1.8 μm; Mobile Phase A: water/10 mmol ammonium carbonate, Mobile Phase B: acetonitrile; Flow rate: 25 mL/min; Gradient: 25% B to 50% B in 5 min, hold 0.5 min; 254 nm) to provide the title compound (68 mg, 0.118 mmol, 52.4% yield) as a white solid. $^1$H NMR (400 MHz, Methanol-d$_4$) δ 8.03 (d, J=2.5 Hz, 1H), 7.95 (d, J=2.5 Hz, 1H), 7.34 (s, 1H), 6.97 (s, 1H), 6.71 (d, J=8.9 Hz, 2H), 3.62 (s, 3H), 1.94 (s, 6H), 1.58 (s, 6H), 1.49 (s, 6H). MS (ESI+) m/z 575.2 (M+H)$^+$.

Example 57

4-[2-(2-chloro-4-fluoro-6-methylphenoxy)-5-(2-hydroxypropan-2-yl)phenyl]-6-methyl-7-oxo-N-(1,1,1-trifluoro-2-methylpropan-2-yl)-6,7-dihydro-1H-pyrrolo[2,3-c]pyridine-2-carboxamide Example 57 was prepared according to the procedure used for the preparation of Example 56, substituting Example 49b for Example 43b, and heating in a microwave reactor at 60° C. for two hours. $^1$H NMR (400 MHz, Methanol-d$_4$) δ 7.54 (d, J=2.4 Hz, 1H), 7.29 (s, 1H), 7.26 (dd, J=8.6, 2.4 Hz, 1H), 7.06 (dd, J=8.1, 3.0 Hz, 1H), 7.02 (s, 1H), 6.96-6.89 (m, 1H), 6.32 (d, J=8.6 Hz, 1H), 3.62 (s, 3H), 2.00 (s, 3H), 1.57 (s, 6H), 1.46 (s, 6H). MS (ESI+) m/z 594.2 (M+H)$^+$.

Example 58

4-[2-(2-chloro-4-fluoro-6-methylphenoxy)-5-(2-hydroxypropan-2-yl)pyridin-3-yl]-6-methyl-7-oxo-N-(1,1,1-trifluoro-2-methylpropan-2-yl)-6,7-dihydro-1H-pyrrolo[2,3-c]pyridine-2-carboxamide The trifluoroacetic acid salt of Example 58 was prepared according to the procedure used for the preparation of Example 56, substituting Example 51b for Example 43b. The mixture was heated in a microwave reactor at 60° C. for two hours, and the crude product was purified by HPLC (C18 column, CH$_3$CN/water (0.1% trifluoroacetic acid)). $^1$H NMR (400 MHz, Methanol-d$_4$) δ 8.03 (d, J=2.4 Hz, 1H), 7.96 (d, J=2.5 Hz, 1H), 7.37 (s, 1H), 6.99-7.04 (m, 2H), 6.90 (dd, J=9.1, 3.1 Hz, 1H), 3.62 (s, 3H), 2.01 (s, 3H), 1.57 (s, 6H), 1.49 (s, 6H). MS (ESI+) m/z 595.2 (M+H)$^+$.

Example 59

4-[2-(2-chloro-4-fluoro-6-methylphenoxy)-5-(2-hydroxypropan-2-yl)phenyl]-N-(2,2-difluoro-1-methyl cyclopropyl)-6-methyl-7-oxo-6,7-dihydro-1H-pyrrolo[2,3-c]pyridine-2-carboxamide A mixture of tris(dibenzylideneacetone)dipalladium(0) (9.19 mg, 10.04 µmol), Example 49b (0.075 g, 0.201 mmol), Example 34c (0.090 g, 0.221 mmol), 1,3,5,7-tetramethyl-6-phenyl-2,4,8-trioxa-6-phosphaadamantane (5.86 mg, 0.020 mmol), and potassium phosphate tribasic (0.128 g, 0.602 mmol) in tetrahydrofuran (4 mL) water (1 mL) was heated in a microwave reactor at 60° C. under nitrogen for 2 hours. After cooling to ambient temperature, the mixture was filtered through a pad of diatomaceous earth and washed with ethyl acetate (30 mL). The filtrate was washed with water (20 mL), and concentrated to dryness. The crude product was purified by Preparative HPLC (Column: Waters HSS C18, 2.1*50 mm, 1.8 µm; Mobile Phase A: water/10 mmol ammonium carbonate, Mobile Phase B: acetonitrile; Flow rate: 25 mL/min; Gradient: 25 B to 50 B in 5 min, hold 0.5 min; 254 nm), and the collected fractions was lyophilized to provide the title compound (0.038 g, 0.066 mmol, 33.0% yield). $^1$H NMR (400 MHz, Methanol-d$_4$) δ 7.54 (d, J=2.4 Hz, 1H), 7.30 (s, 1H), 7.25 (dd, J=8.7, 2.4 Hz, 1H), 7.06 (dd, J=8.1, 3.0 Hz, 1H), 6.95-6.88 (m, 2H), 6.31 (d, J=8.6 Hz, 1H), 3.61 (s, 3H), 1.99 (s, 3H), 1.45-1.55 (m, 2H), 1.46 (s, 6H), 1.43 (s, 3H). MS (ESI+) m/z 594.2 (M+H)$^+$.

Example 60

N-(2,2-difluoro-1-methylcyclopropyl)-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide Example 60 was prepared according to the procedure used for the preparation of Example 59, substituting Example 35c for Example 49b, and heating in a microwave reactor at 70° C. for two hours. $^1$H NMR (400 MHz, Methanol-d$_4$) δ 7.52 (s, 1H), 7.2-7.3 (m, 2H), 6.87 (s, 1H), 6.73 (d, J=8.9 Hz, 2H), 6.30 (d, J=8.6 Hz, 1H), 3.62 (s, 3H), 1.95 (s, 6H), 1.35-1.55 (m, 11H). MS (ESI+) m/z 554.2 (M+H)$^+$.

Example 61

N-(2,2-difluoro-1-methylcyclopropyl)-4-[2-(4-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide Example 61 was prepared according to the procedure used for the preparation of Example 59, substituting Example 43b for Example 49b, and heating in a microwave reactor at 70° C. for two hours. $^1$H NMR (400 MHz, Methanol-d$_4$) δ 8.02 (d, J=2.5 Hz, 1H), 7.95 (d, J=2.5 Hz, 1H), 7.34 (s, 1H), 6.87 (s, 1H), 6.70 (d, J=8.9 Hz, 2H), 3.62 (s, 3H), 1.93 (s, 6H), 1.45-1.55 (m, 8H), 1.43 (q, J=2.7 Hz, 3H).). MS (ESI+) m/z 555.2 (M+H)$^+$.

Example 62

4-[2-(2-chloro-4-fluoro-6-methylphenoxy)-5-(2-hydroxypropan-2-yl)pyridin-3-yl]-N-(2,2-difluoro-1-methylcyclopropyl)-6-methyl-7-oxo-6,7-dihydro-1H-pyrrolo[2,3-c]pyridine-2-carboxamide Example 62 was prepared according to the procedure used for the preparation of Example 59, substituting Example 51b for Example 49b. $^1$H NMR (400 MHz, Methanol-d$_4$) δ 8.03 (d, J=2.4 Hz, 1H), 7.97 (d, J=2.5 Hz, 1H), 7.40 (s, 1H), 7.03 (dd, J=8.1, 3.0 Hz, 1H), 6.88-6.98 (m, 2H), 3.62 (s, 3H), 2.02 (s, 3H), 1.45-1.55 (m, 8H), 1.44 (s, 3H). MS (ESI+) m/z 575.2 (M+H)$^+$.

Example 63

N-(bicyclo[1.1.1]pentan-1-yl)-4-[2-(2-chloro-6-methylphenoxy)-5-(2-hydroxypropan-2-yl)pyridin-3-yl]-6-methyl-7-oxo-6,7-dihydro-1H-pyrrolo[2,3-c]pyridine-2-carboxamide Example 63a N-(bicyclo[1.1.1]pentan-1-yl)-4-bromo-6-methyl-7-oxo-6,7-dihydro-1H-pyrrolo[2,3-c]pyridine-2-carboxamide Example 63a was prepared according to the procedure used for the preparation of Example 32b, replacing 2-methylpropan-2-amine with bicyclo[1.1.1]pentan-1-amine.

Example 63b

N-(bicyclo[1.1.1]pentan-1-yl)-6-methyl-7-oxo-4-(4,4,5,5-tetramethyl-1,3,2-dioxaborolan-2-yl)-6,7-dihydro-1H-pyrrolo[2,3-c]pyridine-2-carboxamide Example 63b was prepared according to the procedure used for the preparation of Example 32c, replacing Example 32b with Example 63a.

Example 63c

N-(bicyclo[1.1.1]pentan-1-yl)-4-[2-(2-chloro-6-methylphenoxy)-5-(2-hydroxypropan-2-yl)pyridin-3-yl]-6-methyl-7-oxo-6,7-dihydro-1H-pyrrolo[2,3-c]pyridine-2-carboxamide A mixture of Example 29b (40 mg, 0.112 mmol), Example 63b (47.3 mg, 0.123 mmol), tris(dibenzylideneacetone)dipalladium(0) (3.80 mg, 4.15 µmol), potassium phosphate tribasic (71.4 mg, 0.336 mmol) and 1,3,5,7-tetramethyl-6-phenyl-2,4,8-trioxa-6-phosphaadamantane (4.39 mg, 0.015 mmol) in tetrahydrofuran (3 mL) and water (0.3 mL) was heated in a microwave reactor at 80° C. for 2 hours under a nitrogen atmosphere. The reaction mixture was cooled to ambient temperature, partitioned between ethyl acetate and water, the aqueous phase was extracted twice with ethyl acetate, and the combined organics were washed with water and saturated aqueous sodium chloride, dried over anhydrous sodium sulfate, filtered, and concentrated. The residue was purified by preparative HPLC (Column: Waters HSS C18, 2.1*50 mm, 1.8 µm; Mobile Phase A:water/10 mmol ammonium carbonate, Mobile Phase B: acetonitrile; Flow rate: 25 mL/min; Gradient:25% B to 50% B in 5 min, hold 0.5 min; 254 nm) to provide the title compound (11 mg, 0.021 mmol, 18.40% yield) as a white solid. $^1$H NMR (400 MHz, Methanol-$d_4$) δ 8.01 (s, 1H), 7.97 (s, 1H), 7.43 (s, 1H), 7.20 (d, J=7.8 Hz, 1H), 7.11 (d, J=7.4 Hz, 1H), 7.02 (t, J=7.7 Hz, 1H), 6.93 (s, 1H), 3.62 (s, 2H), 2.38 (s, 1H), 2.08 (s, 6H), 2.02 (s, 3H), 1.50 (s, 6H). MS (ESI+) m/z 533.2 (M+H)$^+$.

Example 64

4-[2-(2,6-dimethylphenoxy)-4-fluoro-5-(2-hydroxypropan-2-yl)phenyl]-N-ethyl-6-methyl-7-oxo-6,7-dihydro-1H-pyrrolo[2,3-c]pyridine-2-carboxamide Example 64a methyl 5-bromo-2,4-difluorobenzoate To a solution of 5-bromo-2,4-difluorobenzoic acid (400 mg, 1.688 mmol) in methanol (8.44 mL) was added thionyl chloride (0.493 mL, 6.75 mmol), and the reaction mixture was stirred at 65° C. for 1 hour. The reaction mixture was poured into 50 mL ice-water and then partitioned with ethyl acetate (3×30 mL). The organic layer was washed with saturated aqueous sodium chloride, dried with anhydrous sodium sulfate, filtered, and concentrated under reduced pressure. The residue was purified by flash chromatography (silica gel, hexanes) to provide the title compound (0.269 g, 1.05 mmol, 62.3% yield).

Example 64b methyl 5-bromo-4-(2,6-dimethylphenoxy)-2-fluorobenzoate

A mixture of cesium carbonate 1.537 g, 4.72 mmol), 2,6-dimethylphenol (0.137 g, 1.120 mmol), and Example 64a (0.296 g, 1.179 mmol) in dimethyl sulfoxide (6 mL) was stirred at 80° C. for 1 hour. The reaction mixture was poured into ice-water (50 mL) and partitioned with ethyl acetate (3×30 mL). The organic layer was washed with saturated aqueous sodium chloride, dried with anhydrous sodium sulfate, filtered, and concentrated under reduced pressure. The residue was purified by flash chromatography (hexanes) to provide the title compound (0.362 g, 1.026 mmol, 87% yield) as colorless oil.

Example 64c 2-(5-bromo-4-(2,6-dimethylphenoxy)-2-fluorophenyl)propan-2-ol

Example 64c was prepared according to the procedure used for the preparation of Example 35c, replacing Example 35b with example 64b.

Example 64d

4-[2-(2,6-dimethylphenoxy)-4-fluoro-5-(2-hydroxypropan-2-yl)phenyl]-N-ethyl-6-methyl-7-oxo-6,7-dihydro-1H-pyrrolo[2,3-c]pyridine-2-carboxamide Example 64d was prepared according to the procedure used for the preparation of Example 1m, substituting Example 64c for Example 1l. $^1$H NMR (400 MHz, Methanol-$d_4$) δ 7.65 (d, J=9.2 Hz, 1H), 7.27 (s, 1H), 7.05-6.93 (m, 3H), 6.86 (s, 1H), 5.98 (d, J=13.2 Hz, 1H), 3.62 (s, 3H), 3.31 (q, J=7.2 Hz, 2H), 1.98 (s, 6H), 1.50 (d, J=1.0 Hz, 6H), 1.12 (t, J=7.2 Hz, 3H). MS (ESI+) m/z 492.2 (M+H)$^+$.

Example 65

N-ethyl-4-[4-fluoro-2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide Example 65a methyl 5-bromo-2-fluoro-4-(4-fluoro-2,6-dimethylphenoxy)benzoate Example 65a was prepared according to the procedure used for the preparation of Example 64b, replacing 2,6-dimethylphenol with 4-fluoro-2,6-dimethylphenol.

Example 65b 2-(5-bromo-2-fluoro-4-(4-fluoro-2,6-dimethylphenoxy)phenyl)propan-2-ol Example 65b was prepared according to the procedure used for the preparation of Example 35c, replacing Example 35b with example 65a.

Example 65c

N-ethyl-4-[4-fluoro-2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide Example 65c was prepared according to the procedure used for the preparation of Example 1m, substituting Example 65b for Example 1l. $^1$H NMR (400 MHz, DMSO-$d_6$) δ 12.21 (d, J=2.3 Hz, 1H), 8.27 (t, J=5.4 Hz, 1H), 7.59 (d, J=9.3 Hz, 1H), 7.27 (s, 1H), 6.95 (d, J=9.1 Hz, 2H), 6.75 (d, J=2.1 Hz, 1H), 6.01 (d, J=12.9 Hz, 1H), 5.22 (s, 1H), 3.26

(s, 2H), 3.20 (m, 2H), 1.96 (s, 6H), 1.42 (s, 6H), 1.05 (t, J=7.2 Hz, 3H). MS (ESI+) m/z 510.2 (M+H)$^+$.

Example 66

4-[5-(1,2-dihydroxypropan-2-yl)-2-(2,6-dimethyl-phenoxy)phenyl]-N-ethyl-6-methyl-7-oxo-6,7-di-hydro-1H-pyrrolo[2,3-c]pyridine-2-carboxamide Example 66a 2-(2-bromo-4-(prop-1-en-2-yl)phenoxy)-1,3-dimethylbenzene To a mixture of methyltriphenylphosponium bromide (3.68 g, 10.34 mmol) in anhydrous tetrahydrofuran (40 mL) was added n-butyllithium in hexane (6.46 mL, 10.34 mmol) at 0° C., and the mixture was stirred at 0° C. for 1 hour. To the mixture was added dropwise a solution of Example 3c (3 g, 9.40 mmol) in anhydrous tetrahydrofuran (10 mL) at 0° C., and the mixture was allowed to warm to room temperature slowly for 16 hours. The mixture was partitioned between water (50 mL) and ethyl acetate (30 mL), extracted with ethyl acetate (30 mL), dried over anhydrous sodium sulfate, filtered, and concentrated under reduced pressure. The residue was purified by flash chromatography (silica gel, eluting with hexane) to provide the title compound (2 g, 6.30 mmol, 67.1% yield) as colorless oil.

Example 66b 2-(3-bromo-4-(2,6-dimethylphenoxy)phenyl)propane-1,2-diol

To a mixture of Example 66a (0.2 g, 0.630 mmol) in water (10 mL) and tert-butanol (10 mL) was added potassium carbonate (0.261 g, 1.891 mmol), potassium osmate hydrate (4.67 mg, 0.013 mmol) and potassium hexacyanoferrate (III) (0.933 g, 2.84 mmol) at 0° C., and the mixture was stirred at ambient temperature for 48 hours. The mixture was diluted with water (20 mL), extracted with ethyl acetate, dried over anhydrous sodium sulfate, filtered, and concentrated to provide the title compound (0.2 g, 0.199 mmol, 31.6% yield), which was contaminated with Example 66a. This material was used in Example 66c without further purification.

Example 66c

4-[5-(1,2-dihydroxypropan-2-yl)-2-(2,6-dimethyl-phenoxy)phenyl]-N-ethyl-6-methyl-7-oxo-6,7-di-hydro-1H-pyrrolo[2,3-c]pyridine-2-carboxamide A mixture of tris(dibenzylideneacetone)dipalladium (7.82 mg, 8.54 µmol), Example 66b (0.2 g, 0.171 mmol), Example 1h (0.071 g, 0.205 mmol), 1,3,5,7-tetramethyl-6-phenyl-2,4,8-trioxa-6-phosphaadamantane (4.99 mg, 0.017 mmol) and potassium phosphate (0.109 g, 0.512 mmol) in tetrahydrofuran (4 mL) and water (1 mL) was heated in a microwave reactor at 60° C. under nitrogen for 2 hours. After cooling to room temperature, the mixture was filtered through a pad of diatomaceous earth, rinsing with ethyl acetate (30 mL). The filtrate was washed with water (20 mL), dried over anhydrous sodium sulfate, filtered, and concentrated to dryness. The crude product was purified by prep-HPLC (Column: Waters HSS C18, 2.1*50 mm, 1.8 µm; Mobile Phase A: water/10 mmol ammonium carbonate, Mobile Phase B: acetonitrile; Flow rate: 25 mL/min; Gradient: 25% B to 50% B in 5 min, hold 0.5 min; 254 nm), and the fractions collected were concentrated under reduced pressure. The residue was lyophilized to provide the title compound (0.03 g, 0.061 mmol, 35.9% yield). $^1$H NMR (400 MHz, DMSO-d$_6$) δ 12.24 (s, 1H), 8.34 (s, 1H), 7.51 (s, 1H), 7.35-7.25 (m, 2H), 7.15-7.00 (m, 3H), 6.86 (s, 1H), 6.26 (d, J=8.2 Hz, 1H), 4.86 (s, 1H), 4.70 (s, 1H), 3.59 (s, 3H), 3.50-3.20 (m, 4H), 2.00 (s, 6H), 1.39 (s, 3H), 1.16-1.05 (m, 3H). MS (ESI+) m/z 490.5 (M+H)$^+$.

Example 67

4-[5-(2,4-dihydroxybutan-2-yl)-2-(2,6-dimethylphe-noxy)phenyl]-N-ethyl-6-methyl-7-oxo-6,7-dihydro-1H-pyrrolo[2,3-c]pyridine-2-carboxamide Example 67a 2-(3-bromo-4-(2,6-dimethylphenoxy)phenyl)but-3-en-2-ol To a solution of Example 3c (0.5 g, 1.566 mmol) in tetrahydrofuran (10 mL) was added vinylmagnesium bromide (1M in tetrahydrofuran, 1.6 mL) at 0° C., and the mixture was stirred at ambient temperature for 16 hours. The mixture was partitioned between water and ethyl acetate, and extracted with ethyl acetate. The combined extracts were concentrated to dryness and the crude product was purified by flash chromatography (silica gel, ethyl acetate/hexanes) to provide the title compound (0.2 g, 0.576 mmol, 36.8% yield).

Example 67b 3-(3-bromo-4-(2,6-dimethylphenoxy)phenyl)butane-1,3-diol

To a solution of Example 67a (0.4 g, 1.152 mmol) in tetrahydrofuran (5 mL) was added borane-tetrahydrofuran complex (2.304 mL, 2.304 mmol) at 0° C., and the mixture was stirred at 0° C. for 3 hours. To the mixture was added 5 M sodium hydroxide in water (0.276 g, 6.91 mmol) slowly, followed by 30% hydrogen peroxide (1.883 mL, 18.43 mmol), and the mixture was stirred at ambient temperature for 16 hours. The mixture was partitioned between water and ethyl acetate, extracted with ethyl acetate, dried over anhydrous sodium sulfate, filtered, and concentrated to provide the title compound (0.4 g, 95% yield).

Example 67c

4-[5-(2,4-dihydroxybutan-2-yl)-2-(2,6-dimethylphe-noxy)phenyl]-N-ethyl-6-methyl-7-oxo-6,7-dihydro-1H-pyrrolo[2,3-c]pyridine-2-carboxamide Example 67c was prepared according to the procedure used for the preparation of Example 1m, substituting Example 67b for Example 1l. $^1$H NMR (400 MHz, Methanol-d$_4$) δ 7.59 (d, J=2.4 Hz, 1H), 7.38 (s, 1H), 7.28 (dd, J=8.7, 2.4 Hz, 1H), 7.13-6.99 (m, 3H), 6.96 (s, 1H), 6.40 (d, J=8.7 Hz, 1H), 3.72 (s, 3H), 3.67-3.49 (m, 2H), 3.40 (q, J=7.2 Hz, 2H), 2.0-2.1 (m, 8H), 1.56 (s, 3H), 1.21 (t, J=7.2 Hz, 4H). MS (ESI+) m/z 504.5 (M+H)$^+$.

Example 68

4-{5-[(2R)-1,2-dihydroxypropan-2-yl]-2-(2,6-dimethylphenoxy)phenyl}-N-ethyl-6-methyl-7-oxo-6,7-dihydro-1H-pyrrolo[2,3-c]pyridine-2-carboxamide Example 68 was obtained as the first eluting enantiomer from the separation of the two enantiomers of Example 66c by chiral SFC-HPLC (70% (CO$_2$):30% methanol (0.1% trifluoroacetic acid as additive, AD-H column (10 mm×250 mm, 5 μm). $^1$H NMR (400 MHz, DMSO-d$_6$) δ 12.17 (bs, 1H), 8.28 (t, J=5.3 Hz, 1H), 7.45 (d, J=2.3 Hz, 1H), 7.27 (s, 1H), 7.22 (dd, J=8.5, 2.3 Hz, 1H), 7.05 (d, J=7.4 Hz, 2H), 6.98 (dd, J=8.5, 6.3 Hz, 1H), 6.80 (s, 1H), 6.21 (d, J=8.6 Hz, 1H), 4.79 (s, 1H), 4.63 (t, J=5.8 Hz, 1H), 3.53 (s, 3H), 3.34 (m, 1H), 3.20 (dd, J=7.3, 5.4 Hz, 1H), 2.01 (s, 1H), 1.95 (s, 6H), 1.33 (s, 3H), 1.05 (t, J=7.2 Hz, 3H). MS (ESI+) m/z 490.5 (M+H)$^+$. Stereochemistry was assigned arbitrarily.

Example 69

4-{5-[(2S)-1,2-dihydroxypropan-2-yl]-2-(2,6-dimethylphenoxy)phenyl}-N-ethyl-6-methyl-7-oxo-6,7-dihydro-1H-pyrrolo[2,3-c]pyridine-2-carboxamide Example 69 was obtained as the second eluting enantiomer from the separation of the two enantiomers of Example 66c by chiral SFC-HPLC (70% (CO$_2$):30% methanol (0.1% trifluoroacetic acid as additive, AD-H column (10 mm×250 mm, 5 μm). $^1$H NMR (400 MHz, DMSO-d$_6$) δ 12.17 (s, 1H), 8.28 (t, J=5.4 Hz, 1H), 7.45 (d, J=2.4 Hz, 1H), 7.27 (s, 1H), 7.22 (dd, J=8.6, 2.3 Hz, 1H), 7.05 (d, J=7.4 Hz, 2H), 6.99 (dd, J=8.5, 6.3 Hz, 1H), 6.80 (s, 1H), 6.21 (d, J=8.6 Hz, 1H), 4.80 (s, 1H), 4.63 (t, J=5.8 Hz, 1H), 3.53 (s, 3H), 3.34 (m, 1H), 3.24-3.15 (m, 1H), 1.95 (s, 6H), 1.33 (s, 3H), 1.17 (s, 1H), 1.05 (t, J=7.3 Hz, 3H). MS (ESI+) m/z 490.5 (M+H)$^+$. Stereochemistry was assigned arbitrarily.

Example 70

4-{2-[2-(difluoromethyl)-6-methylphenoxy]-5-(2-hydroxypropan-2-yl)phenyl}-N-ethyl-6-methyl-7-oxo-6,7-dihydro-1H-pyrrolo[2,3-c]pyridine-2-carboxamide Example 70a methyl 3-bromo-4-(2-formyl-6-methylphenoxy)benzoate Example 70a was prepared according to the procedure used for the preparation of Example 35b, substituting 2-hydroxy-3-methylbenzaldehyde for Example 35a.

Example 70b methyl 3-bromo-4-(2-(difluoromethyl)-6-methylphenoxy)benzoate

Example 70a (0.56 g, 1.604 mmol) in dichloromethane (20 mL) was treated with DAST (diethylaminosulfur trifluoride) (0.636 mL, 4.81 mmol) at ambient temperature. The reaction mixture was stirred at ambient temperature overnight, and treated with saturated aqueous sodium carbonate. The aqueous layer was extracted with additional dichloromethane three times. The combined organic layers were washed with brine, dried over anhydrous magnesium sulfate, filtered, and concentrated. The residue was purified by flash column chromatography on silica gel eluting with 10% ethyl acetate in heptanes to provide the title compound (0.52 g, 1.401 mmol, 87% yield).

Example 70c 2-(3-bromo-4-(2-(difluoromethyl)-6-methylphenoxy)phenyl)propan-2-ol

Example 70c was prepared according to the procedure used for the preparation of Example 28d, substituting Example 70b for Example 28c.

Example 70d

4-{2-[2-(difluoromethyl)-6-methylphenoxy]-5-(2-hydroxypropan-2-yl)phenyl}-N-ethyl-6-methyl-7-oxo-6,7-dihydro-1H-pyrrolo[2,3-c]pyridine-2-carboxamide Example 70d was prepared according to the procedure used for the preparation of Example 1m, substituting Example 70c for Example 1l. $^1$H NMR (501 MHz, DMSO-d$_6$) δ 12.22 (d, J=2.3 Hz, 1H), 8.33 (t, J=5.4 Hz, 1H), 7.54 (d, J=2.4 Hz, 1H), 7.50 (d, J=7.7 Hz, 1H), 7.46 (d, J=7.5 Hz, 1H), 7.39 (s, 1H), 7.35-7.30 (m, 2H), 6.94 (J=57.4 Hz, 1H), 6.84 (t, J=2.2 Hz, 1H), 6.31 (d, J=8.6 Hz, 1H), 3.57 (s, 3H), 3.26 (qd, J=7.2, 5.3 Hz, 2H), 1.90 (s, 3H), 1.43 (s, 6H), 1.11 (t, J=7.2 Hz, 3H). MS (ESI+) m/z 510.1 (M+H)$^+$.

Example 71

N-tert-butyl-4-{2-[2-(difluoromethyl)-6-methylphenoxy]-5-(2-hydroxypropan-2-yl)phenyl}-6-methyl-7-oxo-6,7-dihydro-1H-pyrrolo[2,3-c]pyridine-2-carboxamide Example 71 was prepared according to the procedure used for the preparation of Example 1m, substituting Example 70c for Example 1l, and substituting Example 32c for Example 1h, respectively. $^1$H NMR (400 MHz, DMSO-d$_6$) δ 12.32 (d, J=2.4 Hz, 1H), 7.82 (s, 1H), 7.69-7.23 (m, 5H), 6.95 (d, J=54.8 Hz, 1H), 6.84 (t, J=2.2 Hz, 1H), 6.30 (d, J=8.6 Hz, 1H), 3.58 (s, 3H), 1.89 (s, 3H), 1.42 (s, 6H), 1.36 (s, 9H). MS (ESI+) m/z 538.1 (M+H)$^+$.

Example 72

4-[2-(4-bromo-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide Example 72a 4-(5-acetyl-2-fluorophenyl)-N-ethyl-6-methyl-7-oxo-6,7-dihydro-1H-pyrrolo[2,3-c]pyridine-2-carboxamide 3'-bromo-4'-fluoroacetophenone (0.126 g, 0.579 mmol), Example 1h (0.2 g, 0.579 mmol), tris(dibenzylideneacetone)dipalladium(0) (0.016 g, 0.017 mmol), 1,3,5,7-tetramethyl-6-phenyl-2,4,8-trioxa-6-phosphaadamantane (0.017 g, 0.058 mmol) and sodium carbonate (0.246 g, 2.317 mmol)

were combined and sparged with argon for 15 minutes. Meanwhile a solution of 4:1 tetrahydrofuran/water (6.0 mL) was sparged with nitrogen for 15 minutes and transferred by syringe into the reaction vessel under argon. The mixture was stirred for 6 hours under argon at 60° C., cooled, and partitioned between water and ethyl acetate. The organic layer was washed with saturated aqueous sodium chloride, dried over anhydrous sodium sulfate, treated with 3-mercaptopropyl functionalized silica gel, filtered and concentrated. Purification by trituration in 1:1 dichloromethane/heptanes (5 mL) provided the title compound as a white powder (0.180 g, 85%).

Example 72b 4-(5-acetyl-2-(4-bromo-2,6-dimethylphenoxy)phenyl)-N-ethyl-6-methyl-7-oxo-6,7-dihydro-1H-pyrrolo[2,3-c]pyridine-2-carboxamide 4-bromo-2,6-dimethylphenol (0.204 g, 1.013 mmol), Example 72a (0.18 g, 0.507 mmol) and cesium carbonate (0.413 g, 1.266 mmol) were combined in dimethyl sulfoxide (1.688 mL) under argon in a sealed tube and heated at 90° C. for 18 hours. The mixture was partitioned between water and ethyl acetate. The organic layer was washed with saturated aqueous sodium chloride, dried over anhydrous sodium sulfate, filtered, and concentrated. Purification by chromatography (silica, 30-60% of 3:1 ethyl acetate/ethanol in heptanes) provided the title compound (0.12 g, 43%).

Example 72c

4-[2-(4-bromo-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide Example 72b (0.03 g, 0.056 mmol) in tetrahydrofuran (1.119 mL) under nitrogen at ambient temperature was treated dropwise with 1.4 M methylmagnesium bromide in tetrahydrofuran (0.160 mL, 0.224 mmol). The mixture was stirred for 16 hours and partitioned between 5% aqueous ammonium chloride and ethyl acetate. The organic layer was washed with saturated aqueous sodium chloride, dried over anhydrous sodium sulfate, filtered, and concentrated. Purification by chromatography (silica, 1-10% methanol in dichloromethane) provided the title compound (0.0018 g, 6%). $^1$H NMR (500 MHz, DMSO-$d_6$) δ 12.25 (s, 1H), 8.32 (t, J=5.3 Hz, 1H), 7.50 (d, J=2.4 Hz, 1H), 7.32-7.28 (m, 2H), 7.19 (d, J=0.8 Hz, 2H), 6.81 (d, J=2.1 Hz, 1H), 6.30 (d, J=8.6 Hz, 1H), 4.97 (s, 1H), 3.58 (s, 3H), 3.24 (qd, J=7.2, 5.3 Hz, 2H), 1.99 (s, 6H), 1.42 (s, 6H), 1.10 (t, J=7.2 Hz, 3H). MS (ESI+) m/z 552 [M+H]$^+$.

Example 73

4-[2-(4-cyano-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide Example 73a 4-(4-acetyl-2-bromophenoxy)-3,5-dimethylbenzonitrile 4-hydroxy-3,5-dimethylbenzonitrile (0.356 g, 2.419 mmol), 3'-bromo-4'-fluoroacetophenone (0.5 g, 2.304 mmol) and cesium carbonate (1.126 g, 3.46 mmol) were combined in dimethyl sulfoxide (7.68 mL) under argon in a sealed tube and heated at 90° C. for 18 hours. The mixture was cooled and partitioned between 5% aqueous sodium bicarbonate and ethyl acetate. The organic layer was washed with saturated aqueous sodium chloride, dried over anhydrous sodium sulfate, filtered, and concentrated. Purification by chromatography (silica, 0-40% ethyl acetate in heptanes) provided the title compound (0.3 g, 51%).

Example 73b 4-(2-bromo-4-(2-hydroxypropan-2-yl)phenoxy)-3,5-dimethylbenzonitrile Example 73a (0.22 g, 0.639 mmol) in tetrahydrofuran (6.39 mL) under nitrogen at 10° C. was treated dropwise with 1.4 M methylmagnesium bromide in tetrahydrofuran (0.913 mL, 1.278 mmol). The mixture was stirred for 1 hour and partitioned between 5% aqueous ammonium chloride and ethyl acetate. The organic layer was washed with saturated aqueous sodium chloride, dried over anhydrous sodium sulfate, filtered and, concentrated. Purification by chromatography (silica, 5-50% ethyl acetate in heptanes) provided the title compound as a white solid (0.21 g, 88%).

Example 73c

4-[2-(4-cyano-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamid Example 73b (0.052 g, 0.145 mmol), Example 1h (0.05 g, 0.145 mmol), tris(dibenzylideneacetone)dipalladium(0) (3.98 mg, 4.35 µmol), 1,3,5,7-tetramethyl-6-phenyl-2,4,8-trioxa-6-phosphaadamantane (4.23 mg, 0.014 mmol) and sodium carbonate (0.061 g, 0.579 mmol) were combined and sparged with argon for 15 minutes. Meanwhile a solution of 4:1 tetrahydrofuran/water (1.5 mL) was sparged with nitrogen for 15 minutes and transferred by syringe into the reaction vessel under argon. The mixture was stirred for 16 hours under argon at 60° C., cooled, and partitioned between water and ethyl acetate. The organic layer was washed with saturated aqueous sodium chloride, dried over anhydrous sodium sulfate, treated with 3-mercaptopropyl functionalized silica gel, filtered, and concentrated. Purification by chromatography (25-60% of 3:1 ethyl acetate/ethanol in heptanes) provided the title compound as a white solid (0.055 g, 73%). $^1$H NMR (400 MHz, DMSO-$d_6$) δ 12.19 (s, 1H), 8.30 (t, J=5.4 Hz, 1H), 7.63 (s, 2H), 7.51 (d, J=2.4 Hz, 1H), 7.30 (m, 2H), 6.80 (s, 1H), 6.29 (d, J=8.6 Hz, 1H), 4.98 (s, 1H), 3.56 (s, 3H), 3.25-3.16 (m, 2H), 2.01 (s, 6H), 1.41 (s, 6H), 1.08 (t, J=7.2 Hz, 3H). MS (ESI+) m/z 499 [M+H].

Example 74

4-{2-[(2,4-dimethylpyridin-3-yl)oxy]-5-(2-hydroxypropan-2-yl)phenyl}-N-ethyl-6-methyl-7-oxo-6,7-dihydro-1H-pyrrolo[2,3-c]pyridine-2-carboxamide Example 74a 1-(3-bromo-4-((2,4-dimethylpyridin-3-yl)oxy)phenyl)ethanone A suspension of 3'-bromo-4'-fluoroacetophenone (1.0128 g, 4.67 mmol), 2,4-dimethylpyridin-3-ol (0.603 g, 4.90 mmol), and cesium carbonate (2.281 g, 7.00 mmol) in dimethyl sulfoxide (15.56 mL) was stirred at about 90° C. overnight. The reaction mixture was partitioned between water and ethyl acetate. The aqueous layer was extracted with ethyl acetate. The combined organic layers were washed with brine, dried over anhydrous magnesium sulfate, filtered, and concentrated. The residue was purified by flash chromatography (10-70% (3:1 ethyl acetate:ethanol):heptanes) to provide the title compound as a colorless oil (1.1753 g, 79%).

Example 74b 2-(3-bromo-4-((2,4-dim ethylpyridin-3-yl)oxy)phenyl)propan-2-ol

To a solution of Example 74a (1.1753 g, 3.67 mmol) in tetrahydrofuran (25 mL) was added methylmagnesium bromide (4.46 mL, 6.24 mmol) dropwise. The reaction mixture was stirred at ambient temperature for 3 hours. The reaction mixture was quenched with saturated ammonium chloride, and extracted with ethyl acetate. The combined organic layers were washed with brine, dried over anhydrous magnesium sulfate, filtered, and concentrated. The residue was purified by flash chromatography (20-80% (3:1 ethyl acetate:ethanol):heptanes) to provide the title compound as a colorless oil that solidified to a white solid upon standing overnight (0.7518 g, 61%).

Example 74c

4-{2-[(2,4-dimethylpyridin-3-yl)oxy]-5-(2-hydroxypropan-2-yl)phenyl}-N-ethyl-6-methyl-7-oxo-6,7-dihydro-1H-pyrrolo[2,3-c]pyridine-2-carboxamide Example 74c (0.0858 g, 61%) was prepared according to the procedure used for the preparation of Example 1m, substituting Example 74b for Example 11. $^1$H NMR (400 MHz, DMSO-$d_6$) δ 12.21 (s, 1H), 8.32 (t, J=5.3 Hz, 1H), 8.17 (d, J=4.9 Hz, 1H), 7.52 (d, J=2.4 Hz, 1H), 7.34 (s, 1H), 7.32 (dd, J=8.6, 2.4 Hz, 1H), 7.16 (d, J=5.0 Hz, 1H), 6.83 (d, J=2.1 Hz, 1H), 6.29 (d, J=8.6 Hz, 1H), 4.99 (s, 1H), 3.58 (s, 3H), 3.31-3.19 (m, 2H), 2.18 (s, 3H), 2.04 (s, 3H), 1.43 (s, 6H), 1.10 (t, J=7.2 Hz, 3H). MS (ESI+) m/z 524.2 (M+H)$^+$.

Example 75

N-(bicyclo[1.1.1]pentan-1-yl)-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide Example 75a ethyl 6-methyl-7-oxo-4-(4,4,5,5-tetramethyl-1,3,2-dioxaborolan-2-yl)-1-tosyl-6,7-dihydro-1H-pyrrolo[2,3-c]pyridine-2-carboxylate Example 75a was prepared according to the procedure used for the preparation of Example 1h, substituting Example 1f for Example 1g.

Example 75b ethyl 4-(2-(4-fluoro-2,6-dimethylphenoxy)-5-(2-hydroxypropan-2-yl)phenyl)-6-methyl-7-oxo-1-tosyl-6,7-dihydro-1H-pyrrolo[2,3-c]pyridine-2-carboxylate A flask charged with Example 75a (3.506 g, 7.01 mmol), cesium carbonate (3.11 g, 9.55 mmol), tris(dibenzylideneacetone)dipalladium(0) (65 mg, 0.071 mmol) and 1,3,5,7-tetramethyl-6-phenyl-2,4,8-trioxa-6-phosphaadamantane (84 mg, 0.287 mmol) was sealed and purged with nitrogen for 15 minutes, followed by addition of a degassed solution of Example 35c (2.056 g, 5.82 mmol) in tetrahydrofuran (40.0 mL)/water (10 mL). The mixture was heated at 60° C. for 5 hours. The reaction mixture was partitioned between water and ethyl acetate. The organic phase was dried over anhydrous sodium sulfate. After filtration and solvent removal, the residues were chromatographed on a 80 g silica cartridge eluting with 0-100% ethyl acetate/heptanes to provide 3.21 g (85%) of the title compound.

Example 75c 4-(2-(4-fluoro-2,6-dimethylphenoxy)-5-(2-hydroxypropan-2-yl)phenyl)-6-methyl-7-oxo-6,7-dihydro-1H-pyrrolo[2,3-c]pyridine-2-carboxylic acid A mixture of Example 75b (3.21 g, 4.96 mmol) and lithium hydroxide monohydrate (2.13 g, 50.8 mmol) in a mixture of 1,4-dioxane (75 mL) and water (25 mL) was heated at 70° C. for 2 hours, then cooled to ambient temperature and adjusted to pH 2-3 with 1 M HCl. The mixture was diluted with 400 mL of ice water, extracted with 2×200 mL of methyl tert-butyl ether. The combined organics were dried over anhydrous sodium sulfate. After filtration and solvent removal, the residues were chromatographed on a 40 g HP silica column eluting with 10-100% 3:1 ethyl acetate:ethanol/heptanes to provide 1.95 g (85%) of the title compound.

Example 75d

N-(bicyclo[1.1.1]pentan-1-yl)-4-(2-(4-fluoro-2,6-dimethylphenoxy)-5-(2-hydroxypropan-2-yl)phenyl)-6-methyl-7-oxo-6,7-dihydro-1H-pyrrolo[2,3-c]pyridine-2-carboxamide A mixture of Example 75c (59.4 mg, 0.128 mmol), $N^1$-(ethylimino)methylene)-$N^3$,$N^3$-dimethylpropane-1,3-diamine hydrochloride (36 mg, 0.188 mmol), 1H-benzo[d][1,2,3]triazol-1-ol hydrate (33 mg, 0.215 mmol), bicyclo[1.1.1]pentan-1-amine, hydrochloride (24.7 mg, 0.207 mmol) and 4-methylmorpholine (65 µl, 0.591 mmol) in dichloromethane (4 mL) was stirred for 16 hours at ambient temperature. The mixture was partitioned between aqueous sodium bicarbonate and dichloromethane. The organics were dried over anhydrous sodium sulfate, filtered, and concentrated. The residues were chromatographed (silica gel, 0-10% ammonia saturated methanol/dichloromethane) to provide the title compound (0.045 g, 66% yield). $^1$H NMR (400 MHz, DMSO-$d_6$) δ 12.14 (s, 1H), 8.85 (s, 1H), 7.49 (d, J=2.4 Hz, 2H), 7.31-7.28 (m, 3H), 6.96 (d, J=9.1 Hz, 1H), 6.83 (s, 1H), 6.29 (d, J=8.6 Hz, 1H), 4.96 (s, 1H), 3.57 (s, 3H), 2.42 (s 1H), 2.02 (s, 6H), 1.93 (s, 6H), 1.42 (s, 6H). MS (ESI+) m/z 530.1 (M+H)$^+$.

Example 76

N-tert-butyl-4-[3-(2,6-dimethylphenoxy)-6-(2-hydroxypropan-2-yl)pyridin-2-yl]-6-methyl-7-oxo-6,7-dihydro-1H-pyrrolo[2,3-c]pyridine-2-carboxamide Example 76a methyl 6-bromo-5-(2,6-dimethylphenoxy)picolinate Example 76a was prepared according to the procedure used for the preparation of Example 35b, substituting 2,6- dimethylphenol for Example 35a, and substituting methyl 6-bromo-5-fluoropicolinate for methyl 3-bromo-4-fluorobenzoate, respectively.

Example 76b 2-(6-bromo-5-(2,6-dimethylphenoxy)pyridin-2-yl)propan-2-ol

Example 76b was prepared according to the procedure used for the preparation of Example 28d, substituting Example 76a for Example 28c.

Example 76c

N-tert-butyl-4-[3-(2,6-dimethylphenoxy)-6-(2-hydroxypropan-2-yl)pyridin-2-yl]-6-methyl-7-oxo-6,7-dihydro-1H-pyrrolo[2,3-c]pyridine-2-carboxamide Example 76c was prepared according to the procedure used for the preparation of Example 37, substituting Example 76b for Example 29b. $^1$H NMR (501 MHz, DMSO-d$_6$) δ 12.23 (d, J=2.4 Hz, 1H), 8.32 (t, J=5.3 Hz, 1H), 7.82 (s, 1H), 7.66-7.57 (m, 2H), 7.57-7.49 (m, 2H), 7.45 (d, J=8.6 Hz, 1H), 7.22 (d, J=2.3 Hz, 1H), 7.16 (d, J=7.4 Hz, 1H), 7.10 (dd, J=8.4, 6.4 Hz, 1H), 6.74 (d, J=8.6 Hz, 1H), 3.61 (s, 3H), 2.03 (s, 3H), 1.48 (s, 6H), 1.37 (s, 9H). MS (ESI+) m/z 503.2 (M+H)$^+$.

Example 77

4-[3-(2,6-dimethylphenoxy)-6-(2-hydroxypropan-2-yl)pyridin-2-yl]-N-ethyl-6-methyl-7-oxo-6,7-dihydro-1H-pyrrolo[2,3-c]pyridine-2-carboxamide The trifluoroacetic acid salt of Example 77 was prepared according to the procedure used for the preparation of Example 1m, substituting Example 76b for Example 11. $^1$H NMR (501 MHz, DMSO-d$_6$) δ 12.23 (d, J=2.4 Hz, 1H), 8.32 (t, J=5.3 Hz, 1H), 7.82 (s, 1H), 7.66-7.57 (m, 2H), 7.57-7.49 (m, 2H), 7.45 (d, J=8.6 Hz, 1H), 7.22 (d, J=2.3 Hz, 1H), 7.16 (d, J=7.4 Hz, 1H), 7.10 (dd, J=8.4, 6.4 Hz, 1H), 6.74 (d, J=8.6 Hz, 1H), 3.61 (s, 3H), 3.27 (qd, J=7.2, 5.2 Hz, 2H), 2.02 (s, 3H), 1.48 (s, 6H), 1.12 (t, J=7.2 Hz, 3H). MS (ESI+) m/z 475.1 (M+H)$^+$.

Example 78

N-ethyl-4-[2-(4-fluoro-2,6-dimethylphenoxy)-5-(1-fluoro-2-hydroxypropan-2-yl)pyridin-3-yl]-6-methyl-7-oxo-6,7-dihydro-1H-pyrrolo[2,3-c]pyridine-2-carboxamide

Example 78a 2-(5-bromo-6-(4-fluoro-2,6-dimethylphenoxy)pyridin-3-yl)-1-fluoropropan-2-ol A solution of Example 43b (0.200 g, 0.565 mmol) and 1-(chloromethyl)-4-fluoro-1,4-diazabicyclo[2.2.2]octane-1,4-diium tetrafluoroborate (0.231 g, 0.652 mmol) in anhydrous acetonitrile (6 mL), was heated at 82° C. in a sealed vial for 68 hours. The mixture was cooled to ambient temperature and partitioned between 50 mL each of saturated aqueous sodium bicarbonate and dichloromethane. The organics were washed twice with water, dried over anhydrous sodium sulfate, filtered, and concentrated. The residue was purified by chromatographed (silica, 0-50% ethyl acetate/heptanes) to provide the title compound (0.052 g, 25%).

Example 78b

N-ethyl-4-(2-(4-fluoro-2,6-dimethylphenoxy)-5-(1-fluoro-2-hydroxypropan-2-yl)pyridin-3-yl)-6-methyl-7-oxo-6,7-dihydro-1H-pyrrolo[2,3-c]pyridine-2-carboxamide Example 78b was prepared according to the procedure used for the preparation of Example 1m, substituting Example 78a for Example 11. $^1$H NMR (400 MHz, DMSO-d$_6$) δ 12.06 (s, 1H), 8.33 (t, J=5.4 Hz, 1H), 8.11 (d, J=2.4 Hz, 1H), 7.96 (d, J=2.4 Hz, 1H), 7.43 (s, 1H), 6.91 (d, J=9.1 Hz, 2H), 6.84 (s, 1H), 5.63 (s, 1H), 4.46 (s, 1H), 4.34 (s, 1H), 3.59 (s, 3H), 3.25 (m, 2H), 1.97 (s, 6H), 1.48 (d, J=2.0 Hz, 3H), 1.10 (t, J=7.2 Hz, 3H). MS (ESI+) m/z=511.2 (M+H)$^+$.

Example 79

N-ethyl-4-[2-(4-fluoro-2,6-dimethylphenoxy)-5-(1,1,1-trifluoro-2-hydroxypropan-2-yl)pyridin-3-yl]-6-methyl-7-oxo-6,7-dihydro-1H-pyrrolo[2,3-c]pyridine-2-carboxamide

Example 79a 5-bromo-6-(4-fluoro-2,6-dimethylphenoxy)nicotinic acid

Example 79a was prepared according to the procedure used for the preparation of Example 3a, substituting methyl 5-bromo-6-chloronicotinate for methyl 3-bromo-4-fluorobenzoate and substituting Example 35a for 2,6-dimethylphenol.

Example 79b 5-bromo-6-(4-fluoro-2,6-dimethylphenoxy)-N-methoxy-N-methylnicotinamide Example 79b was prepared according to the procedure used for the preparation of Example 1j, substituting Example 79a for Example 1i.

Example 79c 1-(5-bromo-6-(4-fluoro-2,6-dimethylphenoxy)pyridin-3-yl)ethanone Example 79c was prepared according to the procedure used for the preparation of Example 1k, substituting Example 79b for Example 1j.

Example 79d 2-(5-bromo-6-(4-fluoro-2,6-dimethylphenoxy)pyridin-3-yl)-1,1,1-trifluoropropan-2-ol A solution of Example 79c (0.585 g, 1.730 mmol) and cesium fluoride (0.284 g, 1.870 mmol) in tetrahydrofuran (12.00 mL) was treated with a solution of trimethyl(trifluoromethyl)silane (2.0 M in tetrahydrofuran, 1.2 mL, 2.400 mmol). The mixture was stirred at ambient temperature for 3 hours and partitioned between ethyl acetate and water. The organics were dried over anhydrous magnesium sulfate, filtered, and concentrated, and the residue purified by chromatography (silica gel, 0-50% ethyl acetate/heptanes) to provide the title compound (0.132 g, 19%).

Example 79e

N-ethyl-4-(2-(4-fluoro-2,6-dimethylphenoxy)-5-(1,1,1-trifluoro-2-hydroxypropan-2-yl)pyridin-3-yl)-6-methyl-7-oxo-6,7-dihydro-1H-pyrrolo[2,3-c]pyridine-2-carboxamide Example 79e was prepared according to the procedure used for the preparation of Example 1m, substituting Example 79d for Example 1l. $^1$H NMR (400 MHz, DMSO-$d_6$) δ 12.33 (s, 1H), 8.33 (t, J=5.4 Hz, 1H), 8.22 (d, J=2.4 Hz, 1H), 8.04 (d, J=2.4 Hz, 1H), 7.45 (s, 1H), 6.92 (d, J=9.1 Hz, 2H), 6.82 (s, 1H), 6.81 (s, 1H), 3.59 (s, 3H), 3.25 (m, 2H), 1.97 (s, 6H), 1.73 (s, 3H), 1.10 (t, J=7.2 Hz, 3H). MS (ESI+) m/z 547.1 (M+H)$^+$.

Example 80

N-ethyl-4-[2-(4-fluoro-2,6-dimethylphenoxy)-5-(1,1,1,3,3,3-hexafluoro-2-hydroxypropan-2-yl)pyridin-3-yl]-6-methyl-7-oxo-6,7-dihydro-1H-pyrrolo[2,3-c]pyridine-2-carboxamide Example 80a (5-bromo-6-(4-fluoro-2,6-dimethylphenoxy)pyridin-3-yl)(1H-imidazol-1-yl)methanone A solution of Example 79a (0.488 g, 1.435 mmol) and di(1H-imidazol-1-yl)methanone (0.282 g, 1.739 mmol) in dichloromethane (10 mL) was stirred overnight at ambient temperature. The mixture was partitioned between pH7 buffer solution and dichloromethane. The organics were dried over anhydrous magnesium sulfate, filtered, and concentrated to provide 0.551 g (98%) of the title compound.

Example 80b 2-(5-bromo-6-(4-fluoro-2,6-dimethylphenoxy)pyridin-3-yl)-1,1,1,3,3,3-hexafluoropropan-2-ol A solution of Example 80a (0.551 g, 1.412 mmol) and cesium fluoride (0.436 g, 2.87 mmol) in tetrahydrofuran (12.00 mL) was treated with a solution of trimethyl(trifluoromethyl)silane, 2.0 M in tetrahydrofuran (2.118 mL, 4.24 mmol). The mixture was stirred at ambient temperature for 90 minutes and partitioned between ethyl acetate and water. The organics were dried over anhydrous magnesium sulfate, filtered, and concentrated. The residue was chromatographed on a 40 g silica cartridge eluting with 0-50% ethyl acetate/heptanes to provide 0.618 g (95%) of the title compound.

Example 80c

N-ethyl-4-[2-(4-fluoro-2,6-dimethylphenoxy)-5-(1,1,1,3,3,3-hexafluoro-2-hydroxypropan-2-yl)pyridin-3-yl]-6-methyl-7-oxo-6,7-dihydro-1H-pyrrolo[2,3-c]pyridine-2-carboxamide Example 80c was prepared according to the procedure used for the preparation of Example 1m, substituting Example 80b for Example 1l. $^1$H NMR (400 MHz, DMSO-$d_6$) δ 12.38 (s, 1H), 9.06 (s, 1H), 8.34 (t, J=5.4 Hz, 1H), 8.32 (d, J=2.4 Hz, 1H), 8.08 (d, J=2.5 Hz, 1H), 6.94 (d, J=9.1 Hz, 2H), 6.80 (s, 1H), 3.59 (s, 3H), 3.26 (m, 2H), 1.97 (s, 6H), 1.10 (t, J=7.2 Hz, 3H). MS (ESI) m/z 601.1 (M+H)$^+$.

Example 81

N-ethyl-4-[2-(2-fluoro-6-methylphenoxy)-5-(2-hydroxypropan-2-yl)phenyl]-6-methyl-7-oxo-6,7-dihydro-1H-pyrrolo[2,3-c]pyridine-2-carboxamide Example 81a methyl 3-bromo-4-(2-fluoro-6-methylphenoxy)benzoate Example 81a was prepared according to the procedure used for the preparation of Example 35b, substituting 2-methyl-6-fluorophenol for Example 35a.

Example 81b

Example 81b was prepared according to the procedure used for the preparation of Example 28d, substituting Example 81a for Example 28c.

Example 81c

N-ethyl-4-[2-(2-fluoro-6-methylphenoxy)-5-(2-hydroxypropan-2-yl)phenyl]-6-methyl-7-oxo-6,7-dihydro-1H-pyrrolo[2,3-c]pyridine-2-carboxamide Example 81c was prepared according to the procedure used for the preparation of Example 1m, substituting Example 81b for Example 1l. $^1$H NMR (400 MHz, DMSO-$d_6$) δ 12.18 (d, J=2.3 Hz, 1H), 8.29 (t, J=5.3 Hz, 1H), 7.49 (d, J=2.4 Hz, 1H), 7.39-7.24 (m, 2H), 7.19-7.03 (m, 2H), 6.82 (d, J=2.3 Hz, 1H), 6.42 (d, J=8.4 Hz, 1H), 3.56 (s, 3H), 3.23 (qd, J=7.2, 5.2 Hz, 4H), 2.09 (s, 3H), 1.41 (s, 6H), 1.08 (t, J=7.2 Hz, 3H). MS (ESI+) m/z 478.1 (M+H)$^+$.

Example 82

N-($d_5$)ethyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide A flask was charged with Example 75c (103 mg, 0.222 mmol), N$^1$-((ethylimino)methylene)-N$^3$,N$^3$-dimethylpropane-1,3-diamine hydrochloride (51 mg, 0.266 mmol), 1H-benzo[d][1,2,3]triazol-1-ol hydrate (41 mg, 0.268 mmol) and 4-methylmorpholine (100 μL, 0.910 mmol) in tetrahydrofuran (4 mL). The flask was fitted with a dry ice condenser and chilled in an ice/water bath. Ethylamine-$d_5$ (1.3 g, 25.9 mmol) from a gas cylinder was streamed into the reaction vessel. The mixture was allowed to warm to ambient temperature while stirring overnight. The mixture was partitioned between ethyl acetate and aqueous sodium bicarbonate, and the organics were dried over anhydrous sodium sulfate, filtered, and concentrated. The residue was chromatographed on a 4 g silica cartridge eluting with 10-100% 3:1 ethyl acetate:ethanol/heptanes to provide 12 mg (11%) of the title compound. $^1$H NMR (400 MHz, DMSO-$d_6$) δ 12.21 (s, 1H), 8.32 (t, J=5.4 Hz, 1H), 7.51 (d, J=2.4 Hz, 1H), 7.37-7.21 (m, 2H), 6.96 (d, J=9.0 Hz, 2H), 6.83 (s, 1H), 6.29

(d, J=8.6 Hz, 1H), 4.96 (s, 1H), 3.58 (s, 3H), 2.00 (s, 6H), 1.42 (s, 6H). MS (ESI+), m/z=497.2 (M+H)$^+$.

Example 83

N-ethyl-4-[2-(4-fluoro-2,6-dimethylphenoxy)-5-(1-fluoro-2-hydroxypropan-2-yl)phenyl]-6-methyl-7-oxo-6,7-dihydro-1H-pyrrolo[2,3-c]pyridine-2-carboxamide

Example 83a 2-(3-bromo-4-(4-fluoro-2,6-dimethylphenoxy)phenyl)-1-fluoropropan-2-ol Example 83a was prepared according to the procedure used for the preparation of Example 78a, substituting Example 35c for Example 43b.

Example 83b

N-ethyl-4-(2-(4-fluoro-2,6-dimethylphenoxy)-5-(1-fluoro-2-hydroxypropan-2-yl)phenyl)-6-methyl-7-oxo-6,7-dihydro-1H-pyrrolo[2,3-c]pyridine-2-carboxamide Example 83b was prepared according to the procedure used for the preparation of Example 1m, substituting Example 83a for Example 1l. $^1$H NMR (501 MHz, DMSO-d$_6$) δ 12.21 (s, 1H), 8.32 (t, J=5.4 Hz, 1H), 7.53 (d, J=2.4 Hz, 1H), 7.34 (m, 1H), 7.33 (s, 1H), 6.97 (d, J=9.1 Hz, 2H), 6.82 (s, 1H), 6.33 (d, J=8.6 Hz, 1H), 5.43 (s, 1H), 4.38 (m, 1H), 4.30 (m, 1H), 3.58 (s, 3H), 3.25 (m, 2H), 2.00 (s, 6H), 1.45 (d, J=2.0 Hz, 3H), 1.10 (t, J=7.2 Hz, 3H). MS (ESI+) m/z 510.1 (M+H)$^+$.

Example 84

4-[2-(4-chloro-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide

Example 84a methyl 3-bromo-4-(4-chloro-2,6-dimethylphenoxy)benzoate 4-chloro-2,6-dimethylphenol (0.672 g, 4.29 mmol), methyl 3-bromo-4-fluorobenzoate (1.0 g, 4.29 mmol) and cesium carbonate (2.097 g, 6.44 mmol) were combined in dimethyl sulfoxide (4.29 mL) under argon in a sealed tube and heated at 80° C. for 3 hours. The mixture was partitioned between water and ethyl acetate. The organic layer was washed with saturated aqueous sodium chloride, dried over anhydrous sodium sulfate, filtered and concentrated. Purification by chromatography (silica, 0-30% ethyl acetate in heptanes) provided the title compound (1.57 g, 93%).

Example 84b 2-(3-bromo-4-(4-chloro-2,6-dimethylphenoxy)phenyl)propan-2-ol

To a solution of Example 84a (0.4 g, 1.082 mmol) in tetrahydrofuran (5.41 mL) under nitrogen at 23° C. was added dropwise methylmagnesium chloride (1.082 mL, 3.25 mmol, 3.0M in diethyl ether). The mixture was stirred for 2 hours at ambient temperature, poured into 5% aqueous ammonium chloride, and partitioned between ethyl acetate and water. The organic layer was washed with saturated aqueous sodium chloride, dried over anhydrous sodium sulfate, filtered, and concentrated. Purification of the resulting residue by chromatography (silica gel, 0-60% ethyl acetate in heptanes) provided the title compound (0.376 g, 81%).

Example 84c

4-[2-(4-chloro-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide Example 1h (0.05 g, 0.145 mmol), Example 84b (0.054 g, 0.145 mmol), tris(dibenzylideneacetone)dipalladium(0) (3.98 mg, 4.35 μmol), 1,3,5,7-tetramethyl-6-phenyl-2,4,8-trioxa-6-phosphaadamantane (4.23 mg, 0.014 mmol) and sodium carbonate (0.061 g, 0.579 mmol) were combined and sparged with argon for 15 minutes. Meanwhile a solution of 4:1 tetrahydrofuran/water (2.0 mL) was sparged with nitrogen for 15 minutes and transferred by syringe into the reaction vessel under argon. The mixture was stirred for 16 hours under argon at 60° C., cooled, and partitioned between ethyl acetate and water. The organic layer was washed with saturated aqueous sodium chloride, dried over anhydrous sodium sulfate, treated with 3-mercaptopropyl functionalized silica gel, filtered, and concentrated. Purification of the resulting residue by chromatography (silica, 25-60% of 3:1 ethyl acetate/ethanol in heptanes) provided the title compound (0.020 g, 25%). $^1$H NMR (500 MHz, DMSO-d$_6$) δ 12.25 (s, 1H), 8.32 (t, J=5.3 Hz, 1H), 7.50 (d, J=2.4 Hz, 1H), 7.32-7.28 (m, 2H), 7.19 (d, J=0.8 Hz, 2H), 6.81 (d, J=2.1 Hz, 1H), 6.30 (d, J=8.6 Hz, 1H), 4.97 (s, 1H), 3.58 (s, 3H), 3.24 (qd, J=7.2, 5.3 Hz, 2H), 1.99 (s, 6H), 1.42 (s, 6H), 1.10 (t, J=7.2 Hz, 3H). MS (ESI+) m/z 508 [M+H]$^+$.

Example 85

N-ethyl-4-{5-(2-hydroxypropan-2-yl)-2-[4-(methanesulfonyl)-2,6-dimethylphenoxy]phenyl}-6-methyl-7-oxo-6,7-dihydro-1H-pyrrolo[2,3-c]pyridine-2-carboxamide

Example 85a methyl 3-bromo-4-(2,6-dimethyl-4-(methylsulfonyl)phenoxy)benzoate 2,6-dimethyl-4-(methylsulfonyl)phenol (0.307 g, 1.533 mmol), methyl 3-bromo-4-fluorobenzoate (0.375 g, 1.609 mmol) and cesium carbonate (0.749 g, 2.299 mmol) were combined in dimethyl sulfoxide (1.533 mL) under argon in a sealed tube and heated at 100° C. for 24 hours. The mixture was partitioned between water and ethyl acetate. The organic layer was washed with saturated aqueous sodium chloride, dried over anhydrous sodium sulfate, filtered, and concentrated. Purification of the resulting residue by chromatography (silica, 20-40% of 3:1 ethyl acetate/ethanol in heptanes) provided material that was 80-90% pure. This material was triturated in 1:1 ethyl acetate/heptane to provide the title compound (0.29 g, 44%).

Example 85b 2-(3-bromo-4-(2,6-dimethyl-4-(methylsulfonyl)phenoxy)phenyl)propan-2-ol To a solution of Example 85a (0.289 g, 0.699 mmol) in tetrahydrofuran (3.50 mL) under nitrogen at ambient temperature was added dropwise methylmagnesium chloride (0.699 mL, 2.098 mmol, 3.0 M in tetrahydrofuran). The mixture was stirred for 2 hours at ambient temperature, poured into 5% aqueous ammonium chloride and partitioned between ethyl acetate and water. The organic layer was washed with saturated aqueous sodium chloride, dried over anhydrous sodium sulfate, filtered, and concentrated. Purification of the resulting residue by chromatography (silica gel, 0-50% ethyl acetate in heptanes) provided the title compound as a tacky white solid (0.162 g, 47%).

Example 85c

N-ethyl-4-{5-(2-hydroxypropan-2-yl)-2-[4-(methanesulfonyl)-2,6-dimethylphenoxy]phenyl}-6-methyl-7-oxo-6,7-dihydro-1H-pyrrolo[2,3-c]pyridine-2-carboxamide Example 1h (0.05 g, 0.145 mmol), Example 85b (0.060 g, 0.145 mmol), tris(dibenzylideneacetone)dipalladium(0) (3.98 mg, 4.35 µmol), 1,3,5,7-tetramethyl-6-phenyl-2,4,8-trioxa-6-phosphaadamantane (4.23 mg, 0.014 mmol) and sodium carbonate (0.061 g, 0.579 mmol) were combined and sparged with argon for 15 minutes. Meanwhile a solution of 4:1 tetrahydrofuran/water (2.0 mL) was sparged with nitrogen for 15 minutes and transferred by syringe into the reaction vessel under argon. The mixture was stirred for 16 hours under argon at 60° C., cooled to ambient temperature, and partitioned between ethyl acetate and water. The organic layer was washed with saturated aqueous sodium chloride, dried over anhydrous sodium sulfate, treated with 3-mercaptopropyl functionalized silica gel, filtered and concentrated. Purification by chromatography (silica, 25-60% of 3:1 ethyl acetate/ethanol in heptanes) provided the title compound as a white solid (0.070 g, 82%). $^1$H NMR (400 MHz, DMSO-$d_6$) δ 12.20 (s, 1H), 8.31 (t, J=5.3 Hz, 1H), 7.66 (s, 2H), 7.52 (d, J=2.4 Hz, 1H), 7.33 (s, 1H), 7.30 (dd, J=8.6, 2.4 Hz, 1H), 6.82 (d, J=1.8 Hz, 1H), 6.31 (d, J=8.6 Hz, 1H), 4.98 (s, 1H), 3.56 (s, 3H), 3.25-3.18 (m, 2H), 3.15 (s, 3H), 2.07 (s, 6H), 1.41 (s, 6H), 1.08 (t, J=7.2 Hz, 3H). MS (ESI+) m/z 552 [M+H]$^+$.

Example 86

N-ethyl-4-[2-(4-fluoro-2,6-dimethylphenoxy)-5-(1,1,1-trifluoro-2-hydroxypropan-2-yl)phenyl]-6-methyl-7-oxo-6,7-dihydro-1H-pyrrolo[2,3-c]pyridine-2-carboxamide

Example 86a 3-bromo-4-(4-fluoro-2,6-dimethylphenoxy)benzoic acid

A solution of Example 35b (2.0 g, 5.66 mmol) and lithium hydroxide hydrate (0.951 g, 22.65 mmol) in a mixture of methanol (3.79 mL), tetrahydrofuran (3.79 mL), and water (1.897 mL) was stirred for 90 minutes. The mixture was concentrated, then diluted with 15 mL of water and acidified to pH 2 with 2M HCl. The precipitate was dried in vacuum oven to provide 1.77 g (92%) of the title compound.

Example 86b 3-bromo-4-(4-fluoro-2,6-dimethylphenoxy)-N-methoxy-N-methylbenzamide Example 86b was prepared according to the procedure used for the preparation of Example 1j, substituting Example 86a for Example 1i.

Example 86c 1-(3-bromo-4-(4-fluoro-2,6-dimethylphenoxy)phenyl)ethanone

Example 86c was prepared according to the procedure used for the preparation of Example 1k, substituting Example 86b for Example 1j.

Example 86d 2-(3-bromo-4-(4-fluoro-2,6-dimethylphenoxy)phenyl)-1,1,1-trifluoropropan-2-ol Example 86d was prepared according to the procedure used for the preparation of Example 79d, substituting Example 86c for Example 79c.

Example 86e

N-ethyl-4-(2-(4-fluoro-2,6-dimethylphenoxy)-5-(1,1,1-trifluoro-2-hydroxypropan-2-yl)phenyl)-6-methyl-7-oxo-6,7-dihydro-1H-pyrrolo[2,3-c]pyridine-2-carboxamide Example 86e was prepared according to the procedure used for the preparation of Example 1m, substituting Example 86d for Example 1l. $^1$H NMR (501 MHz, DMSO-$d_6$) δ 12.12 (s, 1H), 8.34 (t, J=5.4 Hz, 1H), 7.62 (d, J=2.4 Hz, 1H), 7.44 (dd, J=8.7, 2.4 Hz, 1H), 7.34 (s, 1H), 6.98 (d, J=9.0 Hz, 2H), 6.80 (s, 1H), 6.58 (s, 1H), 6.40 (d, J=8.7 Hz, 1H), 3.58 (s, 3H), 3.25 (qd, J=7.2, 5.3 Hz, 2H), 2.00 (s, 6H), 1.68 (s, 3H), 1.10 (t, J=7.2 Hz, 3H). MS (ESI) M/Z 544.1 (M+H)$^+$.

Example 87

N-tert-butyl-4-[2-(4-fluoro-2,6-dimethylphenoxy)-5-(1-fluoro-2-hydroxypropan-2-yl)phenyl]-6-methyl-7-oxo-6,7-dihydro-1H-pyrrolo[2,3-c]pyridine-2-carboxamide Example 32c (0.05 g, 0.134 mmol), Example 83a (0.050 g, 0.134 mmol), tris(dibenzylideneacetone)dipalladium(0) (3.68 mg, 4.02 µmol), 1,3,5,7-tetramethyl-6-phenyl-2,4,8-trioxa-6-phosphaadamantane (3.92 mg, 0.013 mmol) and sodium carbonate (0.057 g, 0.536 mmol) were combined and sparged with argon for 15 minutes. Meanwhile a solution of 4:1 tetrahydrofuran/water (2.0 mL) was sparged with nitrogen for 15 minutes and transferred by syringe into the reaction vessel under argon. The mixture was stirred for 3 hours under argon at 60° C., cooled, and partitioned between ethyl acetate and water. The organic layer was washed with saturated aqueous sodium chloride, dried over anhydrous sodium sulfate, treated with 3-mercaptopropyl functional-

113 ized silica gel, filtered, and concentrated. Purification of the resulting residue by chromatography (silica, 25-60% of 3:1 ethyl acetate/ethanol in heptanes) provided the title compound as a white solid (0.0491 g, 62%). $^1$H NMR (400 MHz, DMSO-$d_6$) δ 12.32 (s, 1H), 7.82 (s, 1H), 7.52 (d, J=2.4 Hz, 1H), 7.36-7.27 (m, 2H), 6.95 (d, J=9.1 Hz, 2H), 6.80 (d, J=2.0 Hz, 1H), 6.31 (d, J=8.6 Hz, 1H), 5.42 (s, 1H), 4.42-4.34 (m, 1H), 4.29-4.23 (m, 1H), 3.57 (s, 3H), 1.98 (s, 6H), 1.43 (d, J=2.0 Hz, 3H), 1.33 (s, 9H). MS (ESI+) m/z 538 [M+H].

Example 88

4-[2-(4-chloro-2,6-dimethylphenoxy)-5-(1-fluoro-2-hydroxypropan-2-yl)phenyl]-N-ethyl-6-methyl-7-oxo-6,7-dihydro-1H-pyrrolo[2,3-c]pyridine-2-carboxamide

Example 88a 2-(3-bromo-4-(4-chloro-2,6-dimethylphenoxy)phenyl)-1-fluoropropan-2-ol A solution of Example 84b (0.3 g, 0.812 mmol) and 1-(chloromethyl)-4-fluoro-1,4-diazabicyclo[2.2.2]octane-1,4-diium tetrafluoroborate (0.316 g, 0.893 mmol) in acetonitrile (8.12 mL) under argon in a sealed tube was heated at 80° C. for 30 minutes. The reaction mixture was cooled and partitioned between ethyl acetate and 5% aqueous sodium bicarbonate. The organic layer was washed with saturated aqueous sodium chloride, dried over anhydrous sodium sulfate, filtered, and concentrated. Purification by chromatography (silica, 5-35% ethyl acetate in heptanes) provided the title compound as a viscous oil that solidified upon standing (0.2 g, 64%).

Example 88b

4-[2-(4-chloro-2,6-dimethylphenoxy)-5-(1-fluoro-2-hydroxypropan-2-yl)phenyl]-N-ethyl-6-methyl-7-oxo-6,7-dihydro-1H-pyrrolo[2,3-c]pyridine-2-carboxamide Example 1h (0.05 g, 0.145 mmol), Example 88a (0.056 g, 0.145 mmol), tris(dibenzylideneacetone)dipalladium(0) (3.98 mg, 4.35 μmol), 1,3,5,7-tetramethyl-6-phenyl-2,4,8-trioxa-6-phosphaadamantane (4.23 mg, 0.014 mmol) and sodium carbonate (0.061 g, 0.579 mmol) were combined and sparged with argon for 15 minutes. Meanwhile a solution of 4:1 tetrahydrofuran/water (2.0 mL) was sparged with nitrogen for 15 minutes and transferred by syringe into the reaction vessel under argon. The mixture was stirred for 18 hours under argon at 60° C., cooled, and partitioned between ethyl acetate and water. The organic layer was washed with saturated aqueous sodium chloride, dried over anhydrous sodium sulfate, treated with 3-mercaptopropyl functionalized silica gel, filtered and concentrated. Purification of the resulting residue by chromatography (silica, 25-60% of 3:1 ethyl acetate/ethanol in heptanes) provided the title compound as a white solid (0.06 g, 79%). $^1$H NMR (500 MHz, DMSO-$d_6$) δ 12.25 (s, 1H), 8.38-8.30 (m, 1H), 7.55 (d, J=2.4 Hz, 1H), 7.36 (d, J=9.0 Hz, 2H), 7.23 (t, J=0.8 Hz, 2H), 6.84 (d, J=1.8 Hz, 1H), 6.37 (d, J=8.6 Hz, 1H), 5.47 (s, 1H), 4.44-4.38 (m, 1H), 4.35-4.28 (m, 1H), 3.60 (s, 3H), 3.27 (qd, J=7.2, 5.3 Hz, 2H), 2.01 (s, 6H), 1.47 (d, J=2.0 Hz, 3H), 1.12 (t, J=7.3 Hz, 3H). MS (ESI+) m/z 526 [M+H]$^+$.

Example 89

4-[2-(2,4-difluorophenyl)-5-(2-hydroxypropan-2-yl)pyridin-3-yl]-N-ethyl-6-methyl-7-oxo-6,7-dihydro-1H-pyrrolo[2,3-c]pyridine-2-carboxamide

Example 89a

Methyl 5-chloro-6-(2,4-difluorophenyl)nicotinate 2-(2,4-Difluorophenyl)-4,4,5,5-tetramethyl-1,3,2-dioxaborolane (1.0095 g, 4.21 mmol), methyl 5,6-dichloronicotinate (0.953 g, 4.63 mmol), sodium carbonate (1.560 g, 14.72 mmol), tris(dibenylidene acetone)dipalladium (0) (0.193 g, 0.210 mmol), and 1,3,5,7-tetramethyl-6-phenyl-2,4,8-trioxa-6-phosphaadamantane (0.209 g, 0.715 mmol) were flow purged with nitrogen for 1 hour. Degassed tetrahydrofuran (11.21 mL) and water (2.80 mL) were added. The reaction mixture was heated at 60° C. for 6 hours. The reaction mixture was cooled to ambient temperature and partitioned between ethyl acetate and water. The organic layer was washed with brine, dried over anhydrous magnesium sulfate, filtered, and concentrated. The residue was purified by flash chromatography (10% ethyl acetate:heptanes to 50% ethyl acetate:heptanes over 20 minutes). The collected fractions were concentrated. The residue was purified by flash chromatography (100% $CH_2Cl_2$ over 15 minutes) to provide the title compound as a white solid (0.8605 g, 72% yield).

Example 89b 2-(5-chloro-6-(2,4-difluorophenyl)pyridin-3-yl)propan-2-ol

To a solution of Example 89a (0.2061 g, 0.727 mmol) in tetrahydrofuran (4.38 mL) was added methylmagnesium bromide (1.557 mL, 2.180 mmol) dropwise. The reaction mixture was stirred at ambient temperature for about 3 hours. The reaction mixture was quenched with saturated ammonium chloride, and extracted with ethyl acetate. The combined organic layers were washed with brine, dried over anhydrous magnesium sulfate, filtered, and concentrated. The residue was purified by flash chromatography (20-60% ethyl acetate/heptanes) to provide the title compound as a colorless oil that solidified to a white solid upon standing overnight (0.1817 g, 88% yield).

Example 89c

4-[2-(2,4-difluorophenyl)-5-(2-hydroxypropan-2-yl)pyridin-3-yl]-N-ethyl-6-methyl-7-oxo-6,7-dihydro-1H-pyrrolo[2,3-c]pyridine-2-carboxamide Example 89c (0.0319 g, 22%) was prepared according to the procedure used for the preparation of Example 1m, substituting Example 89b for Example 1l. $^1$H NMR (500 MHz, DMSO-$d_6$) δ 12.29-12.15 (m, 1H), 8.81 (d, J=2.3 Hz, 1H), 8.30-8.23 (m, 1H), 7.95 (d, J=2.3 Hz, 1H), 7.54-7.45 (m, 1H), 7.13-7.01 (m, 2H), 7.02 (s, 1H), 6.52 (d, J=1.7 Hz, 1H), 5.38 (s, 1H), 3.42 (s, 3H), 3.24 (qd, J=7.2, 5.3 Hz, 2H), 1.56 (s, 6H), 1.11 (t, J=7.2 Hz, 3H). MS (ESI+) m/z 467.2 (M+H)$^+$.

Example 90

N-tert-butyl-4-{5-(2-hydroxypropan-2-yl)-2-[4-(methanesulfonyl)-2,6-dimethylphenoxy]phenyl}-6-methyl-7-oxo-6,7-dihydro-1H-pyrrolo[2,3-c]pyridine-2-carboxamide Example 32c (0.04 g, 0.107 mmol), Example 85b (0.044 g, 0.107 mmol), tris(dibenzylideneacetone)dipalladium(0) (2.94 mg, 3.21 µmol), 1,3,5,7-tetramethyl-6-phenyl-2,4,8-trioxa-6-phosphaadamantane (3.13 mg, 10.72 µmol) and sodium carbonate (0.045 g, 0.429 mmol) were combined and sparged with argon for 15 minutes. Meanwhile a solution of 4:1 tetrahydrofuran/water (1.4 mL) was sparged with nitrogen for 15 minutes and transferred by syringe into the reaction vessel under argon. The mixture was stirred for 4 hours under argon at 60° C., cooled, and partitioned between ethyl acetate and water. The organic layer was washed with saturated aqueous sodium chloride, dried over anhydrous sodium sulfate, treated with 3-mercaptopropyl functionalized silica gel, filtered, and concentrated. Purification of the residue by chromatography (silica, 25-60% of 3:1 ethyl acetate/ethanol in heptanes) provided the title compound (0.056 g, 88%). $^1$H NMR (400 MHz, DMSO-$d_6$) δ 12.34 (s, 1H), 7.84 (s, 1H), 7.69 (s, 2H), 7.54 (d, J=2.4 Hz, 1H), 7.35 (s, 1H), 7.31 (dd, J=8.5, 2.4 Hz, 1H), 6.84 (d, J=1.8 Hz, 1H), 6.32 (d, J=8.5 Hz, 1H), 5.01 (s, 1H), 3.59 (s, 3H), 3.17 (s, 3H), 2.09 (s, 6H), 1.43 (s, 6H), 1.35 (s, 9H). MS (ESI+) m/z 580 [M+H]$^+$.

Example 91

N-ethyl-4-[2-(3-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide

Example 91a methyl 6-(3-amino-2,6-dimethylphenoxy)-5-bromonicotinate

The mixture of methyl 5-bromo-6-fluoronicotinate (900 mg, 3.85 mmol), Example 99d (528 mg, 3.85 mmol) and cesium carbonate (2506 mg, 7.69 mmol) in dimethyl sulfoxide (12 mL) was stirred at 65° C. for 2 hours. The reaction mixture was partitioned between water (80 mL) and ethyl acetate (150 mL). The aqueous layer was extracted with ethyl acetate once more and the combined organic layers were washed with brine, dried over anhydrous sodium sulfate, filtered, and concentrated. The residue was purified by column chromatography (silica gel, 20% to 50% ethyl acetate in petroleum ether) to provide the title compound (365 mg, 0.831 mmol, 21.62% yield).

Example 91b methyl 5-bromo-6-(3-fluoro-2,6-dimethylphenoxy)nicotinate

Example 91b was prepared according to the procedure used for the preparation of Example 104a, substituting Example 91a for Example 99e.

Example 91c 2-(5-bromo-6-(3-fluoro-2,6-dimethylphenoxy)pyridin-3-yl)propan-2-ol Example 91c was prepared according to the procedure used for the preparation of Example 28d, substituting Example 91b for Example 28c.

Example 91d

N-ethyl-4-[2-(3-fluoro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide Example 91d was prepared according to the procedure used for the preparation of Example 1m, substituting Example 91c for Example 1l. $^1$H NMR (400 MHz, Methanol-$d_4$) δ 8.14 (s, 1H), 8.08 (s, 1H), 7.47 (s, 1H), 7.06 (d, J=7.0 Hz, 1H), 6.97 (s, 1H), 6.87 (t, J=8.8 Hz, 1H), 3.74 (s, 3H), 3.43 (d, J=6.9 Hz, 2H), 2.02 (s, 3H), 1.99 (s, 3H), 1.61 (s, 6H), 1.24 (t, J=6.9 Hz, 3H). MS (ESI+) m/z 493 (M+H)$^+$.

Example 92

N-tert-butyl-4-{5-(2-hydroxypropan-2-yl)-2-[4-(methanesulfonyl)-2,6-dimethylphenoxy]pyridin-3-yl}-6-methyl-7-oxo-6,7-dihydro-1H-pyrrolo[2,3-c]pyridine-2-carboxamide

Example 92a methyl 5-bromo-6-(2,6-dimethyl-4-(methylsulfonyl)phenoxy)nicotinate 2,6-dimethyl-4-(methylsulfonyl)phenol (0.420 g, 2.096 mmol), methyl 5-bromo-6-chloronicotinate (0.5 g, 1.996 mmol) and cesium carbonate (0.976 g, 2.99 mmol) were combined in dimethyl sulfoxide (4.0 mL) under argon in a sealed tube and stirred at 80° C. for 4 hours. The mixture was cooled, diluted with 100 mL of water and stirred for 15 minutes. The solid was collected by filtration, and dried to constant mass to provide the title compound as a tan solid (0.62 g, 75%).

Example 92b 2-(5-bromo-6-(2,6-dimethyl-4-(methylsulfonyl)phenoxy)pyridin-3-yl)propan-2-ol To a solution of Example 92a (0.62 g, 1.497 mmol) in tetrahydrofuran (7.48 mL) under nitrogen at ambient temperature was added dropwise methylmagnesium chloride (1.497 mL, 4.49 mmol, 3.0M in tetrahydrofuran). The mixture was stirred for 2 hours at ambient temperature, poured into 5% aqueous ammonium chloride and partitioned between ethyl acetate and water. The organic layer was washed with saturated aqueous sodium chloride, dried over anhydrous sodium sulfate, filtered, and concentrated. Purification of the residue by chromatography (silica gel, 0-50% ethyl acetate in heptanes) provided the title compound 1 (0.17 g, 27%).

Example 92c

N-tert-butyl-4-{5-(2-hydroxypropan-2-yl)-2-[4-(methanesulfonyl)-2,6-dimethylphenoxy]pyridin-3-yl}-6-methyl-7-oxo-6,7-dihydro-1H-pyrrolo[2,3-c]pyridine-2-carboxamide Example 32c (0.045 g, 0.121 mmol), Example 92b (0.05 g, 0.121 mmol), tris(dibenzylideneacetone)dipalladium(0) (3.32 mg, 3.62 µmol), 1,3,5,7-tetramethyl-6-phenyl-2,4,8-trioxa-6-phosphaadamantane (3.53 mg, 0.012 mmol) and sodium carbonate (0.051 g, 0.483 mmol) were combined and sparged with argon for 15 minutes. Meanwhile a solution of 4:1 tetrahydrofuran/water (1.8 mL) was sparged with nitrogen for 15 minutes and transferred by syringe into the reaction vessel under argon. The mixture was stirred for 4 hours under argon at 60° C., cooled, and partitioned between ethyl acetate and water. The organic layer was washed with saturated aqueous sodium chloride, dried over anhydrous sodium sulfate, treated with 3-mercaptopropyl functionalized silica gel, filtered, and concentrated. Purification by chromatography (silica, 25-60% of 3:1 ethyl acetate/ethanol in heptanes) provided the title compound (0.065 g, 90%). $^1$H NMR (400 MHz, DMSO-$d_6$) δ 12.42 (s, 1H), 8.07 (d, J=2.4 Hz, 1H), 7.97 (d, J=2.4 Hz, 1H), 7.84 (s, 1H), 7.64 (s, 2H), 7.44 (s, 1H), 6.85 (d, J=1.9 Hz, 1H), 5.19 (s, 1H), 3.58 (s, 3H), 3.16 (s, 3H), 2.05 (s, 6H), 1.44 (s, 6H), 1.34 (s, 9H). MS (ESI+) m/z 581 [M+H]$^+$.

Example 93

N-ethyl-4-{5-(2-hydroxypropan-2-yl)-2-[4-(methanesulfonyl)-2,6-dimethylphenoxy]pyridin-3-yl}-6-methyl-7-oxo-6,7-dihydro-1H-pyrrolo[2,3-c]pyridine-2-carboxamide Example 1h (0.042 g, 0.121 mmol), Example 92b (0.05 g, 0.121 mmol), tris(dibenzylideneacetone)dipalladium(0) (3.32 mg, 3.62 µmol), 1,3,5,7-tetramethyl-6-phenyl-2,4,8-trioxa-6-phosphaadamantane (3.53 mg, 0.012 mmol) and sodium carbonate (0.051 g, 0.483 mmol) were combined and sparged with argon for 15 minutes. Meanwhile a solution of 4:1 tetrahydrofuran/water (2.0 mL) was sparged with nitrogen for 15 minutes and transferred by syringe into the reaction vessel under argon. The mixture was stirred for 4 hours under argon at 60° C., cooled, and partitioned between ethyl acetate and water. The organic layer was washed with saturated aqueous sodium chloride, dried over anhydrous sodium sulfate, treated with 3-mercaptopropyl functionalized silica gel, filtered, and concentrated. Purification of the residue by chromatography (silica, 25-60% of 3:1 ethyl acetate/ethanol in heptanes) provided the title compound as a white solid (0.060, 87%). $^1$H NMR (400 MHz, DMSO-$d_6$) δ 12.35-12.26 (m, 1H), 8.31 (t, J=5.3 Hz, 1H), 8.08 (d, J=2.4 Hz, 1H), 7.96 (d, J=2.4 Hz, 1H), 7.63 (s, 2H), 7.44 (s, 1H), 6.84 (d, J=1.8 Hz, 1H), 5.18 (s, 1H), 3.57 (s, 3H), 3.27-3.19 (m, 2H), 3.16 (s, 3H), 2.05 (s, 6H), 1.45 (s, 6H), 1.09 (t, J=7.2 Hz, 3H). MS (ESI+) m/z 553 [M+H]$^+$.

Example 94

4-[2-(4-chloro-2,6-dimethylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide

Example 94a methyl 5-bromo-6-(4-chloro-2,6-dimethylphenoxy)nicotinate

Methyl 5-bromo-6-chloronicotinate (1.50 g, 6.00 mmol), 4-chloro-2,6-dimethylphenol (0.940 g, 6.00 mmol), and cesium carbonate (2.93 g, 9.00 mmol) were combined in dimethyl sulfoxide (6 mL). The reaction mixture was heated at 60° C. for 2 hours, cooled to ambient temperature and diluted with water. The resulting precipitate was collected by filtration, washed with water, and dried to provide the title compound (2.01 g, 90%).

Example 94b 2-(5-bromo-6-(4-chloro-2,6-dimethylphenoxy)pyridin-3-yl)propan-2-ol To a solution of Example 94a (2.00 g, 5.40 mmol) in tetrahydrofuran (15 mL) was added 3M methylmagnesium chloride in tetrahydrofuran (5.40 mL, 16.2 mmol) at 0° C. The reaction mixture was stirred at ambient temperature for 2 hours, treated with 5% aqueous ammonium chloride carefully, and partitioned with ethyl acetate and water. The organic layer was washed with saturated aqueous sodium chloride, dried with anhydrous sodium sulfate, filtered, and concentrated. The residue was purified by flash chromatography (silica gel, 20-40% ethyl acetate in heptanes) to provide the title compound (1.01 g, 51%).

Example 94c

4-[2-(4-chloro-2,6-dimethylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide Example 94c (38 mg, 75%) was prepared according to the procedure used for the preparation of Example 1m, substituting Example 94b for Example 1l. $^1$H NMR (500 MHz, DMSO-$d_6$) δ 12.30 (s, 1H), 8.33 (t, J=5.4 Hz, 1H), 8.09 (d, J=2.4 Hz, 1H), 7.94 (d, J=2.5 Hz, 1H), 7.42 (s, 1H), 7.14 (s, 2H), 6.84 (s, 1H), 5.18 (s, 1H), 3.59 (s, 3H), 3.30-3.20 (m, 2H), 1.96 (s, 6H), 1.46 (s, 6H), 1.10 (t, J=7.2 Hz, 3H). MS (ESI+) m/z 509 (M+H)$^+$.

Example 95

N-tert-butyl-4-[2-(4-chloro-2,6-dimethylphenoxy)-5-(2-hydroxypropan-2-yl)pyridin-3-yl]-6-methyl-7-oxo-6,7-dihydro-1H-pyrrolo[2,3-c]pyridine-2-carboxamide Example 95 (47 mg, 88%) was prepared according to the procedure used for the preparation of Example 37, substituting Example 94b for Example 29b. $^1$H NMR (500 MHz, DMSO-$d_6$) δ 12.41 (s, 1H), 8.08 (d, J=2.4 Hz, 1H), 7.94 (d, J=2.4 Hz, 1H), 7.85 (s, 1H), 7.43 (s, 1H), 7.14 (s, 2H), 6.84 (d, J=1.5 Hz, 1H), 5.18 (s, 1H), 3.59 (s, 3H), 1.97 (s, 6H), 1.46 (s, 6H), 1.35 (s, 9H). MS (ESI+) m/z 537 (M+H)$^+$.

Example 96

N-ethyl-4-[3-(4-fluoro-2,6-dimethylphenoxy)-6-(2-hydroxypropan-2-yl)pyridin-2-yl]-6-methyl-7-oxo-6,7-dihydro-1H-pyrrolo[2,3-c]pyridine-2-carboxamide

Example 96a methyl 6-bromo-5-(4-fluoro-2,6-dimethylphenoxy)picolinate

Example 96a was prepared according to the procedure used for the preparation of Example 35b, substituting methyl 6-bromo-5-fluoropicolinate for methyl 3-bromo-4-fluorobenzoate.

Example 96b 2-(6-bromo-5-(4-fluoro-2,6-dimethylphenoxy)pyridin-2-yl)propan-2-ol Example 96b was prepared according to the procedure used for the preparation of Example 28d, substituting Example 96a for Example 28c.

Example 96c

N-ethyl-4-[3-(4-fluoro-2,6-dimethylphenoxy)-6-(2-hydroxypropan-2-yl)pyridin-2-yl]-6-methyl-7-oxo-6,7-dihydro-1H-pyrrolo[2,3-c]pyridine-2-carboxamide The trifluoroacetic acid salt of Example 96c was prepared according to the procedure used for the preparation of Example 1m, substituting Example 96b for Example 11. $^1$H NMR (400 MHz, DMSO-$d_6$) δ 12.23 (d, J=2.4 Hz, 1H), 8.31 (t, J=5.3 Hz, 1H), 7.79 (s, 1H), 7.46 (d, J=8.6 Hz, 1H), 7.19 (d, J=2.2 Hz, 1H), 7.03 (d, J=9.1 Hz, 2H), 6.78 (d, J=8.6 Hz, 1H), 3.61 (s, 3H), 3.27 (qd, J=7.2, 5.1 Hz, 2H), 2.02 (s, 6H), 1.47 (s, 6H), 1.12 (t, J=7.2 Hz, 3H). MS (ESI+) m/z 493.1 (M+H)$^+$.

Example 97

N-tert-butyl-4-[3-(4-fluoro-2,6-dimethylphenoxy)-6-(2-hydroxypropan-2-yl)pyridin-2-yl]-6-methyl-7-oxo-6,7-dihydro-1H-pyrrolo[2,3-c]pyridine-2-carboxamide The trifluoroacetic acid salt of Example 97 was prepared according to the procedure used for the preparation of Example 37, substituting Example 96b for Example 29b. The crude product was purified by HPLC (C18 column, CH$_3$CN/water (0.1% trifluoroacetic acid)). $^1$H NMR (400 MHz, DMSO-$d_6$) δ 12.39 (s, 1H), 7.84 (dd, J=16.6, 2.7 Hz, 1H), 7.53-7.36 (m, 1H), 7.22 (t, J=2.5 Hz, 1H), 7.03 (dd, J=9.2, 2.7 Hz, 1H), 6.87-6.71 (m, 1H), 3.61 (s, 3H), 2.02 (s, 6H), 1.48 (s, 6H), 1.36 (s, 9H). MS (ESI+) m/z 521.1 (M+H)$^+$.

Example 98

4-{2-[2-(difluoromethyl)-4-fluoro-6-methylphenoxy]-5-(2-hydroxypropan-2-yl)phenyl}-N-ethyl-6-methyl-7-oxo-6,7-dihydro-1H-pyrrolo[2,3-c]pyridine-2-carboxamide

Example 98a 2-(dimethoxymethyl)-4-fluoro-6-methylphenol

A solution of 5-fluoro-2-hydroxy-3-methylbenzaldehyde (0.38 g, 2.47 mmol) in methanol (12.4 mL) at 0° C. under a nitrogen atmosphere was treated with titanium (IV) chloride (60 μL, 0.06 mmol) and stirred at 0° C. for 20 minutes. Triethylamine (100 μL, 0.72 mmol) was added and the reaction mixture was stirred at 0° C. for 1 hour. The temperature was allowed to gradually increase to 10° C. while stirring for another 4.5 hours. The reaction mixture was then partitioned between ethyl acetate and water. The aqueous layer was extracted with ethyl acetate (2×50 mL). The organic layers were combined, dried over anhydrous magnesium sulfate, filtered, and concentrated to provide the title compound (0.339 g, 62% yield, 90% purity).

Example 98b methyl 3-bromo-4-(2-(dimethoxymethyl)-4-fluoro-6-methylphenoxy)benzoate Example 98b was prepared according to the procedure used for the preparation of Example 35b, substituting Example 98a for Example 35a. The mixture was heated for 5 hours instead of 2 hours.

Example 98c methyl 3-bromo-4-(4-fluoro-2-formyl-6-methylphenoxy)benzoate

A solution of Example 98b (0.29 g, 0.7 mmol) in tetrahydrofuran (6 mL) was treated with hydrogen chloride solution (2 M aqueous, 0.35 mL, 0.7 mmol) and stirred at 50° C. for 1.25 hours. The reaction mixture was then cooled to ambient temperature, neutralized with saturated sodium bicarbonate solution, partitioned between ethyl acetate and water, washed with brine, dried over anhydrous magnesium sulfate, filtered, and concentrated to provide the title compound (0.251 g, 98%).

Example 98d methyl 3-bromo-4-(2-(difluoromethyl)-4-fluoro-6-methylphenoxy)benzoate A solution of Example 98c (0.25 g, 0.68 mmol) in dichloromethane (5 mL) was added dropwise to a solution of diethylaminosulfur trifluoride (0.25 mL, 1.9 mmol) in dichloromethane (5 mL) at 0° C. The resulting solution was stirred at 0° C. for 1 hour and then at ambient temperature for 3.5 hours. The reaction mixture was carefully quenched with saturated sodium bicarbonate solution. The layers were separated and the organic layer was washed with brine. The aqueous layers were combined and extracted with dichloromethane (2×40 mL). The organic layers were combined, dried over anhydrous magnesium sulfate, filtered, and concentrated. The residue was purified by flash chromatography (silica gel 50 g Biotage KP-Sil Snap column, 0 to 12% ethyl acetate in heptanes) to provide the title compound (0.26 g, 97%).

Example 98e 2-(3-bromo-4-(2-(difluoromethyl)-4-fluoro-6-methylphenoxy)phenyl)propan-2-ol Example 98e was prepared according to the procedure used for the preparation of Example 35c, substituting Example 98d for Example 35b. The reaction mixture was stirred overnight instead of 30 minutes.

Example 98f

4-{2-[2-(difluoromethyl)-4-fluoro-6-methylphenoxy]-5-(2-hydroxypropan-2-yl)phenyl}-N-ethyl-6-methyl-7-oxo-6,7-dihydro-1H-pyrrolo[2,3-c]pyridine-2-carboxamide Example 98f was prepared according to the procedure used for the preparation of Example 1m, substituting Example 98e for Example 1l. The reaction mixture was heated at 60° C. overnight instead of 3 hours. $^1$H NMR (501 MHz, DMSO-$d_6$) δ 12.23 (s, 1H), 8.34 (t, J=5.4 Hz, 1H), 7.55 (d, J=2.4 Hz, 1H), 7.36 (m, 3H), 6.95 (t, J=54.1 Hz, 1H), 6.84 (s, 1H), 6.37 (d, J=8.6 Hz, 1H), 5.03 (s, 1H), 3.59 (s, 3H), 3.27 (qd, J=7.2, 5.7 Hz, 2H), 1.92 (s, 3H), 1.45 (s, 6H), 1.12 (t, J=7.2 Hz, 3H). MS (ESI+) m/z 528.2 (M+H)$^+$.

Example 99

4-[2-(3-chloro-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide Example 99a 2,6-dimethylphenyl acetate To a solution of 2,6-dimethylphenol (10 g, 82 mmol) in acetic anhydride (30 mL) was added 4 drops of concentrated $H_2SO_4$ at 0° C. and the reaction mixture was stirred at 20° C. for 1 hour. Then ice water was added and the product was extracted with ethyl acetate (3×100 mL). The combined organic layers were washed with saturated sodium bicarbonate solution (3×30 mL) and brine, dried over anhydrous sodium sulfate, filtered, and concentrated to provide the title compound (17.6 g, 77 mmol, 94% yield).

Example 99b 2,6-dimethyl-3-nitrophenyl acetate

To a solution of Example 99a (17.6 g, 77 mmol) in acetic anhydride (10 mL) was added dropwise the suspension of cupric nitrate trihydrate (51.9 g, 215 mmol) in acetic anhydride (10 mL) at the rate that the internal temperature was maintained below 10° C. After the addition was finished, the mixture was stirred at this temperature for 20 minutes, then warmed to 40° C. and stirred for 1 hour. The reaction mixture was poured onto ice water and the product was extracted with ethyl acetate (3×150 mL). The combined organic layers were washed with sodium carbonate solution (3×30 mL) and brine, dried over anhydrous sodium sulfate, filtered, and concentrated to provide the title compound, (17.8 g, 55.7 mmol, 72.6% yield), as colorless oil.

Example 99c 2,6-dimethyl-3-nitrophenol

To a solution of sodium hydroxide (1.682 g, 42.1 mmol) in water (20 mL) was added Example 99b (1.1 g, 5.26 mmol) and the mixture was stirred at 20° C. for 18 hours. The pH was adjusted to 2-3 with 15% HCl solution. The product was extracted with ethyl acetate (4×20 mL), The organic layer was washed with brine, dried over anhydrous sodium sulfate, filtered, and concentrated to provide the title compound (810 mg, 4.85 mmol, 92% yield), as yellow solid.

Example 99d 3-amino-2,6-dimethylphenol

To a solution of Example 99c (5 g, 29.9 mmol) in acetic acid (20 mL) was added zinc (1.956 g, 29.9 mmol) and the reaction mixture was stirred at 90° C. for 90 min. After cooling, the reaction mixture was filtered and adjusted the pH to about 8 with solid sodium carbonate. Then the mixture was extracted with ethyl acetate three times. The combined organic layers were washed with brine, dried over anhydrous sodium sulfate, filtered, and concentrated. The residue was purified by flash chromatography (silica gel, 5% methanol in dichloromethane) to provide the title compound (3.6 g, 23.09 mmol, 77% yield).

Example 99e methyl 4-(3-amino-2,6-dimethylphenoxy)-3-bromobenzoate

Example 99e was prepared according to the procedure used for the preparation of Example 35b, substituting Example 99d for Example 35a.

Example 99f methyl 3-bromo-4-(3-chloro-2,6-dimethylphenoxy)benzoate

A solution of copper (II) sulfate (54.7 mg, 0.343 mmol) and sodium chloride (53.4 mg, 0.914 mmol) in water (6 mL) was heated to 95° C., and then a solution of sodium hydroxide (13.71 mg, 0.343 mmol) and sodium metabisulfite (19.54 mg, 0.103 mmol) in water (5 mL) was added to the hot solution. The reaction mixture was stirred at this temperature for 20 minutes, then cooled to 75° C. Example 99e (80 mg, 0.228 mmol) was dissolved in dioxane (1 mL), concentrated HCl (2 mL), and water (1 mL), and the mixture was cooled to −5-0° C. To this solution was added sodium nitrite (17.34 mg, 0.251 mmol) in 1 mL of water. The reaction mixture was stirred at this temperature for 30 min. This reaction mixture was then added to the freshly prepared CuCl solution at 75° C. The reaction mixture was stirred for 1 hour, and then cooled to ambient temperature. The mixture was extracted with ethyl acetate (3×30 mL) and the combined organic layers were washed with brine, dried over anhydrous sodium sulfate, filtered, and concentrated. The residue was purified by silica gel column chromatography (eluted with 5% ethyl acetate in petroleum ether) to provide the title compound, (38 mg, 0.074 mmol, 32.4% yield).

Example 99g 2-(3-bromo-4-(3-chloro-2,6-dimethylphenoxy)phenyl)propan-2-ol

Example 99g was prepared according to the procedure used for the preparation of Example 28d, substituting Example 99f for Example 28c.

Example 99h

4-[2-(3-chloro-2,6-dimethylphenoxy)-5-(2-hydroxypropan-2-yl)phenyl]-N-ethyl-6-methyl-7-oxo-6,7-dihydro-1H-pyrrolo[2,3-c]pyridine-2-carboxamide Example 99h was prepared according to the procedure used for the preparation of Example 1m, substituting Example 99g for Example 1l. $^1$H NMR (400 MHz, Methanol-$d_4$) δ 7.65 (d, J=2.4 Hz, 1H), 7.38 (s, 1H), 7.36 (dd, J=8.7, 2.5 Hz, 1H), 7.09 (d, J=8.3 Hz, 1H), 6.96 (s, 1H), 6.38 (d, J=8.6 Hz, 1H), 3.73 (s, 3H), 3.42 (q, J=7.3 Hz, 2H), 2.12 (s, 3H), 2.06 (s, 3H), 1.58 (s, 6H), 1.23 (t, J=7.3 Hz, 3H). MS (ESI+) m/z 508.1 (M+H)$^+$.

Example 100

N-tert-butyl-4-[2-(2,6-dichloro-4-fluorophenoxy)-5-(2-hydroxypropan-2-yl)pyridin-3-yl]-6-methyl-7-oxo-6,7-dihydro-1H-pyrrolo[2,3-c]pyridine-2-carboxamide

Example 100a methyl 5-bromo-6-(2,6-dichloro-4-fluorophenoxy)nicotinate

Methyl 5-bromo-6-chloronicotinate (1.384 g, 5.53 mmol), 2,6-dichloro-4-fluorophenol (1.0 g, 5.53 mmol) and cesium carbonate (2.70 g, 8.29 mmol) were combined in dimethyl sulfoxide (11.05 mL) under argon in a sealed tube and stirred at 50° C. for 18 hours. The mixture was partitioned between water and ethyl acetate. The organic layer was washed with saturated aqueous sodium chloride, dried over anhydrous sodium sulfate, filtered, and concentrated. Purification of the residue by trituration in 9:1 heptanes/ethyl acetate provided the title compound (1.386 g, 69%).

Example 100b 2-(5-bromo-6-(2,6-dichloro-4-fluorophenoxy)pyridin-3-yl)propan-2-ol To a slurry of cerium(III) chloride (1.135 g, 4.61 mmol) in tetrahydrofuran (16 mL) under nitrogen at 5° C. was added dropwise a solution of Example 100a (1.516 g, 3.84 mmol) in tetrahydrofuran (16 mL). The mixture was stirred for 1.5 hours, cooled to −78° C. and treated dropwise with methylmagnesium chloride (3.84 mL, 11.51 mmol, 3.0 M in tetrahydrofuran). The mixture was stirred for 2 hours and allowed to warm to ambient temperature, poured into 5% aqueous ammonium chloride and partitioned between ethyl acetate and water. The organic layer was washed with saturated aqueous sodium chloride, dried over anhydrous sodium sulfate, filtered, and concentrated. Purification of the residue by chromatography (silica gel, 0-50% ethyl acetate in heptanes) provided the title compound as a viscous oil that solidified upon standing (1.19 g, 78%).

Example 100c

N-tert-butyl-4-[2-(2,6-dichloro-4-fluorophenoxy)-5-(2-hydroxypropan-2-yl)pyridin-3-yl]-6-methyl-7-oxo-6,7-dihydro-1H-pyrrolo[2,3-c]pyridine-2-carboxamide Example 32c (0.05 g, 0.134 mmol), Example 100b (0.053 g, 0.134 mmol), tris(dibenzylideneacetone)dipalladium(0) (3.68 mg, 4.02 μmol), 1,3,5,7-tetramethyl-6-phenyl-2,4,8-trioxa-6-phosphaadamantane (3.92 mg, 0.013 mmol) and sodium carbonate (0.057 g, 0.536 mmol) were combined and sparged with argon for 15 minutes. Meanwhile a solution of 4:1 tetrahydrofuran/water (1.8 mL) was sparged with nitrogen for 15 minutes and transferred by syringe into the reaction vessel under argon. The mixture was stirred for 18 hours under argon at 50° C., cooled, and partitioned between ethyl acetate and water. The organic layer was washed with saturated aqueous sodium chloride, dried over anhydrous sodium sulfate, treated with 3-mercaptopropyl functionalized silica gel, filtered, and concentrated. Purification of the residue by chromatography (silica, 25-60% of 3:1 ethyl acetate/ethanol in heptanes) provided the title compound as a white solid (0.05 g, 63%). $^1$H NMR (400 MHz, DMSO-$d_6$) δ 12.42 (s, 1H), 8.11 (d, J=2.4 Hz, 1H), 8.00 (d, J=2.4 Hz, 1H), 7.84 (s, 1H), 7.63 (d, J=8.2 Hz, 2H), 7.46 (s, 1H), 6.98 (s, 1H), 5.22 (s, 1H), 3.59 (s, 3H), 1.46 (s, 6H), 1.35 (s, 9H). MS (ESI+) m/z 561 [M+H]$^+$.

Example 101

4-[2-(2,6-dichloro-4-fluorophenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide Example 1h (0.05 g, 0.145 mmol), Example 100b (0.057 g, 0.145 mmol), tris(dibenzylideneacetone)dipalladium(0) (3.98 mg, 4.35 μmol), 1,3,5,7-tetramethyl-6-phenyl-2,4,8-trioxa-6-phosphaadamantane (4.23 mg, 0.014 mmol) and sodium carbonate (0.061 g, 0.579 mmol) were combined and sparged with argon for 15 minutes. Meanwhile a solution of 4:1 tetrahydrofuran/water (2.0 mL) was sparged with nitrogen for 15 minutes and transferred by syringe into the reaction vessel under argon. The mixture was stirred for 4 hours under argon at 60° C., cooled, and partitioned between ethyl acetate and water. The organic layer was washed with saturated aqueous sodium chloride, dried over anhydrous sodium sulfate, treated with 3-mercaptopropyl functionalized silica gel, filtered, and concentrated. Purification of the residue by chromatography (silica, 25-60% of 3:1 ethyl acetate/ethanol in heptanes) provided the title compound as a white solid (0.-55 g, 68%). $^1$H NMR (400 MHz, DMSO-$d_6$) δ 12.31 (s, 1H), 8.32 (t, J=5.4 Hz, 1H), 8.12 (d, J=2.3 Hz, 1H), 7.99 (d, J=2.4 Hz, 1H), 7.62 (d, J=8.2 Hz, 2H), 7.46 (s, 1H), 6.98 (s, 1H), 5.22 (s, 1H), 3.58 (s, 3H), 3.28-3.16 (m, 2H), 1.46 (s, 6H), 1.10 (t, J=7.2 Hz, 3H). MS (ESI+) m/z 533 [M+H]$^+$.

Example 102

4-[2-(4-chloro-2,6-dimethylphenoxy)-5-(1-fluoro-2-hydroxypropan-2-yl)pyridin-3-yl]-N-ethyl-6-methyl-7-oxo-6,7-dihydro-1H-pyrrolo[2,3-c]pyridine-2-carboxamide

Example 102a 2-(5-bromo-6-(4-chloro-2,6-dimethylphenoxy)pyridin-3-yl)-1-fluoropropan-2-ol Example 94b (556 mg, 1.50 mmol) and Selectfluor (1-chloromethyl-4-fluoro-1,4-diazoniabicyclo[2.2.2]octane bis(tetrafluoroborate), 585 mg, 1.65 mmol) were combined in acetonitrile (10 mL). The reaction mixture was heated at 80° C. for 44 hours, cooled to ambient temperature, and partitioned between ethyl acetate and saturated aqueous sodium bicarbonate. The organic layer was washed with saturated aqueous sodium chloride, dried with anhydrous sodium sulfate, filtered, and concentrated. The residue was purified by flash chromatography (silica gel, 10-20% ethyl acetate in heptanes) to provide the title compound (250 mg, 43%).

Example 102b

4-[2-(4-chloro-2,6-dimethylphenoxy)-5-(1-fluoro-2-hydroxypropan-2-yl)pyridin-3-yl]-N-ethyl-6-methyl-7-oxo-6,7-dihydro-1H-pyrrolo[2,3-c]pyridine-2-carboxamide Example 102b was prepared according to the procedure used for the preparation of Example 1m, substituting Example 102a for Example 1l. The crude product was purified by flash chromatography (silica gel, 20-40% 3:1 ethyl acetate/ethanol in heptanes) and then by reverse phase HPLC (C18, 20-80% acetonitrile/0.1% trifluoroacetic acid in water) provided the title compound (27 mg, 42%) as a trifluoroacetic acid salt. $^1$H NMR (400 MHz, DMSO-$d_6$) δ 12.31 (s, 1H), 8.32 (t, J=5.4 Hz, 1H), 8.11 (d, J=2.4 Hz, 1H), 7.97 (d, J=2.4 Hz, 1H), 7.43 (s, 1H), 7.14 (s, 2H), 6.84 (d, J=2.2 Hz, 1H), 5.56 (s, br, 1H), 4.46 (s, 1H), 4.34 (s, 1H), 3.59 (s, 3H), 3.30-3.20 (m, 2H), 1.96 (s, 6H), 1.48 (d, J=2.0 Hz, 3H), 1.10 (t, J=7.2 Hz, 3H). MS (ESI+) m/z 527 (M+H)$^+$.

Example 103

N-tert-butyl-4-[2-(4-chloro-2,6-dimethylphenoxy)-5-(1-fluoro-2-hydroxypropan-2-yl)pyridin-3-yl]-6-methyl-7-oxo-6,7-dihydro-1H-pyrrolo[2,3-c]pyridine-2-carboxamide Example 103 was prepared according to the procedure used for the preparation of Example 37, substituting Example 102a for Example 29b. Purification by flash chromatography (silica gel, 20-40% 3:1 ethyl acetate/ethanol in heptanes) and then by reverse phase HPLC (C18, 20-80% acetonitrile/0.1% trifluoroacetic acid in water) provided the title compound (28 mg, 42%) as a trifluoroacetic acid salt. $^1$H NMR (400 MHz, DMSO-$d_6$) δ 12.43 (s, 1H), 8.10 (d, J=2.5 Hz, 1H), 7.97 (d, J=2.4 Hz, 1H), 7.85 (s, 1H), 7.43 (s, 1H), 7.15 (s, 2H), 6.84 (d, J=2.2 Hz, 1H), 5.55 (s, br, 1H), 4.46 (s, 1H), 4.34 (s, 1H), 3.59 (s, 3H), 1.97 (s, 6H), 1.48 (d, J=2.0 Hz, 3H), 1.35 (s, 9H). MS (ESI+) m/z 555 (M+H)$^+$.

Example 104

N-ethyl-4-[2-(3-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide

Example 104a methyl 3-bromo-4-(3-fluoro-2,6-dimethylphenoxy)benzoate

A solution of sodium nitrite (21.67 mg, 0.314 mmol) in water (1 mL) was added dropwise to a solution of Example 99e (100 mg, 0.286 mmol) in pyridine-HF solution (4 mL) at an internal temperature of 5° C., and the mixture was sealed and stirred at this temperature for 30 minutes. This suspension was then heated to 85° C. for 3 hours. The reaction mixture was cooled to ambient temperature and the mixture extracted with ethyl acetate (3×30 mL). The combined organic layers were washed with brine, dried over anhydrous sodium sulfate, filtered, and concentrated. The residue was purified by column chromatography (silica gel, 10% ethyl acetate in petroleum ether) to provide the title compound, (59 mg, 0.120 mmol, 42.0% yield), as white solid.

Example 104b 2-(3-bromo-4-(3-fluoro-2,6-dimethylphenoxy)phenyl)propan-2-ol

Example 104b was prepared according to the procedure used for the preparation of Example 28d, substituting Example 104a for Example 28c.

Example 104c

N-ethyl-4-[2-(3-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide Example 104c was prepared according to the procedure used for the preparation of Example 1m, substituting Example 104b for Example 1l. $^1$H NMR (400 MHz, Methanol-$d_4$) δ 7.65 (d, J=2.4 Hz, 1H), 7.38 (s, 1H), 7.36 (dd, J=8.7, 2.4 Hz, 1H), 7.14-7.06 (m, 1H), 6.97 (s, 1H), 6.89 (t, J=8.8 Hz, 1H), 6.41 (d, J=8.6 Hz, 1H), 3.74 (s, 3H), 3.42 (q, J=7.2 Hz, 2H), 2.05 (s, 3H), 2.00 (d, J=1.7 Hz, 3H), 1.58 (s, 6H), 1.23 (t, J=7.3 Hz, 3H). MS (ESI+) m/z 492 (M+H)$^+$.

Example 105

4-[2-(2,6-dimethylphenoxy)-5-(2-hydroxy-4-methylpentan-2-yl)phenyl]-N-ethyl-6-methyl-7-oxo-6,7-dihydro-1H-pyrrolo[2,3-c]pyridine-2-carboxamide

Example 105a 2-(3-bromo-4-(2,6-dimethylphenoxy)phenyl)-4-methylpentan-2-ol

Example 105a was prepared according to the procedure used for the preparation of Example 3d (Method A), substituting isobutylmagnesium chloride for methylmagnesium chloride.

Example 105b

4-[2-(2,6-dimethylphenoxy)-5-(2-hydroxy-4-methylpentan-2-yl)phenyl]-N-ethyl-6-methyl-7-oxo-6,7-dihydro-1H-pyrrolo[2,3-c]pyridine-2-carboxamide Example 105b was prepared according to the procedure used for the preparation of Example 1m, substituting Example 105a for Example 1l. $^1$H NMR (400 MHz, DMSO-$d_6$) δ 12.20 (d, J=2.3 Hz, 1H), 8.29 (t, J=5.3 Hz, 2H), 7.45 (d, J=2.3 Hz, 1H), 7.28 (s, 1H), 7.22 (dd, J=8.6, 2.4 Hz, 1H), 7.07 (d, J=7.3 Hz, 2H), 7.01 (dd, J=8.5, 6.3 Hz, 1H), 6.80 (d, J=2.3 Hz, 1H), 6.25 (d, J=8.6 Hz, 1H), 3.57 (s, 3H), 3.24 (qd, J=7.2, 5.1 Hz, 2H), 1.97 (s, 6H), 1.64-1.50 (m, 3H), 1.40 (s, 3H), 1.09 (t, J=7.2 Hz, 3H), 0.81 (dd, J=8.9, 6.2 Hz, 3H), 0.63 (d, J=5.9 Hz, 3H). MS (ESI+) m/z 516.2 (M+H)+.

Example 106

N-tert-butyl-4-[2-(2,6-dimethylphenoxy)-5-(2-hydroxy-4-methylpentan-2-yl)phenyl]-6-methyl-7-oxo-6,7-dihydro-1H-pyrrolo[2,3-c]pyridine-2-carboxamide Example 106 was prepared according to the procedure used for the preparation of Example 37, substituting Example 105a for Example 29b. $^1$H NMR (400 MHz, DMSO-d$_6$) δ 12.34 (d, J=2.3 Hz, 1H), 7.83 (s, 1H), 7.46 (d, J=2.3 Hz, 1H), 7.31-7.14 (m, 2H), 7.15-6.92 (m, 2H), 6.79 (d, J=2.2 Hz, 1H), 6.25 (d, J=8.6 Hz, 1H), 3.58 (s, 5H), 1.97 (s, 6H), 1.68-1.51 (m, 2H), 1.40 (s, 2H), 1.34 (s, 9H), 0.79 (d, J=6.2 Hz, 2 3H), 0.63 (d, J=6.2 Hz, 3H). MS (ESI+) m/z 516.2 (M+H)+.

Example 107

N-ethyl-4-{5-(2-hydroxypropan-2-yl)-2-[4-(2-hydroxypropan-2-yl)-2,6-dimethylphenoxy]phenyl}-6-methyl-7-oxo-6,7-dihydro-1H-pyrrolo[2,3-c]pyridine-2-carboxamide

Example 107a methyl 4-(4-acetyl-2,6-dimethylphenoxy)-3-bromobenzoate

Methyl 3-bromo-4-fluorobenzoate (699 mg, 3.00 mmol), 1-(4-hydroxy-3,5-dimethylphenyl)ethanone (493 mg, 3.00 mmol), and cesium carbonate (1.47 g, 4.50 mmol) were combined in dimethyl sulfoxide (3 mL). The reaction mixture was heated at 100° C. for 16 hours, cooled to ambient temperature, and partitioned with ethyl acetate and water. The organic layer was washed with saturated aqueous sodium chloride, dried with anhydrous sodium sulfate, filtered, and concentrated. The residue was purified by flash chromatography (silica gel, 10-20% ethyl acetate in heptanes) to provide the title compound (540 mg, 48%).

Example 107b 2-(4-(2-bromo-4-(2-hydroxypropan-2-yl)phenoxy)-3,5-dimethylphenyl)propan-2-ol To a solution of Example 107a (528 mg, 1.40 mmol) in tetrahydrofuran (10 mL) was added 3M methylmagnesium chloride in tetrahydrofuran (2.80 mL, 8.40 mmol) dropwise at −78° C. The reaction mixture was stirred at ambient temperature for 3 hours. The reaction mixture was cooled to −78° C. and additional 3M methylmagnesium chloride in tetrahydrofuran (2.80 mL, 8.40 mmol) was added dropwise. The reaction mixture was stirred at ambient temperature for another 3 hours, treated with 5% aqueous ammonium chloride carefully, and partitioned with ethyl acetate and water. The organic layer was washed with saturated aqueous sodium chloride, dried with anhydrous sodium sulfate, filtered, and concentrated. The residue was purified by flash chromatography (silica gel, 20-40% ethyl acetate in heptanes) to provide the title compound (375 mg, 68%).

Example 107c

N-ethyl-4-{5-(2-hydroxypropan-2-yl)-2-[4-(2-hydroxypropan-2-yl)-2,6-dimethylphenoxy]phenyl}-6-methyl-7-oxo-6,7-dihydro-1H-pyrrolo[2,3-c]pyridine-2-carboxamide Example 107c (50 mg, 94%) was prepared according to the procedure used for the preparation of Example 1m, substituting Example 107b for Example 1l. $^1$H NMR (400 MHz, DMSO-d$_6$) δ 12.18 (s, 1H), 8.30 (t, J=5.3 Hz, 1H), 7.49 (d, J=2.4 Hz, 1H), 7.31 (s, 1H), 7.27 (dd, J=8.6, 2.4 Hz, 1H), 7.15 (s, 2H), 6.83 (s, 1H), 6.25 (d, J=8.6 Hz, 1H), 4.93 (s, 1H), 4.90 (s, 1H), 3.57 (s, 3H), 3.28-3.20 (m, 2H), 1.98 (s, 6H), 1.41 (s, 6H), 1.37 (s, 6H), 1.08 (t, J=7.2 Hz, 3H). MS (ESI−) m/z 530 (M−H)+.

Example 108

N-tert-butyl-4-{5-(2-hydroxypropan-2-yl)-2-[4-(2-hydroxypropan-2-yl)-2,6-dimethylphenoxy]phenyl}-6-methyl-7-oxo-6,7-dihydro-1H-pyrrolo[2,3-c]pyridine-2-carboxamide Example 108 (54 mg, 96%) was prepared according to the procedure used for the preparation of Example 37, substituting Example 107b for 29b. $^1$H NMR (400 MHz, DMSO-d$_6$) δ 12.31 (s, 1H), 7.83 (s, 1H), 7.50 (d, J=2.4 Hz, 1H), 7.31 (s, 1H), 7.27 (dd, J=8.6, 2.4 Hz, 1H), 7.16 (s, 2H), 6.83 (s, 1H), 6.25 (d, J=8.5 Hz, 1H), 4.94 (s, 1H), 4.90 (s, 1H), 3.57 (s, 3H), 1.98 (s, 6H), 1.41 (s, 6H), 1.37 (s, 6H), 1.34 (s, 9H). MS (ESI−) m/z 558 (M−H)+.

Example 109

4-[2-(3-chloro-2,6-dimethylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide

Example 109a methyl 5-bromo-6-(3-chloro-2,6-dimethylphenoxy)nicotinate

Example 109a was prepared according to the procedure used for the preparation of Example 99f, substituting Example 91a for Example 99e.

Example 109b 2-(5-bromo-6-(3-chloro-2,6-dimethylphenoxy)pyridin-3-yl)propan-2-ol Example 109b was prepared according to the procedure used for the preparation of Example 28d, substituting Example 109a for Example 28c.

Example 109c

4-[2-(3-chloro-2,6-dimethylphenoxy)-5-(2-hydroxypropan-2-yl)pyridin-3-yl]-N-ethyl-6-methyl-7-oxo-6,7-dihydro-1H-pyrrolo[2,3-c]pyridine-2-carboxamide Example 109c was prepared according to the procedure used for the preparation of Example 1m, substituting Example 109b for Example 1l. ¹H NMR (400 MHz, Methanol-d₄) δ 8.14 (d, J=2.5 Hz, 1H), 8.08 (d, J=2.5 Hz, 1H), 7.47 (s, 1H), 7.18 (d, J=8.4 Hz, 1H), 7.07 (d, J=8.2 Hz, 1H), 6.97 (s, 1H), 3.74 (s, 3H), 3.43 (q, J=7.2 Hz, 2H), 2.11 (s, 3H), 2.04 (s, 3H), 1.61 (s, 6H), 1.24 (t, J=7.3 Hz, 3H). MS (ESI+) m/z 509.2 (M+H)⁺.

Example 110

N-ethyl-4-[4-(2-hydroxypropan-2-yl)-4'-(trifluoromethoxy)[1,1'-biphenyl]-2-yl]-6-methyl-7-oxo-6,7-dihydro-1H-pyrrolo[2,3-c]pyridine-2-carboxamide

Example 110a 2-(3-bromo-4-chlorophenyl)propan-2-ol

Example 110a was prepared according to the procedure used for the preparation of Example 35c, substituting methyl 3-bromo-4-chlorobenzoate for Example 35b. The reaction mixture was stirred overnight instead of 30 minutes.

Example 110b 4-(2-chloro-5-(2-hydroxypropan-2-yl)phenyl)-N-ethyl-6-methyl-7-oxo-6,7-dihydro-1H-pyrrolo[2,3-c]pyridine-2-carboxamide Example 110b was prepared according to the procedure used for the preparation of Example 1m, substituting Example 110a for Example 1l. The reaction mixture was heated for 6 hours instead of 3 hours.

Example 110c

N-ethyl-4-[4-(2-hydroxypropan-2-yl)-4'-(trifluoromethoxy)[1,1'-biphenyl]-2-yl]-6-methyl-7-oxo-6,7-dihydro-1H-pyrrolo[2,3-c]pyridine-2-carboxamide Example 110b (0.035 g, 0.09 mmol), (4-(trifluoromethoxy)phenyl)boronic acid (0.028 g, 0.135 mmol), tris(dibenzylideneacetone)dipalladium(0) (0.0083 g, 0.009 mmol), dicyclohexyl(2',6'-dimethoxy-[1,1'-biphenyl]-2-yl)phosphine (0.011 g, 0.027 mmol) and potassium fluoride (0.026 g, 0.45 mmol) were combined and sparged with nitrogen for 30 minutes. To this mixture were added nitrogen-sparged dioxane (0.9 mL) and water (0.1 mL) via syringe. The reaction mixture was stirred at 90° C. overnight and then partitioned between ethyl acetate and water. The organic layer was washed with brine, treated with 3-mercaptopropyl-functionalized silica gel for 20 minutes, dried over anhydrous magnesium sulfate, filtered through a plug of diatomaceous earth, and concentrated. The residue was purified by flash chromatography (silica gel 12 g Grace Reveleris column, 12 to 50% of a 3:1 mixture of ethyl acetate/ethanol in heptanes) to provide the title compound and some fractions. The mixed fractions were purified by a second flash chromatography (silica gel 12 g Grace Reveleris column, 2 to 35% of a 3:1 mixture of ethyl acetate/ethanol in heptanes). A combined yield of 0.024 g (52%) of the title compound was obtained. ¹H NMR (501 MHz, DMSO-d₆) δ 12.09 (s, 1H), 8.20 (t, J=5.3 Hz, 1H), 7.58 (dd, J=8.0, 1.9 Hz, 1H), 7.56 (d, J=1.8 Hz, 1H), 7.44 (d, J=8.0 Hz, 1H), 7.31 (m, 2H), 7.19 (d, J=8.1 Hz, 2H), 6.97 (s, 1H), 6.41 (d, J=1.3 Hz, 1H), 5.13 (s, 1H), 3.42 (s, 3H), 3.22 (qd, J=7.2, 5.4 Hz, 2H), 1.50 (s, 6H), 1.08 (t, J=7.2 Hz, 3H). MS (ESI+) m/z 514.0 (M+H)⁺.

Example 111

4-[4',4'-difluoro-4-(2-hydroxypropan-2-yl)[2',3',4',5'-tetrahydro[1,1'-biphenyl]]-2-yl]-N-ethyl-6-methyl-7-oxo-6,7-dihydro-1H-pyrrolo[2,3-c]pyridine-2-carboxamide Example 111 was prepared according to the procedure used for the preparation of Example 110c, substituting 2-(4,4-difluorocyclohex-1-en-1-yl)-4,4,5,5-tetramethyl-1,3,2-dioxaborolane for (4-(trifluoromethoxy)phenyl)boronic acid. ¹H NMR (400 MHz, DMSO-d₆) δ 12.21 (s, 1H), 8.32 (t, J=5.3 Hz, 1H), 7.47 (s, 1H), 7.44 (dd, J=8.0, 1.6 Hz, 1H), 7.24 (d, J=8.0 Hz, 1H), 7.09 (s, 1H), 6.68 (s, 1H), 5.51 (s, 1H), 5.05 (s, 1H), 3.53 (s, 3H), 3.25 (m, 2H), 2.49 (m, 2H), 2.18 (t, J=5.7 Hz, 2H), 1.81 (dt, J=14.6, 7.4 Hz, 2H), 1.46 (s, 6H), 1.11 (t, J=7.2 Hz, 3H). MS (ESI+) m/z 470.1 (M+H)⁺.

Example 112

4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide 1-Hydroxybenzotriazole hydrate (9.0 mg, 0.059 mmol), Example 75c (17 mg, 0.037 mmol) were dissolved in dichloromethane (2.5 mL). Ammonia (0.5 M in dioxane, 1.0 mL, 0.500 mmol) was added and the mixture was stirred at ambient temperature as 1-(3-dimethylaminopropyl)-3-ethylcarbodiimide hydrochloride (13.1 mg, 0.068 mmol) was added. The mixture was stirred for 23 hours, and the resulting white suspension was concentrated under vacuum. The residue was purified by HPLC (30×100 mm)(Bridge column, eluted with 10 mM aqueous (NH₄)₂CO₃—CH₃CN, 80:20-0:100 over 15 minutes) to provide the title compound (13 mg). ¹H NMR (400 MHz, DMSO-d₆) δ 12.23 (s, 1H), 7.81 (s, 1H), 7.52 (d, J=2.2 Hz, 1H), 7.44 (s, 1H), 7.36-7.26 (m, 2H), 6.98 (d, J=8.9 Hz, 2H), 6.84 (s, 1H), 6.31 (d, J=8.6 Hz, 1H), 4.98 (s, 1H), 3.60 (s, 3H), 2.01 (s, 6H), 1.44 (s, 6H). MS (ESI+) m/z 464 (M+H)⁺.

Example 113

N-ethyl-4-[4-(2-hydroxypropan-2-yl)-4'-methyl[2',3',4',5'-tetrahydro[1,1'-biphenyl]]-2-yl]-6-methyl-7-oxo-6,7-dihydro-1H-pyrrolo[2,3-c]pyridine-2-carboxamide Example 113 was prepared according to the procedure used for the preparation of Example 110c, substituting (4-methylcyclohex-1-en-1-yl)boronic acid for (4-(trifluoromethoxy)phenyl)boronic acid. ¹H NMR (500 MHz, DMSO-d₆) δ 12.17 (s, 1H), 8.32 (t, J=5.5 Hz, 1H), 7.42 (d, J=1.9 Hz, 1H), 7.40 (dd, J=8.0, 2.0 Hz, 1H), 7.20 (d, J=8.0 Hz, 1H), 7.08 (s, 1H), 6.66 (s, 1H), 5.58 (m, 1H), 5.03 (s, 1H), 3.53 (s, 3H), 3.26 (m, 2H), 2.07 (dt, J=16.6, 4.5 Hz, 1H), 1.93 (m, 2H), 1.53 (m, 3H), 1.45 (s, 6H), 1.10 (t, J=7.2 Hz, 3H), 0.96 (m, 1H), 0.81 (d, J=6.4 Hz, 3H). MS (ESI+) m/z 448.2 (M+H)⁺.

Example 114

4-[2-(cyclopent-1-en-1-yl)-5-(2-hydroxypropan-2-yl)phenyl]-N-ethyl-6-methyl-7-oxo-6,7-dihydro-1H-pyrrolo[2,3-c]pyridine-2-carboxamide Example 114 was prepared according to the procedure used for the preparation of Example 110c, substituting 2-(cyclopent-1-en-1-yl)-4,4,5,5-tetramethyl-1,3,2-dioxaborolane for (4-(trifluoromethoxy)phenyl)boronic acid. Additional purification by reverse phase HPLC (C18, acetonitrile/water (0.1% trifluroacetic acid), 10-80%) provided the title compound. $^1$H NMR (501 MHz, DMSO-$d_6$) δ 12.16 (s, 1H), 8.30 (t, J=5.3 Hz, 1H), 7.43 (dd, J=8.1, 2.0 Hz, 1H), 7.39 (d, J=1.9 Hz, 1H), 7.34 (d, J=8.1 Hz, 1H), 7.11 (s, 1H), 6.54 (d, J=2.2 Hz, 1H), 5.62 (p, J=2.2 Hz, 1H), 5.03 (s, 1H), 3.55 (s, 3H), 3.24 (qd, J=7.2, 5.3 Hz, 2H), 2.28 (m, 2H), 2.18 (m, J=9.2, 7.6, 2.2 Hz, 2H), 1.66 (p, J=7.5 Hz, 2H), 1.45 (s, 6H), 1.10 (t, J=7.2 Hz, 3H). LCMS (APCI+) m/z 420.5 (M+H)$^+$.

Example 115

4-[2-(2-chloro-6-methylphenoxy)-5-(1,2-dihydroxypropan-2-yl)phenyl]-N-ethyl-6-methyl-7-oxo-6,7-dihydro-1H-pyrrolo[2,3-c]pyridine-2-carboxamide

Example 115a 1-(3-bromo-4-(2-chloro-6-methylphenoxy)phenyl)ethan-1-one

Example 115a was prepared according to the procedure used for the preparation of Example 35b, substituting 2-methy-6-chlorophenol for Example 35a, and substituting 1-(3-bromo-4-fluorophenyl)ethan-1-one for methyl 3-bromo-4-fluorobenzoate, respectively.

Example 115b 2-(2-bromo-4-(prop-1-en-2-yl)phenoxy)-1-chloro-3-methylbenzene

To a solution of methyltriphenylphosphonium bromide (1.893 g, 5.30 mmol) in tetrahydrofuran (12 mL) was added 2.5 M n-butyllithium (2.120 mL, 5.30 mmol) at 0° C. The reaction mixture was stirred at this temperature for 1 hour, and then Example 115a (900 mg, 2.65 mmol) in 2 mL of tetrahydrofuran was added to the reaction solution. The reaction mixture was allowed to warm to ambient temperature gradually and stirred for 16 hours. The reaction mixture was then quenched with water. The mixture was partitioned between water (15 mL) and ethyl acetate (15 mL), extracted with ethyl acetate (10 mL), dried over anhydrous sodium sulfate, filtered, and concentrated. The crude product was purified by flash chromatography on silica gel eluting with 100:5 hexane:acetate to provide the title compound, (810 mg, 2.267 mmol, 86% yield), as a colorless oil.

Example 115c 2-(3-bromo-4-(2-chloro-6-methylphenoxy)phenyl)propane-1,2-diol

To a solution of Example 115b (810 mg, 2.399 mmol) and potassium carbonate (995 mg, 7.20 mmol) in water (15 mL) and tert-butanol (15.000 mL) was added potassium hexacyanoferrate (III) (3.949 g, 12.00 mmol) and potassium osmate dihydrate (35.4 mg, 0.096 mmol) at ambient temperature. The reaction mixture was stirred at ambient temperature for 48 hours. The mixture was partitioned between water (15 mL) and ethyl acetate (25 mL), extracted with ethyl acetate (3×20 mL), dried over anhydrous sodium sulfate, filtered, and concentrated. The crude product was purified by flash chromatography (silica gel, ethyl acetate/petroleum 1:2) to provide the title compound (620 mg, 1.668 mmol, 69.5% yield).

Example 115d

4-[2-(2-chloro-6-methylphenoxy)-5-(1,2-dihydroxypropan-2-yl)phenyl]-N-ethyl-6-methyl-7-oxo-6,7-dihydro-1H-pyrrolo[2,3-c]pyridine-2-carboxamide Example 115d was prepared according to the procedure used for the preparation of Example 1m, substituting Example 115c for Example 1l. $^1$H NMR (400 MHz, DMSO-$d_6$) δ 12.21 (s, 1H), 8.34 (t, J=5.3 Hz, 1H), 7.55 (d, J=2.3 Hz, 1H), 7.41 (d, J=7.9 Hz, 1H), 7.37 (s, 1H), 7.35-7.28 (m, 2H), 7.19 (t, J=7.8 Hz, 1H), 6.93 (s, 1H), 6.30 (d, J=8.6 Hz, 1H), 4.89 (s, 1H), 4.71 (t, J=5.8 Hz, 1H), 3.60 (s, 3H), 3.43 (dd, J=5.6, 2.7 Hz, 2H), 3.32-3.22 (m, 2H), 2.08 (s, 3H), 1.41 (s, 3H), 1.12 (t, J=7.2 Hz, 3H). MS (ESI+) m/z 510.1 (M+H)$^+$.

Example 116

N-tert-butyl-4-[2-(2-chloro-6-methylphenoxy)-5-(1,2-dihydroxypropan-2-yl)phenyl]-6-methyl-7-oxo-6,7-dihydro-1H-pyrrolo[2,3-c]pyridine-2-carboxamide Example 116 was prepared according to the procedure used for the preparation of Example 37, substituting Example 115c for Example 29b. $^1$H NMR (400 MHz, DMSO-$d_6$) δ 12.35 (s, 1H), 7.86 (s, 1H), 7.55 (d, J=2.2 Hz, 1H), 7.42 (d, J=7.2 Hz, 1H), 7.37 (s, 1H), 7.34-7.27 (m, 2H), 7.20 (t, J=7.8 Hz, 1H), 6.93 (s, 1H), 6.30 (d, J=8.6 Hz, 1H), 4.90 (s, 1H), 4.71 (t, J=5.8 Hz, 1H), 3.60 (s, 3H), 3.46-3.39 (m, 2H), 2.09 (s, 3H), 1.41 (s, 3H), 1.37 (s, 9H). MS (ESI+) m/z 538.1 (M+H)$^+$.

Example 117

4-[2-(2,6-dimethylphenoxy)-5-(2-hydroxypropan-2-yl)phenyl]-6-methyl-7-oxo-6,7-dihydro-1H-pyrrolo[2,3-c]pyridine-2-carboxamide

Example 117a ethyl 4-(2-(2,6-dimethylphenoxy)-5-(2-hydroxypropan-2-yl)phenyl)-6-methyl-7-oxo-1-tosyl-6,7-dihydro-1H-pyrrolo[2,3-c]pyridine-2-carboxylate Example 117a (615 mg, 98%) was prepared according to the procedure used for the preparation of Example 75b, substituting Example 3d for Example 35c.

Example 117b 4-(2-(2,6-dimethylphenoxy)-5-(2-hydroxypropan-2-yl)phenyl)-6-methyl-7-oxo-6,7-dihydro-1H-pyrrolo[2,3-c]pyridine-2-carboxylic acid Example 117a (610 mg, 0.970 mmol) and lithium hydroxide (232 mg, 9.70 mmol) were combined in the mixture of dioxane (15 mL) and water (5 mL). The reaction mixture was heated at 70° C. for 2 hours, cooled, diluted with water, adjusted pH to 4 by addition of 1M HCl, filtered, washed with water and dried to provide the title compound (322 mg, 74%).

Example 117c

4-[2-(2,6-dimethylphenoxy)-5-(2-hydroxypropan-2-yl)phenyl]-6-methyl-7-oxo-6,7-dihydro-1H-pyrrolo[2,3-c]pyridine-2-carboxamide Example 117b (89 mg, 0.20 mmol), 1-hydroxybenzotriazole hydra (49 mg, 0.32 mmol), 1-ethyl-3-[3-(dimethylamino)propyl]-carbodiimide hydrochloride (61 mg, 0.32 mmol) and 0.5 M ammonia in dioxane (6.0 mL, 3.0 mmol) were combined in dichloromethane (1 mL). The reaction mixture was stirred at ambient temperature for 48 hours. To this reaction mixture was added 0.5 M ammonia in dioxane (6.0 mL, 3.0 mmol) again. The reaction mixture stirred at ambient temperature for another 48 hours. To this reaction mixture was added 0.5 M ammonia in dioxane (6.0 mL, 3.0 mmol) again. The reaction mixture stirred at ambient temperature for another 48 hours and concentrated. The residue was purified by flash chromatography (silica gel, 20-40% 3:1 ethyl acetate/ethanol in heptanes) to provide the title compound (25 mg, 28%). $^1$H NMR (400 MHz, DMSO-$d_6$) δ 12.21 (s, 1H), 7.80 (s, 1H), 7.51 (d, J=2.4 Hz, 1H), 7.43 (s, 1H), 7.33 (s, 1H), 7.28 (dd, J=8.6, 2.4 Hz, 1H), 7.13-7.00 (m, 3H), 6.84 (s, 1H), 6.26 (d, J=8.6 Hz, 1H), 4.96 (s, 1H), 3.59 (s, 3H), 2.00 (s, 6H), 1.42 (s, 6H). MS (ESI+) m/z 446 (M+H)$^+$.

Example 118

N-tert-butyl-4-[2-(2-chloro-4-fluoro-6-methylphenoxy)-5-(1,2-dihydroxypropan-2-yl)phenyl]-6-methyl-7-oxo-6,7-dihydro-1H-pyrrolo[2,3-c]pyridine-2-carboxamide

Example 118a 1-(3-bromo-4-(2-chloro-4-fluoro-6-methylphenoxy)phenyl)ethan-1-one Example 118a was prepared according to the procedure used for the preparation of Example 35b, substituting 2-methy-4-fluoro-6-chlorolphenol for Example 35a, and substituting 1-(3-bromo-4-fluorophenyl)ethan-1-one for methyl 3-bromo-4-fluorobenzoate respectively.

Example 118b 2-(2-bromo-4-(prop-1-en-2-yl)phenoxy)-1-chloro-5-fluoro-3-methylbenzene Example 118b was prepared according to the procedure used for the preparation of Example 115b, substituting Example 118a for Example 115a.

Example 118c 2-(5-bromo-6-(3-fluoro-2,6-dimethylphenoxy)pyridin-3-yl)propan-2-ol Example 118c was prepared according to the procedure used for the preparation of Example 115c, substituting Example 118b for Example 115b.

Example 118d

N-tert-butyl-4-[2-(2-chloro-4-fluoro-6-methylphenoxy)-5-(1,2-dihydroxypropan-2-yl)phenyl]-6-methyl-7-oxo-6,7-dihydro-1H-pyrrolo[2,3-c]pyridine-2-carboxamide Example 118d was prepared according to the procedure used for the preparation of Example 37, substituting Example 118c for Example 29b. $^1$H NMR (400 MHz, Methanol-$d_4$) δ 7.67 (d, J=2.3 Hz, 1H), 7.41 (s, 1H), 7.37 (dd, J=8.7, 2.3 Hz, 1H), 7.18 (dd, J=8.0, 3.0 Hz, 1H), 7.09-7.00 (m, 2H), 6.44 (d, J=8.6 Hz, 1H), 3.73 (s, 3H), 3.70-3.60 (m, J=5.9 Hz, 2H), 2.10 (s, 3H), 1.55 (s, 3H), 1.46 (s, 9H). MS (ESI+) m/z 556.2 (M+H)$^+$.

Example 119

4-[2-(2-chloro-4-fluoro-6-methylphenoxy)-5-(1,2-dihydroxypropan-2-yl)phenyl]-N-ethyl-6-methyl-7-oxo-6,7-dihydro-1H-pyrrolo[2,3-c]pyridine-2-carboxamide Example 119 was prepared according to the procedure used for the preparation of Example 1m, substituting Example 118c for Example 1l. $^1$H NMR (400 MHz, Methanol-$d_4$) δ 7.69 (d, J=2.3 Hz, 1H), 7.43 (s, 1H), 7.38 (dd, J=8.7, 2.3 Hz, 1H), 7.17 (dd, J=8.1, 3.0 Hz, 1H), 7.06-6.99 (m, 2H), 6.45 (d, J=8.7 Hz, 1H), 3.72 (s, 3H), 3.66 (q, J=5.6 Hz, 2H), 3.42 (q, J=7.3 Hz, 2H), 2.11 (s, 3H), 1.56 (s, 3H), 1.23 (t, J=7.2 Hz, 3H). MS (ESI+) m/z 528.2 (M+H)$^+$.

Example 120

4-[2-(4-fluoro-2,6-dimethylphenoxy)-5-(2-hydroxypropan-2-yl)phenyl]-N,6-dimethyl-7-oxo-6,7-dihydro-1H-pyrrolo[2,3-c]pyridine-2-carboxamide

Example 120a 4-bromo-N,6-dimethyl-7-oxo-6,7-dihydro-1H-pyrrolo[2,3-c]pyridine-2-carboxamide Example 32a (1.084 g, 4 mmol) in dichloromethane (25 mL) was treated with oxalyl dichloride (0.700 mL, 8.00 mmol) and N,N-dimethylformamide (0.062 mL, 0.800 mmol). Gas was generated, and the reaction mixture turned from a white suspension to a yellow fine suspension. The reaction mixture was stirred at ambient temperature for 2 hours. The solvent was evaporated under reduced pressure, and the residue was treated with tetrahydrofuran (20 mL) and N,N-dimethylformamide (10 mL). To this reaction mixture was added 2.0 N methanamine in tetrahydrofuran (20.00 mL, 40.0 mmol). The white suspension was stirred at ambient temperature for 2 hours. Excess tetrahydrofuran was removed under reduced pressure. The remaining mixture was poured into water (300 mL). The resulting solid was collected by filtration to provide the title compound (0.95 g, 84% yield) after drying in a vacuum oven overnight.

Example 120b 2-(4-(4-fluoro-2,6-dimethylphenoxy)-3-(4,4,5,5-tetramethyl-1,3,2-dioxaborolan-2-yl)phenyl)propan-2-ol A solution of Example 35c (21 g, 59.5 mmol) in tetrahydrofuran (396 ml) was cooled to −78° C. and n-butyl lithium (71.3 mL, 178 mmol) was added. The reaction mixture was stirred for 30 minutes. Neat 2-isopropoxy-4,4,5,5-tetramethyl-1,3,2-dioxaborolane (37.6 mL, 184 mmol) was added. The cold bath was removed after 10 minutes and the reaction mixture was allowed to warm to ambient temperature for one hour. The reaction mixture was quenched by addition of saturated aqueous sodium carbonate and extracted with ethyl acetate. The organic phase was separated, dried over anhydrous magnesium sulfate, filtered, and concentrated under reduced pressure. The crude material was purified via flash chromatography using a Grace silica gel column eluting with 10-25% ethyl acetate/heptanes to give the title compound (15 g, 63%) as a white solid.

Example 120c

4-[2-(4-fluoro-2,6-dimethylphenoxy)-5-(2-hydroxypropan-2-yl)phenyl]-N,6-dimethyl-7-oxo-6,7-dihydro-1H-pyrrolo[2,3-c]pyridine-2-carboxamide A mixture of Example 120a (0.057 g, 0.2 mmol), Example 120b (0.096 g, 0.240 mmol), tetrakis(triphenylphosphine)palladium(0) (0.012 g, 10.00 µmol), and cesium fluoride (0.091 g, 0.600 mmol) in dimethoxyethane (1 mL) and methanol (0.5 mL) was heated at 120° C. for 40 minutes under microwave heating conditions. The reaction mixture was loaded onto a 15 g silica gel cartridge, and dried. It was then loaded onto a 12 g silica gel column, eluted with 15:85 methanol:ethyl acetate to give crude product, which was then purified by reverse phase Preparative HPLC (C18 column, acetonitrile/water (0.1% trifluoroacetic acid)) to give the title compound (0.062 g, 0.130 mmol, 64.9% yield). $^1$H NMR (400 MHz, DMSO-$d_6$) δ 12.26-12.09 (m, 1H), 8.31 (q, J=4.5 Hz, 1H), 7.50 (d, J=2.4 Hz, 1H), 7.34-7.26 (m, 2H), 6.96 (d, J=9.0 Hz, 2H), 6.80 (d, J=2.2 Hz, 1H), 6.29 (d, J=8.6 Hz, 1H), 3.58 (s, 3H), 2.74 (d, J=4.5 Hz, 3H), 1.99 (s, 6H), 1.42 (s, 6H). MS (ESI+) m/z 478.1 (M+H)$^+$.

Example 121

N-cyclopropyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide

Example 121a 4-bromo-N-cyclopropyl-6-methyl-7-oxo-6,7-dihydro-1H-pyrrolo[2,3-c]pyridine-2-carboxamide A solution of Example 32a (1 g, 3.69 mmol) in dimethyl sulfoxide (18.5 mL) was treated with 2-(3H-[1,2,3]triazolo[4,5-b]pyridin-3-yl)-1,1,3,3-tetramethylisouronium hexafluorophosphate(V) (HATU, 1.543 g, 4.06 mmol) and N-ethyl-N-isopropylpropan-2-amine (2 mL, 11.45 mmol). The resulting mixture was stirred at ambient temperature for 5 minutes and was then treated with cyclopropanamine (0.3 mL, 4.33 mmol). The resulting mixture was stirred at ambient temperature overnight. Water (80 mL) was added to the reaction mixture, inducing precipitation of a light yellow solid. The solid was collected by filtration, rinsed with 300 mL of water and 50 mL of heptanes, and dried in a vacuum oven at 65° C. to provide 0.966 g (84%) of the title compound.

Example 121b

N-cyclopropyl-4-(2-(4-fluoro-2,6-dimethylphenoxy)-5-(2-hydroxypropan-2-yl)phenyl)-6-methyl-7-oxo-6,7-dihydro-1H-pyrrolo[2,3-c]pyridine-2-carboxamide Example 121a (0.12 g, 0.387 mmol), Example 120b (0.155 g, 0.387 mmol), tris(dibenzylideneacetone)dipalladium(0) (0.018 g, 0.019 mmol), 1,3,5,7-tetramethyl-6-phenyl-2,4,8-trioxa-6-phosphaadamantane (0.017 g, 0.058 mmol) and sodium carbonate (0.176 g, 1.664 mmol) were combined and sparged with nitrogen for 30 minutes. To this mixture were added nitrogen-sparged tetrahydrofuran (2 mL) and water (0.5 mL) via syringe. The reaction mixture was stirred at 60° C. for 4.5 hours. The reaction mixture was then partitioned between ethyl acetate and water. The organic layer was washed with saturated aqueous sodium chloride, treated with 3-mercaptopropyl-functionalized silica gel overnight, dried over anhydrous magnesium sulfate, filtered through a plug of diatomaceous earth, and concentrated. The residue was purified by flash chromatography (silica gel 24 g Grace Reveleris column, eluting with a gradient of 0 to 60% of a 3:1 mixture of ethyl acetate/ethanol in heptanes) to provide the title compound as a mixture. The material was purified by a second flash chromatography (silica gel 24 g Grace Reveleris column, 15 to 35% of a 3:1 mixture of ethyl acetate/ethanol in heptanes) to provide 0.147 g (75%) of the title compound. $^1$H NMR (501 MHz, DMSO-$d_6$) δ 12.17 (s, 1H), 8.35 (d, J=4.2 Hz, 1H), 7.51 (d, J=2.4 Hz, 1H), 7.33 (s, 1H), 7.32 (dd, J=9.0, 2.5 Hz, 1H), 6.98 (d, J=9.1 Hz, 2H), 6.83 (s, 1H), 6.31 (d, J=8.6 Hz, 1H), 4.98 (s, 1H), 3.59 (s, 3H), 2.82 (tq, J=7.7, 4.0 Hz, 1H), 2.01 (s, 6H), 1.44 (s, 6H), 0.70 (td, J=7.0, 4.9 Hz, 2H), 0.52 (m, 2H). MS (ESI+) m/z 504.1 (M+H)$^+$.

Example 122

N-ethyl-4-[2-(4-fluoro-2,6-dimethylphenoxy)-5-(1-hydroxycyclobutyl)phenyl]-6-methyl-7-oxo-6,7-dihydro-1H-pyrrolo[2,3-c]pyridine-2-carboxamide

Example 122a 2-(2-bromo-4-iodophenoxy)-5-fluoro-1,3-dimethylbenzene

A mixture of 2-bromo-1-fluoro-4-iodobenzene (3.01 g, 10 mmol), Example 35a (1.472 g, 10.50 mmol), and cesium carbonate (3.42 g, 10.50 mmol) in dimethylsulfoxide (20 mL) was heated at 110° C. overnight. After cooling to ambient temperature, the reaction mixture was partitioned between water and ethyl acetate. The aqueous layer was extracted with additional ethyl acetate twice. The combined organic layers were washed with brine, dried over anhydrous magnesium sulfate, filtered, and concentrated. The residue was purified by column chromatography on silica gel eluting with heptanes to give the title compound (3.21 g, 76% yield) as a white solid.

Example 122b 1-(3-bromo-4-(4-fluoro-2,6-dimethylphenoxy)phenyl)cyclobutan-1-ol Example 122a (0.421 g, 1.0 mmol) in hexane (10 mL) was cooled to −78° C. To this solution was added 1.7 M tert-butyllithium (0.647 mL, 1.1 mmol) at −78° C. The reaction was stirred at −78° C. for 1 hour. Then toluene (3 mL) was added, and the solution became clear. To this solution was added cyclobutanone (0.105 g, 1.5 mmol) in toluene (1 mL). The reaction was allowed to warm up to ambient temperature slowly overnight. The reaction mixture was quenched with saturated NH$_4$Cl. It was then partitioned between water and ethyl acetate. The aqueous layer was extracted with additional ethyl acetate twice. The combined organic layers were washed with brine, dried over MgSO$_4$, filtered, and concentrated. The residue was purified by column chromatography on silica gel eluting with 10% ethyl acetate in haptanes to give the title compound (0.086 g, 0.235 mmol, 24% yield).

Example 122c

N-ethyl-4-[2-(4-fluoro-2,6-dimethylphenoxy)-5-(1-hydroxycyclobutyl)phenyl]-6-methyl-7-oxo-6,7-dihydro-1H-pyrrolo[2,3-c]pyridine-2-carboxamide Example 122c was prepared according to the procedure for the preparation of Example 28e, substituting Example 122b for Example 28d. $^1$H NMR (400 MHz, DMSO-d$_6$) δ 12.21 (s, 1H), 8.32 (t, J=5.4 Hz, 1H), 7.50 (d, J=2.3 Hz, 1H), 7.37-7.30 (m, 2H), 6.97 (d, J=9.1 Hz, 2H), 6.83 (s, 1H), 6.33 (d, J=8.6 Hz, 1H), 5.44 (s, 1H), 3.58 (s, 3H), 3.31-3.19 (m, 2H), 2.49-2.38 (m, 2H), 2.24 (ddd, J=11.6, 9.2, 7.2 Hz, 2H), 2.00 (s, 6H), 1.98-1.81 (m, 1H), 1.68-1.55 (m, 1H), 1.16-1.05 (m, 3H). MS (ESI+) m/z 504.1 (M+H)$^+$.

Example 123

N-ethyl-4-[2-(4-fluoro-2,6-dimethylphenoxy)-5-(3-hydroxyoxetan-3-yl)phenyl]-6-methyl-7-oxo-6,7-dihydro-1H-pyrrolo[2,3-c]pyridine-2-carboxamide

Example 123a 3-(3-bromo-4-(4-fluoro-2,6-dimethylphenoxy)phenyl)oxetan-3-ol

Example 123a was prepared according to the procedure for the preparation of Example 122b, substituting oxetan-3-one for cyclobutanone.

Example 123b

N-ethyl-4-[2-(4-fluoro-2,6-dimethylphenoxy)-5-(3-hydroxyoxetan-3-yl)phenyl]-6-methyl-7-oxo-6,7-dihydro-1H-pyrrolo[2,3-c]pyridine-2-carboxamide Example 123b was prepared according to the procedure for the preparation of Example 28e, substituting Example 123a for Example 28d. $^1$H NMR (400 MHz, DMSO-d$_6$) δ 12.23 (s, 1H), 8.31 (t, J=5.3 Hz, 1H), 7.62 (d, J=2.4 Hz, 1H), 7.46 (dd, J=8.6, 2.4 Hz, 1H), 7.36 (s, 1H), 6.98 (d, J=9.1 Hz, 2H), 6.84 (s, 1H), 6.40 (d, J=8.6 Hz, 1H), 6.33 (s, 1H), 4.78-4.67 (m, 4H), 3.58 (s, 3H), 3.25 (qd, J=7.2, 5.3 Hz, 2H), 2.01 (s, 6H), 1.10 (t, J=7.2 Hz, 3H). MS (ESI+) m/z 506.1 (M+H)$^+$.

Example 124

N-ethyl-4-{5-(2-hydroxypropan-2-yl)-2-[4-(2-hydroxypropan-2-yl)-2,6-dimethylphenoxy]pyridin-3-yl}-6-methyl-7-oxo-6,7-dihydro-1H-pyrrolo[2,3-c]pyridine-2-carboxamide

Example 124a methyl 6-(4-acetyl-2,6-dimethylphenoxy)-5-bromonicotinate

Methyl 5-bromo-6-chloronicotinate (751 mg, 3.00 mmol), 1-(4-hydroxy-3,5-dimethylphenyl)ethanone (493 mg, 3.00 mmol), and cesium carbonate (1.47 g, 4.50 mmol) were combined in dimethyl sulfoxide (3 mL). The reaction mixture was heated at 100° C. for 2 hours, cooled to ambient temperature, and partitioned between ethyl acetate and water. The organic layer was washed with saturated aqueous sodium chloride, dried with anhydrous sodium sulfate, filtered, and concentrated to provide the title compound (980 mg, 86%).

Example 124b 2-(4-((3-bromo-5-(2-hydroxypropan-2-yl)pyridin-2-yl)oxy)-3,5-dimethylphenyl)propan-2-ol To a solution of Example 124a (970 mg, 2.56 mmol) in tetrahydrofuran (15 mL) was added 3M methylmagnesium chloride in tetrahydrofuran (5.13 mL, 15.4 mmol) dropwise at −78° C. The reaction mixture was stirred at ambient temperature for 2 hours, treated carefully with 5% aqueous ammonium chloride, and partitioned between ethyl acetate and water. The organic layer was washed with saturated aqueous sodium chloride, dried with anhydrous sodium sulfate, filtered, and concentrated. The residue was purified by flash chromatography (silica gel, 20-40% ethyl acetate in heptanes) to provide the title compound (854 mg, 84%).

Example 124c

N-ethyl-4-{5-(2-hydroxypropan-2-yl)-2-[4-(2-hydroxypropan-2-yl)-2,6-dimethylphenoxy]pyridin-3-yl}-6-methyl-7-oxo-6,7-dihydro-1H-pyrrolo[2,3-c]pyridine-2-carboxamide Example 1h (34.5 mg, 0.100 mmol), Example 124b (39.4 mg, 0.100 mmol), sodium carbonate (37.1 mg, 0.350 mmol), tris(dibenzylideneacetone)dipalladium(0) (2.75 mg, 3.00 μmol) and 1,3,5,7-tetramethyl-6-phenyl-2,4,8-trioxa-6-phosphaadamantane (2.63 mg, 9.00) were combined in a microwave tube and purged with nitrogen for 15 minutes. A mixture of tetrahydrofuran (2 mL) and water (0.5 mL) was purged with nitrogen for 15 minutes and transferred to the reaction vessel. The reaction mixture was heated at 60° C. for 3 hours, cooled to ambient temperature, and partitioned between ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20-60% 3:1 ethyl acetate/ethanol in heptanes) to provide the title compound (50 mg, 94%). $^1$H NMR (500 MHz, DMSO-d$_6$) δ ppm 12.33 (d, J=1.8 Hz, 1H), 8.36 (t, J=5.4 Hz, 1H), 8.10 (d, J=2.4 Hz, 1H), 7.95 (d, J=2.4 Hz, 1H), 7.45 (s, 1H), 7.14 (s, 2H), 6.89 (d, J=2.2 Hz, 1H), 5.19 (s, 1H), 4.93 (s, 1H), 3.61 (s, 3H), 3.31-3.25 (m, 2H), 1.99 (s, 6H), 1.48 (s, 6H), 1.41 (s, 6H), 1.13 (t, J=7.2 Hz, 3H). (ESI+) m/z 533 (M+H)$^+$.

Example 125

N-tert-butyl-4-{5-(2-hydroxypropan-2-yl)-2-[4-(2-hydroxypropan-2-yl)-2,6-dimethylphenoxy]pyridin-3-yl}-6-methyl-7-oxo-6,7-dihydro-1H-pyrrolo[2,3-c]pyridine-2-carboxamide Example 125 was prepared according to the procedure used for the preparation of Example 124c, substituting Example 32c for Example 1h. Purification by flash chromatography (silica gel, 20-40% 3:1 ethyl acetate/ethanol in heptanes) provided the title compound (49 mg, 87%). $^1$H NMR (500 MHz, DMSO-$d_6$) δ ppm 12.45 (s, 1H), 8.10 (d, J=2.4 Hz, 1H), 7.96 (d, J=2.4 Hz, 1H), 7.89 (s, 1H), 7.46 (s, 1H), 7.15 (s, 2H), 6.90 (d, J=1.7 Hz, 1H), 5.20 (s, 1H), 4.93 (s, 1H), 3.62 (s, 3H), 1.99 (s, 6H), 1.48 (s, 6H), 1.41 (s, 6H), 1.38 (s, 9H). (ESI+) m/z 561 (M+H)$^+$.

Example 126

4-{5-(1,2-dihydroxypropan-2-yl)-2-[2-methyl-6-(trifluoromethyl)phenoxy]phenyl}-N-ethyl-6-methyl-7-oxo-6,7-dihydro-1H-pyrrolo[2,3-c]pyridine-2-carboxamide Example 126a 1-(3-bromo-4-(2-methyl-6-(trifluoromethyl)phenoxy)phenyl)ethan-1-one A mixture of 2-methyl-6-(trifluoromethyl)phenol (213 mg, 1.21 mmol), cesium carbonate (751 mg, 2.30 mmol), and 1-(3-bromo-4-fluorophenyl)ethanone (250 mg, 1.15 mmol) in dimethyl sulfoxide (3 mL) was stirred at 60° C. in sealed tube for 2 days and then at 80° C. for another day. The reaction mixture was cooled to ambient temperature and partitioned between ethyl acetate (50 mL) and water (20 mL). The aqueous layer was extracted with ethyl acetate twice. The combined organic layers were washed with saturated aqueous sodium chloride, dried over anhydrous sodium sulfate, filtered, and concentrated. The residue was purified by flash column chromatography (silica gel, 5% to 20% ethyl acetate in petroleum ether) to give the title compound (180 mg, 39% yield). MS (ESI+) m/z 373.0, 375.0 (M, M+2)$^+$.

Example 126b 2-(2-bromo-4-(prop-1-en-2-yl)phenoxy)-1-methyl-3-(trifluoromethyl)benzene To a solution of methyltriphenylphosphonium bromide (402 mg, 1.13 mmol) in anhydrous tetrahydrofuran (10 mL) was added n-butyl lithium (0.703 mL, 1.6 M in tetrahydrofuran, 1.13 mmol) at 0° C. and the reaction mixture was stirred at this temperature for 1 hour. Then Example 126a (280 mg, 0.750 mmol) in 2 mL of tetrahydrofuran was added to the reaction solution and the reaction mixture was allowed to warm to 15° C. for 16 hours. The mixture was partitioned between water (10 mL) and ethyl acetate (30 mL). The organic layer was separated and the aqueous layer was extracted with ethyl acetate (20 mL) once more. The combined organic layers were dried over anhydrous sodium sulfate, filtered, and concentrated. The residue was purified by flash chromatography (silica gel, 5% to 10% ethyl acetate in petroleum ether) to give the title compound (230 mg, 83% yield). $^1$H NMR (400 MHz, CDCl$_3$) δ 7.73 (s, 1H), 7.58 (d, J=7.8 Hz, 1H), 7.46 (d, J=7.5 Hz, 1H), 7.29 (d, J=7.7 Hz, 1H), 7.21 (d, J=8.6 Hz, 1H), 6.29 (d, J=8.6 Hz, 1H), 5.30 (s, 1H), 5.05 (s, 1H), 2.09 (s, 6H).

Example 126c 2-(3-bromo-4-(2-methyl-6-(trifluoromethyl)phenoxy)phenyl)propane-1,2-diol To a solution of Example 126b (230 mg, 0.620 mmol) and potassium carbonate (257 mg, 1.86 mmol) in water (15 mL) and tert-butanol (15 mL) was added potassium hexacyanoferrate(III) (1020 mg, 3.10 mmol) and potassium osmate dehydrate (9.13 mg, 0.025 mmol) at 15° C. The reaction mixture was stirred at 15° C. for 18 hours. Water was added and the product was extracted with ethyl acetate (3×30 mL). The combined organic layers were washed with saturated aqueous sodium chloride, dried over anhydrous sodium sulfate, filtered, and concentrated. The residue was purified by flash chromatography (silica gel, 50% to 100% ethyl acetate in petroleum ether) to give the title compound (230 mg, 92% yield). MS (ESI+) m/z 387.0, 389.1 (M-18, M-16)$^+$.

Example 126d

4-{5-(1,2-dihydroxypropan-2-yl)-2-[2-methyl-6-(trifluoromethyl)phenoxy]phenyl}-N-ethyl-6-methyl-7-oxo-6,7-dihydro-1H-pyrrolo[2,3-c]pyridine-2-carboxamide Example 126d was prepared according to the procedure used for the preparation of Example 1m, substituting Example 126c for Example 1l. $^1$H NMR (400 MHz, DMSO-$d_6$) δ 12.25 (s, 1H), 8.34 (s, 1H), 7.69-7.59 (m, 2H), 7.56 (s, 1H), 7.37 (t, J=7.8 Hz, 1H), 7.34-7.25 (m, 2H), 6.83 (s, 1H), 6.33 (d, J=8.6 Hz, 1H), 4.91 (s, 1H), 4.73 (t, J=5.8 Hz, 1H), 3.57 (s, 3H), 3.45-3.38 (m, 2H), 3.29-3.23 (m, 2H), 1.93 (s, 3H), 1.41 (s, 3H), 1.12 (t, J=7.2 Hz, 3H). MS (ESI+) m/z 544.1 (M+H)$^+$.

Example 127

N-tert-butyl-4-{5-(1,2-dihydroxypropan-2-yl)-2-[2-methyl-6-(trifluoromethyl)phenoxy]phenyl}-6-methyl-7-oxo-6,7-dihydro-1H-pyrrolo[2,3-c]pyridine-2-carboxamide Example 127 was prepared according to the procedure used for the preparation of Example 32d, substituting Example 126d for Example 3d. $^1$H NMR (400 MHz, DMSO-$d_6$) δ 12.35 (s, 1H), 7.86 (s, 1H), 7.67-7.59 (m, 2H), 7.57 (d, J=2.1 Hz, 1H), 7.37 (t, J=7.7 Hz, 1H), 7.33-7.27 (m, 2H), 6.82 (s, 1H), 6.33 (d, J=8.6 Hz, 1H), 4.93 (s, 1H), 4.73 (t, J=5.7 Hz, 1H), 3.58 (s, 3H), 3.41 (d, J=5.8 Hz, 2H), 1.93 (s, 3H), 1.41 (s, 3H), 1.38 (s, 9H). MS (ESI+) m/z 572.1 (M+H)$^+$.

Example 128

4-[5-(2,5-dihydroxypentan-2-yl)-2-(4-fluoro-2,6-dimethylphenoxy)phenyl]-N-ethyl-6-methyl-7-oxo-6,7-dihydro-1H-pyrrolo[2,3-c]pyridine-2-carboxamide

Example 128a 2-(2-bromo-4-iodophenoxy)-5-fluoro-1,3-dimethylbenzene

A mixture of 2-bromo-1-fluoro-4-iodobenzene (3.01 g, 10 mmol), 4-fluoro-2,6-dimethylphenol (1.47 g, 10.5 mmol), and cesium carbonate (3.42 g, 10.5 mmol) in dimethyl sulfoxide (20 mL) was heated at 110° C. for 16 hours. The reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash chromatography (silica gel, 2% ethyl acetate in heptanes) to give the title compound (3.21 g, 76% yield). $^1$H NMR (400 MHz, DMSO-$d_6$) δ 7.98 (d, J=2.1 Hz, 1H), 7.51 (dd, J=8.6, 2.1 Hz, 1H), 7.03 (dt, J=9.1, 0.7 Hz, 2H), 6.15 (d, J=8.6 Hz, 1H), 2.00 (t, J=0.6 Hz, 6H).

Example 128b 1-(3-bromo-4-(4-fluoro-2,6-dimethylphenoxy)phenyl)-4-hydroxybutan-1-one A mixture of Example 128a (0.421 g, 1.0 mmol), tributyl(4,5-dihydrofuran-2-yl)stannane (0.395 g, 1.100 mmol) and tetrakis(triphenylphosphine)palladium(0) (0.058 g, 0.050 mmol) in toluene (5 mL) was heated at 90° C. for 2 hours. The solvent was evaporated under reduced pressure, and the residue was purified by flash chromatography (silica gel, 20% ethyl acetate in heptanes) to give the title compound (0.29 g, 76% yield).

Example 128c 4-(3-bromo-4-(4-fluoro-2,6-dimethylphenoxy)phenyl)pentane-1,4-diol Example 128b (0.1 g, 0.262 mmol) in tetrahydrofuran (5 mL) was treated with methylmagnesium bromide (0.350 mL, 3 M in tetrahydrofuran, 1.049 mmol) at ambient temperature overnight. The reaction mixture was quenched carefully with methanol and then partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash chromatography (silica gel eluting, 30% ethyl acetate in heptanes) to give the title compound (0.079 g, 76% yield). $^1$H NMR (501 MHz, DMSO-$d_6$) δ 7.70 (d, J=2.2 Hz, 2H), 7.22 (dd, J=8.6, 2.2 Hz, 2H), 7.09-7.02 (m, 4H), 6.30 (d, J=8.6 Hz, 2H), 4.97 (s, 2H), 4.33 (t, J=5.2 Hz, 2H), 3.29 (tdd, J=6.7, 5.2, 1.5 Hz, 4H), 2.05 (d, J=0.6 Hz, 11H), 1.70-1.56 (m, 4H), 1.38 (s, 6H), 1.23-1.10 (m, 3H). MS (DCI+) m/z 398.1 (M+H)$^+$.

Example 128d

4-[5-(2,5-dihydroxypentan-2-yl)-2-(4-fluoro-2,6-dimethylphenoxy)phenyl]-N-ethyl-6-methyl-7-oxo-6,7-dihydro-1H-pyrrolo[2,3-c]pyridine-2-carboxamide Example 128d was prepared according to the procedure used for the preparation of Example 1m, substituting Example 128c for Example 1l. $^1$H NMR (501 MHz, DMSO-$d_6$) δ 12.21 (d, J=2.4 Hz, 1H), 8.31 (t, J=5.4 Hz, 1H), 7.45 (d, J=2.4 Hz, 1H), 7.31 (s, 1H), 7.25 (dd, J=8.6, 2.4 Hz, 1H), 6.96 (d, J=9.1 Hz, 2H), 6.81 (d, J=2.2 Hz, 1H), 6.30 (d, J=8.6 Hz, 1H), 3.58 (s, 3H), 3.34-3.20 (m, 4H), 2.00 (s, 6H), 1.72-1.59 (m, 2H), 1.41 (s, 3H), 1.45-1.35 (m, 1H), 1.24 (ddd, J=12.3, 8.8, 5.8 Hz, 1H), 1.10 (t, J=7.2 Hz, 3H). MS (ESI+) m/z 536.2 (M+H)$^+$.

Example 129

N-ethyl-4-[2-(4-fluoro-2,6-dimethylphenoxy)-5-(4-hydroxyoxan-4-yl)phenyl]-6-methyl-7-oxo-6,7-dihydro-1H-pyrrolo[2,3-c]pyridine-2-carboxamide

Example 129a 4-(3-bromo-4-(4-fluoro-2,6-dimethylphenoxy)phenyl)tetrahydro-2H-pyran-4-ol Example 128a (0.842 g, 2 mmol) in hexanes (20 mL) was cooled to −78° C. To this solution was added tert-butyllithium (1.35 mL, 2.30 mmol) at −78° C. The reaction mixture was stirred at −78° C. for 1 hour. Then the reaction mixture was allowed to worm to ambient temperature, and stirred at ambient temperature for 1 hour. The reaction mixture was cooled back to −78° C. again. To this solution was added dihydro-2H-pyran-4(3H)-one (0.200 g, 2 mmol) in toluene (1 mL). The reaction mixture was allowed to warm up to ambient temperature overnight. The reaction mixture was quenched with saturated aqueous ammonium chloride. The reaction mixture was partitioned between water and ethyl acetate. The aqueous was extracted with additional ethyl acetate twice. The combined organic layers were washed with saturated aqueous sodium chloride, dried over anhydrous magnesium sulfate, filtered, and concentrated. The residue was purified by column chromatography (silica gel, 10% ethyl acetate in heptanes) to give the title compound (0.14 g, 18% yield). $^1$H NMR (501 MHz, DMSO-$d_6$) δ 7.76 (d, J=2.2 Hz, 1H), 7.30 (dd, J=8.6, 2.3 Hz, 1H), 7.08-7.02 (m, 2H), 6.31 (d, J=8.6 Hz, 1H), 5.08 (d, J=1.0 Hz, 1H), 3.77-3.54 (m, 4H), 2.6 (s, 6H), 1.89 (td, J=12.7, 5.2 Hz, 2H), 1.58 (td, J=12.6, 5.9 Hz, 2H). MS (ESI−) m/z 394.9 (M−H)$^-$.

Example 129b

N-ethyl-4-[2-(4-fluoro-2,6-dimethylphenoxy)-5-(4-hydroxyoxan-4-yl)phenyl]-6-methyl-7-oxo-6,7-dihydro-1H-pyrrolo[2,3-c]pyridine-2-carboxamide Example 129b was prepared according to the procedure used for the preparation of Example 1m, substituting Example 129a for Example 1l. $^1$H NMR (400 MHz, DMSO-$d_6$) δ 12.21-12.22 (m, 1H), 8.32 (t, J=5.3 Hz, 1H), 7.53 (d, J=2.4 Hz, 1H), 7.37-7.29 (m, 2H), 6.97 (d, J=9.1 Hz, 2H), 6.83 (d, J=2.2 Hz, 1H), 6.33 (d, J=8.6 Hz, 1H), 3.81-3.64 (m, 4H), 3.59 (s, 3H), 3.24 (td, J=7.3, 5.2 Hz, 2H), 2.00 (s, 6H), 1.94 (dt, J=12.5, 6.7 Hz, 2H), 1.55 (d, J=13.0 Hz, 2H), 1.10 (t, J=7.2 Hz, 3H). MS (ESI+) m/z 534.1 (M+H)+.

g. Biological Examples

Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BDI: amino acids K57-E168) and second (BDII: amino acids E352-M457) bromodomains of BRD4 were expressed and purified. An Alexa647-labeled BET-inhibitor was used as the fluorescent probe in the assay.

Synthesis of Alexa647-Labeled Bromodomain Inhibitor Compound 2-((6S,Z)-4-(4-chlorophenyl)-2,3,9-trimethyl-6H-thieno[3,2-f][1,2,4]triazolo[4,3-a][1,4]diazepin-6-yl)acetic acid Methyl 24(6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623)(100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)+] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate)

2-((6S,Z)-4-(4-chlorophenyl)-2,3,9-trimethyl-6H-thieno[3,2-f][1,2,4]triazolo[4,3-a][1,4]diazepin-6-yl)acetic acid) (85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide: water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)+]; 529.1 [(M−H)−] and (S,Z)—N,N'-(2,2'-(ethane-1,2-diylbis(oxy))bis(ethane-2,1-diyl))bis(2-((6S,Z)-4-(4-chlorophenyl)-2,3,9-trimethyl-6H-thieno[3,2-f][1,2,4]triazolo[4,3-a][1,4]diazepin-6-yl)acetamide)bis(2,2,2-trifluoroacetate) (3.0 mg, 1.5%); ESI-MS m/z=913.2 [(M+H)+]; 911.0 [(M−H)−].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate)

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)+] as a dark blue powder.

Assay

Compound dilution series were prepared in DMSO via an approximately 3-fold serial dilution. Compound dilutions were added directly into white, low-volume assay plates (Perkin Elmer Proxiplate 384 Plus#6008280) using a Labcyte Echo in conjunction with Labcyte Access and Thermo Multidrop CombinL robotics. Compounds were then suspended in eight microliters (μL) of assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) containing His-tagged bromodomain, Europium-conjugated anti-His antibody (Invitrogen PV5596) and Alexa-647-conjugated probe.

The final concentration of 1× assay mixture contained 2% DMSO, 12 nM His tagged BRD4 (BDI_K57-E168) and 100 nM probe or 4 nM His tagged BRD4 (BDII_E352-M457) and 30 nM probe, and 1 nM Europium-conjugated anti-His-tag antibody, and compound concentrations in the range of: 49.02 μM-0.61 nM or 0.98 μM-0.15 nM.

After a one-hour equilibration at room temperature, TR-FRET ratios were determined using an Envision multilabel plate reader (Ex 340, Em 495/520).

TR-FRET data were normalized to the means of 24 no-compound controls ("high") and 8 controls containing 1 μM un-labeled probe ("low"). Percent inhibition was plotted as a function of compound concentration and the data were fit with the 4 parameter logistic equation to obtain $IC_{50}$s. Inhibition constants ($K_i$) were calculated from the $IC_{50}$s, probe $K_d$ and probe concentration.

The mean $K_i$ values are reported in Table 1.

TABLE 1

| Example # | TR-FRET Binding Ki: BRD4 (BDI_K57-E168) (μM) | TR-FRET Binding Ki: BRD4 (BDII_E352-M457) (μM) |
|---|---|---|
| 1 | 0.462 | 0.0023 |
| 2 | 0.220 | 0.0030 |
| 3 | 0.404 | 0.0011 |
| 4 | 0.215 | 0.0031 |
| 5 | 0.187 | 0.0016 |
| 6 | 0.273 | 0.0023 |
| 7 | 0.632 | 0.0041 |

TABLE 1-continued

| Example # | TR-FRET Binding Ki: BRD4 (BDI_K57-E168) (μM) | TR-FRET Binding Ki: BRD4 (BDII_E352-M457) (μM) |
|---|---|---|
| 8 | 0.359 | 0.0023 |
| 9 | 0.601 | 0.0038 |
| 10 | 0.715 | 0.0054 |
| 11 | 0.170 | 0.0026 |
| 12 | 0.097 | 0.0019 |
| 13 | 0.114 | 0.0020 |
| 14 | 0.965 | 0.0023 |
| 15 | 1.84 | 0.0265 |
| 16 | 0.333 | 0.0023 |
| 17 | 0.467 | 0.0030 |
| 18 | 0.449 | 0.0038 |
| 19 | 0.196 | 0.0040 |
| 20 | 0.363 | 0.0031 |
| 21 | 0.521 | 0.0015 |
| 22 | 2.50 | 0.0105 |
| 23 | 0.701 | 0.0032 |
| 24 | 0.079 | 0.0017 |
| 25 | 0.171 | 0.0030 |
| 26 | 0.015 | 0.0015 |
| 27 | 0.044 | 0.0018 |
| 28 | 1.18 | 0.0054 |
| 29 | 0.594 | 0.0013 |
| 30 | 0.279 | 0.0019 |
| 31 | 0.260 | 0.0033 |
| 32 | 0.599 | 0.0028 |
| 33 | 0.921 | 0.0064 |
| 34 | 0.729 | 0.0051 |
| 35 | 0.426 | 0.0014 |
| 36 | 0.579 | 0.0034 |
| 37 | 0.195 | 0.0037 |
| 38 | 0.241 | 0.0057 |
| 39 | 0.640 | 0.0113 |
| 40 | 0.773 | 0.0021 |
| 41 | 0.759 | 0.0048 |
| 42 | 0.704 | 0.0057 |
| 43 | 0.525 | 0.0050 |
| 44 | 0.323 | 0.0073 |
| 45 | 1.08 | 0.0125 |
| 46 | 2.52 | 0.0195 |
| 47 | 2.06 | 0.0244 |
| 48 | 1.60 | 0.0060 |
| 49 | 0.284 | 0.0010 |
| 50 | 0.318 | 0.0013 |
| 51 | 0.263 | 0.0049 |
| 52 | 0.325 | 0.0009 |
| 53 | 0.432 | 0.0046 |
| 54 | 4.52 | 0.0060 |
| 55 | 4.69 | 0.0069 |
| 56 | 0.917 | 0.0047 |
| 57 | 2.89 | 0.0175 |
| 58 | 0.723 | 0.0081 |
| 59 | 1.77 | 0.0074 |
| 60 | 3.51 | 0.0075 |
| 61 | 1.58 | 0.0120 |
| 62 | 1.11 | 0.0102 |
| 63 | 0.406 | 0.0015 |
| 64 | 0.181 | 0.0004 |
| 65 | 0.222 | 0.0013 |
| 66 | 0.289 | 0.0014 |
| 67 | 0.259 | 0.0011 |
| 68 | 0.341 | 0.0022 |
| 69 | 0.499 | 0.0023 |
| 70 | 1.34 | 0.0037 |
| 71 | 2.31 | 0.0075 |
| 72 | 0.794 | 0.0013 |
| 73 | 0.417 | 0.0015 |
| 74 | 0.551 | 0.0030 |
| 75 | 0.743 | 0.0029 |
| 76 | 0.927 | 0.0087 |
| 77 | 0.606 | 0.0022 |
| 78 | 0.253 | 0.0022 |
| 79 | 0.225 | 0.0025 |
| 80 | 0.486 | 0.0052 |
| 81 | 0.043 | 0.0011 |
| 82 | 1.03 | 0.0014 |
| 83 | 0.350 | 0.0011 |
| 84 | 0.610 | 0.0019 |
| 85 | 0.433 | 0.0018 |
| 86 | 0.416 | 0.0014 |
| 87 | 0.501 | 0.0028 |
| 88 | 0.389 | 0.0011 |
| 89 | 0.281 | 0.0017 |
| 90 | 0.158 | 0.0020 |
| 91 | 0.271 | 0.0016 |
| 92 | 0.410 | 0.0121 |
| 93 | 0.502 | 0.0109 |
| 94 | 0.236 | 0.0037 |
| 95 | 0.333 | 0.0048 |
| 96 | 0.801 | 0.0091 |
| 97 | 0.657 | 0.0247 |
| 98 | 0.682 | 0.0096 |
| 99 | 0.431 | 0.0018 |
| 100 | 0.115 | 0.0056 |
| 101 | 0.11 | 0.0025 |
| 102 | 0.309 | 0.0025 |
| 103 | 0.450 | 0.0033 |
| 104 | 0.375 | 0.0012 |
| 105 | 1.34 | 0.0025 |
| 106 | 6.69 | 0.0066 |
| 107 | 0.231 | 0.0008 |
| 108 | 0.175 | 0.0016 |
| 109 | 0.169 | 0.0011 |
| 110 | 0.224 | 0.0020 |
| 111 | 0.150 | 0.0014 |
| 112 | 0.332 | 0.0023 |
| 113 | 0.098 | 0.0015 |
| 114 | 0.096 | 0.0013 |
| 115 | 0.323 | 0.0014 |
| 116 | 0.756 | 0.0029 |
| 117 | 0.215 | 0.0015 |
| 118 | 1.39 | 0.0104 |
| 119 | 0.346 | 0.0022 |
| 120 | 0.161 | 0.0008 |
| 121 | 0.356 | 0.0006 |
| 122 | 0.308 | 0.0020 |
| 123 | 0.168 | 0.0010 |
| 124 | 0.269 | 0.0017 |
| 125 | 0.140 | 0.0035 |
| 126 | 1.51 | 0.0063 |
| 127 | 6.58 | 0.0205 |
| 128 | 0.469 | 0.0013 |
| 129 | 0.649 | 0.0023 |
| Compound X | 0.00209 | 0.000952 |
| Compound Y | 0.0216 | 0.00132 |
| Compound Z | 0.0699 | 0.0155 |

Compound X is N-[4-(2,4-difluorophenoxy)-3-(6-methyl-7-oxo-6,7-dihydro-1H-pyrrolo[2,3-c]pyridin-4-yl)phenyl]ethanesulfonamide;

Compound Y is 4-[2-(2,4-difluorophenoxy)-5-(methylsulfonyl)phenyl]-N-ethyl-6-methyl-7-oxo-6,7-dihydro-1H-pyrrolo[2,3-c]pyridine-2-carboxamide; and Compound Z is 4-[5-(hydroxymethyl)-2-phenoxyphenyl]-6-methyl-1,6-dihydro-7H-pyrrolo[2,3-c]pyridin-7-one.

All tested compounds were found to have selectivity for BRD4 BDII over BRD4 BDI in the TR-FRET assay described above, and are at least 10 fold selective for BRD4 BDII over BRD4 BDI. In one embodiment, the present compounds are about 50 to about 100 fold selective for BRD4 BDII over BRD4 BDI. In one embodiment, the present compounds are about 100 to about 200 fold selective for BRD4 BDII over BRD4 BDI. In one embodiment, the present compounds are at least about 200 fold selective for BRD4 BDII over BRD4 BDI.

Xenograft Tumor Growth Inhibition Assay

The effect of compound of Example 32, 35 and Compound X to inhibit the growth of SKM-1_FP1 and LNCaP- FGC xenograft tumors was evaluated. Female SCID Beige mice (Charles River) were utilized for the SKM-1_FP1 flank xenograft model. Male NSG mice (JAX Labs) were used for the LNCaP-FGC study. Cells were suspended in PBS, mixed with Matrigel (phenol red free, Becton Dickinson Biosciences Discovery Labware) in a ratio of 1:4 (V/V) and inoculated subcutaneously into the flank (five million cells per site) of the mice. Inoculated mice were randomized into groups and treatment was initiated when mean tumor volume was 0.2-0.25 cm$^3$. The compounds were administered orally in (volume %): 1.5% DMSO, 30% PEG 400, and 68.5% Phosol 53 MCT. Tumor growth in the flank was assessed by measuring tumor size with calipers and calculating volume using the formula (L×W$^2$/2). Study groups were terminated prior to tumor volume reaching 3 cm$^3$. Inhibition of tumor growth was assessed at the time the vehicle-treated group was terminated by calculating the ratio of the mean volume of the test drug group to the mean volume of the untreated (control) group (T/C) and calculating percent tumor growth inhibition (% TGI).

% TGI=((1−T/C)×100). Results are reported in Table 2. Efficacy and Exposure Margins of BDII Selective BET Inhibitors Efficacy in AML (acute myeloid leukemia) and prostate cancer was studied with two BDII selective BET inhibitor compounds (Example 35 and Example 32), and a pan BET inhibitor (Compound X), in mouse SKM-1 (AML) and LNCaP (prostate) xenograft (Table 2).

Fourteen day rat toxicology studies were conducted with Example 35, Example 32, and Compound X, and maximum tolerated exposures were determined based on in-life observations including clinical signs, body weight, and food consumption. Compounds were dosed orally once daily, in Sprague-Dawley rats. Exposure margins calculated from the tolerated exposures in rat relative to the efficacious exposures in mouse xenograft models are reported in Table 2.

TABLE 2

| | Mouse efficacy results from xenograft studies | | | | | | Rat maximum tolerated exposure | AUC ratio (rat maximum tolerated exposure/mouse efficacious exposure) | |
|---|---|---|---|---|---|---|---|---|---|
| | AML (SKM-1) | | | Prostate (LNCaP) | | | | | |
| Example | AUC (μg * hr/mL) | Dose (mg/kg) | % TGI | AUC (ug * hr/mL) | Dose (mg/kg) | % TGI | AUC (μg * hr/ml) (dose) | AML (SKM-1) | Prostate (LNCaP) |
| Ex. 35 | 0.84 | 4.7 | 74 | 1.1 | 4.7 | 64 | 27.5 (30 mg/kg) | 32x | 25x |
| Ex. 32 | 5 | 9.4 | 76 | 12.6 | 30 | 60 | 69.2 (30 mg/kg) | 14x | 5.5x |
| Compound X | 1.2 | 1 | 76 | 1.2 | 1 | 64 | 0.725 (1 mg/kg) | 0.6x | 0.6x |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:

1. N-ethyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide or a pharmaceutically acceptable salt thereof.

2. N-ethyl-4-[2-(4-fluoro-2,6-dimethylphenoxy)-5-(2-hydroxypropan-2-yl)phenyl]-6-methyl-7-oxo-6,7-dihydro-1H-pyrrolo[2,3-c]pyridine-2-carboxamide.

* * * * *